US009193789B2

(12) United States Patent
Coyle et al.

(10) Patent No.: US 9,193,789 B2
(45) Date of Patent: Nov. 24, 2015

(54) ANTI-ICOS ANTIBODIES AND THEIR USE IN TREATMENT OF ONCOLOGY, TRANSPLANTATION AND AUTOIMMUNE DISEASE

(75) Inventors: Anthony Coyle, Boston, MA (US); Yihong Yao, Boyds, MD (US); Bahija Jallal, Potomac, MD (US); Gianluca Carlesso, Rockville, MD (US); Michael Bowen, Rockville, MD (US)

(73) Assignee: MedImmune, LLC, Gaithersburg, MD (US)

( * ) Notice: Subject to any disclaimer, the term of this patent is extended or adjusted under 35 U.S.C. 154(b) by 209 days.

(21) Appl. No.: 13/605,468

(22) Filed: Sep. 6, 2012

(65) Prior Publication Data

US 2013/0142783 A1    Jun. 6, 2013

Related U.S. Application Data

(63) Continuation of application No. 12/971,469, filed on Dec. 17, 2010, now abandoned, which is a continuation of application No. 12/116,512, filed on May 7, 2008, now abandoned.

(60) Provisional application No. 60/916,400, filed on May 7, 2007, provisional application No. 61/049,131, filed on Apr. 30, 2008.

(51) Int. Cl.
*C07K 16/28* (2006.01)
*A61K 39/395* (2006.01)
*A61K 39/00* (2006.01)

(52) U.S. Cl.
CPC ............. *C07K 16/28* (2013.01); *C07K 16/2818* (2013.01); *A61K 2039/505* (2013.01); *C07K 2317/41* (2013.01); *C07K 2317/56* (2013.01); *C07K 2317/72* (2013.01); *C07K 2317/732* (2013.01)

(58) Field of Classification Search
None
See application file for complete search history.

(56) References Cited

U.S. PATENT DOCUMENTS

| 6,737,056 B1 * | 5/2004 | Presta .................... 424/133.1 |
| 6,803,039 B2 * | 10/2004 | Tsuji et al. ................. 424/144.1 |
| 6,808,710 B1 | 10/2004 | Wood et al. |
| 6,946,292 B2 * | 9/2005 | Kanda et al. .................... 435/326 |
| 2002/0102658 A1 | 8/2002 | Tsuji et al. |
| 2003/0115614 A1 | 6/2003 | Kanda et al. |
| 2005/0014224 A1 | 1/2005 | Collins et al. |
| 2005/0054832 A1 | 3/2005 | Lazar et al. |
| 2005/0276803 A1 | 12/2005 | Chan et al. |
| 2006/0034826 A1 | 2/2006 | Carreno et al. |
| 2007/0036799 A1 | 2/2007 | Stavenhagen et al. |

FOREIGN PATENT DOCUMENTS

| EP | 1 158 004 A2 | 11/2001 |
| WO | WO 2005/103086 A1 | 3/2005 |

OTHER PUBLICATIONS

Carlesso, Gianluca et al., 2010, "ICOS and B7RP-1: Novel targets for monoclonal antibodies", New Drugs and Targets for Asthma and COPD, vol. 39, pp. 63-66.
Chelius, Dirk et al., 2005, "Identification and Characterization of Deamidation Sites in the Conserved Regions of Human Immunoglobulin Gamma Antibodies", Analytical Chemistry, vol. 77, No. 18:6004-6011.
European Search Report corresponding to EP 13 18 2513; mailed Feb. 14, 2014.
Herbst, Ronald et al., 2010, "B-Cell Depletion In Vitro and In Vivo with an Afucosylated Anti-CD19 Antibody", The Journal of Pharmacology and Experimental Therapeutics, Vo. 335, No. 1:213-222.
International Search Report corresponding to PCT/US2008/062859 mailed Oct. 24, 2008.
Kanda, Yutaka et al., 2006, "Comparison of biological activity among nonfucosylated therapeutic IgG1 antibodies with three different N-linked Fc oligosaccharides: the high-mannose, hybrid, and complex types", Glycobiology, vol. 17., No. 1:104-118.
Ogawa, Shu-hei et al., 2001, "Opposing Effects of Anti-Activation-Inducible Lymphocyte-Immunomodulatory Molecule/Inducible Costimulator Antibody on the Development of Acute Versus Chronic Graft-Versus-Host Disease", The Journal of Immunology, 167:5741-5748.
Peng, Baowei et al., 2008, "Transient blockade of the inducible costimulator pathway generates long-term tolerance to factor VIII after nonviral gene transfer into hemophilia A mice", Blood, vol. 112(5): 1662-1672.
Shields, Robert L. et al., 2001, "High Resolution Mapping of the Binding Site on Human IgG1 for FcγRI, FcγRII, FcγRIII, and FcRn and Design of IgG1 Variants with Improved Binding to the FcγR", The Journal of Biological Chemistry, vol. 276(9):6591-6604.
Shields, Robert L. et al., 2002, "Lack of Fucose on Human IgG1 N-Linked Oligosaccharide Improves Binding to Human FcγRIII and Antibody-dependent Cellular Toxicity", The Journal of Biological Chemistry, vol. 277(30):26733-26740.
Tamatani, Takuya et al., 2000, "AILIM/ICOS: a novel lymphocyte adhesion molecule", International Immunology, vol. 12(1):51-55.
Techman, A., 2007, "MedImmune In-Licenses from Japan Tobacco anti-ICOS Monoclonal Antibody for Inflammatory Diseases", Musculoskeletal Report.
Lazar, Greg A., 2006, "Engineered antibody Fc variants with enhanced effector function", Proceedings of the National Academy of Sciences, vol. 103(11):4005-4010.
Partial European Search Report corresponding to EP. Application No. 13182515.0 dated Oct. 6, 2014.

* cited by examiner

*Primary Examiner* — Ilia Ouspenski

(57) ABSTRACT

The present invention provides anti-human ICOS antibodies with increased effector function. The invention further relates to pharmaceutical compositions, immunotherapeutic compositions, and methods using therapeutic antibodies that bind to the human ICOS antigen and that may mediate ADCC, CDC, and/or antibody-dependent phagocytosis (opsonization) for the treatment and prevention of T cell-mediated diseases and disorders, such as, but not limited to, chronic infection, autoimmune disease or disorder, inflammatory disease or disorder, graft-versus-host disease (GVHD), transplant rejection, and T cell proliferative disorder.

20 Claims, 34 Drawing Sheets

Figure 3:
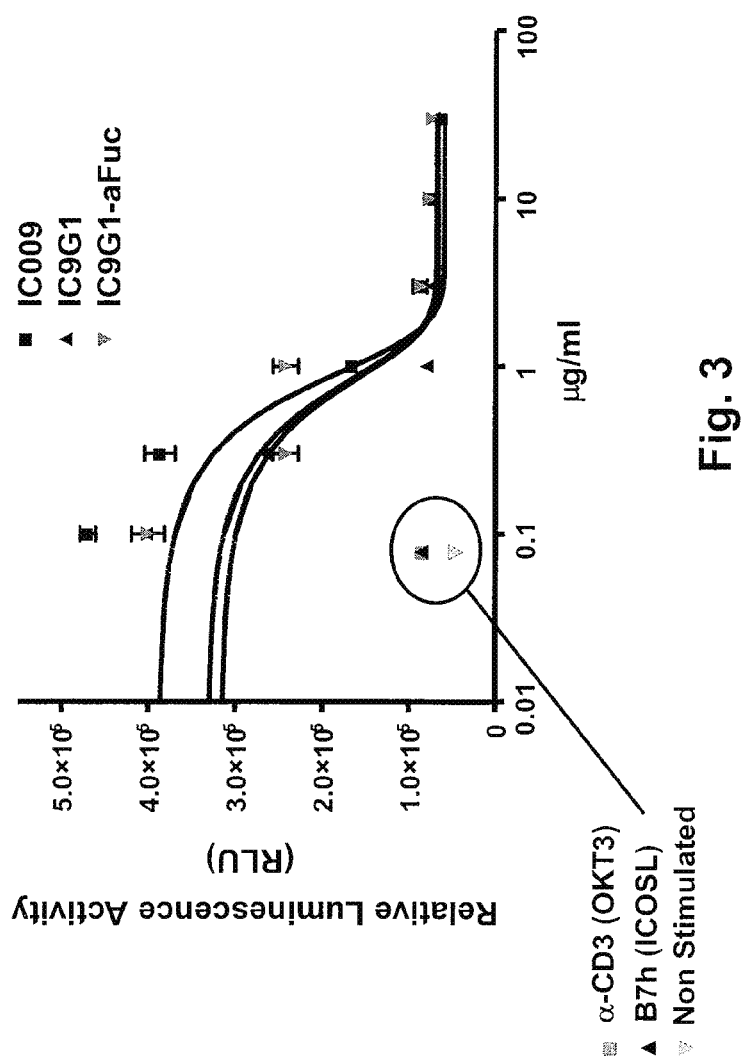

A) DIQMTQSPSSVSASVGDRVTITCRASQGISRLLAWYQQKPGKAPKLLIYVASSLQSGVPSRFSGSGSGTDFTLTISSLQPEDFATYYCQQANSFPWTFGQGTKVEIK

B) QVQLVQSGAEVKKPGASVKVSCKASGYTFTGYYMHWVRQAPGQGLEWMGWINPHSGGTNYAQKFQGRVTMTRDTSISTAYMELSRLRSDDTAVYYCARTYYYDSSGYYHDAFDIWGQGTMVTVSS

Fig. 1

| MAb | Human FcγRIIIa | Cynomolgus FcγRIIIa | Human FcγRIIa | Cynomolgus FcγRIIa | Human FcγRIIb | Cynomolgus FcγRIIb |
|---|---|---|---|---|---|---|
| IC009 | 8300 | 5750 | 1490 | 1280 | | 686 |
| IC9G1 | 2810 (F) 719 (V) | 394 | 3310 | 5280 | | 2370 |
| IC9G1-aFuc | 288 (F) 62 (V) | 21 | 2010 | 3140 | 14000 | 1950 |

Fig. 2

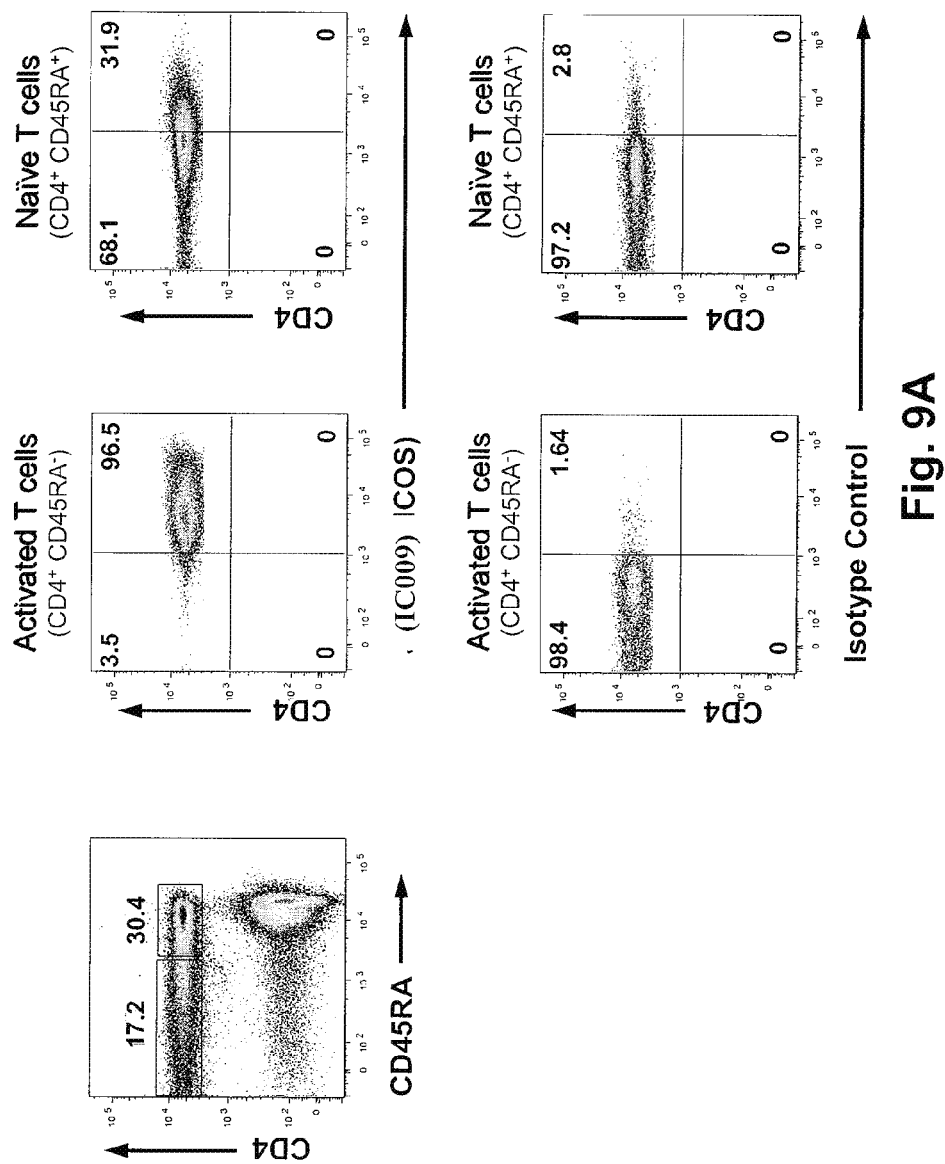

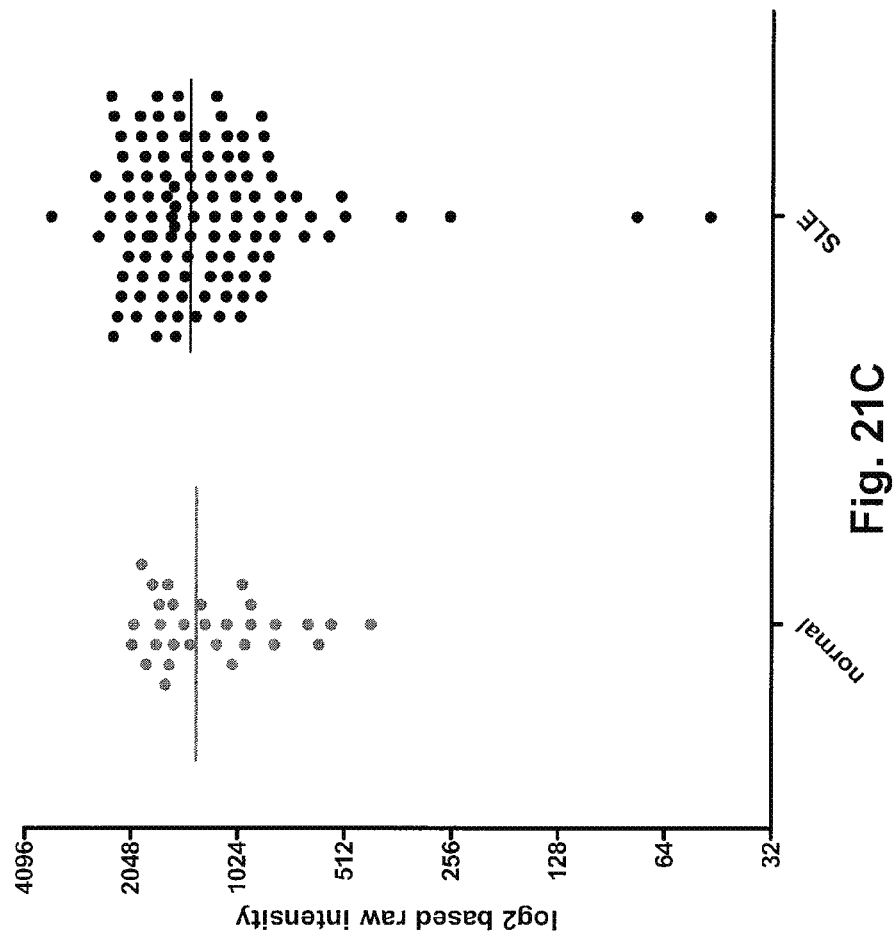

US 9,193,789 B2

ANTI-ICOS ANTIBODIES AND THEIR USE IN TREATMENT OF ONCOLOGY, TRANSPLANTATION AND AUTOIMMUNE DISEASE

This application is a Continuation of U.S. application Ser. No. 12/971,469, filed on Dec. 17, 2010, said application Ser. No. 12/971,469 is a Continuation of U.S. application Ser. No. 12/116,512 filed on May 7, 2008, said application Ser. No. 12/116,512 claims the benefit under 35 U.S.C. §119 (e) of U.S. Provisional Application Nos. 60/916,400, filed May 7, 2007, and 61/049,131, filed Apr. 30, 2008, the disclosures of each of which are incorporated herein in its entirety for all purposes.

1. INTRODUCTION

The present invention relates to anti-ICOS antibodies with enhanced effector function. The present invention is also directed to compositions comprising anti-ICOS antibodies with enhanced effector function that may mediate one or more of the following: complement-dependent cell-mediated cytotoxicity (CDC), antigen-dependent cell-mediated-cytotoxicity (ADCC), and antibody-dependent phagocytosis (opsonisation). The present invention is further directed to compositions comprising anti-ICOS antibodies of the IgG1 and/or IgG3 human isotype, as well as to compositions comprising anti-ICOS antibodies of the IgG2 and/or IgG4 human isotype that may mediate human ADCC, CDC, and/or antibody-dependent phagocytosis.

The present invention is further directed to methods for the treatment and prevention of T cell-mediated diseases and disorders, such as, but not limited to, chronic infection, autoimmune disease or disorder, inflammatory disease or disorder, graft-versus-host disease (GVHD), transplant rejection, and T cell proliferative disorder using therapeutic anti-ICOS antibodies with enhanced effector function.

2. BACKGROUND

ICOS is a type I transmembrane protein comprising an extracellular (Ig) V-like domain. ICOS serves as the receptor for the B7h co-stimulatory molecule. ICOS expression is low on naïve human T cells but becomes upregulated within hours after TCR engagement. ICOS expression persists on activated T cells subpopulations such as Th1, Th2, and Th17 CD4+ cells.

Given that ICOS expression is concentrated on activated T helper cell populations, the therapeutic use of an anti-ICOS antibody with enhanced effector function holds the promise of improving the efficacy of treatment and prevention of T cell-mediated diseases and disorders, such as, but not limited to, chronic infection, autoimmune disease or disorder, inflammatory disease or disorder, graft-versus-host disease (GVHD), transplant rejection, and T cell proliferative disorder using therapeutic anti-ICOS antibodies with enhanced effector function.

3. SUMMARY

The present invention relates to anti-ICOS antibodies with enhanced effector function that bind to the human ICOS molecule, as well as to compositions comprising those antibodies. In one embodiment, the present invention provides JMab-136 anti-ICOS antibodies (see, U.S. Pat. No. 6,803, 039) that are able to mediate an antibody effector function more efficiently than the parental JMab-136 antibody. In one embodiment, an anti-ICOS antibody of the invention comprises a variant Fc region. In one embodiment, an anti-ICOS antibody of the invention comprises a glycosylation pattern different from that of the parental antibody.

The present invention also provides pharmaceutical compositions comprising an anti-ICOS antibody with enhanced effector function.

The present invention also relates to methods of treating or preventing T cell-mediated diseases and disorders, such as, but not limited to, chronic infection, autoimmune disease or disorder, inflammatory disease or disorder, graft-versus-host disease (GVHD), transplant rejection, and T cell proliferative disorder using therapeutic anti-ICOS antibodies with enhanced effector function.

3.1. DEFINITIONS

As used herein, the terms "antibody" and "antibodies" (immunoglobulins) encompass monoclonal antibodies (including full-length monoclonal antibodies), polyclonal antibodies, multispecific antibodies (e.g., bispecific antibodies) formed from at least two intact antibodies, human antibodies, humanized antibodies, camelised antibodies, chimeric antibodies, single-chain Fvs (scFv), single-chain antibodies, single domain antibodies, domain antibodies, Fab fragments, F(ab')2 fragments, antibody fragments that exhibit the desired biological activity, disulfide-linked Fvs (sdFv), and anti-idiotypic (anti-Id) antibodies (including, e.g., anti-Id antibodies to antibodies of the invention), intrabodies, and epitope-binding fragments of any of the above. In particular, antibodies include immunoglobulin molecules and immunologically active fragments of immunoglobulin molecules, i.e., molecules that contain an antigen-binding site Immunoglobulin molecules can be of any type (e.g., IgG, IgE, IgM, IgD, IgA and IgY), class (e.g., IgG1, IgG2, IgG3, IgG4, IgA1 and IgA2) or subclass.

Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Light chains are classified as either lambda chains or kappa chains based on the amino acid sequence of the light chain constant region. The variable domain of a kappa light chain may also be denoted herein as VK. The term "variable region" may also be used to describe the variable domain of a heavy chain or light chain. Particular amino acid residues are believed to form an interface between the light and heavy chain variable domains. Such antibodies may be derived from any mammal, including, but not limited to, humans, monkeys, pigs, horses, rabbits, dogs, cats, mice, etc.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in segments called Complementarity Determining Regions (CDRs) both in the light chain and the heavy chain variable domains. The more highly conserved portions of the variable domains are called the framework regions (FW). The variable domains of native heavy and light chains each comprise four FW regions, largely adopting a β-sheet configuration, connected by three CDRs, which form loops connecting, and in some cases forming part of, the β-sheet structure. The CDRs in each chain are held together in close proximity by the FW regions and, with the CDRs from the other chain, contribute to the formation of the antigen-binding site of antibodies (see, Kabat et al., Sequences of Proteins of Immunological Interest, 5th Ed. Public Health Service, National Institutes of Health, Bethesda, Md. (1991)). The constant domains are generally not involved directly in antigen binding, but may influence antigen binding affinity and may exhibit various effector functions, such as participation of the antibody in ADCC, CDC, antibody-dependent phagocytosis and/or apoptosis.

The term "hypervariable region" when used herein refers to the amino acid residues of an antibody which are associated with its binding to antigen. The hypervariable regions encompass the amino acid residues of the "complementarity determining regions" or "CDRs" (e.g., residues 24-34 (L1), 50-56 (L2) and 89-97 (L3) of the light chain variable domain and residues 31-35 (H1), 50-65 (H2) and 95-102 (H3) of the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, J. Mol. Biol., 196:901-917 (1987)). "Framework" or "FW" residues are those variable domain residues flanking the CDRs. FW residues are present in chimeric, humanized, human, domain antibodies, diabodies, vaccibodies, linear antibodies, and bispecific antibodies.

As used herein "Fc region" includes the polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat et al. (1991, NIH Publication 91-3242, National Technical Information Service, Springfield, Va.). The "EU index as set forth in Kabat" refers to the residue numbering of the human IgG1 EU antibody as described in Kabat et al. supra. Fc may refer to this region in isolation, or this region in the context of an antibody, antibody fragment, or Fc fusion protein. An Fc variant protein may be an antibody, Fc fusion, or any protein or protein domain that comprises an Fc region. Particularly preferred are proteins comprising variant Fc regions, which are non-naturally occurring variants of an Fc region. The amino acid sequence of a non-naturally occurring Fc region (also referred to herein as a "variant Fc region") comprises a substitution, insertion and/or deletion of at least one amino acid residue compared to the wild type amino acid sequence. Any new amino acid residue appearing in the sequence of a variant Fc region as a result of an insertion or substitution may be referred to as a non-naturally occurring amino acid residue.

Note: Polymorphisms have been observed at a number of Fc positions, including but not limited to Kabat 270, 272, 312, 315, 356, and 358, and thus slight differences between the presented sequence and sequences in the prior art may exist.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, monoclonal antibodies are advantageous in that they can be synthesized by hybridoma cells that are uncontaminated by other immunoglobulin producing cells. Alternative production methods are known to those trained in the art, for example, a monoclonal antibody may be produced by cells stably or transiently transfected with the heavy and light chain genes encoding the monoclonal antibody.

The modifier "monoclonal" indicates the character of the antibody as being obtained from a substantially homogeneous population of antibodies, and is not to be construed as requiring engineering of the antibody by any particular method. The term "monoclonal" is used herein to refer to an antibody that is derived from a clonal population of cells, including any eukaryotic, prokaryotic, or phage clone, and not the method by which the antibody was engineered. For example, the monoclonal antibodies to be used in accordance with the present invention may be made by the hybridoma method first described by Kohler et al., Nature, 256:495 (1975), or may be made by any recombinant DNA method (see, e.g., U.S. Pat. No. 4,816,567), including isolation from phage antibody libraries using the techniques described in Clackson et al., Nature, 352:624-628 (1991) and Marks et al., J. Mol. Biol., 222:581-597 (1991), for example. These methods can be used to produce monoclonal mammalian, chimeric, humanized, human, domain antibodies, diabodies, vaccibodies, linear antibodies, and bispecific antibodies.

A "human antibody" can be an antibody derived from a human or an antibody obtained from a transgenic organism that has been "engineered" to produce specific human antibodies in response to antigenic challenge and can be produced by any method known in the art. In certain techniques, elements of the human heavy and light chain loci are introduced into strains of the organism derived from embryonic stem cell lines that contain targeted disruptions of the endogenous heavy chain and light chain loci. The transgenic organism can synthesize human antibodies specific for human antigens, and the organism can be used to produce human antibody-secreting hybridomas. A human antibody can also be an antibody wherein the heavy and light chains are encoded by a nucleotide sequence derived from one or more sources of human DNA. A fully human antibody also can be constructed by genetic or chromosomal transfection methods, as well as phage display technology, or in vitro activated ICOS expressing T cells, all of which are known in the art.

"Antibody-dependent cell-mediated cytotoxicity" and "ADCC" refer to a cell-mediated reaction in which non-specific cytotoxic cells (e.g., Natural Killer (NK) cells, neutrophils, and macrophages) recognize bound antibody on a target cell and subsequently cause lysis of the target cell. In one embodiment, such cells are human cells. While not wishing to be limited to any particular mechanism of action, these cytotoxic cells that mediate ADCC generally express Fc receptors (FcRs). The primary cells for mediating ADCC, NK cells, express FcγRIII, whereas monocytes express FcγRI, FcγRII, FcγRIII and/or FcγRIV. FcR expression on hematopoietic cells is summarized in Ravetch and Kinet, Annu. Rev. Immunol., 9:457-92 (1991). To assess ADCC activity of a molecule, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecules of interest may be assessed in vivo, e.g., in an animal model such as that disclosed in Clynes et al., Proc. Natl. Acad. Sci. (USA), 95:652-656 (1998).

"Complement dependent cytotoxicity" or "CDC" refers to the ability of a molecule to initiate complement activation and lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santaro et al., J. Immunol. Methods, 202:163 (1996), may be performed.

"Antibody-dependent phagocytosis" or "opsonization" as used herein refers to the cell-mediated reaction wherein non-specific cytotoxic cells that express FcγRs recognize bound antibody on a target cell and subsequently cause phagocytosis of the target cell.

"Effector cells" are leukocytes which express one or more FcRs and perform effector functions. The cells express at least FcγRI, FCγRII, FcγRIII and/or FcγRIV and carry out ADCC effector function. Examples of human leukocytes which mediate ADCC include peripheral blood mononuclear cells (PBMC), natural killer (NK) cells, monocytes, cytotoxic T cells and neutrophils.

The terms "Fc receptor" or "FcR" are used to describe a receptor that binds to the Fc region of an antibody. In one embodiment, the FcR is a native sequence human FcR. Moreover, in certain embodiments, the FcR is one which binds an IgG antibody (a gamma receptor) and includes receptors of the FcγRI, FcγRII, FcγRIII, and FcγRIV subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (See, Daëron, Annu. Rev. Immunol., 15:203-234 (1997)). FcRs are reviewed in Ravetch and Kinet, Annu. Rev. Immunol., 9:457-92 (1991); Capel et al., Immunomethods, 4:25-34 (1994); and de Haas et al., J. Lab. Clin. Med., 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., Immunol., 117:587 (1976) and Kim et al., J. Immunol., 24:249 (1994)).

"Affinity" of an antibody for an epitope to be used in the treatment(s) described herein is a term well understood in the art and means the extent, or strength, of binding of antibody to epitope. Affinity may be measured and/or expressed in a number of ways known in the art, including, but not limited to, equilibrium dissociation constant (KD or Kd), apparent equilibrium dissociation constant (KD' or Kd'), and IC50 (amount needed to effect 50% inhibition in a competition assay). It is understood that, for purposes of this invention, an affinity is an average affinity for a given population of antibodies which bind to an epitope. Values of KD' reported herein in terms of mg IgG per mL or mg/mL indicate mg Ig per mL of serum, although plasma can be used. When antibody affinity is used as a basis for administration of the treatment methods described herein, or selection for the treatment methods described herein, antibody affinity can be measured before and/or during treatment, and the values obtained can be used by a clinician in assessing whether a human patient is an appropriate candidate for treatment.

As used herein, the term "avidity" is a measure of the overall binding strength (i.e., both antibody arms) with which an antibody binds an antigen. Antibody avidity can be determined by measuring the dissociation of the antigen-antibody bond in antigen excess using any means known in the art, such as, but not limited to, by the modification of indirect fluorescent antibody as described by Gray et al., J. Virol. Meth., 44:11-24. (1993)

An "epitope" is a term well understood in the art and means any chemical moiety that exhibits specific binding to an antibody. An "antigen" is a moiety or molecule that contains an epitope, and, as such, also specifically binds to antibody.

The term "antibody half-life" as used herein means a pharmacokinetic property of an antibody that is a measure of the mean survival time of antibody molecules following their administration. Antibody half-life can be expressed as the time required to eliminate 50 percent of a known quantity of immunoglobulin from the patient's body or a specific compartment thereof, for example, as measured in serum or plasma, i.e., circulating half-life, or in other tissues. Half-life may vary from one immunoglobulin or class of immunoglobulin to another. In general, an increase in antibody half-life results in an increase in mean residence time (MRT) in circulation for the antibody administered.

The term "isotype" refers to the classification of an antibody's heavy or light chain constant region. The constant domains of antibodies are not involved in binding to antigen, but exhibit various effector functions. Depending on the amino acid sequence of the heavy chain constant region, a given human antibody or immunoglobulin can be assigned to one of five major classes of immunoglobulins: IgA, IgD, IgE, IgG, and IgM. Several of these classes may be further divided into subclasses (isotypes), e.g., IgG1 (gamma 1), IgG2 (gamma 2), IgG3 (gamma 3), and IgG4 (gamma 4), and IgA1 and IgA2. The heavy chain constant regions that correspond to the different classes of immunoglobulins are called α, δ, ε, γ, and μ, respectively. The structures and three-dimensional configurations of different classes of immunoglobulins are well-known. Of the various human immunoglobulin classes, only human IgG1, IgG2, IgG3, IgG4, and IgM are known to activate complement. Human IgG1 and IgG3 are known to mediate ADCC in humans. Human light chain constant regions may be classified into two major classes, kappa and lambda As used herein, the term "immunogenicity" means that a compound is capable of provoking an immune response (stimulating production of specific antibodies and/or proliferation of specific T cells).

As used herein, the term "antigenicity" means that a compound is recognized by an antibody or may bind to an antibody and induce an immune response.

By the terms "treat," "treating" or "treatment of" (or grammatically equivalent terms) it is meant that the severity of the subject's condition is reduced or at least partially improved or ameliorated and/or that some alleviation, mitigation or decrease in at least one clinical symptom is achieved and/or there is an inhibition or delay in the progression of the condition and/or prevention or delay of the onset of a disease or illness. Thus, the terms "treat," "treating" or "treatment of" (or grammatically equivalent terms) refer to both prophylactic and therapeutic treatment regimes.

As used herein, a "sufficient amount" or "an amount sufficient to" achieve a particular result refers to an amount of an antibody or composition of the invention that is effective to produce a desired effect, which is optionally a therapeutic effect (i.e., by administration of a therapeutically effective amount). For example, a "sufficient amount" or "an amount sufficient to" can be an amount that is effective to deplete ICOS expressing T cells.

A "therapeutically effective" amount as used herein is an amount that provides some improvement or benefit to the subject. Stated in another way, a "therapeutically effective" amount is an amount that provides some alleviation, mitigation, and/or decrease in at least one clinical symptom. Clinical symptoms associated with the disorders that can be treated by the methods of the invention are well-known to those skilled in the art. Further, those skilled in the art will appreciate that the therapeutic effects need not be complete or curative, as long as some benefit is provided to the subject.

4. BRIEF DESCRIPTION OF THE DRAWINGS

FIG. 1. Amino acid sequence of the VH (A) and VL (B) domains of the JMab-136 anti-ICOS antibody. CDR residues, defined according to Kabat, are in boxed bold letters. Potential O-glycosylation sites (T or S residue) and deamidation sites (DS or DG residues) are highlighted in gray.

FIG. 2. Enhanced binding affinity of IC9G1-aFuc to human and cynomolgus FcgRIIIa. Binding affinity (nM) of IC9G1-aFuc to recombinant human and cynomolgus FcγRs was measured as compared to a control antibodies (IC009 and IC9G1) and is summarized in this Figure.

FIG. 3. IC9G1-aFuc inhibits CD3/ICOSL induced human T Cell proliferation. Human T cells were incubated for 72 hrs on a plate coated with B7h-Fc (50 μl of 4 μg/ml) and anti-CD3 antibody (50 μl of 0.2 μg/ml) in the presence of increasing amounts of the IC9G1-aFuc antibody. T cell proliferation as a function of IC9G1-aFuc antibody concentration is shown. Data obtained from control experiments using the IC009 and IC9G1 antibodies are also shown.

Figure 4:
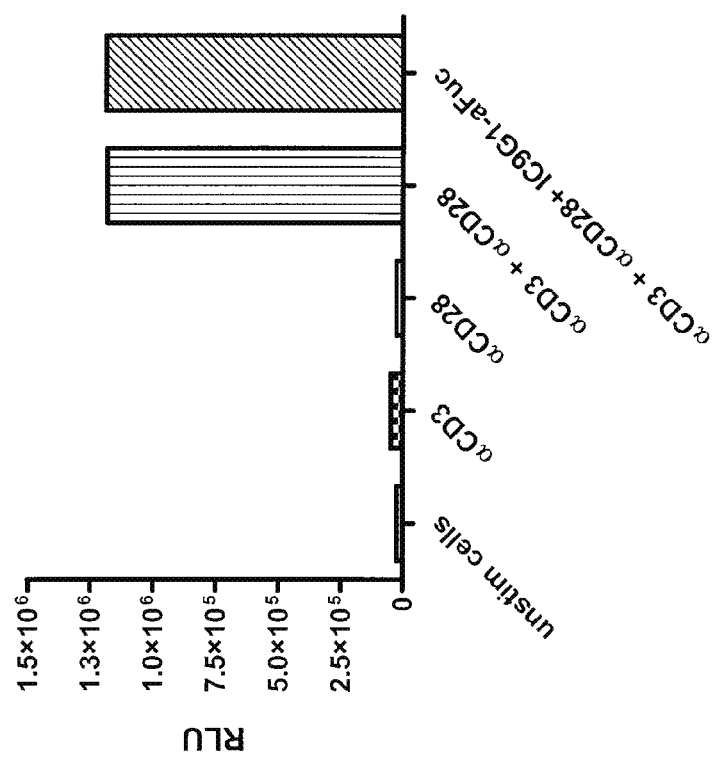

FIG. 4. IC9G1-aFuc does not inhibit anti-CD3/anti-CD28 antibody mediated proliferation of human tonsillar T cells. Isolated human tonsillar T cells were incubated for 72 hrs on a plate coated with anti-CD3 and/or anti-CD28 antibodies. Cell proliferation detected in the presence of 10 microg/ml of IC9G1 is shown.

FIG. 5. The ADCC activity of IC9G1-aFuc is higher than that of the IC9G1 or IC009 antibodies. ADCC activity was measured using stable tranfectants (A) HPB-ALL cells (HPB-ALL h-ICOS) and (B) Jurkat cells (Jurkat h-ICOS) expressing a human ICOS as target cells. The EC50 activity of the IC9G1-aFuc and IC9G1 antibodies on HPB-ALL h-ICOS cells was 138 pM and 648 pM, respectively. The EC50 activity of the IC9G1-aFuc and IC9G1 antibodies on transgenic Jurkat h-ICOS cells was 5.7 pM and 61 pM, respectively.

Figure 6:
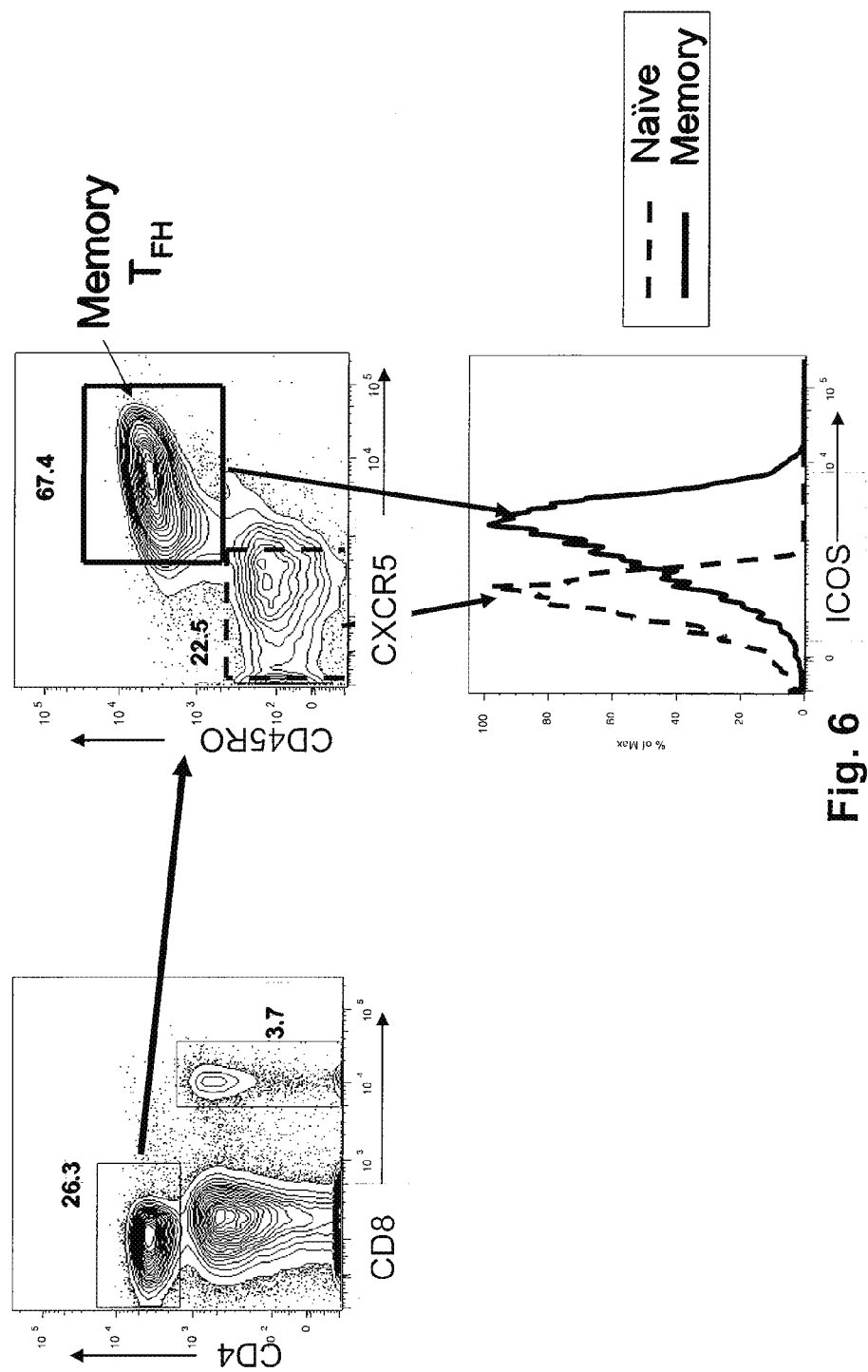

FIG. 6. ICOS expression in human tonsil is restricted to CD4+ memory $T_{FH}$ cells. The anti-ICOS staining pattern of CD4+CD45RO-CXCR5-naïve T cells and CD4+CD45RO+ CXCR5+ memory $T_{FH}$ is shown.

Figure 7:
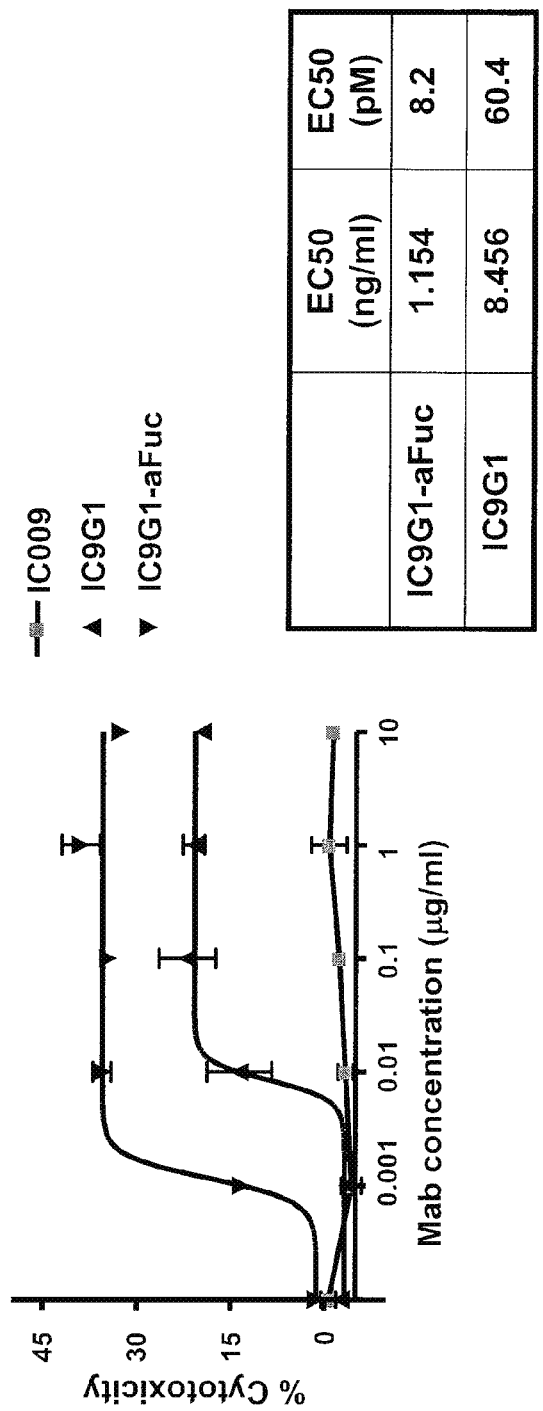

FIG. 7. The ADCC activity of IC9G1-aFuc is higher than that of the IC9G1 or IC009 antibodies. ADCC activity was measured using isolated human tonsillar T cells as target cells. The EC50 activity of the IC9G1-aFuc and IC9G1 antibodies was 8.2 pM and 60.4 pM, respectively, in this assay.

Figure 8A:
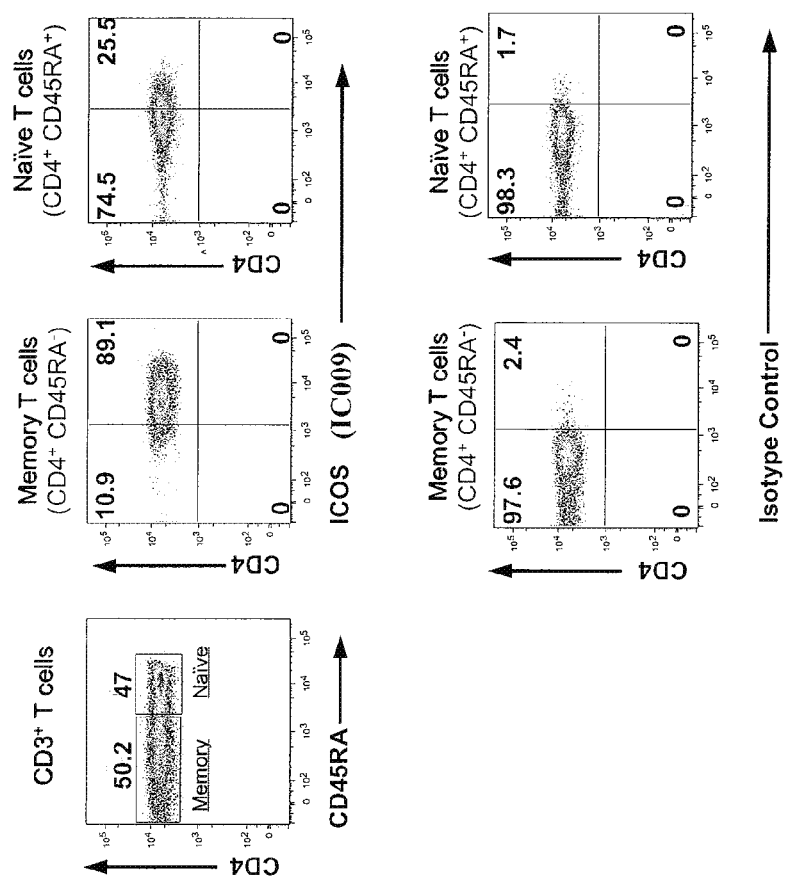
Figure 8B:
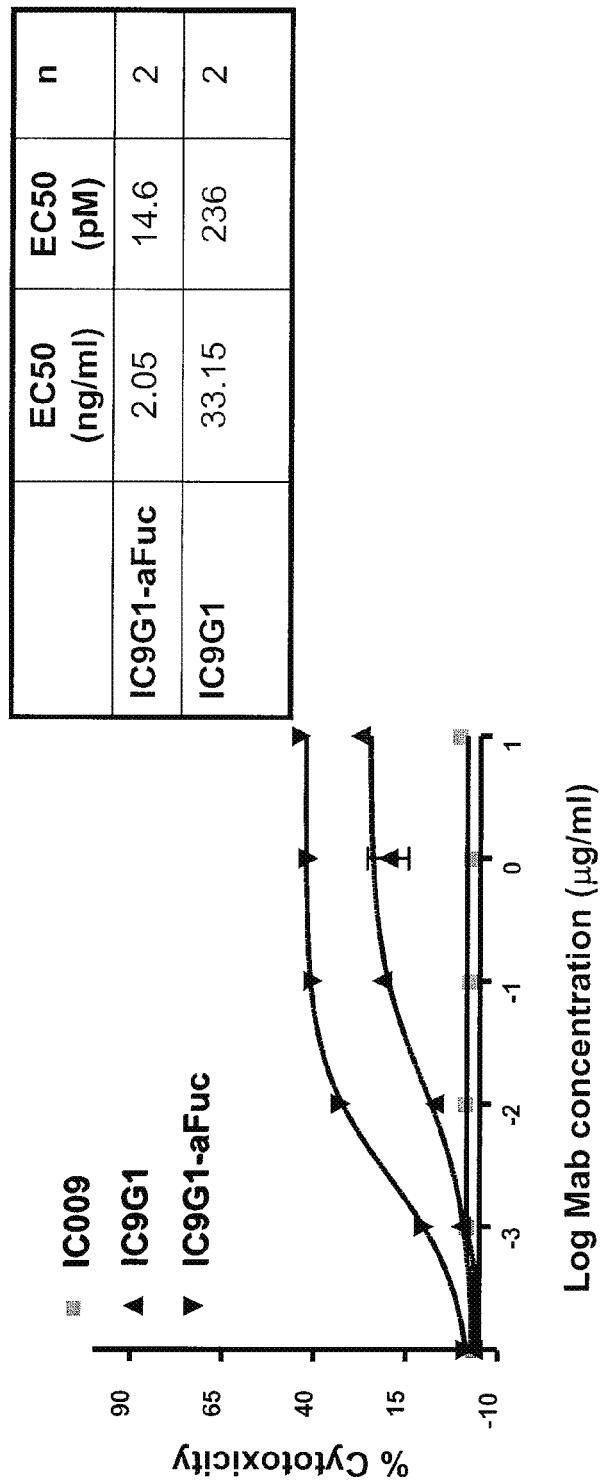

FIG. 8. IC9G1-aFuc mediated ADCC activity on freshly isolated cynomolgus splenic T cell targets. (A) ICOS expression profile of isolated cynomolgus splenic CD4+CD45RA+ naïve T cells and CD4+CD45RA− memory T cells was determined using flow cytometry. Flow cytometry plots of stained cells are shown. ICOS expression level of CD4+CD45RA− memory T cells is significantly higher than that of the CD4+CD45RA+naïve T cells. (B) ADCC cytotoxicity curves of IC009, IC9G1 and IC9G1-aFuc antibodies measured using isolated cynomolgus splenic T cells is shown. The ADCC activity of IC9G1-aFuc is higher than that of either the IC009 or IC9G1 antibodies. The EC50 activity of the IC9G1-aFuc and IC9G1 antibodies was 14.6 pM and 236 pM, respectively, in this assay.

Figure 9B:
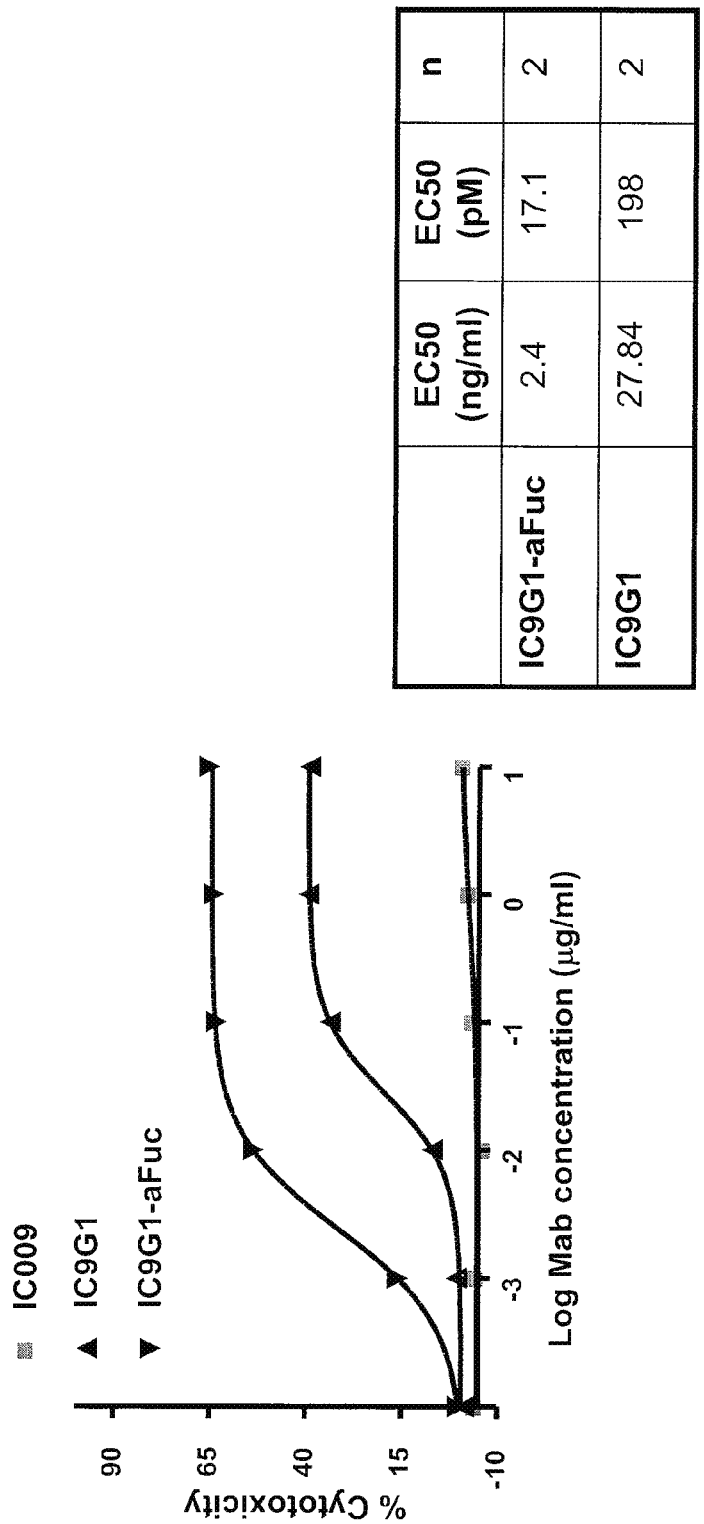

FIG. 9. IC9G1-aFuc mediated ADCC activity on freshly isolated cynomolgus mesenteric lymph node (MLN) T cell targets. (A) ICOS expression profile of isolated cynomolgus MLN CD4+CD45RA+naïve T cells and CD4+CD45RA− activated T cells was determined flow cytometry. Flow cytometry plots of stained cells are shown. ICOS expression level of CD4+CD45RA− activated T cells is significantly higher than that of the CD4+CD45RA+naïve T cells. (B) ADCC cytotoxicity curves of IC009, IC9G1 and IC9G1-aFuc antibodies measured using isolated cynomolgus MLN T cells is shown. The ADCC activity of IC9G1-aFuc is higher than that of either the IC009 or IC9G1 antibodies. The EC50 activity of the IC9G1-aFuc and IC9G1 antibodies was 17.1 pM and 198 pM, respectively, in this assay.

Figure 10:
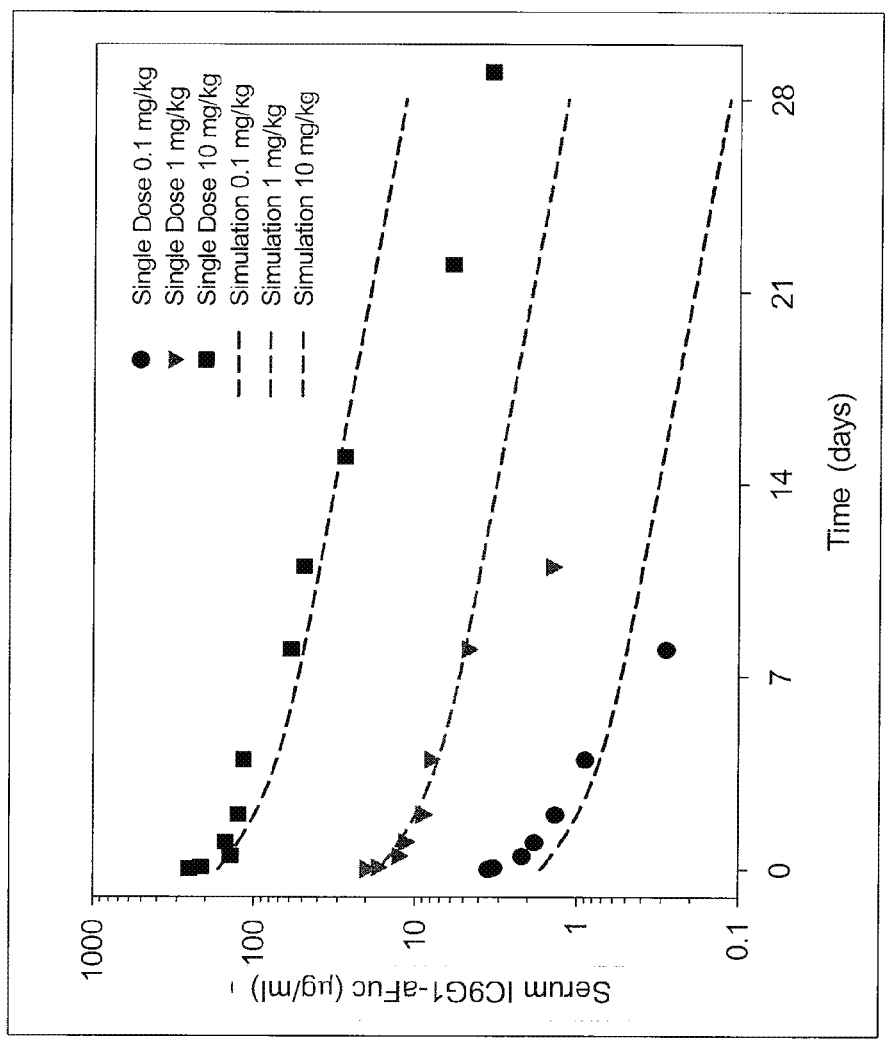

FIG. 10. IC9G1-aFuc PK profile in cynomolgus monkeys. A single dose of 0.1 mg/kg, 1 mg/kg or 10 mg/kg of IC9G1-aFuc antibody was administered intravenously to cynomolgus monkeys. Serum concentration of the IC9G1-aFuc antibody was measured for 4 weeks post-administration. IC9G1-aFuc serum concentration as a function of time is shown.

Figure 11:
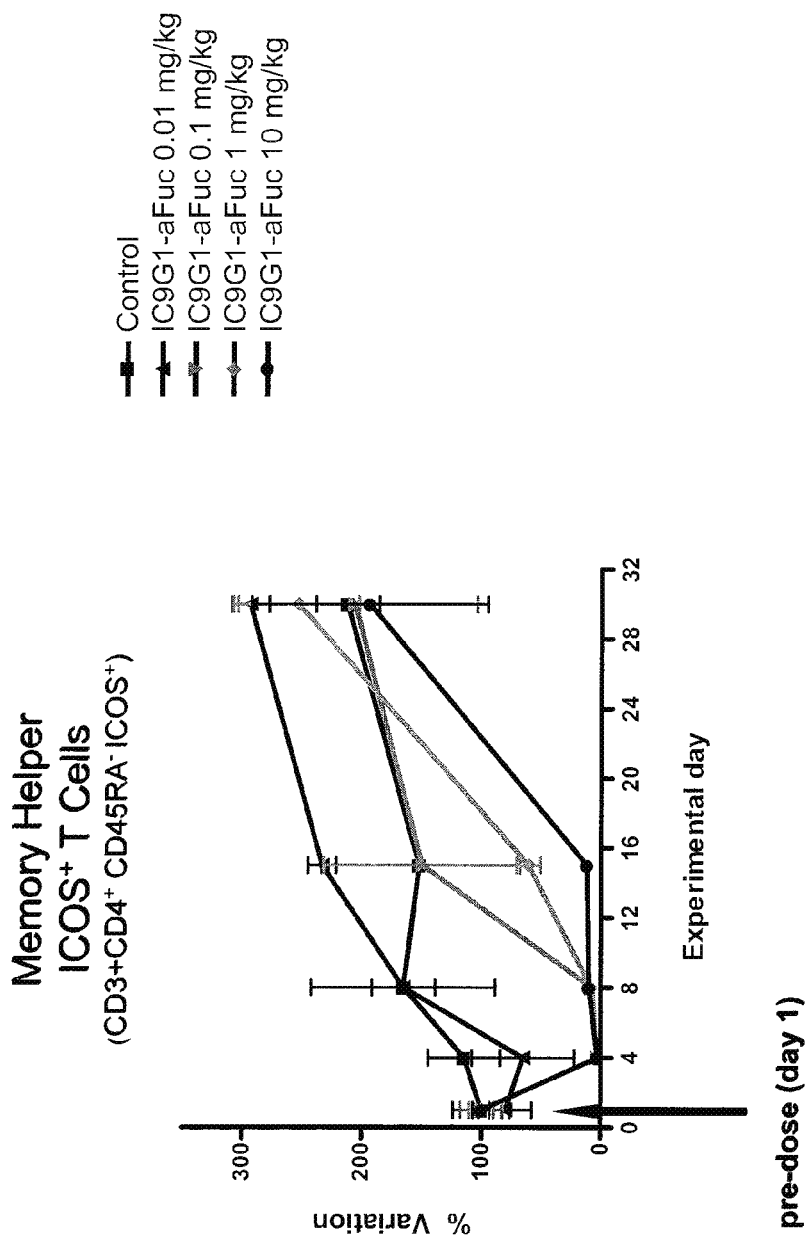

FIG. 11. A single IV dose of IC9G1-aFuc significantly depletes the level of CD3+CD4+CD45RA_ICOS+ memory T cells in cynomolgus monkeys in vivo. A single dose of 0.01 mg/kg, 0.1 mg/kg, 1 mg/kg or 10 mg/kg of IC9G1-aFuc antibody was administered intravenously to cynomolgus monkeys. The level CD3+CD4+CD45RA−ICOS+ memory T cells was monitored over time. Normalized memory T cell levels as a function of time after IC9G1-aFuc administration is shown. Administration of a single dose of 0.1 mg/kg, 1 mg/kg or 10 mg/kg of IC9G1-aFuc antibody achieved essentially complete elimination of CD3+CD4+CD45RA_ICOS+ memory T cells by day 4. The recovery of the ICOS+ memory T cells was dose dependent.

Figure 12:
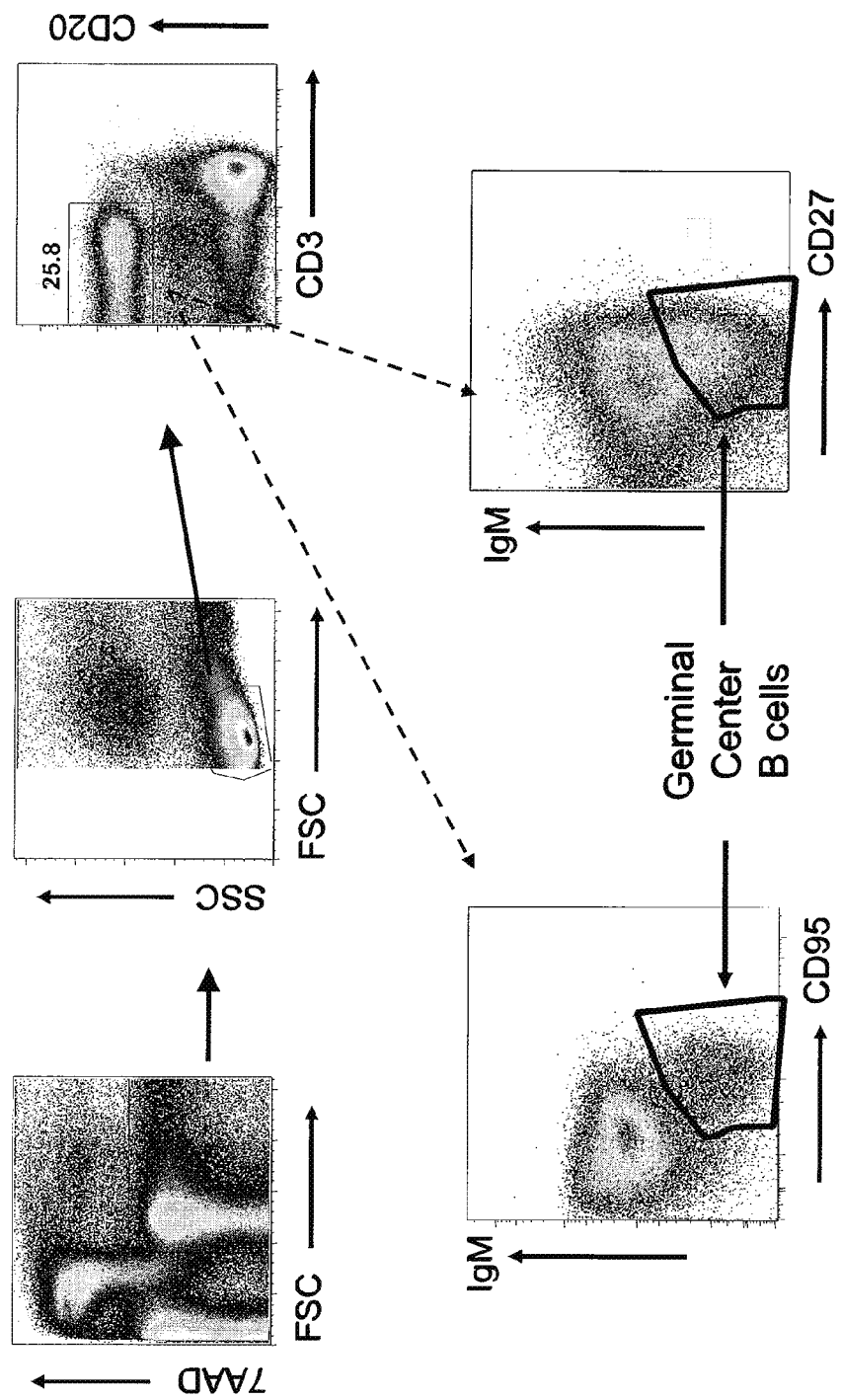

FIG. 12. Flow cytometry based characterization of germinal center B cells. Cynomolgus germinal center B cells were identified either as CD3−CD20+IgM-CD95+ cells or CD3−CD20+IgM-CD27+ cells.

FIG. 13. A single IV dose of IC9G1-aFuc significantly reduces the level of mesenteric lymph node (MLN) memory helper ICOS+ T cells and MLN germinal center B cells in cynomolgus monkeys in vivo. A single dose of 0.1 mg/kg, or 10 mg/kg of IC9G1-aFuc antibody was administered intravenously to cynomolgus monkeys. Control animals were treated with 10 mg/kg IC009 or PBS. The level MLN memory ICOS+ T cells and MLN germinal center B cells were monitored over time. MLN memory helper T cells were identified as CD3+CD4+CD45RA− ICOS+ cells. MLN germinal center B cells were identified as CD20+CD95+IgM− cells. (A) Total number of MLN T cells and MLN germinal center B cells on day 8 after treatment are shown. (B) Percent depletion of ICOS+ T cells and % dissolution of germinal center B cells on day 8 after treatment are shown. IC9G1-aFuc administration resulted in a dose dependent depletion of the memory helper ICOS+ T cells and germinal center B cells from the MLN.

FIG. 14. A single IV dose of IC9G1-aFuc significantly reduces the level of splenic memory helper ICOS+ T cells and germinal center B cells in cynomolgus monkeys in vivo. A single dose of 0.1 mg/kg, or 10 mg/kg of IC9G1-aFuc antibody was administered intravenously to cynomolgus monkeys. Control animals were treated with 10 mg/kg IC009 or PBS. The level of splenic memory ICOS+ T cells and germinal center B cells were monitored over time. Splenic memory helper T cells were identified as CD3+CD4+CD45RA−ICOS+ cells; germinal center B cells were identified as CD3-CD20+CD95+IgM− cells. (A) Total number of splenic memory helper T cells and germinal center B cells on days 8 and 30 after treatment are shown. (B) Percent depletion of T cells and % dissolution of germinal center B cells on days 8 and 29 after treatment are shown. IC9G1-aFuc administration resulted in a significant depletion of the memory helper T cells and germinal center B cells from the spleen. Depletion levels were significantly higher in animals receiving IC9G1-aFuc than in control animals receiving the IC009 antibody. Maximum depletion of T cells was achieved by day 8 after IC9G1-aFuc administration. Maximum level of germinal center B cell depletion was seen on day 29 after IC9G1-aFuc administration.

FIG. 15. Splenic germinal centers were atrophied on day 29 after administration of a single dose of IC9G1-aFuc antibody to cynomolgus monkeys. The morphology of splenic white pulp was examined following the administration of a single dose f IC9G1-aFuc antibody. Histological sections of the spleen isolated on day 8 (A) and day 29 (B) after IC9G1-aFuc antibody administration are shown. IC9G1-aFuc administration results in severe atrophy of splenic follicles by day 29.

Figure 16:
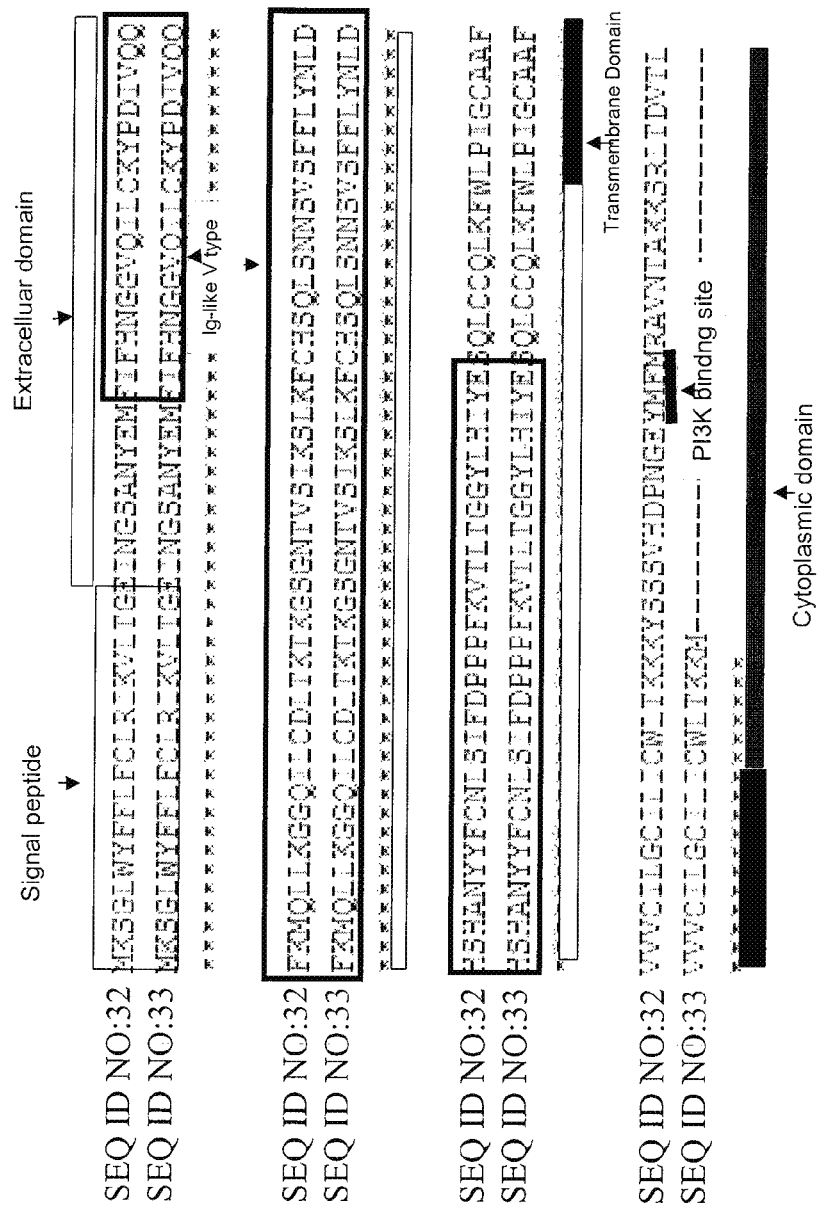

FIG. 16. Amino acid sequence alignment of long and short isoforms of human ICOS (SEQ ID NO: 32 and 33, respectively).

Figure 17:
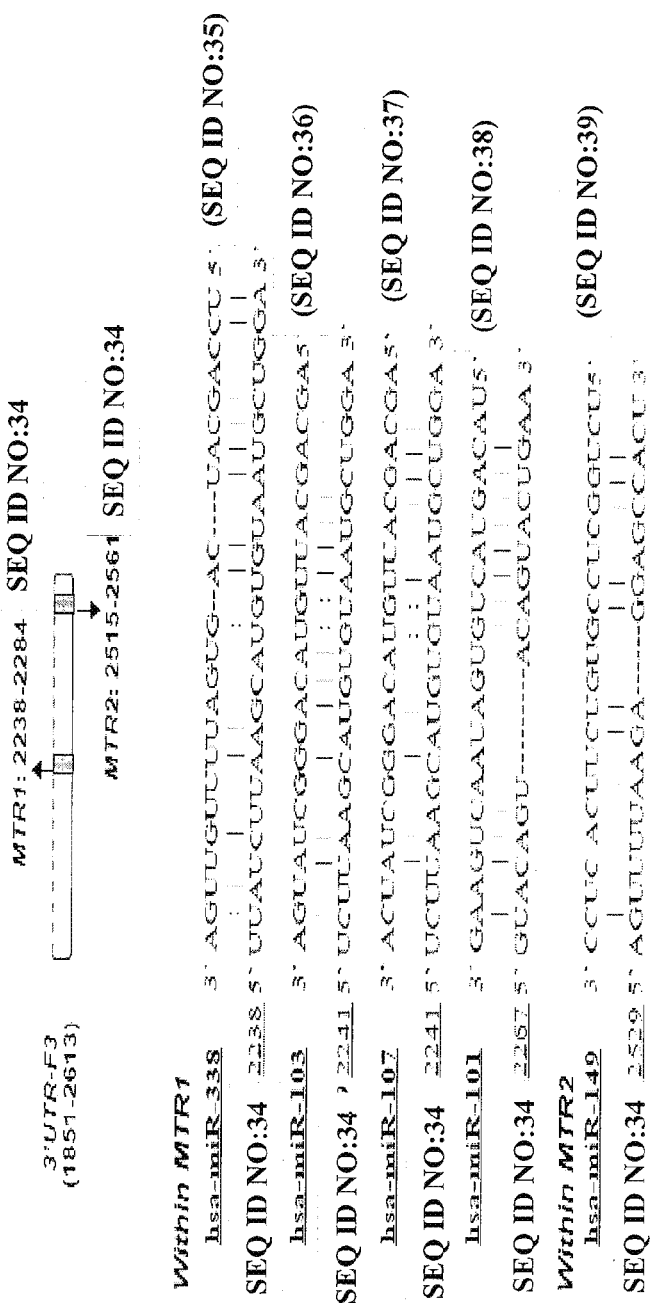

FIG. 17. Nucleotide sequence complementarity of ICOS mRNA (SEQ ID NO:34) and selected micro RNA molecules.

Figure 18:
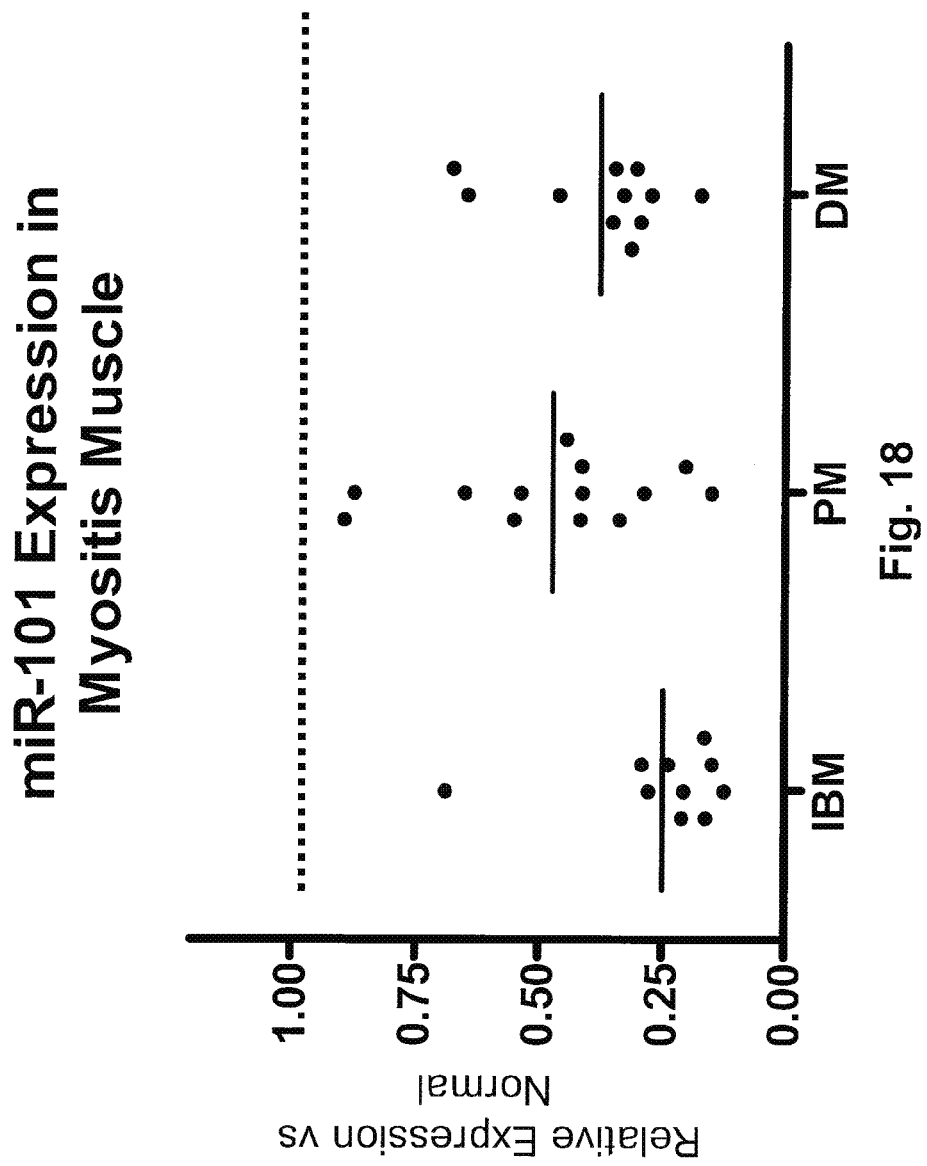

FIG. 18. Relative expression level of miR-101 in muscle specimen from inclusion-body myositis (IBM), polymyositis (PM), and dermatomyositis (DM) patients compared to healthy normal controls as measured by TaqMan QRT-PCR.

FIG. 19. Relative levels of (A) ICOS and ICOS-L, (B) CD4 and (C) CDR mRNA in muscle specimen from inclusion-body myositis (IBM), polymyositis (PM), and dermatomyositis (DM) patients compared with normal controls as measured by Affymetrix whole genome array. (D) ICOS and ICOS-L mRNA expression levels in whole blood (WB) samples isolated from inclusion-body myositis (IBM), polymyositis (PM), and dermatomyositis (DM) patients compared to normal controls as measured by TaqMan QRT-PCR.

FIG. 20. Relative mRNA expression levels of (A) ICOS and ICOSL, (B) CD4 and (C) CDR3ε in affected skin lesions of SLE patients compared to normal controls as measured by TaqMan QRT-PCR.

FIG. 21. Relative mRNA expression levels of (A) CD28, CTLA4, ICOS, ICOS-L, (B) CD4 and (C) CDR3ε in whole blood (WB) from SLE patients compared to normal controls as measured by TaqMan QRT-PCR.

5. DETAILED DESCRIPTION

The present invention relates to methods for generating anti-ICOS antibodies with enhanced effector function. Using the methods of the invention, an anti-ICOS parental antibody is modified to yield an anti-ICOS antibody with enhanced effector function, such as, but not limited to, enhanced ADCC, enhanced CDC, and enhanced antibody-dependent phagocytosis. Any anti-ICOS antibody that specifically binds to the human ICOS antigen may serve as a parental antibody for the purpose of practicing a method of the present invention. In one embodiment, anti-ICOS antibodies disclosed in U.S. Pat. No. 6,803,039 serve as parental antibody. In a specific embodiment, the JMAb-136 (IgG2) anti-ICOS antibody serves as the parental antibody.

The present invention provides anti-ICOS antibodies with enhanced effector function. In one embodiment, an anti-ICOS antibody of the invention mediates an antibody dependent effector function more efficiently than the parental anti-ICOS antibody. In a specific embodiment, an anti-ICOS antibody of the invention mediates an antibody dependent effector function more efficiently than the JMAb-136 (see, U.S. Pat. No. 6,803,039).

In one embodiment, an anti-ICOS antibody described herein mediates an antibody dependent effector function more efficiently than the parental anti-ICOS antibody wherein said effector function is selected from the group consisting of: antibody-dependent cell-mediated cytotoxicity (ADCC), complement mediated cytotoxicity (CDC), antibody-dependent phagocytosis. In one embodiment, an anti-ICOS antibody of the invention mediates antibody-dependent cell-mediated cytotoxicity (ADCC) more efficiently than the parental anti-ICOS antibody. In another embodiment, an anti-ICOS antibody of the invention mediates complement mediated cytotoxicity (CDC) more efficiently than the parental anti-ICOS antibody. In a further embodiment, an anti-ICOS antibody of the invention mediates antibody-dependent phagocytosis more efficiently than the parental anti-ICOS antibody.

In one embodiment, an anti-ICOS antibody of the invention mediates antibody-dependent cell-mediated cytotoxicity (ADCC) more efficiently than the parental anti-ICOS antibody wherein the ADCC activity is determined using an in vitro cytotoxicity assay. In a specific embodiment, an anti-ICOS antibody of the invention mediates at least about 5%, at least about 10%, at least about 20%, at least about 30%, at least about 40%, at least about 50%, at least about 75%, at least about 100% higher maximum cytotoxicity in an in vitro ADCC assay than the parental anti-ICOS antibody. In another specific embodiment, an anti-ICOS antibody of the invention mediates at least 2 fold, at least 3 fold, at least 4 fold, at least 5 fold or at least 10 fold higher maximum cytotoxicity in an in vitro ADCC assay than the parental anti-ICOS antibody.

In one embodiment, an anti-ICOS antibody of the invention mediates antibody-dependent cell-mediated cytotoxicity (ADCC) more efficiently than the JMab-136 anti-ICOS antibody wherein the ADCC activity is determined using an in vitro cytotoxicity assay. In a specific embodiment, an anti-ICOS antibody of the invention mediates at least about 5%, at least about 10%, at least about 20%, at least about 30%, at least about 40%, at least about 50%, at least about 75%, at least about 100% higher maximum cytotoxicity in an in vitro ADCC assay than the JMab-136 anti-ICOS antibody. In another specific embodiment, an anti-ICOS antibody of the invention mediates at least 2 fold, at least 3 fold, at least 4 fold, at least 5 fold or at least 10 fold higher maximum cytotoxicity in an in vitro ADCC assay than the JMab-136 anti-ICOS antibody.

In one embodiment, the EC50 of an anti-ICOS antibody of the invention in an in vitro ADCC assay is at least about 2×, at least about 5×, at least about 10×, at least about 20×, at least about 50×, or at least about 100× lower than that of the parental anti-ICOS antibody. In another embodiment, the EC50 of an anti-ICOS antibody of the invention in an in vitro ADCC assay is at least about 2×, at least about 5×, at least about 10×, at least about 20×, at least about 50×, or at least about 100× lower than that of the JMab-136 anti-ICOS antibody.

In one embodiment, an anti-ICOS antibody of the invention mediates antibody-dependent cell-mediated cytotoxicity (ADCC) more efficiently than the parental anti-ICOS antibody wherein the ADCC activity is determined using an in vivo cytotoxicity assay. In a specific embodiment, an anti-ICOS antibody of the invention mediates at least about 5%, at least about 10%, at least about 20%, at least about 30%, at least about 40%, at least about 50%, at least about 75%, at least about 100% higher maximum cytotoxicity in an in vivo ADCC assay than the parental anti-ICOS antibody.

In one embodiment, an anti-ICOS antibody of the invention mediates antibody-dependent cell-mediated cytotoxicity (ADCC) more efficiently than the JMab-136 anti-ICOS antibody wherein the ADCC activity is determined using an in vivo cytotoxicity assay. In a specific embodiment, an anti-ICOS antibody of the invention mediates at least about 5%, at least about 10%, at least about 20%, at least about 30%, at least about 40%, at least about 50%, at least about 75%, at least about 100% higher maximum cytotoxicity in an in vivo ADCC assay than the JMab-136 anti-ICOS antibody.

In one embodiment, an anti-ICOS antibody of the invention mediates complement-dependent cytotoxicity (CDC) more efficiently than the parental anti-ICOS antibody wherein the CDC activity is determined using an in vitro cytotoxicity assay. In a specific embodiment, an anti-ICOS antibody of the invention mediates at least about 5%, at least about 10%, at least about 20%, at least about 30%, at least about 40%, at least about 50%, at least about 75%, at least about 100% higher maximum cytotoxicity in an in vitro CDC assay than the parental anti-ICOS antibody.

In one embodiment, an anti-ICOS antibody of the invention mediates complement-dependent cytotoxicity (CDC) more efficiently than the JMab-136 anti-ICOS antibody wherein the CDC activity is determined using an in vitro cytotoxicity assay. In a specific embodiment, an anti-ICOS antibody of the invention mediates at least about 5%, at least about 10%, at least about 20%, at least about 30%, at least about 40%, at least about 50%, at least about 75%, at least about 100% higher maximum cytotoxicity in an in vitro CDC assay than the JMab-136 anti-ICOS antibody.

In one embodiment, the EC50 of an anti-ICOS antibody of the invention in an in vitro CDC assay is at least about 2×, at least about 5×, at least about 10×, at least about 20×, at least about 50×, or at least about 100× lower than that of the parental anti-ICOS antibody. In another embodiment, the EC50 of an anti-ICOS antibody of the invention in an in vitro CDC assay is at least about 2×, at least about 5×, at least about 10×, at least about 20×, at least about 50×, or at least about 100× lower than that of the JMab-136 anti-ICOS antibody.

In one embodiment, an anti-ICOS antibody of the invention mediates antibody-dependent phagocytosis more efficiently than the parental anti-ICOS antibody wherein the antibody-dependent phagocytosis activity is determined using an in vitro cytotoxicity assay. In a specific embodiment, an anti-ICOS antibody of the invention mediates at least about 5%, at least about 10%, at least about 20%, at least about 30%, at least about 40%, at least about 50%, at least about 75%, at least about 100% higher maximum cytotoxicity in an in vitro antibody-dependent phagocytosis assay than the parental anti-ICOS antibody.

In one embodiment, an anti-ICOS antibody of the invention mediates antibody-dependent phagocytosis more efficiently than the JMab-136 anti-ICOS antibody wherein the antibody-dependent phagocytosis activity is determined using an in vitro cytotoxicity assay. In a specific embodiment, an anti-ICOS antibody of the invention mediates at least about 5%, at least about 10%, at least about 20%, at least about 30%, at least about 40%, at least about 50%, at least about 75%, at least about 100% higher maximum cytotoxicity in an in vitro antibody-dependent phagocytosis assay than the JMab-136 anti-ICOS antibody.

In one embodiment, the EC50 of an anti-ICOS antibody of the invention in an in vitro antibody-dependent phagocytosis assay is at least about 2×, at least about 5×, at least about 10×, at least about 20×, at least about 50×, or at least about 100× lower than that of the parental anti-ICOS antibody. In another embodiment, the EC50 of an anti-ICOS antibody of the invention in an in vitro antibody-dependent phagocytosis assay is at least about 2×, at least about 5×, at least about 10×, at least about 20×, at least about 50×, or at least about 100× lower than that of the JMab-136 anti-ICOS antibody.

In one embodiment, an anti-ICOS antibody of the invention comprises a variant Fc region. In another embodiment, an anti-ICOS antibody of the invention comprises a variant Fc region that has an altered affinity for an Fc ligand protein. In a further embodiment, an anti-ICOS antibody of the invention comprises a variant Fc region that has an altered affinity for an Fc ligand selected from the group consisting of: FcγRIA, FcγRIIIA, FcγRIIB, FcγRIIIA, FcγRIIIB, FcγRIV, and C1q. In a specific embodiment, an anti-ICOS antibody of the invention comprises a variant Fc region that has an altered affinity for the FcγRIIIA protein. In a further embodiment, an anti-ICOS antibody of the invention comprises a variant Fc region that has an altered affinity for the C1q protein. In a specific embodiment, an Fc ligand protein may be a mouse, human or primate (e.g., cynomolgus) Fc ligand protein.

In one embodiment, an anti-ICOS antibody of the invention comprises a variant Fc region that has an increased affinity for an Fc ligand protein. In a further embodiment, an anti-ICOS antibody of the invention comprises a variant Fc region that has an increased affinity for an Fc ligand selected from the group consisting of: FcγRIA, FcγRIIIA, FcγRIIB, FcγRIIIA, FcγRIIIB, FcγRIV, and C1q. In a specific embodiment, an anti-ICOS antibody of the invention comprises a variant Fc region that has an increased affinity for the FcγRIIIA protein. In a further embodiment, an anti-ICOS antibody of the invention comprises a variant Fc region that has an increased affinity for the C1q protein. In a specific embodiment, an Fc ligand protein may be a mouse, human or primate (e.g., cynomolgus) Fc ligand protein.

In one embodiment, an anti-ICOS antibody of the invention comprises a variant Fc region wherein said variant Fc region comprises at least one amino acid substitution, insertion or deletion. In another embodiment, an anti-ICOS antibody of the invention comprises a variant Fc region comprising at least one amino acid substitution, insertion or deletion wherein said at least one amino acid residue sunstitution, insertion or deletion results in an increased affinity for an Fc ligand selected from the group consisting of: FcγRIA, FcγRIIA, FcγRIIB, FcγRIIIA, FcγRIIIB, FcγRIV, and C1q. In a specific embodiment, an anti-ICOS antibody of the invention comprises a variant Fc region comprising at least one amino acid substitution, insertion or deletion wherein said at least one amino acid residue sunstitution, insertion or deletion results in an increased affinity for the FcγRIIIA protein. In a further embodiment, an anti-ICOS antibody of the invention comprises a variant Fc region comprising at least one amino acid substitution, insertion or deletion wherein said at least one amino acid residue sunstitution, insertion or deletion results in an increased affinity for the C1q protein. In a specific embodiment, an Fc ligand protein may be a mouse, human or primate (e.g., cynomolgus) Fc ligand protein.

In one embodiment, an anti-ICOS antibody of the invention comprises a variant Fc region comprising at least one amino acid substitution, insertion or deletion wherein said at least one amino acid residue is selected from the group consisting of: residue 239, 330, and 332, wherein amino acid residues are numbered following the EU index. In another embodiment, an anti-ICOS antibody of the invention comprises a variant Fc region comprising at least one amino acid substitution, insertion or deletion wherein said at least one substituted, inserted or deleted amino acid residue is selected from the group consisting of: residue 239, 330, and 332, wherein amino acid residues are numbered following the EU index. In a further embodiment, an anti-ICOS antibody described herein comprises a variant Fc region comprising at least one amino acid substitution wherein said at least one substituted amino acid residue is selected from the group consisting of: residue 239, 330, and 332, wherein amino acid residues are numbered following the EU index. In another embodiment, an anti-ICOS antibody described herein comprises a variant Fc region comprising at least one amino acid substitution wherein said at least one amino acid substitution is selected from the group consisting of: S239D, A330L, A330Y, and I332E, wherein amino acid residues are numbered following the EU index. In a specific embodiment, an anti-ICOS antibody of the invention comprises a variant Fc region comprising the S239D, A330L, and I332E amino acid substitutions, wherein amino acid residues are numbered following the EU index.

In one embodiment, an anti-ICOS antibody of the invention comprises a variant Fc region comprising at least one of the amino acid residues selected from the group consisting of: D at residue 239, E at residue 239, L at residue 330, Y at residue 330, E at residue 332, and D at residue 332, wherein amino acid residues are numbered following the EU index. In a specific embodiment, an anti-ICOS antibody of the invention comprises a variant Fc region comprising D at residue 239, L at residue 330, and E at residue 332, wherein amino acid residues are numbered following the EU index.

In one embodiment, an anti-ICOS antibody of the invention comprises an engineered Fc region wherein the engineered Fc region comprises a posttranslational modification that is different from that of the parental anti-ICOS antibody. In a specific embodiment, an anti-ICOS antibody of the invention comprises an engineered Fc region wherein said engineered Fc region comprises complex N-glycoside-linked sugar chains in which fucose is not bound to N-acetylglucosamine in the reducing end in the sugar chain.

In one embodiment, an anti-ICOS antibody of the invention comprises an engineered Fc region that has an altered affinity for an Fc ligand protein. In a further embodiment, an anti-ICOS antibody of the invention comprises an engineered Fc region that has an altered affinity for an Fc ligand selected from the group consisting of: FcγRIA, FcγRIIA, FcγRIIB, FcγRIIIA, FcγRIIIB, FcγRIV, and C1q. In a specific embodiment, an anti-ICOS antibody of the invention comprises an engineered Fc region that has an altered affinity for the FcγRIIIA protein. In a further embodiment, an anti-ICOS antibody of the invention comprises an engineered Fc region that has an altered affinity for the C1q protein.

In one embodiment, an anti-ICOS antibody of the invention comprises an engineered Fc region that has an increased affinity for an Fc ligand protein. In a further embodiment, an anti-ICOS antibody of the invention comprises an engineered Fc region that has an increased affinity for an Fc ligand selected from the group consisting of: FcγRIA, FcγRIIA, FcγRIIB, FcγRIIIA, FcγRIIIB, FcγRIV, and C1q. In a specific embodiment, an anti-ICOS antibody of the invention comprises an engineered Fc region that has an increased affinity for the FcγRIIIA protein. In a further embodiment, an anti-ICOS antibody of the invention comprises an engineered Fc region that has an increased affinity for the C1q protein.

In one embodiment, an anti-ICOS antibody of the invention comprises an engineered Fc region wherein said engineered Fc region comprises a reduced level of fucose compared to a native antibody. In another embodiment, an anti-ICOS antibody of the invention comprises an engineered Fc region comprising a reduced level of fucose, wherein said reduction in fucose level results in an increased affinity for an Fc ligand selected from the group consisting of: FcγRIA, FcγRIIA, FcγRIIB, FcγRIIIA, FcγRIIIB, FcγRIV, and C1q. In a specific embodiment, an anti-ICOS antibody of the invention comprises an engineered Fc region comprising a reduced level of fucose, wherein said reduction in fucose level results in an increased affinity for the FcγRIIIA protein. In a further embodiment, an anti-ICOS antibody of the invention comprises an engineered Fc region comprising a reduced level of fucose, wherein said reduction in fucose level results in an increased affinity for the C1q protein.

Anti-ICOS antibodies described herein comprise Fc regions having a high binding affinity for the human FcγRIIIA protein. In one embodiment, an anti-ICOS antibody of the invention comprises an Fc region that has an affinity constant or $K_a$ ($k_{on}/k_{off}$) of at least $10^3$ $M^{-1}$, at least $5×10^3$ $M^{-1}$, at least $10^4$ $M^{-1}$, at least $5×10^4$ $M^{-1}$, at least $10^5$ $M^{-1}$, at least $5×10^5$ $M^{-1}$, at least $10^6$ $M^{-1}$, at least $5×10^6$ $M^{-1}$, at least $10^7$ $M^{-1}$, at least $5×10^7$ $M^{-1}$, at least $10^8$ $M^{-1}$, at least $5×10^8$ $M^{-1}$, at least $10^9$ $M^{-1}$, at least $5×10^9$ $M^{-1}$, at least $10^{10}$ $M^{-1}$, at least $5×10^{10}$ $M^{-1}$, at least $10^{11}$ $M^{-1}$, at least $5×10^{11}$ $M^{-1}$, at least $10^{12}$ $M^{-1}$, or at least $5×10^{12}$ $M^{-1}$. In another embodiment, an anti-ICOS antibody of the invention comprises an Fc region that has a dissociation constant or $K_d$ ($k_{off}/k_{on}$) of less than $5×10^{-3}$ M, less than $10^{-3}$ M, less than $5×10^{-4}$ M, less than $10^{-4}$ M, less than $5×10^{-5}$ M, less than $10^{-5}$ M, less than $5×10^{-6}$ M, less than $10^{-6}$ M, less than $5×10^{-7}$ M, less than $10^{-7}$ M, less than $5×10^{-8}$ M, less than $10^{-8}$ M, less than $5×10^{-9}$ M, less than $10^{-9}$ M, less than $5×10^{-10}$ M, less than $10^{-10}$ M less than $5×10^{-11}$ M, less than $10^{-11}$ M, less than $5×10^{-12}$ M, or less than $10^{-12}$ M.

An antibody used in accordance with a method described herein may comprise an Fc region that binds to human FcγRIIIA with a dissociation constant ($K_d$) of less than 3000 nM, less than 2500 nM, less than 2000 nM, less than 1500 nM, less than 1000 nM, less than 750 nM, less than 500 nM, less than 250 nM, less than 200 nM, less than 150 nM, less than 100 nM, less than 75 nM, less than 50 nM, less than 25 nM, less than 10 nM, less than 5 nM, less than 1 nM as assessed using a method described herein or known to one of skill in the art (e.g., a BIAcore assay, ELISA) (Biacore International AB, Uppsala, Sweden). In a specific embodiment, an antibody used in accordance with a method described herein may comprise an Fc region that binds to human FcγRIIIA with a dissociation constant ($K_d$) of between 1 to 3000 nM, 1 to 3000 nM, 1 to 2000 nM, 1 to 1500 nM, 1 to 1000 nM, 1 to 750 nM, 1 to 500 nM, 1 to 250 nM, 1 to 100 nM, 1 to 50 nM, 1 to 25 nM, 1 to 10 nM as assessed using a method described herein or known to one of skill in the art (e.g., a BIAcore assay, ELISA). In another embodiment, an anti-ICOS antibody used in accordance with a method described herein may comprise an Fc region that binds to human FcγRIIIA with a dissociation constant ($K_d$) of 500 nM, 250 nM, 100 nM, 75 nM, 50 nM, 25 nM, 10 nM or 1 nM as assessed using a method described herein or known to one of skill in the art (e.g., a BIAcore assay, ELISA).

Anti-ICOS antibodies described herein comprise Fc regions having a high binding affinity for the non-human primate (e.g., cynomolgus) FcγRIIIA protein. In one embodiment, an anti-ICOS antibody of the invention comprises an Fc region that has an affinity constant or $K_a$ ($k_{on}/k_{off}$) of at least $10^3$ $M^{-1}$, at least $5\times10^3$ $M^{-1}$, at least $10^4$ $M^{-1}$, at least $5\times10^4$ $M^{-1}$, at least $10^5$ $M^{-1}$, at least $5\times10^5$ $M^{-1}$, at least $10^6$ $M^{-1}$, at least $5\times10^6$ $M^{-1}$, at least $10^7$ $M^{-1}$, at least $5\times10^7$ $M^{-1}$, at least $10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or at least $5\times10^{12}$ M. In another embodiment, an anti-ICOS antibody of the invention comprises an Fc region that has a dissociation constant or $K_a$ ($k_{off}/k_{on}$) of less than $5\times10^{-3}$ M, less than $10^{-3}$ M, less than $5\times10^{-4}$ M, less than $10^{-4}$ M, less than $5\times10^{-5}$ M, less than $10^{-5}$ M, less than $5\times10^{-6}$ M, less than $10^{-6}$ M, less than $5\times10^{-7}$ M, less than $10^{-7}$ M, less than $5\times10^{-8}$ M, less than $10^{-8}$ M, less than $5\times10^{-9}$ M, less than $10^{-9}$ M, less than $5\times10^{-10}$ M, less than $10^{-10}$ M, less than $5\times10^{-11}$ M, less than $10^{-11}$ M, less than $5\times10^{-12}$ M, or less than $10^{-12}$ M.

An antibody used in accordance with a method described herein may comprise an Fc region that binds to non-human primate (e.g., cynomolgus) FcγRIIIA with a dissociation constant ($K_d$) of less than 3000 nM, less than 2500 nM, less than 2000 nM, less than 1500 nM, less than 1000 nM, less than 750 nM, less than 500 nM, less than 250 nM, less than 200 nM, less than 150 nM, less than 100 nM, less than 75 nM, less than 50 nM, less than 25 nM, less than 10 nM, less than 5 nM, less than 1 nM as assessed using a method described herein or known to one of skill in the art (e.g., a BIAcore assay, ELISA) (Biacore International AB, Uppsala, Sweden). In a specific embodiment, an antibody used in accordance with a method described herein may comprise an Fc region that binds to non-human primate (e.g., cynomolgus) FcγRIIIA with a dissociation constant ($K_d$) of between 1 to 3000 nM, 1 to 3000 nM, 1 to 2000 nM, 1 to 1500 nM, 1 to 1000 nM, 1 to 750 nM, 1 to 500 nM, 1 to 250 nM, 1 to 100 nM, 1 to 50 nM, 1 to 25 nM, 1 to 10 nM as assessed using a method described herein or known to one of skill in the art (e.g., a BIAcore assay, ELISA). In another embodiment, an anti-ICOS antibody used in accordance with a method described herein may comprise an Fc region that binds to non-human primate (e.g., cynomolgus) FcγRIIIA with a dissociation constant ($K_d$) of 500 nM, 250 nM, 100 nM, 75 nM, 50 nM, 25 nM, 10 nM or 1 nM as assessed using a method described herein or known to one of skill in the art (e.g., a BIAcore assay, ELISA).

Anti-ICOS antibodies described herein comprise Fc regions having a high binding affinity for the mouse FcγRIIIA protein. In one embodiment, an anti-ICOS antibody of the invention comprises an Fc region that has an affinity constant or $K_a$ ($k_{on}/k_{off}$) of at least $10^3$ $M^{-1}$, at least $5\times10^3$ $M^{-1}$, at least $10^4$ $M^{-1}$, at least $5\times10^4$ $M^{-1}$, at least $10^5$ $M^{-1}$, at least $5\times10^5$ $M^{-1}$, at least $10^6$ $M^{-1}$, at least $5\times10^6$ $M^{-1}$, at least $10^7$ $M^{-1}$, at least $5\times10^7$ $M^{-1}$, at least $10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$ or at least $5\times10^{12}$ $M^{-1}$. In another embodiment, an anti-ICOS antibody of the invention comprises an Fc region that has a dissociation constant or $K_a$ ($k_{off}/k_{on}$) of less than $5\times10^{-3}$ M, less than $10^{-3}$ M, less than $5\times10^{-4}$ M, less than $10^{-4}$ M, less than $5\times10^{-5}$ M, less than $10^{-5}$ M, less than $5\times10^{-6}$ M, less than $10^{-6}$ M, less than $5\times10^{-7}$ M, less than $10^{-7}$ M, less than $5\times10^{-8}$ M, less than $10^{-8}$ M, less than $5\times10^{-9}$ M, less than $10^{-9}$ M, less than $5\times10^{-10}$ M, less than $10^{-10}$ M, less than $5\times10^{-11}$ M, less than $10^{-11}$ M, less than $5\times10^{-12}$ M, or less than $10^{-12}$ M.

An antibody used in accordance with a method described herein may comprise an Fc region that binds to mouse FcγRIIIA with a dissociation constant ($K_d$) of less than 3000 nM, less than 2500 nM, less than 2000 nM, less than 1500 nM, less than 1000 nM, less than 750 nM, less than 500 nM, less than 250 nM, less than 200 nM, less than 150 nM, less than 100 nM, less than 75 nM, less than 50 nM, less than 25 nM, less than 10 nM, less than 5 nM, less than 1 nM as assessed using a method described herein or known to one of skill in the art (e.g., a BIAcore assay, ELISA) (Biacore International AB, Uppsala, Sweden). In a specific embodiment, an antibody used in accordance with a method described herein may comprise an Fc region that binds to mouse FcγRIIIA with a dissociation constant ($K_d$) of between 1 to 3000 nM, 1 to 3000 nM, 1 to 2000 nM, 1 to 1500 nM, 1 to 1000 nM, 1 to 750 nM, 1 to 500 nM, 1 to 250 nM, 1 to 100 nM, 1 to 50 nM, 1 to 25 nM, 1 to 10 nM as assessed using a method described herein or known to one of skill in the art (e.g., a BIAcore assay, ELISA). In another embodiment, an anti-ICOS antibody used in accordance with a method described herein may comprise an Fc region that binds to mouse FcγRIIIA with a dissociation constant ($K_d$) of 500 nM, 250 nM, 100 nM, 75 nM, 50 nM, 25 nM, 10 nM or 1 nM as assessed using a method described herein or known to one of skill in the art (e.g., a BIAcore assay, ELISA).

In one embodiment, anti-ICOS antibodies of the invention comprise one, two, three, four, five, or all six of the CDRs of JMAb-136 (see, U.S. Pat. No. 6,803,039).

The amino acid sequences for CDR1, CDR2, and CDR3 of the heavy chain variable region of JMAb-136 defined according to Kabat are identified as SEQ ID NO:8, SEQ ID NO:9, and SEQ ID NO:10, respectively. The amino acid sequences for CDR1, CDR2 and CDR3 of the light chain variable region of JMAb-136 defined according to Kabat are identified as SEQ ID NO:3, SEQ ID NO:4, and SEQ ID NO:5, respectively.

Kabat numbering is based on the seminal work of Kabat et al. (1991) *Sequences of Proteins of Immunological Interest*, Publication No. 91-3242, published as a three volume set by the National Institutes of Health, National Technical Information Service (hereinafter "Kabat"). Kabat provides multiple sequence alignments of immunoglobulin chains from numerous species antibody isotypes. The aligned sequences are numbered according to a single numbering system, the Kabat numbering system. The Kabat sequences have been updated since the 1991 publication and are available as an electronic sequence database (latest downloadable version 1997). Any immunoglobulin sequence can be numbered according to Kabat by performing an alignment with the Kabat reference sequence. Accordingly, the Kabat numbering system provides a uniform system for numbering immunoglobulin chains. Unless indicated otherwise, all immunoglobulin amino acid sequences described herein are numbered according to the Kabat numbering system. Similarly, all single amino acid positions referred to herein are numbered according to the Kabat numbering system.

In certain embodiments, an anti-ICOS antibody described herein may comprise a heavy chain variable region, VH, comprising at least one CDR having the amino acid sequence selected from the group consisting of SEQ ID NO:8, SEQ ID NO:9, and SEQ ID NO:10. In certain embodiments, an anti-ICOS antibody of the invention may comprise a VH domain having the amino acid sequence of SEQ ID NO:7.

In certain embodiments, an anti-ICOS antibody described herein may comprise a light chain variable region, VK, comprising at least one CDR having an amino acid sequence selected from the group consisting of SEQ ID NO:3, SEQ ID NO:4, and SEQ ID NO:5. In certain embodiments, an anti-ICOS antibody of the invention may comprise a VK domain having the amino acid sequence of SEQ ID NO:2.

In one embodiment, an anti-ICOS antibody of the invention comprises a VK domain having the amino acid sequence of SEQ ID NO:2 and further comprises a VH domain having the amino acid sequence of SEQ ID NO:7.

The present invention encompasses antibodies that bind to human ICOS, comprising derivatives of the VH domain, VH CDR1, VH CDR2, VH CDR3, VK domain, VK CDR1, VK CDR2, or VK CDR3 described herein that may bind to human ICOS. Standard techniques known to those of skill in the art can be used to introduce mutations (e.g., additions, deletions, and/or substitutions) in the nucleotide sequence encoding an antibody, including, for example, site-directed mutagenesis and PCR-mediated mutagenesis that are routinely used to generate amino acid substitutions. In one embodiment, the VH and/or VK CDR derivatives may include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, less than 2 amino acid substitutions, or 1 amino acid substitution relative to the original VH and/or VK CDRs of the JMab-136 anti-ICOS antibody. In another embodiment, the VH and/or VK CDR derivatives may have conservative amino acid substitutions (e.g. supra) made at one or more predicted non-essential amino acid residues (i.e., amino acid residues which are not critical for the antibody to specifically bind to human ICOS). Mutations can also be introduced randomly along all or part of the VH and/or VK CDR coding sequences, such as by saturation mutagenesis, and the resultant mutants can be screened for biological activity to identify mutants that retain activity. Following mutagenesis, the encoded antibody can be expressed and the activity of the antibody can be determined.

The present invention further encompasses antibodies that bind to human ICOS, said antibodies or antibody fragments comprising one or more CDRs wherein said CDRs comprise an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of one or more CDRs of the JMab-136 anti-ICOS antibody. The percent identity of two amino acid sequences can be determined by any method known to one skilled in the art, including, but not limited to, BLAST protein searches.

The present invention further encompasses antibodies that bind to human ICOS, said antibodies or antibody fragments comprising a VH and/or a VK domain wherein said VH and/or VK domains comprise an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the VH and VK domain of the JMab-136 anti-ICOS antibody. The percent identity of two amino acid sequences can be determined by any method known to one skilled in the art, including, but not limited to, BLAST protein searches.

In one embodiment, an anti-ICOS antibody of the invention may bind to human ICOS with an affinity comparable to that of the JMab-136 anti-ICOS antibody.

In one embodiment, an anti-ICOS antibody of the invention specifically binds the same epitope of ICOS as the JMab-136 anti-ICOS antibody.

In one embodiment, an anti-ICOS antibody specifically competes the JMab-136 anti-ICOS antibody for ICOS binding. The competition assay may be performed using any binding assay known in the art, for example, but not limited to ELISA assay, radioimmunoassay, flow cytometry.

The invention further provides polynucleotides comprising a nucleotide sequence encoding an anti-ICOS antibody with enhanced effector function. The invention also encompasses polynucleotides that hybridize under stringent or lower stringency hybridization conditions, as defined herein, to polynucleotides that encode an anti-ICOS antibody with enhanced effector function.

In one embodiment, a polynucleotide of the invention encoding an effector function enhanced anti-ICOS antibody described herein comprises an optimized polynucleotide sequence. In a specific embodiment, a polynucleotide of the invention encoding the VH domain of an antibody described herein comprises the nucleotide sequence of SEQ ID NO: 28. In a specific embodiment, a polynucleotide of the invention encoding the VK domain of an antibody described herein comprises the nucleotide sequence of SEQ ID NO: 29. In a specific embodiment, a polynucleotide of the invention encoding the heavy chain of an antibody described herein comprises the nucleotide sequence of SEQ ID NO: 30. In a specific embodiment, a polynucleotide of the invention encoding the light chain of an antibody described herein comprises the nucleotide sequence of SEQ ID NO: 31.

Another embodiment of the invention is a vector comprising one or more nucleotide sequences encoding an anti-ICOS antibody with enhanced effector function.

In one embodiment, a vector of the invention comprises one or more nucleotide sequences encoding an anti-ICOS antibody with enhanced effector function wherein the nucleotide sequence is an optimized nucleotide sequence. In a specific embodiment, a vector of the invention comprises the nucleotide sequence of SEQ ID NO: 28. In a specific embodiment, a vector of the invention comprises the nucleotide sequence of SEQ ID NO: 29. In a specific embodiment, a vector of the invention comprises the nucleotide sequence of SEQ ID NO: 30. In a specific embodiment, a vector of the invention comprises the nucleotide sequence of SEQ ID NO: 31. In a further specific embodiment, a vector of the invention comprises one or more nucleotide sequences encoding an anti-ICOS antibody with enhanced effector function wherein the nucleotide sequence is selected from the group comprising SEQ ID NO:28-31. In a further specific embodiment, a vector of the invention comprises one or more nucleotide sequences encoding an anti-ICOS antibody with enhanced effector function wherein the nucleotide sequence is selected from the group consisting of SEQ ID NO:28-31.

The present invention further relates to an isolated cell comprising a vector wherein said vector comprises one or more nucleotide sequences encoding an anti-ICOS antibody with enhanced effector function. In a specific embodiment, an isolated cell of the invention comprises a polynucleotide comprising the nucleotide sequence selected from the group comprising SEQ ID NO:28-31. In a further specific embodiment, an isolated cell of the invention comprises a polynucleotide comprising the nucleotide sequence selected from the group consisting of SEQ ID NO:28-31.

Anti-ICOS antibodies of the invention include those of the IgG1, IgG2, IgG3, or IgG4 human isotype.

The present invention further relates to pharmaceutical compositions comprising an anti-ICOS antibody with enhanced effector function.

In still another other aspect, the present invention is directed toward methods of treating and preventing T cell-mediated diseases and disorders, such as, but not limited to, chronic infection, autoimmune disease or disorder, inflammatory disease or disorder, graft-versus-host disease (GVHD), transplant rejection, and T cell proliferative disorder, comprising administering to a human in need thereof a therapeutically-effective amount of a an anti-ICOS antibody with enhanced effector function.

The present invention relates to anti-ICOS antibodies with enhanced effector function, as well as to compositions comprising those antibodies. In certain embodiments, an anti-ICOS antibody of the invention may mediate antigen-dependent-cell-mediated-cytotoxicity (ADCC). In other embodiments, the present invention is directed toward compositions comprising an anti-ICOS antibody of the IgG1 and/or IgG3 human isotype, as well as to an anti-ICOS antibody of the IgG2 and/or IgG4 human isotype, that may mediate human ADCC, CDC, and/or antibody-dependent phagocytosis.

Anti-ICOS antibodies described herein may have a high binding affinity for the human ICOS antigen. For example, an antibody described herein may have an association rate constant or $k_{on}$ rate (antibody (Ab)+antigen (Ag)$^{k-on}$→Ab-Ag) of at least $2\times10^5 M^{-1} s^{-1}$, at, least $5\times10^5 M^{-1} s^{-1}$, at least $10^6 M^{-1} s^{-1}$ at least $5\times10^6$ at least $10^7 M^{-1} s^{-1}$, at least $5\times10^7 M^{-1} s^{-1}$, or at least $10^8 M^{-1} s^{-1}$.

In another embodiment, an anti-ICOS antibody may have a $k_{off}$ rate ((Ab-Ag)$^{k-off}$→antibody (Ab)+antigen (Ag)) of less than $5\times10^{-1} s^{-1}$, less than $10^{-1} s^{-1}$, less than $5\times10^{-2} s^{-1}$, less than $10^{-2} s^{-1}$, less than $5\times10^{-3} s^{-1}$, less than $10^{-3} s^{-1}$, less than $5\times10^{-4} s^{-1}$, or less than $10^{-4} s^{-1}$. In a another embodiment, an antibody of the invention has a $k_{off}$ of less than $5\times10^{-5} s^{-1}$, less than $10^{-5} s^{-1}$, less than $5\times10^{-6} s^{-1}$, less than $10^{-6} s^{-1}$, less than $5\times10^{-7} s^{-1}$, less than $10^{-7} s^{-1}$, less than $5\times10^{-8} s^{-1}$, less than $10^{-8} s^{-1}$, less than $5\times10^{-9} s^{-1}$, less than $10^{-9} s^-$, or less than $10^{-10} s^{-1}$.

In another embodiment, an anti-ICOS antibody may have an affinity constant or $K_a$ ($k_{on}/k_{off}$) of at least $10^2 M^{-1}$, at least $5\times10^2 M^{-1}$, at least $10^3 M^{-1}$, at least $5\times10^3 M^{-1}$, at least $10^4 M^{-1}$, at least $5\times10^4 M^{-1}$, at least $10^5 M^{-1}$, at least $5\times10^5 M^{-1}$, at least $10^6 M^{-1}$, at least $5\times10^6 M^{-1}$, at least $10^7 M^{-1}$, at least $5\times10^7 M^{-1}$, at least $10^8 M^{-1}$, at least $5\times10^8 M^{-1}$, at least $10^9 M^{-1}$, at least $5\times10^9 M^{-1}$, at least $10^{10} M^{-1}$, at least $5\times10^{10} M^{-1}$ at least $10^{11} M^{-1}$, at least $5\times10^{11} M^{-1}$, at least $10^{12} M^{-1}$, at least $5\times10^{12} M^{-1}$, at least $10^{13} M^{-1}$, at least $5\times10^{13} M^{-1}$, at least $10^{14} M^{-1}$, at least $5\times10^{14} M^{-1}$, at least $10^{15} M^{-1}$, or at least $5\times10^{15} M^{-1}$. In yet another embodiment, an anti-ICOS antibody may have a dissociation constant or $K_d$ ($k_{off}/k_{on}$) of less than $5\times10^{-2} M$, less than $10^{-2} M$, less than $5\times10^{-3} M$, less than $10^{-3} M$, less than $5\times10^{-4} M$, less than $10^{-4} M$, less than $5\times10^{-5} M$, less than $10^{-5} M$, less than $5\times10^{-6} M$, less than $10^{-6} M$, less than $5\times10^{-7} M$, less than $10^{-7} M$, less than $5\times10^{-8} M$, less than $10^{-8} M$, less than $5\times10^{-9} M$, less than $10^{-9} M$, less than $5\times10^{-10} M$, less than $10^{-10} M$, less than $5\times10^{-11} M$, less than $10^{-11} M$, less than $5\times10^{-1} M$, less than $10^{-12} M$, less than $5\times10^{-13} M$, less than $10^{-13} M$, less than $5\times10^{-14} M$, less than $10^{-14} M$, less than $5\times10^{-15} M$, or less than $10^{-15} M$.

An antibody used in accordance with a method described herein may immunospecifically bind to ICOS and may have a dissociation constant ($K_d$) of less than 3000 pM, less than 2500 pM, less than 2000 pM, less than 1500 pM, less than 1000 pM, less than 750 pM, less than 500 pM, less than 250 pM, less than 200 pM, less than 150 pM, less than 100 pM, less than 75 pM as assessed using a method described herein or known to one of skill in the art (e.g., a BIAcore assay, ELISA) (Biacore International AB, Uppsala, Sweden). In a specific embodiment, an antibody used in accordance with a method described herein may immunospecifically bind to a human ICOS antigen and may have a dissociation constant ($K_d$) of between 25 to 3400 pM, 25 to 3000 pM, 25 to 2500 pM, 25 to 2000 pM, 25 to 1500 pM, 25 to 1000 pM, 25 to 750 pM, 25 to 500 pM, 25 to 250 pM, 25 to 100 pM, 25 to 75 pM, 25 to 50 pM as assessed using a method described herein or known to one of skill in the art (e.g., a BIAcore assay, ELISA). In another embodiment, an anti-ICOS antibody used in accordance with a method described herein may immunospecifically bind to ICOS and may have a dissociation constant ($K_d$) of 500 pM, 100 pM, 75 pM or 50 pM as assessed using a method described herein or known to one of skill in the art (e.g., a BIAcore assay, ELISA).

The invention further provides polynucleotides comprising a nucleotide sequence encoding an anti-ICOS antibody with enhanced effector function. The invention also encompasses polynucleotides that hybridize under stringent or lower stringency hybridization conditions, e.g., as defined herein, to polynucleotides that encode an anti-ICOS antibody with enhanced effector function.

Stringent hybridization conditions include, but are not limited to, hybridization to filter-bound DNA in 6× sodium chloride/sodium citrate (SSC) at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 60° C., or any other stringent hybridization conditions known to those skilled in the art (see, for example, Ausubel, F. M. et al., eds. 1989 Current Protocols in Molecular Biology, vol. 1, Green Publishing Associates, Inc. and John Wiley and Sons, Inc., NY at pages 6.3.1 to 6.3.6 and 2.10.3).

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

A polynucleotide encoding an antibody may also be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably polyA+RNA, isolated from, any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

The present invention further provides for antibodies that efficiently deplete ICOS expressing cells in a mouse xenograft model system. In one embodiment, administration of one or more therapeutic doses of an anti-ICOS antibody of the invention may achieve at least about 20%, at least about 30%, at least about 40%, at least about 50%, at least about 60%, at least about 70%, at least about 80%, at least about 90%, at least about 95%, at least about 97%, at least about 99%, or at least about 100% depletion of ICOS expressing cells in a mouse xenograft model system.

In one embodiment, administration of one or more therapeutic doses of an anti-ICOS antibody of the invention depletes ICOS expressing cells in a mouse xenograft model more efficiently than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention depletes ICOS expressing cells in a mouse xenograft model more efficiently than that of the fucosylated JMab-136 anti-ICOS antibody.

In one embodiment, administration of one or more therapeutic doses of an anti-ICOS antibody of the invention achieves at least about 2-fold, at least about 3-fold, at least about 5-fold, or at least about 10-fold higher depletion of ICOS expressing cells in a mouse xenograft model than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In one embodiment, administration of one or more therapeutic doses of an anti-ICOS antibody of the invention achieves at least about 2-fold, at least about 3-fold, at least about 5-fold, or at least about 10-fold higher depletion of ICOS expressing cells in a mouse xenograft model than that of the fucosylated JMab-136 anti-ICOS antibody.

In one embodiment, the EC50 value of an anti-ICOS antibody of the invention for the depletion of ICOS expressing cells in a mouse xenograft model is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, the EC50 value of an anti-ICOS antibody of the invention for the depletion of ICOS expressing cells in a mouse xenograft model is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC).

In one embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of ICOS expressing cells in a mouse xenograft model than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of ICOS expressing cells in a mouse xenograft model than that of the fucosylated JMab-136 anti-ICOS antibody.

In one embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of ICOS expressing cells in a mouse xenograft model than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of ICOS expressing cells in a mouse xenograft model than that of the fucosylated JMab-136 anti-ICOS antibody.

The present invention further provides for antibodies that efficiently deplete ICOS expressing cells in a transgenic mouse model system. In one embodiment, administration of one or more therapeutic doses of an anti-ICOS antibody of the invention may achieve at least about 20%, at least about 30%, at least about 40%, at least about 50%, at least about 60%, at least about 70%, at least about 80%, at least about 90%, at least about 95%, at least about 97%, at least about 99%, or at least about 100% depletion of ICOS expressing cells in a transgenic mouse model system.

In one embodiment, administration of one or more therapeutic doses of an anti-ICOS antibody of the invention depletes ICOS expressing cells in a transgenic mouse model more efficiently than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention depletes ICOS expressing cells in a transgenic mouse model more efficiently than that of the fucosylated JMab-136 anti-ICOS antibody.

In one embodiment, administration of one or more therapeutic doses of an anti-ICOS antibody of the invention achieves at least about 2-fold, at least about 3-fold, at least about 5-fold, or at least about 10-fold higher depletion of ICOS expressing cells in a transgenic mouse model than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In one embodiment, administration of one or more therapeutic doses of an anti-ICOS antibody of the invention achieves at least about 2-fold, at least about 3-fold, at least about 5-fold, or at least about 10-fold higher depletion of ICOS expressing cells in a transgenic mouse model than that of the fucosylated JMab-136 anti-ICOS antibody.

In one embodiment, the EC50 value of an anti-ICOS antibody of the invention for the depletion of ICOS expressing cells in a transgenic mouse model is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, the EC50 value of an anti-ICOS antibody of the invention for the depletion of ICOS expressing cells in a transgenic mouse model is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC).

In one embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of ICOS expressing cells in a transgenic mouse model than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of ICOS expressing cells in a transgenic mouse model than that of the fucosylated JMab-136 anti-ICOS antibody.

In one embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of ICOS expressing cells in a transgenic mouse model than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of ICOS expressing cells in a transgenic mouse model than that of the fucosylated JMab-136 anti-ICOS antibody.

The present invention also provides for antibodies that efficiently deplete ICOS expressing cells in a primate (non-human primate or human). In one embodiment, administration of one or more therapeutic doses of an anti-ICOS antibody of the invention may achieve at least about 20%, at least about 30%, at least about 40%, at least about 50%, at least about 60%, at least about 70%, at least about 80%, at least about 90%, at least about 95%, at least about 97%, at least about 99%, or at least about 100% depletion of ICOS expressing cells in a primate (non-human primate or human).

In one embodiment, administration of one or more therapeutic doses of an anti-ICOS antibody of the invention depletes ICOS expressing cells in a primate (non-human primate or human) more efficiently than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention depletes ICOS expressing cells in a primate (non-human primate or human) more efficiently than that of the fucosylated JMab-136 anti-ICOS antibody.

In one embodiment, administration of one or more therapeutic doses of an anti-ICOS antibody of the invention achieves at least about 2-fold, at least about 3-fold, at least about 5-fold, or at least about 10-fold higher depletion of ICOS expressing cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In one embodiment, administration of one or more therapeutic doses of an anti-ICOS antibody of the invention achieves at least about 2-fold, at least about 3-fold, at least about 5-fold, or at least about 10-fold higher depletion of ICOS expressing cells in a primate (non-human primate or human) than that of the fucosylated JMab-136 anti-ICOS antibody.

In one embodiment, the EC50 value of an anti-ICOS antibody of the invention for the depletion of ICOS expressing cells in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, the EC50 value of an anti-ICOS antibody of the invention for the depletion of ICOS expressing cells in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC).

In one embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of ICOS expressing cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of ICOS expressing cells in a primate (non-human primate or human) than that of the fucosylated JMab-136 anti-ICOS antibody.

In one embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of ICOS expressing cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of ICOS expressing cells in a primate (non-human primate or human) than that of the fucosylated JMab-136 anti-ICOS antibody.

The present invention also provides for antibodies that efficiently deplete ICOS expressing T cells in a primate (non-human primate or human). In one embodiment, administration of one or more therapeutic doses of an anti-ICOS antibody of the invention may achieve at least about 20%, at least about 30%, at least about 40%, at least about 50%, at least about 60%, at least about 70%, at least about 80%, at least about 90%, at least about 95%, at least about 97%, at least about 99%, or at least about 100% depletion of ICOS expressing T cells in a primate (non-human primate or human).

In one embodiment, administration of one or more therapeutic doses of an anti-ICOS antibody of the invention depletes ICOS expressing T cells in a primate (non-human primate or human) more efficiently than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention depletes ICOS expressing T cells in a primate (non-human primate or human) more efficiently than that of the fucosylated JMab-136 anti-ICOS antibody.

In one embodiment, administration of one or more therapeutic doses of an anti-ICOS antibody of the invention achieves at least about 2-fold, at least about 3-fold, at least about 5-fold, or at least about 10-fold higher depletion of ICOS expressing T cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In one embodiment, administration of one or more therapeutic doses of an anti-ICOS antibody of the invention achieves at least about 2-fold, at least about 3-fold, at least about 5-fold, or at least about 10-fold higher depletion of ICOS expressing T cells in a primate (non-human primate or human) than that of the fucosylated JMab-136 anti-ICOS antibody.

In one embodiment, the EC50 value of an anti-ICOS antibody of the invention for the depletion of ICOS expressing T cells in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, the EC50 value of an anti-ICOS antibody of the invention for the depletion of ICOS expressing T cells in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC).

In one embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of ICOS expressing T cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of ICOS expressing T cells in a primate (non-human primate or human) than that of the fucosylated JMab-136 anti-ICOS antibody.

In one embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of ICOS expressing T cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of ICOS expressing T cells in a primate (non-human primate or human) than that of the fucosylated JMab-136 anti-ICOS antibody.

The present invention also provides for antibodies that efficiently deplete ICOS expressing T helper cells in a primate (non-human primate or human). In one embodiment, administration of one or more therapeutic doses of an anti-ICOS antibody of the invention may achieve at least about 20%, at least about 30%, at least about 40%, at least about 50%, at least about 60%, at least about 70%, at least about 80%, at least about 90%, at least about 95%, at least about 97%, at least about 99%, or at least about 100% depletion of ICOS expressing T helper cells in a primate (non-human primate or human).

In one embodiment, administration of one or more therapeutic doses of an anti-ICOS antibody of the invention depletes ICOS expressing T helper cells in a primate (non-human primate or human) more efficiently than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention depletes ICOS expressing T helper cells in a primate (non-human primate or human) more efficiently than that of the fucosylated JMab-136 anti-ICOS antibody.

In one embodiment, administration of one or more therapeutic doses of an anti-ICOS antibody of the invention achieves at least about 2-fold, at least about 3-fold, at least about 5-fold, or at least about 10-fold higher depletion of ICOS expressing T helper cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In one embodiment, administration of one or more therapeutic doses of an anti-ICOS antibody of the invention achieves at least about 2-fold, at least about 3-fold, at least about 5-fold, or at least about 10-fold higher depletion of ICOS expressing T helper cells in a primate (non-human primate or human) than that of the fucosylated JMab-136 anti-ICOS antibody.

In one embodiment, the EC50 value of an anti-ICOS antibody of the invention for the depletion of ICOS expressing T helper cells in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, the EC50 value of an anti-ICOS antibody of the invention for the depletion of ICOS expressing T helper cells in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC).

In one embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of ICOS expressing T helper cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of ICOS expressing T helper cells in a primate (non-human primate or human) than that of the fucosylated JMab-136 anti-ICOS antibody.

In one embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of ICOS expressing T helper cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of ICOS expressing T helper cells in a primate (non-human primate or human) than that of the fucosylated JMab-136 anti-ICOS antibody.

The present invention also provides for antibodies that efficiently deplete ICOS expressing Th1 cells in a primate (non-human primate or human). In one embodiment, administration of one or more therapeutic doses of an anti-ICOS antibody of the invention may achieve at least about 20%, at least about 30%, at least about 40%, at least about 50%, at least about 60%, at least about 70%, at least about 80%, at least about 90%, at least about 95%, at least about 97%, at least about 99%, or at least about 100% depletion of ICOS expressing Th1 cells in a primate (non-human primate or human).

In one embodiment, administration of one or more therapeutic doses of an anti-ICOS antibody of the invention depletes ICOS expressing Th1 cells in a primate (non-human primate or human) more efficiently than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention depletes ICOS expressing Th1 cells in a primate (non-human primate or human) more efficiently than that of the fucosylated JMab-136 anti-ICOS antibody.

In one embodiment, administration of one or more therapeutic doses of an anti-ICOS antibody of the invention achieves at least about 2-fold, at least about 3-fold, at least about 5-fold, or at least about 10-fold higher depletion of ICOS expressing Th1 cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In one embodiment, administration of one or more therapeutic doses of an anti-ICOS antibody of the invention achieves at least about 2-fold, at least about 3-fold, at least about 5-fold, or at least about 10-fold higher depletion of ICOS expressing Th1 cells in a primate (non-human primate or human) than that of the fucosylated JMab-136 anti-ICOS antibody.

In one embodiment, the EC50 value of an anti-ICOS antibody of the invention for the depletion of ICOS expressing Th1 cells in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, the EC50 value of an anti-ICOS antibody of the invention for the depletion of ICOS expressing Th1 cells in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC).

In one embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of ICOS expressing Th1 cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of ICOS expressing Th1 cells in a primate (non-human primate or human) than that of the fucosylated JMab-136 anti-ICOS antibody.

In one embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of ICOS expressing Th1 cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of ICOS expressing Th1 cells in a primate (non-human primate or human) than that of the fucosylated JMab-136 anti-ICOS antibody.

The present invention also provides for antibodies that efficiently deplete ICOS expressing Th2 cells in a primate (non-human primate or human). In one embodiment, administration of one or more therapeutic doses of an anti-ICOS antibody of the invention may achieve at least about 20%, at least about 30%, at least about 40%, at least about 50%, at least about 60%, at least about 70%, at least about 80%, at least about 90%, at least about 95%, at least about 97%, at least about 99%, or at least about 100% depletion of ICOS expressing Th2 cells in a primate (non-human primate or human).

In one embodiment, administration of one or more therapeutic doses of an anti-ICOS antibody of the invention depletes ICOS expressing Th2 cells in a primate (non-human primate or human) more efficiently than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention depletes ICOS expressing Th2 cells in a primate (non-human primate or human) more efficiently than that of the fucosylated JMab-136 anti-ICOS antibody.

In one embodiment, administration of one or more therapeutic doses of an anti-ICOS antibody of the invention achieves at least about 2-fold, at least about 3-fold, at least about 5-fold, or at least about 10-fold higher depletion of ICOS expressing Th2 cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In one embodiment, administration of one or more therapeutic doses of an anti-ICOS antibody of the invention achieves at least about 2-fold, at least about 3-fold, at least about 5-fold, or at least about 10-fold higher depletion of ICOS expressing Th2 cells in a primate (non-human primate or human) than that of the fucosylated JMab-136 anti-ICOS antibody.

In one embodiment, the EC50 value of an anti-ICOS antibody of the invention for the depletion of ICOS expressing Th2 cells in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, the EC50 value of an anti-ICOS antibody of the invention for the depletion of ICOS expressing Th2 cells in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC).

In one embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of ICOS expressing Th2 cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of ICOS expressing Th2 cells in a primate (non-human primate or human) than that of the fucosylated JMab-136 anti-ICOS antibody.

In one embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of ICOS expressing Th2 cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of ICOS expressing Th2 cells in a primate (non-human primate or human) than that of the fucosylated JMab-136 anti-ICOS antibody.

The present invention also provides for antibodies that efficiently deplete ICOS expressing Th17 cells in a primate (non-human primate or human). In one embodiment, administration of one or more therapeutic doses of an anti-ICOS antibody of the invention may achieve at least about 20%, at least about 30%, at least about 40%, at least about 50%, at least about 60%, at least about 70%, at least about 80%, at least about 90%, at least about 95%, at least about 97%, at least about 99%, or at least about 100% depletion of ICOS expressing Th17 cells in a primate (non-human primate or human).

In one embodiment, administration of one or more therapeutic doses of an anti-ICOS antibody of the invention depletes ICOS expressing Th17 cells in a primate (non-human primate or human) more efficiently than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention depletes ICOS expressing Th17 cells in a primate (non-human primate or human) more efficiently than that of the fucosylated JMab-136 anti-ICOS antibody.

In one embodiment, administration of one or more therapeutic doses of an anti-ICOS antibody of the invention achieves at least about 2-fold, at least about 3-fold, at least about 5-fold, or at least about 10-fold higher depletion of ICOS expressing Th17 cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In one embodiment, administration of one or more therapeutic doses of an anti-ICOS antibody of the invention achieves at least about 2-fold, at least about 3-fold, at least about 5-fold, or at least about 10-fold higher depletion of ICOS expressing Th17 cells in a primate (non-human primate or human) than that of the fucosylated JMab-136 anti-ICOS antibody.

In one embodiment, the EC50 value of an anti-ICOS antibody of the invention for the depletion of ICOS expressing Th17 cells in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, the EC50 value of an anti-ICOS antibody of the invention for the depletion of ICOS expressing Th17 cells in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC).

In one embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of ICOS expressing Th17 cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of ICOS expressing Th17 cells in a primate (non-human primate or human) than that of the fucosylated JMab-136 anti-ICOS antibody.

In one embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of ICOS expressing Th17 cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of ICOS expressing Th17 cells in a primate (non-human primate or human) than that of the fucosylated JMab-136 anti-ICOS antibody.

The present invention also provides for antibodies that efficiently deplete ICOS expressing memory helper T cells in a primate (non-human primate or human). In one embodiment, administration of one or more therapeutic doses of an anti-ICOS antibody of the invention may achieve at least about 20%, at least about 30%, at least about 40%, at least about 50%, at least about 60%, at least about 70%, at least about 80%, at least about 90%, at least about 95%, at least about 97%, at least about 99%, or at least about 100% depletion of ICOS expressing memory helper T cells in a primate (non-human primate or human).

In one embodiment, administration of one or more therapeutic doses of an anti-ICOS antibody of the invention depletes ICOS expressing memory helper T cells in a primate (non-human primate or human) more efficiently than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention depletes ICOS expressing memory helper T cells in a primate (non-human primate or human) more efficiently than that of the fucosylated JMab-136 anti-ICOS antibody.

In one embodiment, administration of one or more therapeutic doses of an anti-ICOS antibody of the invention achieves at least about 2-fold, at least about 3-fold, at least about 5-fold, or at least about 10-fold higher depletion of ICOS expressing memory helper T cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In one embodiment, administration of one or more therapeutic doses of an anti-ICOS antibody of the invention achieves at least about 2-fold, at least about 3-fold, at least about 5-fold, or at least about 10-fold higher depletion of ICOS expressing memory helper T cells in a primate (non-human primate or human) than that of the fucosylated JMab-136 anti-ICOS antibody.

In one embodiment, the EC50 value of an anti-ICOS antibody of the invention for the depletion of ICOS expressing memory helper T cells in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, the EC50 value of an anti-ICOS antibody of the invention for the depletion of ICOS expressing memory helper T cells in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC).

In one embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of ICOS expressing memory helper T cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of ICOS expressing memory helper T cells in a primate (non-human primate or human) than that of the fucosylated JMab-136 anti-ICOS antibody.

In one embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of ICOS expressing memory helper T cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of ICOS expressing memory helper T cells in a primate (non-human primate or human) than that of the fucosylated JMab-136 anti-ICOS antibody.

Depletion of a particular cell type may lead to the depletion of a secreted product of said cell type. For example, depletion of Th17 cells using an effector function enhanced anti-ICOS antibody of the invention may lead to depletion of IL-17. The present invention also provides for antibodies that efficiently deplete IL-17 in a primate (non-human primate or human). In one embodiment, administration of one or more therapeutic doses of an anti-ICOS antibody of the invention may achieve at least about 20%, at least about 30%, at least about 40%, at least about 50%, at least about 60%, at least about 70%, at least about 80%, at least about 90%, at least about 95%, at least about 97%, at least about 99%, or at least about 100% depletion of IL-17 in a primate (non-human primate or human).

In one embodiment, administration of one or more therapeutic doses of an anti-ICOS antibody of the invention depletes IL-17 in a primate (non-human primate or human) more efficiently than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention depletes IL-17 in a primate (non-human primate or human) more efficiently than that of the fucosylated JMab-136 anti-ICOS antibody.

In one embodiment, administration of one or more therapeutic doses of an anti-ICOS antibody of the invention achieves at least about 2-fold, at least about 3-fold, at least about 5-fold, or at least about 10-fold higher depletion of IL-17 in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In one embodiment, administration of one or more therapeutic doses of an anti-ICOS antibody of the invention achieves at least about 2-fold, at least about 3-fold, at least about 5-fold, or at least about 10-fold higher depletion of IL-17 in a primate (non-human primate or human) than that of the fucosylated JMab-136 anti-ICOS antibody.

In one embodiment, the EC50 value of an anti-ICOS antibody of the invention for the depletion of IL-17 in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, the EC50 value of an anti-ICOS antibody of the invention for the depletion of IL-17 in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC).

In one embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of IL-17 in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of IL-17 in a primate (non-human primate or human) than that of the fucosylated JMab-136 anti-ICOS antibody.

In one embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of IL-17 in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of IL-17 in a primate (non-human primate or human) than that of the fucosylated JMab-136 anti-ICOS antibody.

The present invention also provides for antibodies that efficiently deplete IL-2 in a primate (non-human primate or human). In one embodiment, administration of one or more therapeutic doses of an anti-ICOS antibody of the invention may achieve at least about 20%, at least about 30%, at least about 40%, at least about 50%, at least about 60%, at least about 70%, at least about 80%, at least about 90%, at least about 95%, at least about 97%, at least about 99%, or at least about 100% depletion of IL-2 in a primate (non-human primate or human).

In one embodiment, administration of one or more therapeutic doses of an anti-ICOS antibody of the invention depletes IL-2 in a primate (non-human primate or human) more efficiently than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention depletes IL-2 in a primate (non-human primate or human) more efficiently than that of the fucosylated JMab-136 anti-ICOS antibody.

In one embodiment, administration of one or more therapeutic doses of an anti-ICOS antibody of the invention achieves at least about 2-fold, at least about 3-fold, at least about 5-fold, or at least about 10-fold higher depletion of IL-2 in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In one embodiment, administration of one or more therapeutic doses of an anti-ICOS antibody of the invention achieves at least about 2-fold, at least about 3-fold, at least about 5-fold, or at least about 10-fold higher depletion of IL-2 in a primate (non-human primate or human) than that of the fucosylated JMab-136 anti-ICOS antibody.

In one embodiment, the EC50 value of an anti-ICOS antibody of the invention for the depletion of IL-2 in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, the EC50 value of an anti-ICOS antibody of the invention for the depletion of IL-2 in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC).

In one embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of IL-2 in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of IL-2 in a primate (non-human primate or human) than that of the fucosylated JMab-136 anti-ICOS antibody.

In one embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of IL-2 in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of IL-2 in a primate (non-human primate or human) than that of the fucosylated JMab-136 anti-ICOS antibody.

ICOS expressing T cells have been implicated in germinal center formation in mouse model systems. Data disclosed herein demonstrates that ICOS expressing cells are also involved in maintaining of the structural integrity and B cell compartment of already formed germinal centers. Without being bound by a particular model, the depletion of ICOS expressing T cells in a primate (non-human primate or human) by administering one or more therapeutic doses of an anti-ICOS antibody of the invention may prevent the formation of germinal centers, may disrupt the architecture of already formed germinal centers, may deplete germinal center B cells from secondary lymphoid organs and/or may deplete circulating class switched B cells. Germinal center formation may be monitored by any method known in the art, for example, but not limited to, histological examination of secondary lymphoid organs or analysis of the lymphoid cells isolated from secondary lymphoid tissues by flow cytometry. The disruption of germinal center architecture may be monitored by any method known in the art, for example, but not limited to, histological examination of secondary lymphoid organs. Depletion of germinal center B cells from secondary lymphoid organs may be monitored by any method known in the art, for example, but not limited to, histological examination of secondary lymphoid organs or analysis of the lymphoid cells isolated from secondary lymphoid tissues by flow cytometry. Depletion of circulating class switched B cells may be monitored by any method known in the art, for example, but not limited to, analysis of circulating lymphoid cells by flow cytometry. Class switched B cells may be identified based on their specific expression, or lack thereof, of cell surface markers, for example, but not limited to, circulating class switched B cells may be identified as CD27+IgM-IgD- B cells.

The present invention provides for antibodies that efficiently prevent germinal center formation in a secondary lymphoid organ of a primate (non-human primate or human). In one embodiment, the secondary lymphoid organ is a lymph node. In another embodiment, the secondary lymphoid organ is the spleen. In a further embodiment, the secondary lymphoid organ is the tonsil. In one embodiment, the secondary lymphoid organ is a mesenteric lymph node.

In one embodiment, the administration of one or more therapeutic doses of an anti-ICOS antibody of the invention prevents germinal center formation in a secondary lymphoid organ of a primate (non-human primate or human) for at least 1 day, at least 2 days at least 5 days, at least 1 week, at least 2 weeks, at least 3 weeks, at least 1 month, at least 2 months, at least 3 months, at least 4 months, at least 5 months, at least 6 months, at least 9 months. In a specific embodiment, the secondary lymphoid organ is the spleen. In another specific embodiment, the secondary lymphoid organ is the tonsil.

In one embodiment, the administration of one or more therapeutic doses of an anti-ICOS antibody of the invention prevents germinal center formation in a secondary lymphoid organ of a primate (non-human primate or human) for a longer time period than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention prevents germinal center formation in a secondary lymphoid organ of a primate (non-human primate or human) for a longer time period than that of the fucosylated JMAb-136 anti-ICOS antibody. In a specific embodiment, the secondary lymphoid organ is the spleen. In another specific embodiment, the secondary lymphoid organ is the tonsil.

In one embodiment, administration of one or more therapeutic doses of an anti-ICOS antibody of the invention prevents germinal center formation in a secondary lymphoid organ of a primate (non-human primate or human) more efficiently than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention prevents germinal center formation in a secondary lymphoid organ of a primate (non-human primate or human) more efficiently than that of the fucosylated JMAb-136 anti-ICOS antibody.

The present invention also provides for antibodies that efficiently disrupt germinal center architecture in a secondary lymphoid organ of a primate (non-human primate or human). In one embodiment, the secondary lymphoid organ is a lymph node. In another embodiment, the secondary lymphoid organ is the spleen. In a further embodiment, the secondary lymphoid organ is the tonsil. In one embodiment, the secondary lymphoid organ is a mesenteric lymph node.

In one embodiment, the administration of one or more therapeutic doses of an anti-ICOS antibody of the invention disrupts germinal center architecture in a secondary lymphoid organ of a primate (non-human primate or human) for at least 1 day, at least 2 days at least 5 days, at least 1 week, at least 2 weeks, at least 3 weeks, at least 1 month, at least 2 months, at least 3 months, at least 4 months, at least 5 months, at least 6 months, at least 9 months. In a specific embodiment, the secondary lymphoid organ is the spleen. In another specific embodiment, the secondary lymphoid organ is the tonsil.

In one embodiment, the administration of one or more therapeutic doses of an anti-ICOS antibody of the invention disrupts germinal center architecture in a secondary lymphoid organ of a primate (non-human primate or human) for a longer time period than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention disrupts germinal center architecture in a secondary lymphoid organ of a primate (non-human primate or human) for a longer time period than that of the fucosylated JMAb-136 anti-ICOS antibody. In a specific embodiment, the secondary lymphoid organ is the spleen. In another specific embodiment, the secondary lymphoid organ is the tonsil.

In one embodiment, administration of one or more therapeutic doses of an anti-ICOS antibody of the invention disrupts germinal center architecture in a secondary lymphoid organ of a primate (non-human primate or human) more efficiently than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention disrupts germinal center architecture in a secondary lymphoid organ of a primate (non-human primate or human) more efficiently than that of the fucosylated JMAb-136 anti-ICOS antibody.

The present invention also provides for antibodies that efficiently deplete germinal center B cells from a secondary lymphoid organ in a primate (non-human primate or human). In one embodiment, the secondary lymphoid organ is a lymph node. In another embodiment, the secondary lymphoid organ is the spleen. In a further embodiment, the secondary lymphoid organ is the tonsil. In one embodiment, the secondary lymphoid organ is a mesenteric lymph node.

In one embodiment, the administration of one or more therapeutic doses of an anti-ICOS antibody of the invention depletes germinal center B cells from a secondary lymphoid organ in a primate (non-human primate or human) for at least 1 day, at least 2 days at least 5 days, at least 1 week, at least 2 weeks, at least 3 weeks, at least 1 month, at least 2 months, at least 3 months, at least 4 months, at least 5 months, at least 6 months, at least 9 months. In a specific embodiment, the secondary lymphoid organ is the spleen. In another specific embodiment, the secondary lymphoid organ is the tonsil. Depletion of germinal center B cells is considered to "substantially persist" during the time period following the administration of one or more doses of anti-ICOS antibody when the number of germinal center B cells is at least 10% lower in the antibody treated sample than the number of germinal center B cells in the untreated control sample.

In one embodiment, the administration of one or more therapeutic doses of an anti-ICOS antibody of the invention depletes germinal center B cells from a secondary lymphoid organ in a primate (non-human primate or human) for a longer time period than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention depletes germinal center B cells from a secondary lymphoid organ in a primate (non-human primate or human) for a longer time period than that of the fucosylated JMAb-136 anti-ICOS antibody. In a specific embodiment, the secondary lymphoid organ is the spleen. In another specific embodiment, the secondary lymphoid organ is the tonsil.

In one embodiment, administration of one or more therapeutic doses of an anti-ICOS antibody of the invention may achieve at least about 20%, at least about 30%, at least about 40%, at least about 50%, at least about 60%, at least about 70%, at least about 80%, at least about 90%, at least about 95%, at least about 97%, at least about 99%, or at least about 100% depletion of germinal center B cells from a secondary lymphoid organ in a primate (non-human primate or human).

In one embodiment, administration of one or more therapeutic doses of an anti-ICOS antibody of the invention depletes germinal center B cells from a secondary lymphoid organ in a primate (non-human primate or human) more efficiently than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention depletes germinal center B cells from a secondary lymphoid organ in a primate (non-human primate or human) more efficiently than that of the fucosylated JMAb-136 anti-ICOS antibody.

In one embodiment, administration of one or more therapeutic doses of an anti-ICOS antibody of the invention achieves at least about 2-fold, at least about 3-fold, at least about 5-fold, or at least about 10-fold higher depletion of germinal center B cells from a secondary lymphoid organ in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In one embodiment, administration of one or more therapeutic doses of an anti-ICOS antibody of the invention achieves at least about 2-fold, at least about 3-fold, at least about 5-fold, or at least about 10-fold higher depletion of germinal center B cells from a secondary lymphoid organ in a primate (non-human primate or human) than that of the fucosylated JMab-136 anti-ICOS antibody.

In one embodiment, the EC50 value of an anti-ICOS antibody of the invention for the depletion of germinal center B cells from a secondary lymphoid organ in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, the EC50 value of an anti-ICOS antibody of the invention for the depletion of germinal center B cells from a secondary lymphoid organ in a primate (non-human primate or human) is at least about 2×, at least about 5×, at least about 10×, at least about 20×, at least about 50×, or at least about 100× lower than that of the parental anti-ICOS antibody.

In one embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of germinal center B cells from a secondary lymphoid organ in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of germinal center B cells from a secondary lymphoid organ in a primate (non-human primate or human) than that of the fucosylated the JMab-136 anti-ICOS antibody.

In one embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of germinal center B cells from a secondary lymphoid organ in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of germinal center B cells from a secondary lymphoid organ in a primate (non-human primate or human) than that of the fucosylated JMab-136 anti-ICOS antibody.

The present invention also provides for antibodies that efficiently deplete circulating class switched B cells in a primate (non-human primate or human). In one embodiment, the administration of one or more therapeutic doses of an anti-ICOS antibody of the invention depletes circulating class switched B cells in a primate (non-human primate or human) for at least 1 day, at least 2 days at least 5 days, at least 1 week, at least 2 weeks, at least 3 weeks, at least 1 month, at least 2 months, at least 3 months, at least 4 months, at least 5 months, at least 6 months, at least 9 months. Depletion of circulating class switched B cells is considered to "substantially persist" during the time period following the administration of one or more doses of anti-ICOS antibody when the number of circulating class switched B cells is at least 10% lower in the antibody treated sample than the number of circulating class switched B cells in the untreated control sample.

In one embodiment, the administration of one or more therapeutic doses of an anti-ICOS antibody of the invention depletes circulating class switched B cells in a primate (non-human primate or human) for a longer time period than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention depletes circulating class switched B cells in a primate (non-human primate or human) for a longer time period than that of the fucosylated JMAb-136 anti-ICOS antibody.

In one embodiment, administration of one or more therapeutic doses of an anti-ICOS antibody of the invention may achieve at least about 20%, at least about 30%, at least about 40%, at least about 50%, at least about 60%, at least about 70%, at least about 80%, at least about 90%, at least about 95%, at least about 97%, at least about 99%, or at least about 100% depletion of circulating class switched B cells in a primate (non-human primate or human).

In one embodiment, administration of one or more therapeutic doses of an anti-ICOS antibody of the invention may deplete circulating class switched B cells to less than 2%, less than 1.5%, less than 1%, less than 0.9%, less than 0.8%, less than 07%, less than 0.6%, less than 0.5%, less than 0.4%, less than 0.3% or less than 0.1% of peripheral blood lymphocytes (PBL) in a primate (non-human primate or human).

In one embodiment, administration of one or more therapeutic doses of an anti-ICOS antibody of the invention depletes circulating class switched B cells in a primate (non-human primate or human) more efficiently than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention depletes circulating class switched B cells in a primate (non-human primate or human) more efficiently than that of the fucosylated JMAb-136 anti-ICOS antibody.

In one embodiment, administration of one or more therapeutic doses of an anti-ICOS antibody of the invention achieves at least about 2-fold, at least about 3-fold, at least about 5-fold, or at least about 10-fold higher depletion of circulating class switched B cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In one embodiment, administration of one or more therapeutic doses of an anti-ICOS antibody of the invention achieves at least about 2-fold, at least about 3-fold, at least about 5-fold, or at least about 10-fold higher depletion of circulating class switched B cells in a primate (non-human primate or human) than that of the fucosylated the JMab-136 anti-ICOS antibody.

In one embodiment, the EC50 value of an anti-ICOS antibody of the invention for the depletion of circulating class switched B cells in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, the EC50 value of an anti-ICOS antibody of the invention for the depletion of circulating class switched B cells in a primate (non-human primate or human) is at least about 2×, at least about 5×, at least about 10×, at least about 20×, at least about 50×, or at least about 100× lower than that of the parental anti-ICOS antibody (e.g., an antibody comprising the same variable domain amino acid sequence, but having 1) a fucosylated Fc domain or 2) an Fc domain amino acid sequence, which has not been modified to increase ADCC).

In one embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of circulating class switched B cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 5%, at least about 10%, at least about 20%, at least about 30%, at least about 40%, at least about 50%, at least about 75%, at least about 100% higher depletion of circulating class switched B cells in a primate (non-human primate or human) than that of the fucosylated the JMAb-136 anti-ICOS antibody.

In one embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of circulating class switched B cells in a primate (non-human primate or human) than that of the parental anti-ICOS antibody (e.g., an antibody comprising the same variable domain amino acid sequence, but having 1) a fucosylated Fc domain or 2) an Fc domain amino acid sequence, which has not been modified to increase ADCC). In another embodiment, administration of one or more therapeutic doses of an anti-ICOS antibody of the invention achieves at least about 2×, at least about 5×, at least about 10×, at least about 15×, at least about 20×, at least about 25×, at least about 50×, or at least about 100× higher depletion of circulating class switched B cells in a primate (non-human primate or human) than that of the fucosylated JMab-136 anti-ICOS antibody.

In one embodiment, an anti-ICOS antibody described herein mediates antibody-dependent cellular cytotoxicity (ADCC), complement-dependent cell-mediated cytotoxicity (CDC), and/or antibody-dependent phagocytosis. In one embodiment, an anti-ICOS antibody of the invention mediates antibody-dependent cellular cytotoxicity (ADCC) and/or antibody-dependent phagocytosis. In one embodiment, an anti-ICOS antibody of the invention has enhanced antibody-dependent cellular cytotoxicity (ADCC).

In one embodiment, an anti-ICOS antibody of the invention comprises a variant Fc region that mediates enhanced antibody-dependent cellular cytotoxicity (ADCC). In a further embodiment, an anti-ICOS antibody of the invention comprises a variant Fc region comprising at least one substitution of an amino acid residue selected from the group consisting of: residue 239, 330, and 332, wherein the amino acid residue positions are determined according to the EU convention. In a specific embodiment, an anti-ICOS antibody of the invention comprises a variant Fc region comprising at least on amino acid substitution selected from the group consisting of: S239D, A330L, and I332E; wherein the amino acid residue positions are determined according to the EU convention. In a further embodiment, an anti-ICOS antibody of the invention comprises at least one amino acid residue selected from the group consisting of: D at position 239, L at position 330, and E at position 332; wherein the amino acid residue positions are determined according to the EU convention.

In one embodiment, an anti-ICOS antibody of the invention comprises an engineered Fc region comprising at least one engineered glycoform, wherein said engineered Fc region mediates enhanced antibody-dependent cellular cytotoxicity (ADCC). In one embodiment, an anti-ICOS antibody of the inventions comprises an engineered Fc region lacking glycosylation. In one embodiment, an anti-ICOS antibody of the invention comprises an engineered Fc region having complex N-glycoside-linked sugar chains linked to Asn297 in which fucose is not bound to N-acetylglucosamine in the reducing end.

In certain embodiments, an anti-ICOS antibody of the invention comprises a variant Fc region that has a higher affinity for an Fc binding protein such as, but not limited to, Fc receptor, C1q than a wild type Fc region. In one embodiment, an anti-ICOS antibody of the invention comprises a variant Fc region that has higher affinity for the FcγRIIIA receptor protein than a wild type Fc region.

In certain embodiments, an anti-ICOS antibody of the invention comprises an engineered Fc region comprising at least one engineered glycoform, wherein said engineered Fc region has a higher affinity for an Fc binding protein such as, but not limited to, Fc receptor, C1q than a wild type Fc region. In one embodiment, an anti-ICOS antibody of the invention comprises an engineered Fc region comprising at least one engineered glycoform, wherein said engineered Fc region has higher affinity for the FcγRIIIA receptor protein than a wild type Fc region.

The present invention also relates to methods of treating and preventing T cell-mediated diseases and disorders, such as, but not limited to, chronic infection, autoimmune disease or disorder, inflammatory disease or disorder, graft-versus-host disease (GVHD), transplant rejection, and T cell proliferative disorder in a human, comprising administering to a human in need thereof an anti-ICOS antibody with enhanced effector function (e.g., antibody-dependent cellular cytotoxicity (ADCC), complement-dependent cell-mediated cytotoxicity (CDC), and/or antibody-dependent phagocytosis) in an amount sufficient to deplete circulating ICOS expressing cells. In a particular aspect, the present invention also concerns methods of treating and preventing T cell-mediated diseases and disorders, such as, but not limited to, chronic infection, autoimmune disease or disorder, inflammatory disease or disorder, graft-versus-host disease (GVHD), transplant rejection, and T cell proliferative disorder in a human comprising administration of a therapeutically effective regimen of an anti-ICOS antibody with enhanced effector function, which is of the IgG1 or IgG3 human isotype.

The invention encompasses methods of identifying, diagnosing, treating, and monitoring disease progression in patients. The patient may have the disease, disorder, or condition as a result of experimental research, e.g., it may be an experimental model developed for the disease, disorder, or condition. Alternatively, the patient may have the disease, disorder, or condition in the absence of experimental manipulation. Patients include humans, mice, rats, horses, pigs, cats, dogs, and any animal used for research.

The patient may comprise a differentially regulated ICOS mRNA or ICOSL mRNA or miR-101 level. A differentially regulated ICOS mRNA or ICOSL mRNA or miR-101 level may be one in which a tissue sample of the patient exhibits increased expression of ICOS mRNA or ICOSL mRNA or miR-101 relative to a control tissue sample of the patient or relative to a healthy control individual. A differentially regulated ICOS mRNA or ICOSL mRNA or miR-101 level may be one in which a tissue sample of the patient exhibits decreased expression of ICOS mRNA or ICOSL mRNA or miR-101 relative to a control sample of the patient or relative to a healthy control individual. The differential increase or decrease in expression may be approximately 10%-500% of the control sample, approximately 10%-400% of the control sample, approximately 10%-300% of the control sample, approximately 10%-250% of the control sample, approximately 10%-200% of the control sample, approximately 10%-150% of the control sample, approximately 10%-100% of the control sample, approximately 10%-50% of the control sample, approximately 100%-500% of the control sample, approximately 200%-500% of the control sample, approximately 300%-500% of the control sample, approximately 400%-500% of the control sample, approximately 50%-100% of the control sample, approximately 100%-200% of the control sample, approximately 100%-400% of the control sample, approximately 200%-400% of the control sample, approximately 10%-50% of the control sample, approximately 20%-100% of the control sample, approximately 25%-75% of the control sample, or approximately 50%-100% of the control sample. It may be 10, 20, 25, 30, 40, 50, 75, 100, 125, 150, 175, 200, 250, 300, 400, or 500 percent of the control sample.

Administration of an anti-ICOS antibody of the invention may result in neutralization of the differentially regulated ICOS mRNA or ICOSL mRNA or miR-101 level. Neutralization of the differentially regulated ICOS mRNA or ICOSL mRNA or miR-101 level may be a reduction of at least 2%, at least 3%, at least 4%, at least 5%, at least 7%, at least 8%, at least 10%, at least 15%, at least 25%, at least 30%, at least 35%, at least 40%, at least 45%, at least 50%, at least 60%, at least 70%, at least 75%, at least 80%, or at least 90% of ICOS mRNA or ICOSL mRNA or miR-101 level. Alternatively, neutralization of the differentially regulated ICOS mRNA or ICOSL mRNA or miR-101 level refers to a reduction of expression of up-regulated ICOS mRNA or ICOSL mRNA or miR-101 that is within at most 50%, at most 45%, at most 40%, at most 35%, at most 30%, at most 25%, at most 20%, at most 15%, at most 10%, at most 5%, at most 4%, at most 3%, at most 2%, or at most 1% of expression levels of the ICOS mRNA or ICOSL mRNA or miR-101 level in a control sample.

The upregulation or downregulation of the ICOS mRNA or ICOSL mRNA or miR-101 in the patient may be by any degree relative to that of a sample from a control (which may be from a sample that is not disease tissue of the patient (e.g., non-lesional skin of a SLE patient) or from a healthy person not afflicted with the disease or disorder). The degree upregulation or downregulation may be at least 10%, at least 15%, at least 20%, at least 25%, at least 30%, at least 40%, at least 50%, at least 60%, at least 70%, at least 75%, at least 80%, at least 90%, at least 100%, at least 125%, at least 150%, or at least 200%, or at least 300%, or at least 400%, or at least 500% that of the control or control sample.

In methods of monitoring or prognosing disease progression of a patient, samples from the patient may be obtained before and after administration of an agent.

Samples include any biological fluid or tissue, such as whole blood, serum, muscle, saliva, urine, synovial fluid, bone marrow, cerebrospinal fluid, nasal secretions, sputum, amniotic fluid, bronchoalveolar lavage fluid, peripheral blood mononuclear cells, total white blood cells, lymph node cells, spleen cells, tonsil cells, or skin. The samples may be obtained by any means known in the art.

ICOS mRNA or ICOSL mRNA or miR-101 levels are obtained in the (before and after agent administration) samples. The ICOS mRNA or ICOSL mRNA or miR-101 levels in the samples are compared.

The sample obtained from the patient may be obtained prior to a first administration of the agent, i.e., the patient is naïve to the agent. Alternatively, the sample obtained from the patient may occur after administration of the agent in the course of treatment. For example, the agent may have been administered prior to the initiation of the monitoring protocol. Following administration of the agent an additional samples may be obtained from the patient. The samples may be of the same or different type, e.g., each sample obtained may be a blood sample, or each sample obtained may be a serum sample. The ICOS mRNA or ICOSL mRNA or miR-101 levels detected in each sample may be the same, may overlap substantially, or may be similar.

The samples may be obtained at any time before and after the administration of the therapeutic agent. The sample obtained after administration of the therapeutic agent may be obtained at least 2, at least 3, at least 4, at least 5, at least 6, at least 7, at least 8, at least 9, at least 10, at least 12, or at least 14 days after administration of the therapeutic agent. The sample obtained after administration of the therapeutic agent may be obtained at least 2, at least 3, at least 4, at least 5, at least 6, at least 7, or at least 8 weeks after administration of the therapeutic agent. The sample obtained after administration of the therapeutic agent may be obtained at least 2, at least 3, at least 4, at least 5, or at least 6 months following administration of the therapeutic agent.

Additional samples may be obtained from the patient following administration of the therapeutic agent. At least 2, at least 3, at least 4, at least 5, at least 6, at least 7, at least 8, at least 9, at least 10, at least 12, at least 15, at least 20, at least 25 samples may be obtained from the patient to monitor progression or regression of the disease or disorder over time. Disease progression may be monitored over a time period of at least 1 week, at least 2 weeks, at least 3 weeks, at least 4 weeks, at least 5 weeks, at least 6 weeks, at least 7 weeks, at least 2 months, at least 3 months, at least 4 months, at least 5 months, at least 6 months, at least 1 year, at least 2 years, at least 3 years, at least 4 years, at least 5 years, at least 10 years, or over the lifetime of the patient. Additional samples may be obtained from the patient at regular intervals such as at monthly, bi-monthly, once a quarter year, twice a year, or yearly intervals. The samples may be obtained from the patient following administration of the agent at regular intervals. For instance, the samples may be obtained from the patient at one week following each administration of the agent, or at two weeks following each administration of the agent, or at three weeks following each administration of the agent, or at one month following each administration of the agent, or at two months following each administration of the agent. Alternatively, multiple samples may be obtained from the patient following each administration of the agent.

The invention also encompasses methods employing ICOS mRNA or ICOSL mRNA or miR-101 levels to treat, diagnose, prognose, and monitor myositis. The ICOS mRNA or ICOSL mRNA or miR-101 levels can also be used to guide dosage and treatment of myositis patients or models of myositis disease.

5.1. Monoclonal Anti-ICOS Antibodies

A monoclonal anti-ICOS antibody exhibits binding specificity to human ICOS antigen and may mediate human ADCC, CDC and/or antibody-dependent phagocytosis. Such an antibody can be generated using a wide variety of techniques known in the art including the use of hybridoma, recombinant, and phage display technologies, or a combination thereof. Antibodies are highly specific, being directed against a single antigenic site. An engineered anti-ICOS antibody can be produced by any means known in the art, including, but not limited to, those techniques described below and improvements to those techniques. Large-scale high-yield production typically involves culturing a host cell that produces the engineered anti-ICOS antibody and recovering the anti-ICOS antibody from the host cell culture.

5.1.1. Hybridoma Technique

Monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling et al., in *Monoclonal Antibodies and T Cell Hybridomas*, 563-681 (Elsevier, N.Y., 1981) (said references incorporated herein by reference in their entireties). For example, in the hybridoma method, a mouse or other appropriate host animal, such as a hamster or macaque monkey, is immunized to elicit lymphocytes that produce or are capable of producing antibodies that will specifically bind to the protein used for immunization. Lymphocytes may also be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the human ICOS antigen. The binding specificity of monoclonal antibodies produced by hybridoma cells can be determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

5.1.2. Recombinant DNA Techniques

DNA encoding an anti-ICOS antibody described herein is readily isolated and sequenced using conventional procedures (e.g., by using oligonucleotide probes that are capable of binding specifically to genes encoding the heavy and light chains of anti-ICOS antibodies). The hybridoma cells serve as a source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of anti-ICOS antibodies in the recombinant host cells.

In phage display methods, functional antibody domains are displayed on the surface of phage particles which carry the polynucleotide sequences encoding them. In particular, DNA sequences encoding $V_H$ and $V_L$ domains are amplified from animal cDNA libraries (e.g., human or murine cDNA libraries of affected tissues). The DNA encoding the $V_H$ and $V_L$ domains are recombined together with an scFv linker by PCR and cloned into a phagemid vector. The vector is electroporated in *E. coli* and the *E. coli* is infected with helper phage. Phage used in these methods is typically filamentous phage including fd and M13 and the $V_H$ and $V_L$ domains are usually recombinantly fused to either the phage gene III or gene VIII. Phage expressing an antigen-binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, *J. Immunol. Methods,* 182:41-50; Ames et al., 1995, *J. Immunol. Methods,* 184:177-186; Kettleborough et al., 1994, *Eur. J. Immunol.,* 24:952-958; Persic et al., 1997, *Gene,* 187:9-18; Burton et al., 1994, *Advances in Immunology,* 57:191-280; International Application No. PCT/GB91/O1 134; International Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108; each of which is incorporated herein by reference in its entirety.

As described in the above references, after phage selection, the antibody coding regions from the phage can be isolated and used to generate whole antibodies, including human antibodies, or any other desired antigen-binding fragment, and expressed in any desired host, including mammalian cells, insect cells, plant cells, yeast, and bacteria, e.g., as described below. Techniques to recombinantly produce Fab, Fab' and F(ab')$_2$ fragments can also be employed using methods known in the art such as those disclosed in PCT Publication No. WO 92/22324; Mullinax et al., 1992, *BioTechniques,* 12(6):864-869; Sawai et al., 1995, *AJRI,* 34:26-34; and Better et al., 1988, *Science,* 240:1041-1043 (said references incorporated by reference in their entireties).

Antibodies may be isolated from antibody phage libraries generated using the techniques described in McCafferty et al., *Nature,* 348:552-554 (1990). Clackson et al., *Nature,* 352: 624-628 (1991). Marks et al., *J. Mol. Biol.,* 222:581-597 (1991) describe the isolation of murine and human antibodies, respectively, using phage libraries. Chain shuffling can be used in the production of high affinity (nM range) human antibodies (Marks et al., *Bio/Technology,* 10:779-783 (1992)), as well as combinatorial infection and in vivo recombination as a strategy for constructing very large phage libraries (Waterhouse et al., *Nuc. Acids. Res.,* 21:2265-2266 (1993)). Thus, these techniques are viable alternatives to traditional monoclonal antibody hybridoma techniques for isolation of anti-ICOS antibodies.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. The vectors for expressing the VH or VL domains may comprise an EF-1α promoter, a secretion signal, a cloning site for the variable domain, constant domains, and a selection marker such as neomycin. The VH and VL domains may also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also may be modified, for example, by substituting the coding sequence for human heavy and light chain constant domains in place of the homologous murine sequences (U.S. Pat. No. 4,816,567; Morrison et al., *Proc. Natl. Acad. Sci. USA,* 81:6851 (1984)), or by covalently joining to the immunoglobulin coding sequence all or part of the coding sequence for a non-immunoglobulin polypeptide.

5.2. Chimeric Antibodies

The anti-ICOS antibodies herein specifically include chimeric antibodies (immunoglobulins) in which a portion of the heavy and/or light chain is identical with or homologous to corresponding sequences in antibodies derived from a particular species or belonging to a particular antibody class or subclass, while another portion of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851-6855 (1984)). Chimeric antibodies of interest herein include "primatized" antibodies comprising variable domain antigen-binding sequences derived from a nonhuman primate (e.g., Old World Monkey, such as baboon, rhesus or cynomolgus monkey) and human constant region sequences (U.S. Pat. No. 5,693,780).

5.3. Altered/Mutant Antibodies

Anti-ICOS antibodies of compositions and methods described herein can be mutant antibodies. As used herein, "antibody mutant" or "altered antibody" refers to an amino acid sequence variant of an anti-ICOS antibody wherein one or more of the amino acid residues of an anti-ICOS antibody have been modified. The modifications to the amino acid sequence of an anti-ICOS antibody include modifications to the sequence that may improve affinity or avidity of the antibody for its antigen, and/or modifications to the Fc portion of the antibody that may improve effector function.

The present invention therefore relates to anti-ICOS antibodies with enhanced effector function disclosed herein as well as altered/mutant derivatives thereof including, but not limited to ones exhibiting altered human ICOS binding characteristics; e.g. altered association constants $k_{ON}$, dissociation constants $k_{OFF}$, and/or equilibrium constant or binding affinity, $K_D$. In certain embodiments the $K_D$ of an anti-ICOS antibody described herein, or an altered/mutant derivative thereof, for human ICOS may be no more than about $10^{-6}$M, $10^{-7}$M, $10^{-8}$M, or $10^{-9}$M. Methods and reagents suitable for determination of such binding characteristics of an antibody of the present invention, or an altered/mutant derivative thereof, are known in the art and/or are commercially available (see above and, e.g., U.S. Pat. No. 6,849,425, U.S. Pat. No. 6,632,926, U.S. Pat. No. 6,294,391, and U.S. Pat. No. 6,143,574, each of which is hereby incorporated by reference in its entirety). Moreover, equipment and software designed for such kinetic analyses are commercially available (e.g. Biacore® A100, and Biacore® 2000 instruments; Biacore International AB, Uppsala, Sweden).

The modifications may be made to any known anti-ICOS antibodies or anti-ICOS antibodies identified as described herein. Such altered antibodies necessarily have less than 100% sequence identity or similarity with a known anti-ICOS antibody. By way of example, an altered antibody may have an amino acid sequence that is within the range of from about 25% to about 95% identical or similar to the amino acid sequence of either the heavy or light chain variable domain of an anti-ICOS antibody as described herein. An altered antibody may have an amino acid sequence having at least 25%, 35%, 45%, 55%, 65%, 75%, 80%, 85%, 90%, or 95% amino acid sequence identity or similarity with the amino acid sequence of either the heavy or light chain variable domain of an anti-ICOS antibody as described herein. In another embodiment, an altered antibody may have an amino acid sequence having at least 25%, 35%, 45%, 55%, 65%, 75%, 80%, 85%, 90%, or 95% amino acid sequence identity or similarity with the amino acid sequence of the heavy chain CDR1, CDR2, or CDR3 of an anti-ICOS antibody as described herein. In one embodiment, an altered antibody may maintain human ICOS binding capability. In certain embodiments, an anti-ICOS antibody as described herein may comprise a VH that is at least or about 10%, 15%, 20%, 25%, 30%, 35%, 40%, 45%, 50%, 55%, 60%, 65%, 70%, 75%, 80%, 85%, 90%, 95% or more identical to the amino acid sequence of SEQ ID NO:7.

In another embodiment, an altered antibody may have an amino acid sequence having at least 25%, 35%, 45%, 55%, 65%, 75%, 80%, 85%, 90%, or 95% amino acid sequence identity or similarity with the amino acid sequence of the light chain CDR1, CDR2, or CDR3 of an anti-ICOS antibody as described herein. In certain embodiments, an anti-ICOS antibody of the invention may comprise a VL that is at least or about 10%, 15%, 20%, 25%, 30%, 35%, 40%, 45%, 50%, 55%, 60%, 65%, 70%, 75%, 80%, 85%, 90%, 95% or more identical to an amino acid sequence of SEQ ID NO:2.

Identity or similarity with respect to a sequence is defined herein as the percentage of amino acid residues in the candidate sequence that are identical (i.e., same residue) or similar (i.e., amino acid residue from the same group based on common side-chain properties, see below) with anti-ICOS antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

"% identity," as known in the art, is a measure of the relationship between two polynucleotides or two polypeptides, as determined by comparing their sequences. In general, the two sequences to be compared are aligned to give a maximum correlation between the sequences. The alignment of the two sequences is examined and the number of positions giving an exact amino acid or nucleotide correspondence between the two sequences determined, divided by the total length of the alignment and multiplied by 100 to give a % identity figure. This % identity figure may be determined over the whole length of the sequences to be compared, which is particularly suitable for sequences of the same or very similar length and which are highly homologous, or over shorter defined lengths, which is more suitable for sequences of unequal length or which have a lower level of homology.

For example, sequences can be aligned with the software clustalw under Unix which generates a file with an ".aln" extension, this file can then be imported into the Bioedit program (Hall, T. A. 1999, *BioEdit: a user-friendly biological sequence alignment editor and analysis program for Windows 95/98/NT. Nucl. Acids. Symp. Ser.* 41:95-98) which opens the .aln file. In the Bioedit window, one can choose individual sequences (two at a time) and alignment them. This method allows for comparison of the entire sequence.

Methods for comparing the identity of two or more sequences are well known in the art. Thus for instance, programs are available in the Wisconsin Sequence Analysis Package, version 9.1 (Devereux J. et al., *Nucleic Acids Res.,* 12:387-395, 1984, available from Genetics Computer Group, Madison, Wis., USA). The determination of percent identity between two sequences can be accomplished using a mathematical algorithm. For example, the programs BESTFIT and GAP, may be used to determine the % identity between two polynucleotides and the % identity between two polypeptide sequences. BESTFIT uses the "local homology" algorithm of Smith and Waterman (*Advances in Applied Mathematics,* 2:482-489, 1981) and finds the best single region of similarity between two sequences. BESTFIT is more suited to comparing two polynucleotide or two polypeptide sequences which are dissimilar in length, the program assuming that the shorter sequence represents a portion of the longer. In comparison, GAP aligns two sequences finding a "maximum similarity" according to the algorithm of Neddleman and Wunsch (*J. Mol. Biol.,* 48:443-354, 1970). GAP is more suited to comparing sequences which are approximately the same length and an alignment is expected over the entire length. Preferably the parameters "Gap Weight" and "Length Weight" used in each program are 50 and 3 for polynucleotides and 12 and 4 for polypeptides, respectively. Preferably % identities and similarities are determined when the two sequences being compared are optimally aligned.

Other programs for determining identity and/or similarity between sequences are also known in the art, for instance the BLAST family of programs (Karlin & Altschul, 1990, *Proc. Natl. Acad. Sci. USA,* 87:2264-2268, modified as in Karlin & Altschul, 1993, *Proc. Natl. Acad. Sci. USA,* 90:5873-5877, available from the National Center for Biotechnology Information (NCB), Bethesda, Md., USA and accessible through the home page of the NCBI at www.ncbi.nlm.nih.gov). These programs are non-limiting examples of a mathematical algorithm utilized for the comparison of two sequences. Such an algorithm is incorporated into the NBLAST and XBLAST programs of Altschul et al., 1990, *J. Mol. Biol.,* 215:403-410. BLAST nucleotide searches can be performed with the NBLAST program, score=100, wordlength=12 to obtain nucleotide sequences homologous to a nucleic acid molecule encoding all or a portion if an anti-ICOS antibody of the invention. BLAST protein searches can be performed with the XBLAST program, score=50, wordlength=3 to obtain amino acid sequences homologous to a protein molecule of the invention. To obtain gapped alignments for comparison purposes, Gapped BLAST can be utilized as described in Altschul et al., 1997, *Nucleic Acids Res.,* 25:3389-3402. PSI-Blast can also be used to perform an iterated search which detects distant relationships between molecules (Id.). When utilizing BLAST, Gapped BLAST, and PSI-Blast programs, the default parameters of the respective programs (e.g., XBLAST and NBLAST) can be used. See, http://www.ncbi.nlm.nih.gov.

Another non-limiting example of a program for determining identity and/or similarity between sequences known in the art is FASTA (Pearson W. R. and Lipman D. J., *Proc. Natl. Acad. Sci. USA,* 85:2444-2448, 1988, available as part of the Wisconsin Sequence Analysis Package). Preferably the BLOSUM62 amino acid substitution matrix (Henikoff S, and Henikoff J. G., *Proc. Natl. Acad. Sci. USA,* 89:10915-10919, 1992) is used in polypeptide sequence comparisons including where nucleotide sequences are first translated into amino acid sequences before comparison.

Yet another non-limiting example of a program known in the art for determining identity and/or similarity between amino acid sequences is SeqWeb Software (a web-based interface to the GCG Wisconsin Package: Gap program)

which is utilized with the default algorithm and parameter settings of the program: blosum62, gap weight 8, length weight 2.

The percent identity between two sequences can be determined using techniques similar to those described above, with or without allowing gaps. In calculating percent identity, typically exact matches are counted.

Preferably the program BESTFIT is used to determine the % identity of a query polynucleotide or a polypeptide sequence with respect to a polynucleotide or a polypeptide sequence of the present invention, the query and the reference sequence being optimally aligned and the parameters of the program set at the default value.

To generate an altered antibody, one or more amino acid alterations (e.g., substitutions) are introduced in one or more of the hypervariable regions of the species-dependent antibody. One or more alterations (e.g., substitutions) of framework region residues may also be introduced in an anti-ICOS antibody where these result in an improvement in the binding affinity of the antibody mutant for the antigen from the second mammalian species. Examples of framework region residues to modify include those which non-covalently bind antigen directly (Amit et al., Science, 233:747-753 (1986)); interact with/effect the conformation of a CDR (Chothia et al., J. Mol. Biol., 196:901-917 (1987)); and/or participate in the $V_L$-$V_H$ interface (EP 239 400B1). In certain embodiments, modification of one or more of such framework region residues results in an enhancement of the binding affinity of the antibody for the antigen from the second mammalian species. For example, from about one to about five framework residues may be altered in this embodiment of the invention. Sometimes, this may be sufficient to yield an antibody mutant suitable for use in preclinical trials, even where none of the hypervariable region residues have been altered. Normally, however, an altered antibody will comprise additional hypervariable region alteration(s).

The hypervariable region residues which are altered may be changed randomly, especially where the starting binding affinity of an anti-ICOS antibody for the antigen from the second mammalian species is such that such randomly produced altered antibody can be readily screened.

One useful procedure for generating such an altered antibody is called "alanine scanning mutagenesis" (Cunningham and Wells, Science, 244:1081-1085 (1989)). Here, one or more of the hypervariable region residue(s) are replaced by alanine or polyalanine residue(s) to affect the interaction of the amino acids with the antigen from the second mammalian species. Those hypervariable region residue(s) demonstrating functional sensitivity to the substitutions then are refined by introducing additional or other mutations at or for the sites of substitution. Thus, while the site for introducing an amino acid sequence variation is predetermined, the nature of the mutation per se need not be predetermined. The Ala-mutants produced this way are screened for their biological activity as described herein.

Another procedure for generating such an altered antibody involves affinity maturation using phage display (Hawkins et al., J. Mol. Biol., 254:889-896 (1992) and Lowman et al., Biochemistry, 30(45):10832-10837 (1991)). Briefly, several hypervariable region sites (e.g., 6-7 sites) are mutated to generate all possible amino acid substitutions at each site. The antibody mutants thus generated are displayed in a monovalent fashion from filamentous phage particles as fusions to the gene III product of M13 packaged within each particle. The phage-displayed mutants are then screened for their biological activity (e.g., binding affinity) as herein disclosed.

Mutations in antibody sequences may include substitutions, deletions, including internal deletions, additions, including additions yielding fusion proteins, or conservative substitutions of amino acid residues within and/or adjacent to the amino acid sequence, but that result in a "silent" change, in that the change produces a functionally equivalent anti-ICOS antibody. Conservative amino acid substitutions may be made on the basis of similarity in polarity, charge, solubility, hydrophobicity, hydrophilicity, and/or the amphipathic nature of the residues involved. For example, non-polar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. In addition, glycine and proline are residues that can influence chain orientation. Non-conservative substitutions will entail exchanging a member of one of these classes for a member of another class. Furthermore, if desired, non-classical amino acids or chemical amino acid analogs can be introduced as a substitution or addition into the antibody sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general.

In another embodiment, the sites selected for modification are affinity matured using phage display (see above).

Any technique for mutagenesis known in the art can be used to modify individual nucleotides in a DNA sequence, for purposes of making amino acid substitution(s) in the antibody sequence, or for creating/deleting restriction sites to facilitate further manipulations. Such techniques include, but are not limited to, chemical mutagenesis, in vitro site-directed mutagenesis (Kunkel, Proc. Natl. Acad. Sci. USA, 82:488 (1985); Hutchinson, C. et al., J. Biol. Chem., 253:6551 (1978)), oligonucleotide-directed mutagenesis (Smith, Ann. Rev. Genet., 19:423-463 (1985); Hill et al., Methods Enzymol., 155:558-568 (1987)), PCR-based overlap extension (Ho et al., Gene, 77:51-59 (1989)), PCR-based megaprimer mutagenesis (Sarkar et al., Biotechniques, 8:404-407 (1990)), etc. Modifications can be confirmed by double-stranded dideoxy DNA sequencing.

In certain embodiments of the invention, an anti-ICOS antibody can be modified to produce fusion proteins; i.e., the antibody, or a fragment thereof, fused to a heterologous protein, polypeptide or peptide. In certain embodiments, the protein fused to the portion of an anti-ICOS antibody is an enzyme component of Antibody-Directed Enzyme Prodrug Therapy (ADEPT). Examples of other proteins or polypeptides that can be engineered as a fusion protein with an anti-ICOS antibody include, but are not limited to toxins such as ricin, abrin, ribonuclease, DNase I, Staphylococcal enterotoxin-A, pokeweed anti-viral protein, gelonin, diphtherin toxin, Pseudomonas exotoxin, and Pseudomonas endotoxin. See, for example, Pastan et al., Cell, 47:641 (1986), and Goldenberg et al., Cancer Journal for Clinicians, 44:43 (1994). Enzymatically active toxins and fragments thereof which can be used include diphtheria A chain, non-binding active fragments of diphtheria toxin, exotoxin A chain (from

*Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of the anti-ICOS antibody or fragments thereof (e.g., an antibody or a fragment thereof with higher affinities and lower dissociation rates). See, generally, U.S. Pat. Nos. 5,605,793; 5,811,238; 5,830,721; 5,834,252; and 5,837,458, and Patten et al., 1997, *Curr. Opinion Biotechnol.*, 8:724-33; Harayama, 1998, *Trends Biotechnol.* 16(2):76-82; Hansson et al., 1999, *J. Mol. Biol.*, 287:265-76; and Lorenzo and Blasco, 1998, *Biotechniques* 24(2):308-313 (each of these patents and publications are hereby incorporated by reference in its entirety). The antibody can further be a binding-domain immunoglobulin fusion protein as described in U.S. Publication 20030118592, U.S. Publication 200330133939, and PCT Publication WO 02/056910, all to Ledbetter et al., which are incorporated herein by reference in their entireties.

5.4. Domain Antibodies

Anti-ICOS antibodies of compositions and methods of the invention can be domain antibodies, e.g., antibodies containing the small functional binding units of antibodies, corresponding to the variable regions of the heavy ($V_H$) or light ($V_L$) chains of human antibodies. Examples of domain antibodies include, but are not limited to, those available from Domantis Limited (Cambridge, UK) and Domantis Inc. (Cambridge, Mass., USA) that are specific to therapeutic targets (see, for example, WO04/058821; WO04/003019; U.S. Pat. Nos. 6,291,158; 6,582,915; 6,696,245; and 6,593,081). Commercially available libraries of domain antibodies can be used to identify anti-ICOS domain antibodies. In certain embodiments, anti-ICOS antibodies comprise an ICOS functional binding unit and a Fc gamma receptor functional binding unit.

In one embodiment, an anti-ICOS domain antibody may comprise any one of, or any combination of the CDRs of the heavy or light chains of the JMab-136 monoclonal antibody.

In another embodiment, an anti-ICOS domain antibody may comprise VH CDR3 of JMab-136 together with any combination of the CDRs comprised by the heavy or light chains variable regions of the JMab-136 monoclonal antibody. An anti-ICOS domain antibody may also comprise VK CDR3 of JMab-136 together with any combination of the CDRs comprised by the heavy or light chains variable regions of the JMab-136 monoclonal antibody.

In yet another embodiment, an anti-ICOS domain antibody may comprise VH CDR3 of JMab-136. An anti-ICOS domain antibody may also comprise VK CDR3 of JMab-136.

5.5. Diabodies

In certain embodiments of the invention, anti-ICOS antibodies are "diabodies". The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

5.6. Vaccibodies

In certain embodiments of the invention, anti-ICOS antibodies are Vaccibodies. Vaccibodies are dimeric polypeptides. Each monomer of a vaccibody consists of a scFv with specificity for a surface molecule on APC connected through a hinge region and a Cγ3 domain to a second scFv. In other embodiments of the invention, vaccibodies containing as one of the scFv's an anti-ICOS antibody fragment may be used to juxtapose those ICOS expressing cells to be destroyed and an effector cell that mediates ADCC. For example, see, Bogen et al., U.S. Patent Application Publication No. 20040253238.

5.7. Linear Antibodies

In certain embodiments of the invention, anti-ICOS antibodies are linear antibodies. Linear antibodies comprise a pair of tandem Fd segments ($V_H$-$C_{H1}$-$V_H$-$C_{H1}$) which form a pair of antigen-binding regions. Linear antibodies can be bispecific or monospecific. See, Zapata et al., *Protein Eng.*, 8(10):1057-1062 (1995).

5.8. Parent Antibody

In certain embodiments of the invention, an anti-ICOS antibody is a parent antibody. A "parent antibody" is an antibody comprising an amino acid sequence which may lack, or may be deficient in, one or more amino acid residues in or adjacent to one or more hypervariable regions thereof compared to an altered/mutant antibody as herein disclosed. Thus, the parent antibody may have a shorter hypervariable region than the corresponding hypervariable region of an antibody mutant as herein disclosed. The parent polypeptide may comprise a native antibody sequence (i.e., a naturally occurring, including a naturally occurring allelic variant) or an antibody sequence with pre-existing amino acid sequence modifications (such as other insertions, deletions and/or substitutions) of a naturally occurring sequence. The parent antibody may be a humanized antibody or a human antibody.

5.9. Antibody Fragments

"Antibody fragments" comprise a portion of a full-length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

Traditionally, these fragments were derived via proteolytic digestion of intact antibodies (see, e.g., Morimoto et al., *Journal of Biochemical and Biophysical Methods*, 24:107-117 (1992) and Brennan et al., *Science*, 229:81 (1985)). However, these fragments can now be produced directly by recombinant host cells. For example, the antibody fragments can be isolated from the antibody phage libraries discussed above. Fab'-SH fragments can also be directly recovered from *E. coli* and chemically coupled to form F(ab')$_2$ fragments (Carter et al., *Bio/Technology*, 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single-chain Fv fragment (scFv). See, for example, WO 93/16185. In certain embodiments, the antibody is not a Fab fragment.

5.10. Bispecific Antibodies

Bispecific antibodies are antibodies that have binding specificities for at least two different epitopes. Exemplary bispecific antibodies may bind to two different epitopes of the ICOS expressing T cell surface marker. Other such antibodies may bind a first ICOS expressing T cell marker and further bind a second ICOS expressing T cell surface marker. An anti-ICOS expressing T cell marker binding arm may also be combined with an arm which binds to a triggering molecule on a leukocyte such as a T cell receptor molecule (e.g., CD2 or CD3), or Fc receptors for IgG (FcγR), so as to focus cellular defense mechanisms to the ICOS expressing T cell. Bispecific antibodies may also be used to localize cytotoxic agents to the ICOS expressing T cell. These antibodies possess a ICOS expressing T cell marker-binding arm and an arm which binds the cytotoxic agent (e.g., saporin, anti-interferon-α, vinca alkaloid, ricin A chain, methola-exate or radioactive isotope hapten). Bispecific antibodies can be prepared as full-length antibodies or antibody fragments (e.g., F(ab'): bispecific antibodies).

Methods for making bispecific antibodies are known in the art. (See, for example, Millstein et al., *Nature*, 305:537-539 (1983); Traunecker et al., *EMBO J.*, 10:3655-3659 (1991); Suresh et al., *Methods in Enzymology*, 121:210 (1986); Kostelny et al., *J. Immunol.*, 148(5):1547-1553 (1992); Hollinger et al., *Proc. Natl. Acad. Sci. USA*, 90:6444-6448 (1993); Gruber et al., *J. Immunol.*, 152:5368 (1994); U.S. Pat. Nos. 4,474,893; 4,714,681; 4,925,648; 5,573,920; 5,601,81; 95,731,168; 4,676,980; and 4,676,980, WO 94/04690; WO 91/00360; WO 92/200373; WO 93/17715; WO 92/08802; and EP 03089.)

In one embodiment, where an anti-ICOS antibody of compositions and methods of the invention is bispecific, the anti-ICOS antibody may be human or humanized and may have specificity for human ICOS and an epitope on a T cell or may be capable of binding to a human effector cell such as, for example, a monocyte/macrophage and/or a natural killer cell to effect cell death.

5.11. Variant Fc Regions

The present invention provides formulation of proteins comprising a variant Fc region. That is, a non naturally occurring Fc region, for example an Fc region comprising one or more non naturally occurring amino acid residues. Also encompassed by the variant Fc regions of present invention are Fc regions which comprise amino acid deletions, additions and/or modifications.

It will be understood that Fc region as used herein includes the polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM and the flexible hinge N-terminal to these domains. For IgA and IgM Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat et al. (1991, NIH Publication 91-3242, National Technical Information Service, Springfield, Va.). The "EU index as set forth in Kabat" refers to the residue numbering of the human IgG1 EU antibody as described in Kabat et al. supra. Fc may refer to this region in isolation, or this region in the context of an antibody, antibody fragment, or Fc fusion protein. An Fc variant protein may be an antibody, Fc fusion, or any protein or protein domain that comprises an Fc region including, but not limited to, proteins comprising variant Fc regions, which are non naturally occurring variants of an Fc. Note: Polymorphisms have been observed at a number of Fc positions, including but not limited to Kabat 270, 272, 312, 315, 356, and 358, and thus slight differences between the presented sequence and sequences in the prior art may exist.

The present invention encompasses Fc variant proteins which have altered binding properties for an Fc ligand (e.g., an Fc receptor, C1q) relative to a comparable molecule (e.g., a protein having the same amino acid sequence except having a wild type Fc region). Examples of binding properties include but are not limited to, binding specificity, equilibrium dissociation constant ($K_D$), dissociation and association rates ($k_{off}$ and $k_{on}$ respectively), binding affinity and/or avidity. It is generally understood that a binding molecule (e.g., a Fc variant protein such as an antibody) with a low $K_D$ may be preferable to a binding molecule with a high $K_D$. However, in some instances the value of the $k_{on}$ or $k_{off}$ may be more relevant than the value of the $K_D$. One skilled in the art can determine which kinetic parameter is most important for a given antibody application.

The affinities and binding properties of an Fc domain for its ligand may be determined by a variety of in vitro assay methods (biochemical or immunological based assays) known in the art for determining Fc-FcγR interactions, i.e., specific binding of an Fc region to an FcγR including but not limited to, equilibrium methods (e.g., enzyme-linked immunoabsorbent assay (ELISA), or radioimmunoassay (RIA)), or kinetics (e.g., BIACORE® analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions.

In one embodiment, the Fc variant protein has enhanced binding to one or more Fc ligand relative to a comparable molecule. In another embodiment, the Fc variant protein has an affinity for an Fc ligand that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold greater than that of a comparable molecule. In a specific embodiment, the Fc variant protein has enhanced binding to an Fc receptor. In another specific embodiment, the Fc variant protein has enhanced binding to the Fc receptor FcγRIIIA In still another specific embodiment, the Fc variant protein has enhanced binding to the Fc receptor FcRn. In yet another specific embodiment, the Fc variant protein has enhanced binding to C1q relative to a comparable molecule.

The serum half-life of proteins comprising Fc regions may be increased by increasing the binding affinity of the Fc region for FcRn. In one embodiment, the Fc variant protein has enhanced serum half life relative to comparable molecule.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the surface of target cells "arm" the cytotoxic cells and are absolutely required for such killing. Lysis of the target cell is extracellular, requires direct cell-to-cell contact, and does not involve complement. It is contemplated that, in addition to antibodies, other proteins comprising Fc regions, specifically Fc fusion proteins, having the capacity to bind specifically to an antigen-bearing target cell will be able to effect cell-mediated cytotoxicity. For simplicity, the cell-mediated cytotoxicity resulting from the activity of an Fc fusion protein is also referred to herein as ADCC activity.

The ability of any particular Fc variant protein to mediate lysis of the target cell by ADCC can be assayed. To assess ADCC activity an Fc variant protein of interest is added to target cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., 1985 79:277-282; Bruggemann et al., 1987, J Exp Med 166:1351-1361; Wilkinson et al., 2001, J Immunol Methods 258:183-191; Patel et al., 1995 J Immunol Methods 184:29-38. ADCC activity of the Fc variant protein of interest may also be assessed in vivo, e.g., in a animal model such as that disclosed in Clynes et al., 1998, *Proc. Natl. Acad. Sci. USA* 95:652-656.

In one embodiment, an Fc variant protein has enhanced ADCC activity relative to a comparable molecule. In a specific embodiment, an Fc variant protein has ADCC activity that is at least 2 fold, or at least 3 fold, or at least 5 fold or at least 10 fold or at least 50 fold or at least 100 fold greater than that of a comparable molecule. In another specific embodiment, an Fc variant protein has enhanced binding to the Fc receptor FcγRIIIA and has enhanced ADCC activity relative to a comparable molecule. In other embodiments, the Fc variant protein has both enhanced ADCC activity and enhanced serum half life relative to a comparable molecule.

"Complement dependent cytotoxicity" and "CDC" refer to the lysing of a target cell in the presence of complement. The complement activation pathway is initiated by the binding of the first component of the complement system (C1q) to a molecule, an antibody for example, complexed with a cognate antigen. To assess complement activation, a CDC assay, e.g. as described in Gazzano-Santoro et al., 1996, J. Immunol. Methods, 202:163, may be performed. In one embodiment, an Fc variant protein has enhanced CDC activity relative to a comparable molecule. In a specific embodiment, an Fc variant protein has CDC activity that is at least 2 fold, or at least 3 fold, or at least 5 fold or at least 10 fold or at least 50 fold or at least 100 fold greater than that of a comparable molecule. In other embodiments, the Fc variant protein has both enhanced CDC activity and enhanced serum half life relative to a comparable molecule.

In one embodiment, the present invention provides compositions, wherein the Fc region comprises a non naturally occurring amino acid residue at one or more positions selected from the group consisting of 234, 235, 236, 237, 238, 239, 240, 241, 243, 244, 245, 247, 251, 252, 254, 255, 256, 262, 263, 264, 265, 266, 267, 268, 269, 279, 280, 284, 292, 296, 297, 298, 299, 305, 313, 316, 325, 326, 327, 328, 329, 330, 332, 333, 334, 339, 341, 343, 370, 373, 378, 392, 416, 419, 421, 440 and 443 as numbered by the EU index as set forth in Kabat. Optionally, the Fc region may comprise a non naturally occurring amino acid residue at additional and/or alternative positions known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752; WO 04/074455; WO 04/099249; WO 04/063351; WO 05/070963; WO 05/040217, WO 05/092925 and WO 06/020114).

In a specific embodiment, the present invention provides an Fc variant protein composition, wherein the Fc region comprises at least one non naturally occurring amino acid residue selected from the group consisting of 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235F, 236E, 239D, 239E, 239N, 239Q, 239F, 239T, 239H, 239Y, 240I, 240A, 240T, 240M, 241W, 241L, 241Y, 241E, 241R, 243W, 243L 243Y, 243R, 243Q, 244H, 245A, 247L, 247V, 247G, 251F, 252Y, 254T, 255L, 256E, 256M, 262I, 262A, 262T, 262E, 263I, 263A, 263T, 263M, 264L, 264I, 264W, 264T, 264R, 264F, 264M, 264Y, 264E, 265G, 265N, 265Q, 265Y, 265F, 265V, 265I, 265L, 265H, 265T, 266I, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 296I, 296H, 269G, 297S, 297D, 297E, 298H, 298I, 298T, 298F, 299I, 299L, 299A, 299S, 299V, 299H, 299F, 299E, 305I, 313F, 316D, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 332D, 332S, 332W, 332F, 332E, 332N, 332Q, 332T, 332H, 332Y, 332A, 339T, 370E, 370N, 378D, 392T, 396L, 416G, 419H, 421K, 440Y and 434W as numbered by the EU index as set forth in Kabat. Optionally, the Fc region may comprise additional and/or alternative non naturally occurring amino acid residues known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217).

In another embodiment, the present invention provides an Fc variant protein composition, wherein the Fc region comprises at least a non naturally occurring amino acid at one or more positions selected from the group consisting of 239, 330 and 332, as numbered by the EU index as set forth in Kabat. In a specific embodiment, the present invention provides an Fc variant protein formulation, wherein the Fc region comprises at least one non naturally occurring amino acid selected from the group consisting of 239D, 330L and 332E, as numbered by the EU index as set forth in Kabat. Optionally, the Fc region may further comprise additional non naturally occurring amino acid at one or more positions selected from the group consisting of 252, 254, and 256, as numbered by the EU index as set forth in Kabat. In a specific embodiment, the present invention provides an Fc variant protein formulation, wherein the Fc region comprises at least one non naturally occurring amino acid selected from the group consisting of 239D, 330L and 332E, as numbered by the EU index as set forth in Kabat and at least one non naturally occurring amino acid at one or more positions are selected from the group consisting of 252Y, 254T and 256E, as numbered by the EU index as set forth in Kabat.

In one embodiment, the Fc variants of the present invention may be combined with other known Fc variants such as those disclosed in Ghetie et al., 1997, Nat. Biotech. 15:637-40; Duncan et al, 1988, Nature 332:563-564; Lund et al., 1991, J. Immunol. 147:2657-2662; Lund et al, 1992, Mol Immunol 29:53-59; Alegre et al, 1994, Transplantation 57:1537-1543; Hutchins et al., 1995, *Proc Natl. Acad Sci USA* 92:11980-11984; Jefferis et al, 1995, Immunol Lett. 44:111-117; Lund et al., 1995, Faseb J 9:115-119; Jefferis et al, 1996, Immunol Lett 54:101-104; Lund et al, 1996, J Immunol 157:4963-4969; Armour et al., 1999, Eur J Immunol 29:2613-2624; Idusogie et al, 2000, J Immunol 164:4178-4184; Reddy et al, 2000, J Immunol 164:1925-1933; Xu et al., 2000, Cell Immunol 200:16-26; Idusogie et al, 2001, J Immunol 166:2571-2575; Shields et al., 2001, J Biol Chem 276:6591-6604; Jefferis et al, 2002, Immunol Lett 82:57-65; Presta et al., 2002, Biochem Soc Trans 30:487-490); U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 6,821,505; 6,277,375; U.S. Patent Publication Nos. 2004/0002587 and PCT Publications WO 94/29351; WO 99/58572; WO 00/42072; WO 02/060919; WO 04/029207; WO 04/099249; WO 04/063351. Also encompassed by the present invention are Fc regions which comprise deletions, additions and/or modifications. Still other modifications/substitutions/additions/deletions of the Fc domain will be readily apparent to one skilled in the art.

Methods for generating non naturally occurring Fc regions are known in the art. For example, amino acid substitutions and/or deletions can be generated by mutagenesis methods, including, but not limited to, site-directed mutagenesis (Kunkel, *Proc. Natl. Acad. Sci. USA* 82:488-492 (1985)), PCR mutagenesis (Higuchi, in "PCR Protocols: A Guide to Methods and Applications", Academic Press, San Diego, pp. 177-183 (1990)), and cassette mutagenesis (Wells et al., Gene 34:315-323 (1985)). Preferably, site-directed mutagenesis is performed by the overlap-extension PCR method (Higuchi, in "PCR Technology: Principles and Applications for DNA Amplification", Stockton Press, New York, pp. 61-70 (1989)). The technique of overlap-extension PCR (Higuchi, ibid.) can also be used to introduce any desired mutation(s) into a target sequence (the starting DNA). For example, the first round of PCR in the overlap-extension method involves amplifying the target sequence with an outside primer (primer 1) and an internal mutagenesis primer (primer 3), and separately with a second outside primer (primer 4) and an internal primer (primer 2), yielding two PCR segments (segments A and B). The internal mutagenesis primer (primer 3) is designed to contain mismatches to the target sequence specifying the desired mutation(s). In the second round of PCR, the products of the first round of PCR (segments A and B) are amplified by PCR using the two outside primers (primers 1 and 4). The resulting full-length PCR segment (segment C) is digested with restriction enzymes and the resulting restriction fragment is cloned into an appropriate vector. As the first step of mutagenesis, the starting DNA (e.g., encoding an Fc fusion protein, an antibody or simply an Fc region), is operably cloned into a mutagenesis vector. The primers are designed to reflect the desired amino acid substitution. Other methods useful for the generation of variant Fc regions are known in the art (see, e.g., U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 6,821,505; 6,277,375; U.S. Patent Publication Nos. 2004/0002587 and PCT Publications WO 94/29351; WO 99/58572; WO 00/42072; WO 02/060919; WO 04/029207; WO 04/099249; WO 04/063351).

In some embodiments, an Fc variant protein comprises one or more engineered glycoforms, i.e., a carbohydrate composition that is covalently attached to the molecule comprising an Fc region. Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTI111), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, Nat. Biotechnol 17:176-180; Davies et al., 20017 Biotechnol Bioeng 74:288-294; Shields et al, 2002, J Biol Chem 277:26733-26740; Shinkawa et al., 2003, J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland). See, e.g., WO 00061739; EA01229125; US 20030115614; Okazaki et al., 2004, JMB, 336: 1239-49.

5.12. Glycosylation of Antibodies

In still another embodiment, the glycosylation of antibodies utilized in accordance with the invention is modified. For example, an aglycoslated antibody can be made (i.e., the antibody lacks glycosylation). Glycosylation can be altered to, for example, increase the affinity of the antibody for a target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861. One or more amino acid substitutions can also be made that result in elimination of a glycosylation site present in the Fc region (e.g., Asparagine 297 of IgG). Furthermore, aglycosylated antibodies may be produced in bacterial cells which lack the necessary glycosylation machinery.

An antibody can also be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) J. Biol. Chem. 277: 26733-26740; Umana et al. (1999) Nat. Biotech. 17:176-1, as well as, U.S. Pat. No. 6,946,292; European Patent No: EP 1,176,195; PCT Publications WO 03/035835; WO 99/54342 each of which is incorporated herein by reference in its entirety.

Antibodies with altered glycosylation pattern may also be generated using lower eukaryotic host cells comprising a modified glycosylation machinery as described in U.S. Pat. No. 7,029,872, US Patent Publication US20060148035A1, each of which is incorporated herein by reference in its entirety.

5.13. Engineering Effector Function

It may be desirable to modify an anti-ICOS antibody of the invention with respect to effector function, so as to enhance the effectiveness of the antibody in treating T cell-mediated diseases, for example. For example, cysteine residue(s) may be introduced in the Fc region, thereby allowing interchain disulfide bond formation in this region. The homodimeric antibody thus generated may have improved internalization capability and/or increased complement-mediated cell killing and/or antibody-dependent cellular cytotoxicity (ADCC) and/or antibody dependent phagocytosis. See, Caron et al., *J. Exp Med.*, 176:1191-1195 (1992) and Shopes, B., *J. Immunol.*, 148:2918-2922 (1992). Homodimeric antibodies with enhanced anti-tumor activity may also be prepared using heterobifunctional cross-linkers as described in Wolff et al., *Cancer Research*, 53:2560-2565 (1993). An antibody can also be engineered which has dual Fc regions and may thereby have enhanced complement lysis, antibody-dependent phagocytosis and/or ADCC capabilities. See, Stevenson et al., *Anti-Cancer Drug Design*, 3:219-230 (1989).

Other methods of engineering Fc regions of antibodies so as to alter effector functions are known in the art (e.g., U.S. Patent Publication No. 20040185045 and PCT Publication No. WO 2004/016750, both to Koenig et al., which describe altering the Fc region to enhance the binding affinity for FcγRIIB as compared with the binding affinity for FCγRIIA; see, also, PCT Publication Nos. WO 99/58572 to Armour et al., WO 99/51642 to Idusogie et al., and U.S. Pat. No. 6,395,272 to Deo et al.; the disclosures of which are incorporated herein in their entireties). Methods of modifying the Fc region to decrease binding affinity to FcγRIIB are also known in the art (e.g., U.S. Patent Publication No. 20010036459 and PCT Publication No. WO 01/79299, both to Ravetch et al., the disclosures of which are incorporated herein in their entireties). Modified antibodies having variant Fc regions with enhanced binding affinity for FcγRIIIA and/or FcγRIIA as compared with a wildtype Fc region have also been described (e.g., PCT Publication Nos. WO 2004/063351, to Stavenhagen et al., the disclosure of which is incorporated herein in its entirety).

In vitro assays known in the art can be used to determine whether anti-ICOS antibodies used in compositions and methods of the invention are capable of mediating ADCC, CDC, and/or antibody-depenedent phagocytosis, such as those described herein.

5.14. Manufacture/Production of Anti-ICOS Antibodies

Once a desired anti-ICOS antibody is engineered, the anti-ICOS antibody can be produced on a commercial scale using methods that are well-known in the art for large scale manufacturing of antibodies. For example, this can be accomplished using recombinant expressing systems such as, but not limited to, those described below.

5.15. Recombinant Expression Systems

Recombinant expression of an antibody or variant thereof, generally requires construction of an expression vector containing a polynucleotide that encodes the antibody. Once a polynucleotide encoding an antibody molecule or a heavy or light chain of an antibody, or portion thereof, has been obtained, the vector for the production of the antibody molecule may be produced by recombinant DNA technology using techniques well-known in the art. See, e.g., U.S. Pat. No. 6,331,415, which is incorporated herein by reference in its entirety. Thus, methods for preparing a protein by expressing a polynucleotide containing an antibody encoding nucleotide sequence are described herein. Methods which are well-known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule (see, e.g., International Publication Nos. WO 86/05807 and WO 89/01036; and U.S. Pat. No. 5,122,464) and the variable domain of the antibody may be cloned into such a vector for expression of the entire heavy, the entire light chain, or both the entire heavy and light chains.

In another embodiment, anti-ICOS antibodies can be made using targeted homologous recombination to produce all or portions of the anti-ICOS antibodies (see, U.S. Pat. Nos. 6,063,630, 6,187,305, and 6,692,737). In certain embodiments, anti-ICOS antibodies can be made using random recombination techniques to produce all or portions of the anti-ICOS antibodies (see, U.S. Pat. Nos. 6,361,972, 6,524,818, 6,541,221, and 6,623,958). Anti-ICOS antibodies can also be produced in cells expressing an antibody from a genomic sequence of the cell comprising a modified immunoglobulin locus using Cre-mediated site-specific homologous recombination (see, U.S. Pat. No. 6,091,001). The host cell line may be derived from human or nonhuman species including but not limited to mouse, and Chinese hamster. Where human or humanized antibody production is desired, the host cell line should be a human cell line. These methods may advantageously be used to engineer stable cell lines which permanently express the antibody molecule.

Once the expression vector is transferred to a host cell by conventional techniques, the transfected cells are then cultured by conventional techniques to produce an antibody. Thus, the invention includes host cells containing a polynucleotide encoding an antibody of the invention or fragments thereof, or a heavy or light chain thereof, or portion thereof, or a single-chain antibody of the invention, operably linked to a heterologous promoter. In certain embodiments for the expression of double-chained antibodies, vectors encoding both the heavy and light chains may be co-expressed in the host cell for expression of the entire immunoglobulin molecule, as detailed below.

A variety of host-expression vector systems may be utilized to express an anti-ICOS antibody or portions thereof that can be used in the engineering and generation of anti-ICOS antibodies (see, e.g., U.S. Pat. No. 5,807,715). For example, mammalian cells such as Chinese hamster ovary cells (CHO), in conjunction with a vector such as the major intermediate early gene promoter element from human cytomegalovirus is an effective expression system for antibodies (Foecking et al., *Gene*, 45:101 (1986); and Cockett et al., *Bio/Technology*, 8:2 (1990)). In addition, a host cell strain may be chosen which modulates the expression of inserted antibody sequences, or modifies and processes the antibody gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any functional immunoglobulin chains), CRL7O3O and HsS78Bst cells.

In one embodiment, human cell lines developed by immortalizing human lymphocytes can be used to recombinantly produce monoclonal human anti-ICOS antibodies. In one embodiment, the human cell line PER.C6. (Crucell, Netherlands) can be used to recombinantly produce monoclonal human anti-ICOS antibodies.

In bacterial systems, a number of expression vectors may be advantageously selected depending upon the use intended for the antibody molecule being expressed. For example, when a large quantity of such an antibody is to be produced, for the generation of pharmaceutical compositions comprising an anti-ICOS antibody, vectors which direct the expression of high levels of fusion protein products that are readily purified may be desirable. Such vectors include, but are not limited to, the *E. coli* expression vector pUR278 (Ruther et al., *EMBO*, 12:1791 (1983)), in which the antibody coding sequence may be ligated individually into the vector in frame with the lac Z coding region so that a fusion protein is produced; pIN vectors (Inouye & Inouye, 1985, *Nucleic Acids Res.* 13:3101-3109 (1985); Van Heeke & Schuster, 1989, *J. Biol. Chem.*, 24:5503-5509 (1989)); and the like. pGEX vectors may also be used to express foreign polypeptides as fusion proteins with glutathione-S-transferase (GST). In general, such fusion proteins are soluble and can easily be purified from lysed cells by adsorption and binding to glutathione-agarose affinity matrix followed by elution in the presence of free glutathione. The pGEX vectors are designed to introduce athrombin and/or factor Xa protease cleavage sites into the expressed polypeptide so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example, the polyhedrin gene) of the virus and placed under control of an AcNPV promoter (for example, the polyhedrin promoter).

In mammalian host cells, a number of virus based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion into a non-essential region of the viral genome (e.g., region E1 or E3) will result in a recombinant virus that is viable and capable of expressing the antibody molecule in infected hosts (e.g., see, Logan & Shenk, *Proc. Natl. Acad. Sci. USA*, 81:355-359 (1984)). Specific initiation signals may also be required for efficient translation of inserted antibody coding sequences. These signals include the ATG initiation codon and adjacent sequences. Furthermore, the initiation codon should generally be in frame with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., *Methods in Enzymol.*, 153:51-544 (1987)).

Stable expression can be used for long-term, high-yield production of recombinant proteins. For example, cell lines which stably express the antibody molecule may be generated. Host cells can be transformed with an appropriately engineered vector comprising expression control elements (e.g., promoter, enhancer, transcription terminators, polyadenylation sites, etc.), and a selectable marker gene. Following the introduction of the foreign DNA, cells may be allowed to grow for 1-2 days in an enriched media, and then are switched to a selective media. The selectable marker in the recombinant plasmid confers resistance to the selection and allows cells that stably integrated the plasmid into their chromosomes to grow and form foci which in turn can be cloned and expanded into cell lines. Plasmids that encode an anti-ICOS antibody can be used to introduce the gene/cDNA into any cell line suitable for production in culture.

A number of selection systems may be used, including, but not limited to, the herpes simplex virus thymidine kinase (Wigler et al., *Cell*, 11:223 (1977)), hypoxanthineguanine phosphoribosyltransferase (Szybalska & Szybalski, *Proc. Natl. Acad. Sci. USA*, 48:202 (1992)), and adenine phosphoribosyltransferase (Lowy et al., *Cell*, 22:8-17 (1980)) genes can be employed in tk−, hgprt− or aptT− cells, respectively. Also, antimetabolite resistance can be used as the basis of selection for the following genes: dhfr, which confers resistance to methotrexate (Wigler et al., *Natl. Acad. Sci. USA*, 77:357 (1980); O'Hare et al., *Proc. Natl. Acad. Sci. USA*, 78:1527 (1981)); gpt, which confers resistance to mycophenolic acid (Mulligan & Berg, *Proc. Natl. Acad. Sci. USA*, 78:2072 (1981)); neo, which confers resistance to the aminoglycoside G-418 (Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); May, TIB TECH 11(5):155-2 15 (1993)); and hygro, which confers resistance to hygromycin (Santerre et al., *Gene*, 30:147 (1984)). Methods commonly known in the art of recombinant DNA technology may be routinely applied to select the desired recombinant clone, and such methods are described, for example, in Ausubel et al. (eds.), *Current Protocols in Molecular Biology*, John Wiley & Sons, NY (1993); Kriegler, *Gene Transfer and Expression, A Laboratory Manual*, Stockton Press, NY (1990); and in Chapters 12 and 13, Dracopoli et al. (eds.), *Current Protocols in Human Genetics*, John Wiley & Sons, NY (1994); Colberre-Garapin et al., 1981, *J. Mol. Biol.*, 150:1, which are incorporated by reference herein in their entireties.

The expression levels of an antibody molecule can be increased by vector amplification (for a review, see, Bebbington and Hentschel, *The use of vectors based on gene amplification for the expression of cloned genes in mammalian cells in DNA cloning*, Vol. 3. Academic Press, New York (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.*, 3:257 (1983)). Antibody expression levels may be amplified through the use recombinant methods and tools known to those skilled in the art of recombinant protein production, including technologies that remodel surrounding chromatin and enhance transgene expression in the form of an active artificial transcriptional domain.

The host cell may be co-transfected with two expression vectors, the first vector encoding a heavy chain derived polypeptide and the second vector encoding a light chain derived polypeptide. The two vectors may contain identical or different selectable markers. A single vector which encodes, and is capable of expressing, both heavy and light chain polypeptides may also be used. In such situations, the light chain should be placed 5' to the heavy chain to avoid an excess of toxic free heavy chain (Proudfoot, *Nature* 322:562-65 (1986); and Kohler, 1980, *Proc. Natl. Acad. Sci. USA*, 77:2197 (1980)). The coding sequences for the heavy and light chains may comprise cDNA or genomic DNA.

Once an antibody molecule has been produced by recombinant expression, it may be purified by any method known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the antibodies of the present invention or fragments thereof may be fused to heterologous polypeptide sequences described herein or otherwise known in the art to facilitate purification.

5.15.1. Antibody Purification and Isolation

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology*, 10:163-167 (1992) describe a procedure for isolating antibodies which are secreted into the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody mutant is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, ion exchange chromatography, gel electrophoresis, dialysis, and/or affinity chromatography either alone or in combination with other purification steps. The suitability of protein A as an affinity ligand depends on the species and isotype of any immunoglobulin Fc domain that is present in the antibody mutant. Protein A can be used to purify antibodies that are based on human γ1, γ2, or γ4 heavy chains (Lindmark et al., *J. Immunol. Methods*, 62:1-13 (1983)). Protein G is recommended for all mouse isotypes and for human γ3 (Guss et al., *EMBO J.*, 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $CH_3$ domain, the Bakerbond ABX resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin, SEPHAROSE chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, and performed at low salt concentrations (e.g., from about 0-0.25 M salt).

5.16. Therapeutic Anti-ICOS Antibodies

An anti-ICOS antibody used in compositions and methods of the invention may be a human antibody or a humanized antibody that may mediate T cell lineage ADCC, antibody-dependent phagocytosis and/or CDC, or can be selected from known anti-ICOS antibodies that may mediate T lineage cell ADCC, antibody-dependent phagocytosis and/or CDC. In certain embodiments, anti-ICOS antibodies can be chimeric antibodies. In certain embodiments, an anti-ICOS antibody can be a monoclonal human, humanized, or chimeric anti-ICOS antibody. An anti-ICOS antibody used in compositions and methods of the invention may be a human antibody or a humanized antibody of the IgG1 or IgG3 human isotype or any IgG1 or IgG3 allele found in the human population. In other embodiments, an anti-ICOS antibody used in compositions and methods of the invention can be a human antibody or a humanized antibody of the IgG2 or IgG4 human isotype or any IgG2 or IgG4 allele found in the human population.

While such antibodies can be generated using the techniques described above, in other embodiments of the invention, the human JMab-136 anti-ICOS antibody (see, U.S. Pat. No. 6,803,039) can be modified to generate an anti-ICOS antibody with enhanced effector function such as, but not limited to, ADCC, antibody-dependent phagocytosis and/or CDC. For example, known anti-ICOS antibodies that can be used include, but are not limited to, anti-human ICOS monoclonal antibodies disclosed in U.S. Pat. No. 6,803,039, and clone ISA-3 (eBioscience, US).

In certain embodiments, the antibody is an isotype switched variant of a known antibody (e.g., to an IgG1 or IgG3 human isotype) such as those described above.

An anti-ICOS antibodies used in compositions and methods of the invention can be naked antibodies, immunoconjugates or fusion proteins. Anti-ICOS antibodies described above for use in compositions and methods of the invention may be able to reduce or deplete ICOS expressing T cells and circulating immunoglobulin in a human treated therewith. Depletion of T cells can be in circulating T cells, or in particular tissues such as, but not limited to, bone marrow, spleen, gut-associated lymphoid tissues, and/or lymph nodes. Such depletion may be achieved via various mechanisms such as antibody-dependent cell-mediated cytotoxicity (ADCC), and/or antibody dependent phagocytosis, and/or by blocking of ICOS interaction with its intended ligand, and/or complement dependent cytotoxicity (CDC). By "depletion" of T cells it is meant a reduction in circulating ICOS expressing T cells and/or ICOS expressing T cells in particular tissue(s) by at least about 25%, 40%, 50%, 65%, 75%, 80%, 85%, 90%, 95% or more. In particular embodiments, virtually all detectable ICOS expressing T cells are depleted from the circulation and/or particular tissue(s). By "depletion" of circulating immunoglobulin (Ig) it is meant a reduction by at least about 25%, 40%, 50%, 65%, 75%, 80%, 85%, 90%, 95% or more. In particular embodiments, virtually all detectable Ig is depleted from the circulation.

5.16.1. Screening of Antibodies for Human ICOS Binding

Binding assays can be used to identify antibodies that bind the human ICOS antigen. Binding assays may be performed either as direct binding assays or as competition-binding assays. Binding can be detected using standard ELISA or standard Flow Cytometry assays. In a direct binding assay, a candidate antibody is tested for binding to human ICOS antigen. In certain embodiments, the screening assays comprise, in a second step, determining the ability to of an antibody to induce downstream signaling events in T cells expressing human ICOS. Competition-binding assays, on the other hand, assess the ability of a candidate antibody to compete with a known anti-ICOS antibody or other compound that binds human ICOS.

In a direct binding assay, the human ICOS antigen is contacted with a candidate antibody under conditions that allow binding of the candidate antibody to the human ICOS antigen. The binding may take place in solution or on a solid surface. The candidate antibody may have been previously labeled for detection. Any detectable compound can be used for labeling, such as, but not limited to, a luminescent, fluorescent, or radioactive isotope or group containing same, or a nonisotopic label, such as an enzyme or dye. After a period of incubation sufficient for binding to take place, the reaction is exposed to conditions and manipulations that remove excess or non-specifically bound antibody. Typically, it involves washing with an appropriate buffer. Finally, the presence of a ICOS-antibody complex is detected.

In a competition-binding assay, a candidate antibody is evaluated for its ability to inhibit or displace the binding of a known anti-ICOS antibody (or other compound) to the human ICOS antigen. A labeled known binder of ICOS may be mixed with the candidate antibody, and placed under conditions in which the interaction between them would normally occur, with and without the addition of the candidate antibody. The amount of labeled known binder of ICOS that binds the human ICOS may be compared to the amount bound in the presence or absence of the candidate antibody.

In one embodiment, the binding assay is carried out with one or more components immobilized on a solid surface to facilitate antibody antigen complex formation and detection. In various embodiments, the solid support could be, but is not restricted to, polyvinylidene fluoride, polycarbonate, polystyrene, polypropylene, polyethylene, glass, nitrocellulose, dextran, nylon, polyacrylamide and agarose. The support configuration can include beads, membranes, microparticles, the interior surface of a reaction vessel such as a microtiter plate, test tube or other reaction vessel. The immobilization of human ICOS, or other component, can be achieved through covalent or non-covalent attachments. In one embodiment, the attachment may be indirect, i.e., through an attached antibody. In another embodiment, the human ICOS antigen and negative controls are tagged with an epitope, such as glutathione S-transferase (GST) so that the attachment to the solid surface can be mediated by a commercially available antibody such as anti-GST (Santa Cruz Biotechnology).

For example, such an affinity binding assay may be performed using the human ICOS antigen which is immobilized to a solid support. Typically, the non-mobilized component of the binding reaction, in this case the candidate anti-ICOS antibody, is labeled to enable detection. A variety of labeling methods are available and may be used, such as luminescent, chromophore, fluorescent, or radioactive isotope or group containing same, and nonisotopic labels, such as enzymes or dyes. In one embodiment, the candidate anti-ICOS antibody is labeled with a fluorophore such as fluorescein isothiocyanate (FITC, available from Sigma Chemicals, St. Louis). Such an affinity binding assay may be performed using the human ICOS antigen immobilized on a solid surface. Anti-ICOS antibodies are then incubated with the antigen and the specific binding of antibodies is detected by methods known in the art including, but not limited to, BiaCore Analyses, ELISA, FMET and RIA methods.

Finally, the label remaining on the solid surface may be detected by any detection method known in the art. For example, if the candidate anti-ICOS antibody is labeled with a fluorophore, a fluorimeter may be used to detect complexes.

The human ICOS antigen can be added to binding assays in the form of intact cells that express human ICOS antigen, or isolated membranes containing human ICOS antigen. Thus, direct binding to human ICOS antigen may be assayed in intact cells in culture or in animal models in the presence and absence of the candidate anti-ICOS antibody. A labeled candidate anti-ICOS antibody may be mixed with cells that express human ICOS antigen, or with crude extracts obtained from such cells, and the candidate anti-ICOS antibody may be added. Isolated membranes may be used to identify candidate anti-ICOS antibodies that interact with human ICOS. For example, in a typical experiment using isolated membranes, cells may be genetically engineered to express human ICOS antigen. Membranes can be harvested by standard techniques and used in an in vitro binding assay. Labeled candidate anti-ICOS antibody (e.g., fluorescent labeled antibody) is bound to the membranes and assayed for specific activity; specific binding is determined by comparison with binding assays performed in the presence of excess unlabeled (cold) candidate anti-ICOS antibody. Soluble human ICOS antigen may also be recombinantly expressed and utilized in non-cell based assays to identify antibodies that bind to human ICOS antigen. The recombinantly expressed human ICOS polypeptides can be used in the non-cell based screening assays. Peptides corresponding to one or more of the binding portions of human ICOS antigen, or fusion proteins containing one or more of the binding portions of human ICOS antigen can also be used in non-cell based assay systems to identify antibodies that bind to portions of human ICOS antigen. In non-cell based assays the recombinantly expressed human ICOS is attached to a solid substrate such as a test tube, microtiter well or a column, by means well-known to those in the art (see, Ausubel et al., supra). The test antibodies are then assayed for their ability to bind to human ICOS antigen.

The binding reaction may also be carried out in solution. In this assay, the labeled component is allowed to interact with its binding partner(s) in solution. If the size differences between the labeled component and its binding partner(s) permit such a separation, the separation can be achieved by passing the products of the binding reaction through an ultrafilter whose pores allow passage of unbound labeled component but not of its binding partner(s) or of labeled component bound to its partner(s). Separation can also be achieved using any reagent capable of capturing a binding partner of the labeled component from solution, such as an antibody against the binding partner and so on.

In another specific embodiment, the solid support is membrane containing human ICOS antigen attached to a microtiter dish. Candidate antibodies, for example, can bind cells that express library antibodies cultivated under conditions that allow expression of the library members in the microtiter dish. Library members that bind to the human ICOS are harvested. Such methods, are generally described by way of example in Parmley and Smith, 1988, *Gene,* 73:305-318; Fowlkes et al., 1992, *BioTechniques,* 13:422-427; PCT Publication No. WO94/18318; and in references cited hereinabove. Antibodies identified as binding to human ICOS antigen can be of any of the types or modifications of antibodies described above.

5.16.2. Screening of Antibodies for Human ADCC Effector Function

Antibodies of the human IgG class, which have functional characteristics such a long half-life in serum and the ability to mediate various effector functions are used in certain embodiments of the invention (*Monoclonal Antibodies: Principles and Applications,* Wiley-Liss, Inc., Chapter 1 (1995)). The human IgG class antibody is further classified into the following 4 subclasses: IgG1, IgG2, IgG3 and IgG4. A large number of studies have so far been conducted for ADCC and CDC as effector functions of the IgG class antibody, and it has been reported that among antibodies of the human IgG class, the IgG1 subclass has the highest ADCC activity and CDC activity in humans (*Chemical Immunology*, 65, 88 (1997)).

Expression of ADCC activity and CDC activity of the human IgG1 subclass antibodies generally involves binding of the Fc region of the antibody to a receptor for an antibody (hereinafter referred to as "FcγR") existing on the surface of effector cells such as killer cells, natural killer cells or activated macrophages. Various complement components can be bound. Regarding the binding, it has been suggested that several amino acid residues in the hinge region and the second domain of C region (hereinafter referred to as "Cγ2 domain") of the antibody are important (*Eur. J. Immunol.*, 23, 1098 (1993), *Immunology*, 86, 319 (1995), *Chemical Immunology*, 65, 88 (1997)) and that a sugar chain in the Cγ2 domain (*Chemical Immunology*, 65, 88 (1997)) is also important.

Anti-ICOS antibodies can be modified with respect to effector function, e.g., so as to enhance ADCC and/or complement dependent cytotoxicity (CDC) of the antibody. This may be achieved by introducing one or more amino acid substitutions in the Fc region of an antibody. Cysteine residue(s) may also be introduced in the Fc region, allowing for interchain disulfide bond formation in this region. In this way a homodimeric antibody can be generated that may have improved internalization capability and or increased complement-mediated cell killing and ADCC (Caron et al., *J. Exp. Med.*, 176:1191-1195 (1992) and Shopes, *J. Immunol.*, 148: 2918-2922 (1992)). Heterobifunctional cross-linkers can also be used to generate homodimeric antibodies with enhanced anti-tumor activity (Wolff et al., *Cancer Research*, 53:2560-2565 (1993)). Antibodies can also be engineered to have two or more Fc regions resulting in enhanced complement lysis and ADCC capabilities (Stevenson et al., *Anti-Cancer Drug Design*, (3)219-230 (1989)).

Other methods of engineering Fc regions of antibodies so as to alter effector functions are known in the art (e.g., U.S. Patent Publication No. 20040185045 and PCT Publication No. WO 2004/016750, both to Koenig et al., which describe altering the Fc region to enhance the binding affinity for FcγRIIB as compared with the binding affinity for FCγRIIA; see also PCT Publication Nos. WO 99/58572 to Armour et al., WO 99/51642 to Idusogie et al., and U.S. Pat. No. 6,395,272 to Deo et al.; the disclosures of which are incorporated herein in their entireties). Methods of modifying the Fc region to decrease binding affinity to FcγRIIB are also known in the art (e.g., U.S. Patent Publication No. 20010036459 and PCT Publication No. WO 01/79299, both to Ravetch et al., the disclosures of which are incorporated herein in their entireties). Modified antibodies having variant Fc regions with enhanced binding affinity for FcγRIIIA and/or FcγRIIA as compared with a wildtype Fc region have also been described (e.g., PCT Publication No. WO 2004/063351, to Stavenhagen et al.; the disclosure of which is incorporated herein in its entirety).

At least four different types of FcγR have been found, which are respectively called FcγRI (CD64), FcγRII (CD32), FcγRIII (CD16), and FcγRIV. In human, FcγRII and FcγRIII are further classified into FcγRIIa and FcγRIIb, and FcγRIIIa and FcγRIIIb, respectively. FcγR is a membrane protein belonging to the immunoglobulin superfamily, FcγRII, FcγRIII, and FcγRIV have an α chain having an extracellular region containing two immunoglobulin-like domains, FcγRI has an α chain having an extracellular region containing three immunoglobulin-like domains, as a constituting component, and the α chain is involved in the IgG binding activity. In addition, FcγRI and FcγRIII have a γ chain or ζ chain as a constituting component which has a signal transduction function in association with the α chain (*Annu. Rev. Immunol.*, 18, 709 (2000), *Annu. Rev. Immunol.*, 19, 275 (2001)). FcγRIV has been described by Bruhns et al., *Clin. Invest. Med.*, (Canada) 27:3 D (2004).

To assess ADCC activity of an anti-ICOS antibody of interest, an in vitro ADCC assay can be used, such as that described in U.S. Pat. No. 5,500,362 or 5,821,337. The assay may also be performed using a commercially available kit, e.g. CytoTox 96® (Promega). Useful effector cells for such assays include, but are not limited to peripheral blood mononuclear cells (PBMC), Natural Killer (NK) cells, and NK cell lines. NK cell lines expressing a transgenic Fc receptor (e.g. CD16) and associated signaling polypeptide (e.g. FCεRI-γ) may also serve as effector cells (see, e.g. WO 2006/023148 A2 to Campbell). For example, the ability of any particular antibody to mediate lysis of the target cell by complement activation and/or ADCC can be assayed. The cells of interest are grown and labeled in vitro; the antibody is added to the cell culture in combination with immune cells which may be activated by the antigen antibody complexes; i.e., effector cells involved in the ADCC response. The antibody can also be tested for complement activation. In either case, cytolysis of the target cells is detected by the release of label from the lysed cells. The extent of target cell lysis may also be determined by detecting the release of cytoplasmic proteins (e.g. LDH) into the supernatant. In fact, antibodies can be screened using the patient's own serum as a source of complement and/or immune cells. The antibodies that are capable of mediating human ADCC in the in vitro test can then be used therapeutically in that particular patient. ADCC activity of the molecule of interest may also be assessed in vivo, e.g., in an animal model such as that disclosed in Clynes et al., *Proc. Natl. Acad. Sci.* (USA) 95:652-656 (1998). Moreover, techniques for modulating (i.e., increasing or decreasing) the level of ADCC, and optionally CDC activity, of an antibody are well-known in the art. See, e.g., U.S. Pat. No. 6,194,551. Antibodies of the present invention may be capable or may have been modified to have the ability of inducing ADCC and/or CDC. Assays to determine ADCC function can be practiced using human effector cells to assess human ADCC function. Such assays may also include those intended to screen for antibodies that induce, mediate, enhance, block cell death by necrotic and/or apoptotic mechanisms. Such methods including assays utilizing viable dyes, methods of detecting and analyzing caspases, and assays measuring DNA breaks can be used to assess the apoptotic activity of cells cultured in vitro with an anti-ICOS antibody of interest.

For example, Annexin V or TdT-mediated dUTP nick-end labeling (TUNEL) assays can be carried out as described in Decker et al., *Blood* (USA) 103:2718-2725 (2004) to detect apoptotic activity. The TUNEL assay involves culturing the cell of interest with fluorescein-labeled dUTP for incorporation into DNA strand breaks. The cells are then processed for analysis by flow cytometry. The Annexin V assay detects the appearance of phosphatidylserine (PS) on the outside of the plasma membrane of apoptotic cells using a fluorescein-conjugated Annexin V that specifically recognizes the exposed PS molecules. Concurrently, a viable dye such as propidium iodide can be used to exclude late apoptotic cells. The cells are stained with the labeled Annexin V and are analyzed by flow cytometry.

5.16.3. Immunoconjugates and Fusion Proteins

According to certain aspects of the invention, therapeutic agents or toxins can be conjugated to anti-ICOS antibodies for use in compositions and methods of the invention. In certain embodiments, these conjugates can be generated as fusion proteins. Examples of therapeutic agents and toxins include, but are not limited to, members of the enediyne family of molecules, such as calicheamicin and esperamicin. Chemical toxins can also be taken from the group consisting of duocarmycin (see, e.g., U.S. Pat. No. 5,703,080 and U.S. Pat. No. 4,923,990), methotrexate, doxorubicin, melphalan, chlorambucil, ARA-C, vindesine, mitomycin C, cis-platinum, etoposide, bleomycin and 5-fluorouracil. Examples of chemotherapeutic agents also include Adriamycin, Doxorubicin, 5-Fluorouracil, Cytosine arabinoside (Ara-C), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Caminomycin, Aminopterin, Dactinomycin, Mitomycins, Esperamicins (see, U.S. Pat. No. 4,675,187), Melphalan, and other related nitrogen mustards.

In certain embodiments, anti-ICOS antibodies are conjugated to a cytostatic, cytotoxic or immunosuppressive agent wherein the cytotoxic agent is selected from the group consisting of an enediyne, a lexitropsin, a duocarmycin, a taxane, a puromycin, a dolastatin, a maytansinoid, and a yinca alkaloid. In certain, more specific embodiments, the cytotoxic agent is paclitaxel, docetaxel, CC-1065, SN-38, topotecan, morpholino-doxorubicin, rhizoxin, cyanomorpholino-doxorubicin, dolastatin-10, echinomycin, combretastatin, calicheamicin, maytansine, DM-1, auristatin E, AEB, AEVB, AEFP, MMAE (see, U.S. patent application Ser. No. 10/983, 340), or netropsin.

In certain embodiments, the cytotoxic agent of an anti-ICOS antibody-cytotoxic agent conjugate of the invention is an anti-tubulin agent. In specific embodiments, the cytotoxic agent is selected from the group consisting of a yinca alkaloid, a podophyllotoxin, a taxane, a baccatin derivative, a cryptophysin, a maytansinoid, a combretastatin, and a dolastatin. In other embodiments, the cytotoxic agent is vincristine, vinblastine, vindesine, vinorelbine, VP-16, camptothecin, paclitaxel, docetaxel, epithilone A, epithilone B, nocodazole, coichicine, colcimid, estramustine, cemadotin, discodermolide, maytansine, DM-1, AEFP, auristatin E, AEB, AEVB, AEFP, MMAE or eleutherobin.

In specific embodiments, an anti-ICOS antibody is conjugated to the cytotoxic agent via a linker, wherein the linker is peptide linker. In other embodiments, an anti-ICOS antibody is conjugated to the cytotoxic agent via a linker, wherein the linker is a val-cit linker, a phe-lys linker, a hydrazone linker, or a disulfide linker.

In certain embodiments, the anti-ICOS antibody of an anti-ICOS antibody-cytotoxic agent conjugate is conjugated to the cytotoxic agent via a linker, wherein the linker is hydrolysable at a pH of less than 5.5. In a specific embodiment the linker is hydrolyzable at a pH of less than 5.0.

In certain embodiments, the anti-ICOS antibody of an anti-ICOS antibody-cytotoxic agent conjugate is conjugated to the cytotoxic agent via a linker, wherein the linker is cleavable by a protease. In a specific embodiment, the protease is a lysosomal protease. In other embodiments, the protease is, inter alia, a membrane-associated protease, an intracellular protease, or an endosomal protease.

Other toxins that can be used in immunoconjugates of the invention include poisonous lectins, plant toxins such as ricin, abrin, modeccin, botulina, and diphtheria toxins. Of course, combinations of the various toxins could also be coupled to one antibody molecule thereby accommodating variable cytotoxicity. Illustrative of toxins which are suitably employed in combination therapies of the invention are ricin, abrin, ribonuclease, DNase I, Staphylococcal enterotoxin-A, pokeweed anti-viral protein, gelonin, diphtherin toxin, *Pseudomonas* exotoxin, and *Pseudomonas* endotoxin. See, for example, Pastan et al., *Cell,* 47:641 (1986), and Goldenberg et al., *Cancer Journal for Clinicians,* 44:43 (1994). Enzymatically active toxins and fragments thereof which can be used include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232 published Oct. 28, 1993.

Suitable toxins and chemotherapeutic agents are described in *Remington's Pharmaceutical Sciences,* 19th Ed. (Mack Publishing Co. 1995), and in Goodman And Gilman's The Pharmacological Basis of Therapeutics, 7th Ed. (MacMillan Publishing Co. 1985). Other suitable toxins and/or chemotherapeutic agents are known to those of skill in the art.

The present invention further encompasses antibodies (including antibody fragments or variants thereof) comprising or conjugated to a radioactive agent suitable for diagnostic purposes. Examples of suitable radioactive materials include, but are not limited to, iodine ($^{121}$I, $^{112}$I, $^{125}$I, $^{131}$I) carbon ($^{14}$C), sulfur ($^{35}$S), tritium ($^{3}$H), indium ($^{111}$In, $^{112}$In, $^{113m}$In, $^{115m}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{135}$Xe), fluorine ($^{18}$F), $^{153}$Sm, $^{177}$Lu, $^{159}$Gd, $^{149}$La, $^{175}$Yb, $^{166}$Ho, $^{90}$Y, $^{47}$Sc, $^{188}$Re, $^{188}$Re, $^{142}$Pr, $^{105}$Rh, and $^{97}$Ru.

Further, an anti-ICOS antibody of the invention (including an scFv or other molecule comprising, or alternatively consisting of, antibody fragments or variants thereof), may be coupled or conjugated to a radioactive metal ion utilized for therapeutic purposes. Examples of suitable radioactive ions include, but are not limited to, alpha-emitters such as $^{213}$Bi, or other radioisotopes such as $^{103}$Pd, $^{135}$Ye, $^{131}$I, $^{68}$Ge, $^{57}$Co, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Y, $^{117}$Tin, $^{186}$Re, $^{188}$Re and $^{166}$Ho. In specific embodiments, an antibody or fragment thereof is attached to macrocyclic chelators that chelate radiometal ions, including but not limited to, $^{177}$Lu, $^{90}$Y, $^{166}$Ho, and $^{153}$Sm, to polypeptides. In specific embodiments, the macrocyclic chelator is 1,4,7,10-tetraazacyclod-odecane-N,N',N", N'''-tetraacetic acid (DOTA). In other specific embodiments, the DOTA is attached to the an antibody of the invention or fragment thereof via a linker molecule. Examples of linker molecules useful for conjugating DOTA to a polypeptide are commonly known in the art—see, for example, DeNardo et al., Clin Cancer Res 4(10):2483-90, 1998; Peterson et al., Bioconjug Chem 10(4):553-7, 1999; and Zimmerman et al., Nucl Med Biol 26(8):943-50, 1999 which are hereby incorporated by reference in their entirety.

An anti-ICOS antibody of the present invention may also be used in ADEPT by conjugating the antibody to a prodrug-activating enzyme which converts a prodrug (e.g., a peptidyl chemotherapeutic agent, see, WO81/01145) to an active anti-cancer drug. See, for example, WO 88/07378 and U.S. Pat. No. 4,975,278. The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with α-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Antibodies with enzymatic activity, also known in the art as "abzymes," can be used as well to convert the prodrugs into free active drugs (see, e.g., Massey, Nature 328:457-458 (1987)). Antibody-abzyme conjugates can be prepared as described herein for delivery of the abzyme as desired to portions of a human affected by a ICOS expressing T cell malignancy.

Antibodies of this invention may be covalently bound to the enzymes by techniques well-known in the art such as the use of the heterobifunctional crosslinking reagents discussed above. Fusion proteins comprising at least the antigen-binding region of an anti-ICOS antibody linked to at least a functionally active portion of an enzyme may also be constructed using recombinant DNA techniques well-known in the art (see, e.g., Neuberger et al., Nature, 312:604-608 (1984)).

Covalent modifications of an anti-ICOS antibody are included within the scope of this invention. They may be made by chemical synthesis or by enzymatic or chemical cleavage of the antibody, if applicable. Other types of covalent modifications of an anti-ICOS antibody are introduced into the molecule by reacting targeted amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Similarly, iodo-reagents may also be used. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction can be performed in 0.1 M sodium cacodylate at pH 6.0.

Lysyl and amino-terminal residues are reacted with succinic or other carboxylic acid anhydrides. Derivatization with these agents has the effect of reversing the charge of the lysinyl residues. Other suitable reagents for derivatizing α-amino-containing residues and/or ε-amino-containing residues include imidoesters such as methyl picolinimidate, pyridoxal phosphate, pyridoxal, chloroborohydride, trinitrobenzenesulfonic acid, 0-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginyl residues generally requires that the reaction be performed in alkaline conditions because of the high pKa of the guanidine functional group. Furthermore, these reagents may react with the ε-amino groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, CRC Grit. Rev. Biochem., pp. 259-306 (1981).

5.17. Chemotherapeutic Combinations

According to the invention, cancer or one or more symptoms thereof may be prevented, treated, managed or ameliorated by the administration of an anti-ICOS mAb in combination with the administration of one or more therapies such as, but not limited to, chemotherapies, radiation therapies, hormonal therapies, and/or biological therapies/immunotherapies.

In a specific embodiment, methods of the invention encompass the administration of one or more angiogenesis antagonists such as but not limited to: Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combretastatin A-4; Endostatin (collagen XVIII fragment); Fibronectin fragment; Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16 kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-b); Vasculostatin; Vasostatin (calreticulin fragment); ZD6126; ZD 6474; farnesyl transferase inhibitors (FTI); and bisphosphonates (such as but are not limited to, alendronate, clodronate, etidronate, ibandronate, pamidronate, risedronate, tiludronate, and zoledronate).

In a specific embodiment, methods of the invention encompass the administration of one or more immunomodulatory agents, such as but not limited to, chemotherapeutic agents and non-chemotherapeutic immunomodulatory agents. Non-limiting examples of chemotherapeutic agents include methotrexate, cyclosporin A, leflunomide, cisplatin, ifosfamide, taxanes such as taxol and paclitaxol, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, cytochalasin B, gramicidin D, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin homologues, and cytoxan. Examples of non-chemotherapeutic immunomodulatory agents include, but are not limited to, anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies (e.g., MEDI-507 (MedImmune, Inc., International Publication Nos. WO 02/098370 and WO 02/069904), anti-CD11a antibodies (e.g., Xanelim (Genentech)), and anti-B7 antibodies (e.g., IDEC-114) (IDEC)); anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-13 antibodies, anti-IL-6 antibodies, anti-IL-8 antibodies (e.g., ABX-IL-8 (Abgenix)), anti-IL-12 antibodies and anti-IL-23 antibodies)); CTLA4-immunoglobulin; LFA-3TIP (Biogen, International Publication No. WO 93/08656 and U.S. Pat. No. 6,162,432); soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof); cytokines or fragments thereof (e.g., interleukin (IL)-2, IL-3, IL-4, IL-5, IL-6, IL-7, IL-8, IL-9, IL-10, IL-11, IL-12, IL-15, IL-23, TNF-α, TNF-β, interferon (IFN)-α, IFN-β, IFN-γ, and GM-CSF); and anti-cytokine antibodies (e.g., anti-IL-2 antibodies, anti-IL-4 antibodies, anti-IL-6 antibodies, anti-IL-10 antibodies, anti-IL-12 antibodies, anti-IL-15 antibodies, anti-TNF-α antibodies, and anti-IFN-γ antibodies), and antibodies that immunospecifically bind to tumor-associated antigens (e.g., Herceptin®). In certain embodiments, an immunomodulatory agent is an immunomodulatory agent other than a chemotherapeutic agent. In other embodiments an immunomodulatory agent is an immunomodulatory agent other than a cytokine or hemapoietic such as IL-1, IL-2, IL-4, IL-12, IL-15, TNF, IFN-α, IFN-β, IFN-γ, M-CSF, G-CSF, IL-3 or erythropoietin. In yet other embodiments, an immunomodulatory agent is an agent other than a chemotherapeutic agent and a cytokine or hemapoietic factor.

In a specific embodiment, methods of the invention encompass the administration of one or more anti-inflammatory agents, such as but not limited to, non-steroidal anti-inflammatory drugs (NSAIDs), steroidal anti-inflammatory drugs, beta-agonists, anticholingeric agents, and methyl xanthines. Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

In another specific embodiment, methods of the invention encompass the administration of one or more antiviral agents (e.g., amantadine, ribavirin, rimantadine, acyclovir, famciclovir, foscarnet, ganciclovir, trifluridine, vidarabine, didanosine, stavudine, zalcitabine, zidovudine, interferon), antibiotics (e.g., dactinomycin (formerly actinomycin), bleomycin, mithramycin, and anthramycin (AMC)), anti-emetics (e.g., alprazolam, dexamethoasone, domperidone, dronabinol, droperidol, granisetron, haloperidol, haloperidol, iorazepam, methylprednisolone, metoclopramide, nabilone, ondansetron, prochlorperazine), anti-fungal agents (e.g., amphotericin, clotrimazole, econazole, fluconazole, flucytosine, griseofulvin, itraconazole, ketoconazole, miconazole and nystatin), anti-parasite agents (e.g., dehydroemetine, diloxanide furoate, emetine, mefloquine, melarsoprol, metronidazole, nifurtimox, paromomycin, pentabidine, pentamidine isethionate, primaquine, quinacrine, quinidine) or a combination thereof.

Specific examples of anti-cancer agents that can be used in various embodiments of the invention, including pharmaceutical compositions and dosage forms and kits, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide;

floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; HMG-CoA reductase inhibitor (such as but not limited to, Lovastatin, Pravastatin, Fluvastatin, Statin, Simvastatin, and Atorvastatin); loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; Vitaxin®; vorozole; zanoterone; zeniplatin; zilascorb; and zinostatin stimalamer. Additional anti-cancer drugs are 5-fluorouracil and leucovorin. These two agents may be useful when used in methods employing thalidomide and a topoisomerase inhibitor. In specific embodiments, an anti-cancer agent is not a chemotherapeutic agent.

In more particular embodiments, the present invention also comprises the administration of an anti-ICOS mAb in combination with the administration of one or more therapies such as, but not limited to, anti-cancer agents such as those disclosed in Table 1, for the treatment of breast, ovary, melanoma, prostate, colon and lung cancers as described above. When used in a combination therapy, the dosages and/or the frequency of administration listed in Table 1 may be decreased.

TABLE 1

Anti-cancer agents

| Therapeutic Agent | Dose/Administration/Formulation | | |
|---|---|---|---|
| doxorubicin hydrochloride (Adriamycin RDF ® and Adriamycin PFS ®) | Intravenous | 60-75 mg/m² on Day 1 | 21 day intervals |
| epirubicin hydrochloride (Ellence ™) | Intravenous | 100-120 mg/m² on Day 1 of each cycle or divided equally and given on Days 1-8 of the cycle | 3-4 week cycles |
| fluorousacil | Intravenous | How supplied: 5 mL and 10 mL vials (containing 250 and 500 mg flourouracil respectively) | |
| docetaxel (Taxotere ®) | Intravenous | 60-100 mg/m² over 1 hour | Once every 3 weeks |
| paclitaxel (Taxol ®) | Intravenous | 175 mg/m² over 3 hours | Every 3 weeks for 4 courses (administered sequentially to doxorubicin-containing combination chemotherapy) |
| tamoxifen citrate (Nolvadex ®) | Oral (tablet) | 20-40 mg Dosages greater than 20 mg should be given in divided doses (morning and evening) | Daily |
| leucovorin calcium for injection | intravenous or intramuscular injection | How supplied: 350 mg vial | Dosage is unclear from text. PDR 3610 |
| luprolide acetate Lupron ® | single subcutaneous injection | 1 mg (0.2 mL or 20 unit mark) | Once a day |
| flutamide (Eulexin ®) | Oral (capsule) | 50 mg (capsules contain 125 mg flutamide each) | 3 times a day at 8 hour intervals (total daily dosage 750 mg) |
| nilutamide (Nilandron ®) | Oral (tablet) | 300 mg or 150 mg (tablets contain 50 or 150 mg nilutamide each) | 300 mg once a day for 30 days followed by 150 mg once a day |
| bicalutamide (Casodex ®) | Oral (tablet) | 50 mg (tablets contain 50 mg bicalutamide each) | Once a day |
| progesterone | Injection | USP in sesame oil 50 mg/mL | |
| ketoconazole Nizoral ®) | Cream | 2% cream applied once or twice daily depending on symptoms | |

TABLE 1-continued

Anti-cancer agents

| Therapeutic Agent | | Dose/Administration/Formulation | |
|---|---|---|---|
| prednisone | Oral (tablet) | Initial dosage may vary from 5 mg to 60 mg per day depending on the specific disease entity being treated. | |
| estramustine phosphate sodium (Emcyt ®) | Oral (capsule) | 14 mg/kg of body weight (i.e. one 140 mg capsule for each 10 kg or 22 lb of body weight) | Daily given in 3 or 4 divided doses |
| etoposide or VP-16 | Intravenous | 5 mL of 20 mg/mL solution (100 mg) | |
| dacarbazine (DTIC-Dome ®) | Intravenous | 2-4.5 mg/kg | Once a day for 10 days. May be repeated at 4 week intervals |
| polifeprosan 20 with carmustine implant (BCNU) (nitrosourea) (Gliadel ®) | wafer placed in resection cavity | 8 wafers, each containing 7.7 mg of carmustine, for a total of 61.6 mg, if size and shape of resection cavity allows | |
| cisplatin | Injection | [n/a in PDR 861] How supplied: solution of 1 mg/mL in multi-dose vials of 50 mL and 100 mL | |
| mitomycin | Injection | supplied in 5 mg and 20 mg vials (containing 5 mg and 20 mg mitomycin) | |
| gemcitabine HCl (Gemzar ®) | Intravenous | For NSCLC—schedules have been investigated and the optimum schedule has not been determined 4 week schedule— administration intravenously at 1000 mg/m$^2$ over 30 minutes on 3 week schedule— Gemzar administered intravenously at 1250 mg/m$^2$ over 30 minutes | 4 week schedule— Days 1, 8 and 15 of each 28-day cycle. Cisplatin intravenously at 100 mg/m$^2$ on day 1 after the infusion of Gemzar. 3 week schedule— Days 1 and 8 of each 21 day cycle. Cisplatin at dosage of 100 mg/m$^2$ administered intravenously after administration of Gemzar on day 1. |
| carboplatin (Paraplatin ®) | Intravenous | Single agent therapy: 360 mg/m$^2$ I.V. on day 1 (infusion lasting 15 minutes or longer) Other dosage calculations: Combination therapy with cyclophosphamide, Dose adjustment recommendations, Formula dosing, etc. | Every 4 weeks |
| ifosamide (Ifex ®) | Intravenous | 1.2 g/m$^2$ daily | 5 consecutive days Repeat every 3 weeks or after recovery from hematologic toxicity |
| topotecan hydrochloride (Hycamtin ®) | Intravenous | 1.5 mg/m$^2$ by intravenous infusion over 30 minutes daily | 5 consecutive days, starting on day 1 of 21 day course |
| Bisphosphonates Pamidronate Alendronate Risedronate | Intravenous or Oral take with 6-8 oz water. | 60 mg or 90 mg single infusion over 4-24 hours to correct hypercalcemia in cancer patients 5 mg/d daily for 2 years and then 10 mg/d for 9 month to prevent or control bone resorption. 5.0 mg to prevent or control bone resorption. | |
| Lovastatin (Mevacor ™) | Oral | 10-80 mg/day in single or two divided dose. | |

The invention also encompasses administration of an anti-ICOS mAb in combination with radiation therapy comprising the use of x-rays, gamma rays and other sources of radiation to destroy the cancer cells. In particular embodiments, the radiation treatment is administered as external beam radiation or teletherapy wherein the radiation is directed from a remote source. In other embodiments, the radiation treatment is administered as internal therapy or brachytherapy wherein a radiaoactive source is placed inside the body close to cancer cells or a tumor mass.

Cancer therapies and their dosages, routes of administration and recommended usage are known in the art and have been described in such literature as the *Physician's Desk Reference* (56$^{th}$ ed., 2002).

5.18. Pharmaceutical Compositions

The invention also relates to immunotherapeutic compositions and methods for the treatment of T cell-mediated diseases and disorders in human subjects, such as, but not limited to, chronic infection, autoimmune disease or disorder, inflammatory disease or disorder, graft-versus-host disease (GVHD), transplant rejection, and T cell proliferative disorder in human subjects, using therapeutic antibodies that bind to the ICOS antigen and mediate human ADCC.

The present invention relates to pharmaceutical compositions comprising effector function enhanced anti-ICOS antibodies of the IgG1 or IgG3 human isotype. The present invention also relates to pharmaceutical compositions comprising human or humanized anti-ICOS antibodies of the IgG2 or IgG4 human isotype that mediate human ADCC. In certain embodiments, the present invention also relates to pharmaceutical compositions comprising monoclonal anti-ICOS antibodies with enahced effectro function that can be produced by means known in the art.

Therapeutic formulations and regimens are described for treating human subjects diagnosed with autoimmune diseases, such as, but not limited to, systemic lupus erythematosis, rheumatoid arthritis, immune thrombocytopenic purpura (ITP), diabetes, psoriasis, and hypersensitivity reactions (e.g., allergies, hay fever, asthma, and acute edema cause type I hypersensitivity reactions). The present invention also relates to formulations and regimens for the treatment of human subjects diagnosed with chronic inflammatory diseases, such as, but not limited to, inflammatory bowel disease (Crohn's disease and ulcerative colitis), Grave's disease, Hashimoto's thyroiditis, and diabetes mellitus.

Therapeutic formulations and regimens are described for treating human subjects diagnosed with T cell malignancies that derive from ICOS expressing T cells and their precursors.

In particular embodiments, anti-ICOS antibodies may mediate ADCC, complement-dependent cellular cytoxicity, or antibody-dependent phagocytosis. Compositions and methods of the present invention also have the advantage of targeting a narrower population of T cells than other T cell directed immunotherapies. For example, anti-ICOS antibodies of the present invention may be effective to specifically target activated T cells, for example, but not limited to, activated T cells. Accordingly, methods and compositions of the invention may be effective to reduce or deplete circulating activated CD4+ T cells as well as activated CD8+ T cells.

Accordingly, in one aspect, the invention provides compositions and methods for the treatment and prevention of GVHD and graft rejection, which are associated with fewer and/or less severe complications than less-targeted therapeutic agents and regimens. In one embodiment, compositions and methods of the invention are used with lower doses of traditional therapeutic agents than would be possible in the absence of the methods and compositions of the invention. In another embodiment, compositions and methods of the invention obviate the need for a more severe form of therapy, such as radiation therapy, high-dose chemotherapy, or splenectomy.

In certain embodiments, anti-ICOS antibodies and compositions may be administered to a transplant recipient patient prior to or following transplantation, alone or in combination with other therapeutic agents or regimens for the treatment or prevention of GVHD and graft rejection. For example, anti-ICOS antibodies and compositions may be used to deplete activated T cells from a transplant recipient prior to or following transplantation of an allogeneic graft. Anti-ICOS antibodies and compositions may also be used to deplete activated T cells from the graft ex vivo, prior to transplantation, or in the donor, or as prophylaxis against GVHD and graft rejection.

5.19. Pharmaceutical Formulations, Administration and Dosing

Pharmaceutical formulations of the invention contain as the active ingredient anti-ICOS antibodies with enhanced effector function. The formulations contain naked antibody, immunoconjugate, or fusion protein in an amount effective for producing the desired response in a unit of weight or volume suitable for administration to a human patient, and are preferably sterile. The response can, for example, be measured by determining the physiological effects of the anti-ICOS antibody composition, such as, but not limited to, T cell depletion, IL-17 depletion, regression of a T cell malignancy, or decrease of disease symptoms. Other assays will be known to one of ordinary skill in the art and can be employed for measuring the level of the response.

5.19.1. Pharmaceutical Formulations

A composition comprising an anti-ICOS antibody with enhanced effector function may be formulated with a pharmaceutically acceptable carrier. The term "pharmaceutically acceptable" means one or more non-toxic materials that do not interfere with the effectiveness of the biological activity of the active ingredients. Such preparations may routinely contain salts, buffering agents, preservatives, compatible carriers, and optionally other therapeutic agents. Such pharmaceutically acceptable preparations may also routinely contain compatible solid or liquid fillers, diluents or encapsulating substances which are suitable for administration into a human. When used in medicine, the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, citric, boric, formic, malonic, succinic, and the like. Also, pharmaceutically acceptable salts can be prepared as alkaline metal or alkaline earth salts, such as sodium, potassium or calcium salts. The term "carrier" denotes an organic or inorganic ingredient, natural or synthetic, with which the active ingredient is combined to facilitate the application. The components of the pharmaceutical compositions also are capable of being co-mingled with the antibodies of the present invention, and with each other, in a manner such that there is no interaction which would substantially impair the desired pharmaceutical efficacy.

According to certain aspects of the invention, anti-ICOS antibody compositions can be prepared for storage by mixing the antibody or immunoconjugate having the desired degree of purity with optional physiologically acceptable carriers, excipients or stabilizers (*Remington's Pharmaceutical Sci-*

*ences*, 16th edition, Osol, A. Ed. (1999)), in the form of lyophilized formulations or aqueous solutions. Acceptable carriers, excipients, or stabilizers are nontoxic to recipients at the dosages and concentrations employed, and include buffers such as histidine, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrolidone; amino acids such as glycine, glutamine, asparagine, histidine, arginine, or lysine; monosaccharides, disaccharides, and other carbohydrates including trehalose, glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, polysorbate 80, PLURONICS™ or polyethylene glycol (PEG).

Anti-ICOS antibody compositions also may contain, optionally, suitable preservatives, such as: benzalkonium chloride; chlorobutanol; parabens and thimerosal.

Anti-ICOS antibody compositions may conveniently be presented in unit dosage form and may be prepared by any of the methods well-known in the art of pharmacy. All methods include the step of bringing the active agent into association with a carrier which constitutes one or more accessory ingredients. In general, anti-ICOS antibody compositions are prepared by uniformly and intimately bringing the active compound into association with a liquid carrier, a finely divided solid carrier, or both, and then, if necessary, shaping the product.

Compositions suitable for parenteral administration conveniently comprise a sterile aqueous or non-aqueous preparation of anti-ICOS antibody, which may be isotonic with the blood of the recipient. This preparation may be formulated according to known methods using suitable dispersing or wetting agents and suspending agents. The sterile injectable preparation also may be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administration can be found in *Remington's Pharmaceutical Sciences*, Mack Publishing Co., Easton, Pa. In certain embodiments, carrier formulation suitable for various routes of administration can be the same or similar to that described for RITUXAN™. See, *Physicians' Desk Reference* (Medical Economics Company, Inc., Montvale, N.J., 2005), pp. 958-960 and 1354-1357, which is incorporated herein by reference in its entirety. In certain embodiments of the invention, anti-ICOS antibody compositions are formulated for intravenous administration with sodium chloride, sodium citrate dihydrate, polysorbate 80, and sterile water where the pH of the composition is adjusted to approximately 6.5. Those of skill in the art are aware that intravenous injection provides a useful mode of administration due to the thoroughness of the circulation in rapidly distributing antibodies. Intravenous administration, however, is subject to limitation by a vascular barrier comprising endothelial cells of the vasculature and the subendothelial matrix. Still, the vascular barrier is a more notable problem for the uptake of therapeutic antibodies by solid tumors. Lymphomas have relatively high blood flow rates, contributing to effective antibody delivery. Intralymphatic routes of administration, such as subcutaneous or intramuscular injection, or by catheterization of lymphatic vessels, also provide a useful means of treating T cell-mediated diseases and disorders. In certain embodiments, anti-ICOS antibodies of compositions and methods of the invention are self-administered subcutaneously. In such embodiments, the composition is formulated as a lyophilized drug or in a liquid buffer (e.g., histidine buffer, PBS, citrate) at about 50 mg/mL.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration are typically sterile. This is readily accomplished by filtration through sterile filtration membranes.

Sustained-release preparations may be prepared. Suitable examples of sustained-release preparations include semipermeable matrices of solid hydrophobic polymers containing an anti-ICOS antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devized for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions. In certain embodiments, the pharmaceutically acceptable carriers used in compositions of the invention do not affect human ADCC or CDC.

Anti-ICOS antibody compositions disclosed herein may also be formulated as immunoliposomes. A "liposome" is a small vesicle composed of various types of lipids, phospholipids and/or surfactant which is useful for delivery of a drug (such as anti-ICOS antibodies disclosed herein) to a human. The components of the liposome are commonly arranged in a bilayer formation, similar to the lipid arrangement of biological membranes. Liposomes containing antibodies of the invention are prepared by methods known in the art, such as described in Epstein et al., *Proc. Natl. Acad. Sci. USA*, 82:3688 (1985); Hwang et al., *Proc. Natl. Acad. Sci. USA*, 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. The antibody of the present invention can be conjugated to the liposomes as described in Martin et al., *J. Biol. Chem.*, 257:286-288 (1982) via a disulfide interchange reaction. A therapeutic agent can also be contained within the liposome. See, Gabizon et al., *J. National Cancer Inst.*, (19)1484 (1989).

Some of the pharmaceutical formulations include, but are not limited to:

(a) a sterile, preservative-free liquid concentrate for intravenous (i.v.) administration of anti-ICOS antibody, supplied at a concentration of 10 mg/ml in either 100 mg (10 mL) or 500 mg (50 mL) single-use vials. The product can be formulated for i.v. administration using sodium chloride, sodium citrate dihydrate, polysorbate and sterile water for injection. For example, the product can be formulated in 9.0 mg/mL sodium chloride, 7.35 mg/mL sodium citrate dihydrate, 0.7 mg/mL polysorbate 80, and sterile water for injection. The pH is adjusted to 6.5.

(b) A sterile, lyophilized powder in single-use glass vials for subcutaneous (s.c.) injection. The product can be formulated with sucrose, L-histidine hydrochloride monohydrate, L-histidine and polysorbate 20. For example, each single-use vial can contain 150 mg anti-ICOS antibody, 123.2 mg sucrose, 6.8 mg L-histidine hydrochloride monohydrate, 4.3 mg L-histidine, and 3 mg polysorbate 20. Reconstitution of the single-use vial with 1.3 ml sterile water for injection yields approximately 1.5 ml solution to deliver 125 mg per 1.25 ml (100 mg/ml) of antibody.

(c) A sterile, preservative-free lyophilized powder for intravenous (i.v.) administration. The product can be formulated with α-trehalose dihydrate, L-histidine HCl, histidine and polysorbate 20 USP. For example, each vial can contain 440 mg anti-ICOS antibody, 400 mg α,α-trehalose dihydrate, 9.9 mg L-histidine HCl, 6.4 mg L-histidine, and 1.8 mg polysorbate 20, USP. Reconstitution with 20 ml of bacteriostatic water for injection (BWFI), USP, containing 1.1% benzyl alcohol as a preservative, yields a multi-dose solution containing 21 mg/ml antibody at a pH of approximately 6.

(d) A sterile, lyophilized powder for intravenous infusion in which an anti-ICOS antibody is formulated with sucrose, polysorbate, monobasic sodium phosphate monohydrate, and dibasic sodium phosphate dihydrate. For example, each single-use vial can contain 100 mg antibody, 500 mg sucrose, 0.5 mg polysorbate 80, 2.2 mg monobasic sodium phosphate monohydrate, and 6.1 mg dibasic sodium phosphate dihydrate. No preservatives are present. Following reconstitution with 10 ml sterile water for injection, USP, the resulting pH is approximately 7.2.

(e) A sterile, preservative-free solution for subcutaneous administration supplied in a single-use, 1 ml pre-filled syringe. The product can be formulated with sodium chloride, monobasic sodium phosphate dihydrate, dibasic sodium phosphate dihydrate, sodium citrate, citric acid monohydrate, mannitol, polysorbate 80 and water for injection, USP. Sodium hydroxide may be added to adjust pH to about 5.2.

For example, each syringe can be formulated to deliver 0.8 ml (40 mg) of drug product. Each 0.8 ml contains 40 mg anti-ICOS antibody, 4.93 mg sodium chloride, 0.69 mg monobasic sodium phosphate dihydrate, 1.22 mg dibasic sodium phosphate dihydrate, 0.24 mg sodium citrate, 1.04 citric acid monohydrate, 9.6 mg mannitol, 0.8 mg polysorbate 80 and water for injection, USP.

(f) A sterile, preservative-free, lyophilized powder contained in a single-use vial that is reconstituted with sterile water for injection (SWFI), USP, and administered as a subcutaneous (s.c.) injection. The product can be formulated with sucrose, histidine hydrochloride monohydrate, L-histidine, and polysorbate. For example, a 75 mg vial can contain 129.6 mg or 112.5 mg of an anti-ICOS antibody, 93.1 mg sucrose, 1.8 mg L-histidine hydrochloride monohydrate, 1.2 mg L-histidine, and 0.3 mg polysorbate 20, and is designed to deliver 75 mg of the antibody in 0.6 ml after reconstitution with 0.9 ml SWFI, USP. A 150 mg vial can contain 202.5 mg or 175 mg anti-ICOS antibody, 145.5 mg sucrose, 2.8 mg L-histidine hydrochloride monohydrate, 1.8 mg L-histidine, and 0.5 mg polysorbate 20, and is designed to deliver 150 mg of the antibody in 1.2 ml after reconstitution with 1.4 ml SWFI, USP.

(g) A sterile, hyophilized product for reconstitution with sterile water for injection. The product can be formulated as single-use vials for intramuscular (IM) injection using mannitol, histidine and glycine. For example, each single-use vial can contain 100 mg anti-ICOS antibody, 67.5 mg of mannitol, 8.7 mg histidine and 0.3 mg glycine, and is designed to deliver 100 mg antibody in 1.0 ml when reconstituted with 1.0 ml sterile water for injection. As another example, each single-use vial can contain 50 mg anti-ICOS antibody, 40.5 mg mannitol, 5.2 mg histidine and 0.2 mg glycine, and is designed to deliver 50 mg of antibody when reconstituted with 0.6 ml sterile water for injection.

(h) A sterile, preservative-free solution for intramuscular (IM) injection, supplied at a concentration of 100 mg/ml. The product can be formulated in single-use vials with histidine, glycine, and sterile water for injection. For example, each single-use vial can be formulated with 100 mg antibody, 4.7 mg histidine, and 0.1 mg glycine in a volume of 1.2 ml designed to deliver 100 mg of antibody in 1 ml. As another example, each single-use vial can be formulated with 50 mg antibody, 2.7 mg histidine and 0.08 mg glycine in a volume of 0.7 ml or 0.5 ml designed to deliver 50 mg of antibody in 0.5 ml.

In certain embodiments, a pharmaceutical composition of the invention is stable at 4° C. In certain embodiments, a pharmaceutical composition of the invention is stable at room temperature.

In one embodiment, a liquid formulation of the invention is an aqueous formulation. In a specific embodiment, a liquid formulation of the invention is an aqueous formulation wherein the aqueous carrier is distilled water.

In one embodiment, a formulation of the invention is sterile. In one embodiment, a formulation of the invention is homogeneous. In one embodiment, a formulation of the invention is isotonic.

In one embodiment, a formulation of the invention comprises at least about 1 mg/ml, at least about 5 mg/ml, at least about 10 mg/ml, at least about 20 mg/ml, at least about 30 mg/ml, at least about 40 mg/ml, at least about 50 mg/ml, at least about 60 mg/ml, at least about 70 mg/ml, at least about 80 mg/ml, at least about 90 mg/ml, at least about 100 mg/ml, at least about 110 mg/ml, at least about 120 mg/ml, at least about 130 mg/ml, at least about 140 mg/ml, at least about 150 mg/ml, at least about 160 mg/ml, at least about 170 mg/ml, at least about 180 mg/ml, at least about 190 mg/ml, at least about 200 mg/ml, or at least about 300 mg/ml of an anti-ICOS antibody or a fragment thereof.

Optionally, the formulations of the invention may comprise common excipients and/or additives such as buffering agents, saccharides, salts and surfactants. Additionally or alternatively, the formulations of the invention may further comprise common excipients and/or additives, such as, but not limited to, solubilizers, diluents, binders, stabilizers, salts, lipophilic solvents, amino acids, chelators, preservatives, or the like.

In certain embodiments, the buffering agent is selected from the group consisting of histidine, citrate, phosphate, glycine, and acetate. In other embodiments the saccharide excipient is selected from the group consisting of trehalose, sucrose, mannitol, maltose and raffinose. In still other embodiments the surfactant is selected from the group consisting of polysorbate 20, polysorbate 40, polysorbate 80, and Pluronic F68. In yet other embodiments the salt is selected from the group consisting of NaCl, KCl, $MgCl_2$, and $CaCl_2$ Optionally, the formulations of the invention may further comprise other common auxiliary components, such as, but not limited to, suitable excipients, polyols, solubilizers, diluents, binders, stabilizers, lipophilic solvents, chelators, preservatives, or the like.

The formulations of the invention include a buffering or pH adjusting agent to provide improved pH control. In one embodiment, a formulation of the invention has a pH of between about 3.0 and about 9.0, between about 4.0 and about 8.0, between about 5.0 and about 8.0, between about 5.0 and about 7.0, between about 5.0 and about 6.5, between about 5.5 and about 8.0, between about 5.5 and about 7.0, or between about 5.5 and about 6.5. In a further embodiment, a formulation of the invention has a pH of about 3.0, about 3.5, about 4.0, about 4.5, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.5, about 8.0, about 8.5, or about 9.0. In a specific embodiment, a formulation of the invention has a pH of about 6.0.

The pH of the formulation generally should not be equal to the isoelectric point of the particular antibody (including antibody fragment thereof) to be used in the formulation (for example, but not limited to, the isoelectric point of 13H5, 13H7 or 7H9) and may range from about 4.0 to about 8.0, or may range from about 5.5 to about 6.5.

Typically, the buffering agent is a salt prepared from an organic or inorganic acid or base. Representative buffering agents include, but are not limited to, organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. In addition, amino acid components can also function in a buffering capacity. Representative amino acid components which may be utilized in the formulations of the invention as buffering agents include, but are not limited to, glycine and histidine. In certain embodiments, the buffering agent is selected from the group consisting of histidine, citrate, phosphate, glycine, and acetate. In a specific embodiment, the buffering agent is histidine. In another specific embodiment, the buffering agent is citrate. The purity of the buffering agent should be at least 98%, or at least 99%, or at least 99.5%. As used herein, the term "purity" in the context of histidine refers to chemical purity of histidine as understood in the art, e.g., as described in The Merck Index, 13$^{th}$ ed., O'Neil et al. ed. (Merck & Co., 2001).

Buffering agents are typically used at concentrations between about 1 mM and about 200 mM or any range or value therein, depending on the desired ionic strength and the buffering capacity required. The usual concentrations of conventional buffering agents employed in parenteral formulations can be found in: Pharmaceutical Dosage Form: Parenteral Medications, Volume 1, 2$^{nd}$ Edition, Chapter 5, p. 194, De Luca and Boylan, "Formulation of Small Volume Parenterals", Table 5: Commonly used additives in Parenteral Products. In certain embodiments, a formulation of the invention comprises a buffering agent. In one embodiment, said buffering agent is selected from the group consisting of histidine, citrate, phosphate, glycine, and acetate. In a specific embodiment, a formulation of the invention comprises histidine as a buffering agent. In a further embodiment, a formulation of the invention comprises a citrate buffer.

In one embodiment, a formulation of the invention comprises at least about 1 mM, at least about 5 mM, at least about 10 mM, at least about 20 mM, at least about 30 mM, at least about 40 mM, at least about 50 mM, at least about 75 mM, at least about 100 mM, at least about 150 mM, or at least about 200 mM buffering agent.

In certain embodiments, the formulations of the invention comprise a carbohydrate excipient. Carbohydrate excipients can act, e.g., as viscosity enhancing agents, stabilizers, bulking agents, solubilizing agents, and/or the like. Carbohydrate excipients are generally present at between about 1% to about 99% by weight or volume. In one embodiment, the carbohydrate excipient is present at between about 0.1% to about 20%. In another embodiment, the carbohydrate excipient is present at between about 0.1% to about 15%. In a specific embodiment, the carbohydrate excipient is present at between about 0.1% to about 5%, or between about 1% to about 20%, or between about 5% to about 15%, or between about 8% to about 10%, or between about 10% and about 15%, or between about 15% and about 20%. In another specific embodiment, the carbohydrate excipient is present at between 0.1% to 20%, or between 5% to 15%, or between 8% to 10%, or between 10% and 15%, or between 15% and 20%. In still another specific embodiment, the carbohydrate excipient is present at between about 0.1% to about 5%. In still another specific embodiment, the carbohydrate excipient is present at between about 5% to about 10%. In yet another specific embodiment, the carbohydrate excipient is present at between about 15% to about 20%. In still other specific embodiments, the carbohydrate excipient is present at 1%, or at 1.5%, or at 2%, or at 2.5%, or at 3%, or at 4%, or at 5%, or at 10%, or at 15%, or at 20%.

Carbohydrate excipients suitable for use in the formulations of the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and the like. In one embodiment, the carbohydrate excipients for use in the present invention are selected from the group consisting of, sucrose, trehalose, lactose, mannitol, and raffinose. In a specific embodiment, the carbohydrate excipient is trehalose. In another specific embodiment, the carbohydrate excipient is mannitol. In yet another specific embodiment, the carbohydrate excipient is sucrose. In still another specific embodiment, the carbohydrate excipient is raffinose. The purity of the carbohydrate excipient should be at least 98%, or at least 99%, or at least 99.5%.

In one embodiment, a formulation of the invention comprises an excipient. In a specific embodiment, a formulation of the invention comprises at least one excipient selected from the group consisting of: sugar, salt, surfactant, amino acid, polyol, chelating agent, emulsifier and preservative. In one embodiment, a formulation of the invention comprises a salt. In one embodiment, a formulation of the invention comprises a salt selected from the group consisting of: NaCl, KCl, $CaCl_2$, and $MgCl_2$. In a specific embodiment, a formulation of the invention comprises NaCl.

In one embodiment, a formulation of the invention comprises at least about 10 mM, at least about 25 mM, at least about 50 mM, at least about 75 mM, at least about 100 mM, at least about 125 mM, at least about 150 mM, at least about 175 mM. at least about 200 mM, or at least about 300 mM sodium chloride.

The formulations of the invention may further comprise a surfactant. The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials. Pharmaceutically acceptable surfactants like polysorbates (e.g. polysorbates 20 or 80); polyoxamers (e.g. poloxamer 188); Triton; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUA™ series (Mona Industries, Inc., Paterson, N.J.), polyethyl glycol, polypropyl glycol, and copolymers of ethylene and propylene glycol (e.g. Pluronics, PF68 etc), can optionally be added to the formulations of the invention to reduce aggregation. Surfactants are particularly useful if a pump or plastic container is used to administer the formulation. The presence of a pharmaceutically acceptable surfactant mitigates the propensity for the protein to aggregate. In a specific embodiment, the formulations of the invention comprise a polysorbate which is at a concentration ranging from between about 0.001% to about 1%, or about 0.001% to about 0.1%, or about 0.01% to about 0.1%. In other specific embodiments, the formulations of the invention comprise a polysorbate which is at a concentration of 0.001%, or 0.002%, or 0.003%, or 0.004%, or 0.005%, or 0.006%, or 0.007%, or 0.008%, or 0.009%, or 0.01%, or 0.015%, or 0.02%. In another specific embodiment, the polysorbate is polysorbate-80.

In one embodiment, a formulation of the invention comprises a surfactant. In one embodiment, a formulation of the invention comprises Polysorbate 20, Polysorbate 40, Polysorbate 60, or Polysorbate 80. In a specific embodiment, a formulation of the invention comprises Polysorbate 80.

Optionally, the formulations of the invention may further comprise other common excipients and/or additives including, but not limited to, diluents, binders, stabilizers, lipophilic solvents, preservatives, adjuvants, or the like. Pharmaceutically acceptable excipients and/or additives may be used in the formulations of the invention. Commonly used excipients/additives, such as pharmaceutically acceptable chelators (for example, but not limited to, EDTA, DTPA or EGTA) can optionally be added to the formulations of the invention to reduce aggregation. These additives are particularly useful if a pump or plastic container is used to administer the formulation.

Preservatives, such as phenol, m-cresol, p-cresol, o-cresol, chlorocresol, benzyl alcohol, phenylmercuric nitrite, phenoxyethanol, formaldehyde, chlorobutanol, magnesium chloride (for example, but not limited to, hexahydrate), alkylparaben (methyl, ethyl, propyl, butyl and the like), benzalkonium chloride, benzethonium chloride, sodium dehydroacetate and thimerosal, or mixtures thereof can optionally be added to the formulations of the invention at any suitable concentration such as between about 0.001% to about 5%, or any range or value therein. The concentration of preservative used in the formulations of the invention is a concentration sufficient to yield an microbial effect. Such concentrations are dependent on the preservative selected and are readily determined by the skilled artisan.

Other contemplated excipients/additives, which may be utilized in the formulations of the invention include, for example, flavoring agents, antimicrobial agents, sweeteners, antioxidants, antistatic agents, lipids such as phospholipids or fatty acids, steroids such as cholesterol, protein excipients such as serum albumin (human serum albumin (HSA), recombinant human albumin (rHA)), gelatin, casein, salt-forming counterions such as sodium and the like. These and additional known pharmaceutical excipients and/or additives suitable for use in the formulations of the invention are known in the art, e.g., as listed in "Remington: The Science & Practice of Pharmacy", $21^{st}$ ed., Lippincott Williams & Wilkins, (2005), and in the "Physician's Desk Reference", $60^{th}$ ed., Medical Economics, Montvale, N.J. (2005). Pharmaceutically acceptable carriers can be routinely selected that are suitable for the mode of administration, solubility and/or stability of Fc variant protein as well known in the art or as described herein.

It will be understood by one skilled in the art that the formulations of the invention may be isotonic with human blood, that is the formulations of the invention have essentially the same osmotic pressure as human blood. Such isotonic formulations will generally have an osmotic pressure from about 250 mOSm to about 350 mOSm. Isotonicity can be measured by, for example, using a vapor pressure or ice-freezing type osmometer. Tonicity of a formulation is adjusted by the use of tonicity modifiers. "Tonicity modifiers" are those pharmaceutically acceptable inert substances that can be added to the formulation to provide an isotonity of the formulation. Tonicity modifiers suitable for this invention include, but are not limited to, saccharides, salts and amino acids.

In certain embodiments, the formulations of the present invention have an osmotic pressure from about 100 mOSm to about 1200 mOSm, or from about 200 mOSm to about 1000 mOSm, or from about 200 mOSm to about 800 mOSm, or from about 200 mOSm to about 600 mOSm, or from about 250 mOSm to about 500 mOSm, or from about 250 mOSm to about 400 mOSm, or from about 250 mOSm to about 350 mOSm.

Concentration of any one or any combination of various components of the formulations of the invention are adjusted to achieve the desired tonicity of the final formulation. For example, the ratio of the carbohydrate excipient to antibody may be adjusted according to methods known in the art (e.g., U.S. Pat. No. 6,685,940). In certain embodiments, the molar ratio of the carbohydrate excipient to antibody may be from about 100 moles to about 1000 moles of carbohydrate excipient to about 1 mole of antibody, or from about 200 moles to about 6000 moles of carbohydrate excipient to about 1 mole of antibody, or from about 100 moles to about 510 moles of carbohydrate excipient to about 1 mole of antibody, or from about 100 moles to about 600 moles of carbohydrate excipient to about 1 mole of antibody.

The desired isotonicity of the final formulation may also be achieved by adjusting the salt concentration of the formulations. Salts that are pharmaceutically acceptable and suitable for this invention as tonicity modifiers include, but are not limited to, sodium chloride, sodium succinate, sodium sulfate, potassuim chloride, magnesium chloride, magnesium sulfate, and calcium chloride. In specific embodiments, formulations of the inventions comprise NaCl, $MgCl_2$, and/or $CaCl_2$. In one embodiment, concentration of NaCl is between about 75 mM and about 150 mM. In another embodiment, concentration of $MgCl_2$ is between about 1 mM and about 100 mM. Amino acids that are pharmaceutically acceptable and suitable for this invention as tonicity modifiers include, but are not limited to, proline, alanine, L-arginine, asparagine, L-aspartic acid, glycine, serine, lysine, and histidine.

In one embodiment the formulations of the invention are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with antibodies, even trace amounts of harmful and dangerous endotoxin must be removed. In certain specific embodiments, the endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg.

When used for in vivo administration, the formulations of the invention should be sterile. The formulations of the invention may be sterilized by various sterilization methods, including sterile filtration, radiation, etc. In one embodiment, the antibody formulation is filter-sterilized with a presterilized 0.22-micron filter. Sterile compositions for injection can be formulated according to conventional pharmaceutical practice as described in "Remington: The Science & Practice of Pharmacy", $21^{st}$ ed., Lippincott Williams & Wilkins, (2005). Formulations comprising antibodies, such as those disclosed herein, ordinarily will be stored in lyophilized form or in solution. It is contemplated that sterile compositions comprising antibodies are placed into a container having a sterile access port, for example, an intravenous solution bag or vial having an adapter that allows retrieval of the formulation, such as a stopper pierceable by a hypodermic injection needle.

The terms "stability" and "stable" as used herein in the context of a formulation comprising an anti-ICOS antibody of the invention refer to the resistance of the antibody in the formulation to aggregation, degradation or fragmentation under given manufacture, preparation, transportation and storage conditions. The "stable" formulations of the invention retain biological activity under given manufacture, preparation, transportation and storage conditions. The stability of said antibody can be assessed by degrees of aggregation, degradation or fragmentation, as measured by HPSEC, static light scattering (SLS), Fourier Transform Infrared Spectroscopy (FTIR), circular dichroism (CD), urea unfolding techniques, intrinsic tryptophan fluorescence, differential scanning calorimetry, and/or ANS binding techniques, compared to a reference formulation. For example, a reference formulation may be a reference standard frozen at −70° C. consisting of 10 mg/ml of an anti-ICOS antibody of the invention in PBS. The overall stability of a formulation comprising an anti-ICOS antibody of the invention can be assessed by various assays including, for example, ELISA assay, radioimmunoassay and ADCC assay. The overall stability of a formulation comprising an anti-ICOS antibody of the invention can also be assessed by in vivo assays including, for example, in vivo depletion assays.

In one embodiment, a formulation of the invention comprises an anti-ICOS antibody. In one embodiment, a formulation of the invention reduces aggregation of an anti-ICOS antibody or fragment thereof. In another embodiment, a formulation of the invention reduces fragmentation of an anti-ICOS antibody or fragment thereof. In a further embodiment, a formulation of the invention reduces deamidation of an anti-ICOS antibody or fragment thereof.

In one embodiment, a formulation of the invention comprises an anti-ICOS antibody of the invention and is stable upon storage at about 40° C. for at least about 1 week, at least about 2 weeks, at least about 3 weeks, or at least about 4 weeks. In one embodiment, a formulation of the invention is stable upon storage at about 40° C. for at least about 1 month, at least about 2 months, at least about 3 months, at least about 4 months, at least about 5 months, or at least about 6 months.

In one embodiment, a formulation of the invention comprises an anti-ICOS antibody of the invention and is stable upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a formulation of the invention is stable upon storage at about 5° C. for at least about 1 year, at least about 2 years, at least about 3 years, at least about 4 years, at least about 5 years, at least about 6 years, at least about 7 years, at least about 8 years, at least about 9 years, at least about 10 years, at least about 11 years, or at least about 12 years.

In a specific embodiment, a formulation of the invention comprises at least about 50 mg/ml of an anti-ICOS antibody described herein, wherein the formulation is stable upon storage at about 40° C. for at least about 1 week, at least about 2 weeks, at least about 3 weeks, at least about 4 weeks, at least about 2 months, at least about 3 months, at least about 4 months, at least about 5 months, or at least about 6 months.

In a specific embodiment, a formulation of the invention comprises at least about 50 mg/ml of an anti-ICOS antibody described herein, wherein the formulation is stable upon storage at about 5° C. for at least about 6 months, at least about 7 months, at least about 8 months, at least about 9 months, at least about 1 year, at least about 2 years, or at least about 3 years.

In a specific embodiment, a formulation of the invention comprises at least about 100 mg/ml of an anti-ICOS antibody described herein, wherein the formulation is stable upon storage at about 40° C. for at least about 1 week, at least about 2 weeks, at least about 3 weeks, at least about 4 weeks, at least about 2 months, at least about 3 months, at least about 4 months, at least about 5 months, or at least about 6 months.

In a specific embodiment, a formulation of the invention comprises at least about 100 mg/ml of an anti-ICOS antibody described herein, wherein the formulation is stable upon storage at about 5° C. for at least about 6 months, at least about 7 months, at least about 8 months, at least about 9 months, at least about 1 year, at least about 2 years, or at least about 3 years.

In a specific embodiment, a formulation of the invention comprises at least about 110 mg/ml of an anti-ICOS antibody described herein, wherein the formulation is stable upon storage at about 40° C. for at least about 1 week, at least about 2 weeks, at least about 3 weeks, at least about 4 weeks, at least about 2 months, at least about 3 months, at least about 4 months, at least about 5 months, or at least about 6 months.

In a specific embodiment, a formulation of the invention comprises at least about 110 mg/ml of an anti-ICOS antibody described herein, wherein the formulation is stable upon storage at about 5° C. for at least about 6 months, at least about 7 months, at least about 8 months, at least about 9 months, at least about 1 year, at least about 2 years, or at least about 3 years.

In a specific embodiment, a formulation of the invention comprises at least about 150 mg/ml of an anti-ICOS antibody described herein, wherein the formulation is stable upon storage at about 40° C. for at least about 1 week, at least about 2 weeks, at least about 3 weeks, at least about 4 weeks, at least about 2 months, at least about 3 months, at least about 4 months, at least about 5 months, or at least about 6 months.

In a specific embodiment, a formulation of the invention comprises at least about 150 mg/ml of an anti-ICOS antibody described herein, wherein the formulation is stable upon storage at about 5° C. for at least about 6 months, at least about 7 months, at least about 8 months, at least about 9 months, at least about 1 year, at least about 2 years, or at least about 3 years.

5.19.2. Antibody Half-Life

In certain embodiments, the half-life of an anti-ICOS antibody of compositions and methods of the invention is at least about 4 to 7 days. In certain embodiments, the mean half-life of an anti-ICOS antibody of compositions and methods of the invention is at least about 2 to 5 days, 3 to 6 days, 4 to 7 days, 5 to 8 days, 6 to 9 days, 7 to 10 days, 8 to 11 days, 8 to 12, 9 to 13, 10 to 14, 11 to 15, 12 to 16, 13 to 17, 14 to 18, 15 to 19, or 16 to 20 days. In other embodiments, the mean half-life of an anti-ICOS antibody of compositions and methods of the invention is at least about 17 to 21 days, 18 to 22 days, 19 to 23 days, 20 to 24 days, 21 to 25, days, 22 to 26 days, 23 to 27 days, 24 to 28 days, 25 to 29 days, or 26 to 30 days. In still further embodiments the half-life of an anti-ICOS antibody of compositions and methods of the invention can be up to about 50 days. In certain embodiments, the half-lives of antibodies of compositions and methods of the invention can be prolonged by methods known in the art. Such prolongation can in turn reduce the amount and/or frequency of dosing of the antibody compositions. Antibodies with improved in vivo half-lives and methods for preparing them are disclosed in U.S. Pat. No. 6,277,375; and International Publication Nos. WO 98/23289 and WO 97/3461.

The serum circulation of anti-ICOS antibodies in vivo may also be prolonged by attaching inert polymer molecules such as high molecular weight polyethyleneglycol (PEG) to the antibodies with or without a multifunctional linker either through site-specific conjugation of the PEG to the N- or C-terminus of the antibodies or via epsilon-amino groups present on lysyl residues. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods known to those of skill in the art, for example, by immunoassays described herein.

Further, the antibodies of compositions and methods of the invention can be conjugated to albumin in order to make the antibody more stable in vivo or have a longer half-life in vivo. The techniques are well known in the art, see, e.g., International Publication Nos. WO 93/15199, WO 93/15200, and WO 01/77137; and European Patent No. EP 413, 622, all of which are incorporated herein by reference.

Additionally, variant Fc regions that confer increased in vivo half-life on antibodies has been described (see, US Patent Publication No: US2003/0190311 A1). The use of Fc variants with extended in vivo half-life in combination with the compositions and methods of the current invention is contemplated. In one embodiment, an anti-ICOS antibody of the invention comprises a variant Fc region with increased in vivo half-life. In a further embodiment, an anti-ICOS antibody of the invention comprises a varian tfc region comprising at least one substitution of an amino acid residue selected from the group consisting of: residue 252, 254, and 256, wherein the amino acid residue positions are determined according to the EU convention. In a specific embodiment, an anti-ICOS antibody of the invention comprises a variant Fc region comprising at least one amino acid substitution selected from the group consisiting of: M252Y, S254T, and T256E; wherein the amino acid residue positions are determined according to the EU convention. In a further embodiment, an anti-ICOS antibody of the invention comprises a variant Fc region comprising at least one amino acid residue selected from the group consisting of: Y at position 252, T at position 254, and E at position 256; wherein the amino acid residue positions are determined according to the EU convention.

5.19.3. Administration and Dosing

Administration of compositions of the invention to a human patient can be by any route, including but not limited to intravenous, intradermal, transdermal, subcutaneous, intramuscular, inhalation (e.g., via an aerosol), buccal (e.g., sub-lingual), topical (i.e., both skin and mucosal surfaces, including airway surfaces), intrathecal, intraarticular, intraplural, intracerebral, intra-arterial, intraperitoneal, oral, intralymphatic, intranasal, rectal or vaginal administration, by perfusion through a regional catheter, or by direct intralesional injection. In one embodiment, compositions of the invention are administered by intravenous push or intravenous infusion given over defined period (e.g., 0.5 to 2 hours). Compositions of the invention can be delivered by peristaltic means or in the form of a depot, although the most suitable route in any given case will depend, as is well known in the art, on such factors as the species, age, gender and overall condition of the subject, the nature and severity of the condition being treated and/or on the nature of the particular composition (i.e., dosage, formulation) that is being administered. In particular embodiments, the route of administration is via bolus or continuous infusion over a period of time, once or twice a week. In other particular embodiments, the route of administration is by subcutaneous injection, optionally once or twice weekly. In one embodiment, compositions, and/or methods of the invention are administered on an outpatient basis.

In certain embodiments, the dose of a composition comprising anti-ICOS antibody is measured in units of mg/kg of patient body weight. In other embodiments, the dose of a composition comprising anti-ICOS antibody is measured in units of mg/kg of patient lean body weight (i.e., body weight minus body fat content). In yet other embodiments, the dose of a composition comprising anti-ICOS antibody is measured in units of mg/m$^2$ of patient body surface area. In yet other embodiments, the dose of a composition comprising anti-ICOS antibody is measured in units of mg per dose administered to a patient. Any measurement of dose can be used in conjunction with compositions and methods of the invention and dosage units can be converted by means standard in the art.

Those skilled in the art will appreciate that dosages can be selected based on a number of factors including the age, sex, species and condition of the subject (e.g., stage of disease), the desired degree of cellular depletion, the disease to be treated and/or the particular antibody or antigen-binding fragment being used and can be determined by one of skill in the art. For example, effective amounts of compositions of the invention may be extrapolated from dose-response curves derived in vitro test systems or from animal model (e.g., the cotton rat or monkey) test systems. Models and methods for evaluation of the effects of antibodies are known in the art (Wooldridge et al., *Blood*, 89(8): 2994-2998 (1997)), incorporated by reference herein in its entirety). In certain embodiments, for particular ICOS expressing T cell malignancies, therapeutic regimens standard in the art for antibody therapy can be used with compositions and methods of the invention.

Examples of dosing regimens that can be used in methods of the invention include, but are not limited to, daily, three times weekly (intermittent), weekly, or every 14 days. In certain embodiments, dosing regimens include, but are not limited to, monthly dosing or dosing every 6-8 weeks.

Those skilled in the art will appreciate that dosages are generally higher and/or frequency of administration greater for initial treatment as compared with maintenance regimens.

In some embodiments of the invention, anti-ICOS antibodies bind to ICOS expressing T cells and may result in efficient (i.e., at low dosage) depletion of ICOS expressing T cells (as described herein). In certain embodiments, dosages of the antibody (optionally in a pharmaceutically acceptable carrier as part of a pharmaceutical composition) are at least about 0.0005, 0.001, 0.05, 0.075, 0.1, 0.25, 0.375, 0.5, 1, 2.5, 5, 10, 20, 37.5, or 50 mg/m$^2$ and/or less than about 500, 475, 450, 425, 400, 375, 350, 325, 300, 275, 250, 225, 200, 175, 150, 125, 100, 75, 60, 50, 37.5, 20, 15, 10, 5, 2.5, 1, 0.5, 0.375, 0.1, 0.075 or 0.01 mg/m$^2$. In certain embodiments, the dosage is between about 0.0005 to about 200 mg/m$^2$, between about 0.001 and 150 mg/m$^2$, between about 0.075 and 125 mg/m$^2$, between about 0.375 and 100 mg/m$^2$, between about 2.5 and 75 mg/m$^2$, between about 10 and 75 mg/m$^2$, and between about 20 and 50 mg/m$^2$. In related embodiments, the dosage of anti-ICOS antibody used is at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5 mg/kg of body weight of a patient. In certain embodiments, the dose of naked anti-ICOS antibody used is at least about 1 to 10, 5 to 15, 10 to 20, or 15 to 25 mg/kg of body weight of a patient. In certain embodiments, the dose of anti-ICOS antibody used is at least about 1 to 20, 3 to 15, or 5 to 10 mg/kg of body weight of a patient. In other embodiments, the dose of anti-ICOS antibody used is at least about 5, 6, 7, 8, 9, or 10 mg/kg of body weight of a patient. In certain embodiments, a single dosage unit of the antibody (optionally in a pharmaceutically acceptable carrier as part of a pharmaceutical composition) can be at least about 0.5, 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 204, 206, 208, 210, 212, 214, 216, 218, 220, 222, 224, 226, 228, 230, 232, 234, 236, 238, 240, 242, 244, 246, 248, or 250 micrograms/m$^2$. In other embodiments, dose is up to 1 g per single dosage unit.

In some embodiments of methods of this invention, antibodies and/or compositions of this invention can be administered at a dose lower than about 375 mg/m$^2$; at a dose lower than about 37.5 mg/m$^2$; at a dose lower than about 0.375 mg/m$^2$; and/or at a dose between about 0.075 mg/m$^2$ and about 125 mg/m$^2$. In certain embodiments of methods of the invention, dosage regimens comprise low doses, administered at repeated intervals. For example, in one embodiment, compositions of the invention can be administered at a dose lower than about 375 mg/m$^2$ at intervals of approximately every 1, 2, 3, 4, 5, 6, 7, 8, 9, 10, 15, 20, 25, 30, 35, 40, 45, 50, 60, 70, 80, 90, 100, 125, 150, 175, or 200 days.

The specified dosage can result in ICOS expressing T cell depletion in the human treated using compositions and methods of the invention for a period of at least about 1, 2, 3, 5, 7, 10, 14, 20, 30, 45, 60, 75, 90, 120, 150 or 180 days or longer. In certain embodiments of methods of the invention, ICOS expressing T cells are depleted by at least 30%, 40%, 50%, 60%, 70%, 80%, 90%, or 100% in comparison to ICOS expressing T cell levels in the patient being treated before use of compositions and methods of the invention. In other embodiments of methods of the invention, ICOS expressing T cells are depleted by at least 30%, 40%, 50%, 60%, 70%, 80%, 90%, or 100% in comparison to typical standard ICOS expressing T cell levels for humans. In related embodiments, the typical standard ICOS expressing T cell levels for humans are determined using patients comparable to the patient being treated with respect to age, sex, weight, and other factors.

In certain embodiments of the invention, a dosage of about 125 mg/m$^2$ or less of an antibody or antigen-binding fragment results in ICOS expressing T cell depletion for a period of at least about 7, 14, 21, 30, 45, 60, 90, 120, 150, or 200 days. In another representative embodiment, a dosage of about 37.5 mg/m$^2$ or less depletes ICOS expressing T cells for a period of at least about 7, 14, 21, 30, 45, 60, 90, 120, 150, or 200 days. In still other embodiments, a dosage of about 0.375 mg/m$^2$ or less results in depletion of ICOS expressing T cells for at least about 7, 14, 21, 30, 45 or 60 days. In another embodiment, a dosage of about 0.075 mg/m$^2$ or less results in depletion of ICOS expressing T cells for a period of at least about 7, 14, 21, 30, 45, 60, 90, 120, 150, or 200 days. In yet other embodiments, a dosage of about 0.01 mg/m$^2$, 0.005 mg/m$^2$ or even 0.001 mg/m$^2$ or less results in depletion of ICOS expressing T cells for at least about 3, 5, 7, 10, 14, 21, 30, 45, 60, 90, 120, 150, or 200 days. According to these embodiments, the dosage can be administered by any suitable route, but is optionally administered by a subcutaneous route.

As another aspect, the invention provides the discovery that ICOS expressing T cell depletion and/or treatment of T cell-mediated disorders can be achieved at lower dosages of antibody or antibody fragments than employed in currently available methods. Thus, in another embodiment, the invention provides a method of depleting ICOS expressing T cells and/or treating a T cell-mediated disorder, comprising administering to a human, an effective amount of an antibody that specifically binds to ICOS, wherein a dosage of about 500, 475, 450, 425, 400, 375, 350, 325, 300, 275, 250, 225, 200, 175, 150, 125, 100, 75, 60, 50, 37.5, 20, 10, 5, 2.5, 1, 0.5, 0.375, 0.25, 0.1, 0.075, 0.05, 0.001, 0.0005 mg/m$^2$ or less results in a depletion of ICOS expressing T cells (circulating and/or tissue ICOS expressing T cells) of 25%, 35%, 50%, 60%, 75%, 80%, 85%, 90%, 95%, 98% or more for a period at least about 3, 5, 7, 10, 14, 21, 30, 45, 60, 75, 90, 120, 150, 180, or 200 days or longer. In representative embodiments, a dosage of about 125 mg/m$^2$ or 75 mg/m$^2$ or less results in at least about 50%, 75%, 85% or 90% depletion of ICOS expressing T cells for at least about 7, 14, 21, 30, 60, 75, 90, 120, 150 or 180 days. In other embodiments, a dosage of about 50, 37.5 or 10 mg/m$^2$ results in at least about a 50%, 75%, 85% or 90% depletion of ICOS expressing T cells for at least about 7, 14, 21, 30, 60, 75, 90, 120 or 180 days. In still other embodiments, a dosage of about 0.375 or 0.1 mg/m$^2$ results in at least about a 50%, 75%, 85% or 90% depletion of ICOS expressing T cells for at least about 7, 14, 21, 30, 60, 75 or 90 days. In further embodiments, a dosage of about 0.075, 0.01, 0.001, or 0.0005 mg/m$^2$ results in at least about a 50%, 75%, 85% or 90% depletion of ICOS expressing T cells for at least about 7, 14, 21, 30 or 60 days.

In certain embodiments of the invention, the dose can be escalated or reduced to maintain a constant dose in the blood or in a tissue, such as, but not limited to, bone marrow. In related embodiments, the dose is escalated or reduced by about 2%, 5%, 8%, 10%, 15%, 20%, 30%, 40%, 50%, 60%, 70%, 80%, 90%, and 95% in order to maintain a desired level of an antibody of compositions and methods of the invention.

In certain embodiments, the dosage can be adjusted and/or the infusion rate can be reduced based on patient's immunogenic response to compositions and methods of the invention.

5.19.4. Toxicity Testing

The tolerance, toxicity and/or efficacy of the compositions and/or treatment regimens of the present invention can be determined by standard pharmaceutical procedures in cell cultures or experimental animals, e.g., for determining the LD50 (the dose lethal to 50% of the population), the ED50 (the dose therapeutically effective in 50% of the population), and IC50 (the dose effective to achieve a 50% inhibition). In one embodiment, the dose is a dose effective to achieve at least a 60%, 70%, 80%, 90%, 95%, or 99% depletion of circulating ICOS expressing T cells. The dose ratio between toxic and therapeutic effects is the therapeutic index and it can be expressed as the ratio LD50/ED50. Therapies that exhibit large therapeutic indices may be preferred. While therapies that exhibit toxic side effects may be used, care should be taken to design a delivery system that targets such agents to ICOS-expressing cells in order to minimize potential damage to ICOS negative cells and, thereby, reduce side effects.

Data obtained from the cell culture assays and animal studies can be used in formulating a range of dosages of the compositions and/or treatment regimens for use in humans. The dosage of such agents may lie within a range of circulating concentrations that include the ED50 with little or no toxicity. The dosage may vary within this range depending upon the dosage form employed and the route of administration utilized. For any therapy used in methods of the invention, a therapeutically effective dose can be estimated by appropriate animal models. Depending on the species of the animal model, the dose can be scaled for human use according to art-accepted formulas, for example, as provided by Freireich et al., Quantitative comparison of toxicity of anticancer agents in mouse, rat, monkey, dog, and human, *Cancer Chemotherapy Reports*, NCI 1966 40:219-244. Data obtained from cell culture assays can be useful for predicting potential toxicity. Animal studies can be used to formulate a specific dose to achieve a circulating plasma concentration range that includes the IC50 (i.e., the concentration of the test compound that achieves a half-maximal inhibition of symptoms) as determined in cell culture. Such information can be used to more accurately determine useful doses in humans. Plasma drug levels may be measured, for example, by high performance liquid chromatography, ELISA, or by cell based assays.

5.20. Therapeutic Uses

Compositions comprising an anti-ICOS antibody with enhanced effector function may be used for the treatment of autoimmune diseases, such as systemic lupus erythematosis, rheumatoid arthritis, multiple sclerosis, diabetes, immune thrombocytopenic purpura (ITP), and psoriasis; chronic inflammatory diseases, such as inflammatory bowel disease (Crohn's disease and ulcerative colitis), Grave's disease, Hashimoto's thyroiditis, and diabetes mellitis. Anti-ICOS compositions described herein may also be used to alleviate toxic shock syndrome, inflammatory bowel disease, allosensitization due to blood transfusions, T-cell dependent B-cell-mediated diseases, and the treatment of graft vs. host disease. In addition, compositions and methods of the invention may be useful in therapeutic indications that call for the inhibition or enhancement of antibody production.

Compositions comprising an anti-ICOS antibody with enhanced effector function may also be used as immunosuppressive agents for bone marrow and organ transplantation and may be used to prolong graft survival. Such compositions may provide significant advantages over existing treatment. Bone marrow and organ transplantation therapy must contend with T-cell-mediated rejection of the foreign cells or tissue by the host. Present therapeutic regimens for inhibiting T-cell-mediated rejection involve treatment with the drugs cyclosporine or FK506. While drugs are effective, patients suffer from serious side effects, including hepatotoxicity, nephrotoxicity, and neurotoxicity. The target for the cyclosporin/FK506 class of therapeutics is calcineurin, a phosphatase with ubiquitous expression. Since ICOS expression is restricted to T-cells, depletion of ICOS expressing T cells may lack the severe side effects observed with the use of the present immunotherapeutic agents.

Hypersensitivity is a normally beneficial immune response that is exaggerated or inappropriate, and leads to inflammatory reactions and tissue damage. Hypersensitivity reactions which are antibody-mediated may be particularly susceptible to antagonism by depletion of ICOS expressing cells. Allergies, hay fever, asthma, and acute edema cause type I hypersensitivity reactions, and these reactions may be suppressed by depletion of ICOS expressing cells.

Diseases that cause antibody-mediated hypersensitivity reactions, including systemic lupus erythematosis, arthritis (rheumatoid arthritis, reactive arthritis, psoriatic arthritis), nephropathies (glomerulo-nephritis, membranous, mesangiocapillary, focal segmental, focal necrotizing, crescentic, proliferative—tubulopathies), skin disorders (pemphigus and pemphigoid, erythema nodosum), endocrinopathies (thyroiditis—Grave's, Hashimoto's—insulin dependent diabetes mellitus), various pneumopathies (especially extrinsic alveolitis), various vasculopathies, coeliac disease, with aberrant production of IgA, many anemias and thrombocytopenias, Guillain-Barre Syndrome, and myasthenia gravis, may be treated using compositions comprising an anti-ICOS antibody with enhanced effector function.

In addition, lymphoproliferative disorders, such as multiple myeloma, Waldenstrom's macroglobulinemia, and crioglobulinemias may be inhibited by administering a composition comprising an anti-ICOS antibody with enhanced effector function. Additionaly, graft versus host disease, an "artificial" immune disorder, may benefit from the depletion of ICOS expressing cells.

The ICOS dependent co-stimulatory pathway is involved in regulating IgE production. IgE is an immunoglobulin isotype specifically involved in mediating allergic responses such as asthma, food allergies, hay fever, type 1 hypersensitivity and sinus inflammation. Upon exposure to an allergen, a process involving T-cell and B cell collaboration results in B cell production of IgE specific for the allergen. Allergen-specific IgE released into the circulation by B cells bind to mast cells and basophils through the high affinity IgE receptor (FceRI). Mast cells and basophils to which IgE is bound become sensitized and subsequent exposure to the allergen results in cross-linking of the surface receptors and release of histamines.

The invention provides for the use of an anti-ICOS antibody to regulate IgE production and to prevent or treat IgE-mediated disorders. By way of example, such disorders include allergic responses such as asthma, food allergies, hay fever, hypersensivity, and sinus inflammation. In one embodiment, an anti-ICOS antibody of the invention is used to partially or completely inhibit IgE production. An anti-ICOS antibody of the invention may be used separately, or in combination, in a treatment regimen for decreasing IgE levels.

The invention also provides for the use of an anti-ICOS antibody in combination with an IgE antagonist to partially or completely inhibit IgE production and to prevent and/or treat disorders characterized by excessive or inappropriate IgE production. As used herein the term "IgE antagonist" refers to a compound capable of disrupting or blocking the interaction of IgE with its high affinity receptor FceRI on cells such that the response to allergen stimulus is attenuated or eliminated. Antagonists include an anti-IgE antibody and fragments thereof, soluble FceRI receptor and fragments thereof, anti-FceRI antibody and fragments thereof, IgE variants and fragments thereof, IgE binding peptides, FceRI receptor binding peptides, and small molecules capable of binding to IgE or competing with IgE for binding to FceRI receptor. An anti-ICOS antibody of the invention may also be used with in combination with antihistamines, allergen desensitization, reduction in exposure to allergen and the like for treatment of allergic disorders.

The invention also provides for the prevention and/or treatment of asthma comprising administering an anti-ICOS antibody of the invention alone or in conjunction with one or more agents for treating asthma. Examples of such agents include bronchodilators (anti-cholinergic agents, .beta-2 adrenergic receptor agonists, lenkotriene D-4 antagonists, neurokinin antagonists, potassium channel openers, substance P antagonists, thromboxane A-2 antagonists, and xanthines), anti-inflammatories (5-lipoxygenase inhibitors, 5-lipoxygenase activating protein inhibitors, phosphodiesterase IV inhibitors, platelet activating factor antagonists, respiratory NSAIDS, steroids, and tyrosine kinase inhibitors), cytokine inhibitors (CD4, IL-4 and IL-5 inhibitors) and IgE antagonists as set forth above.

Compositions and methods according to this invention are able to control (suppress or stimulate) proliferation of ICOS expressing cells or production of cytokine (for example, IL-17) by ICOS expressing cells, thereby enabling suppression of various pathological conditions and treatment or prevention of various disorders caused by diverse physiological phenomena related to signal transduction mediated by ICOS.

Compositions comprising an anti-ICOS antibody of this invention enables suppression, prevention and/or treatment of, for example, but not limited to, rheumatoid arthritis, multiple sclerosis, autoimmune thyroiditis, allergic contact-type dermatitis, chronic inflammatory dermatosis (e.g., lichen planus), systemic lupus erythematosus, insulin-dependent diabetes mellitus, psoriasis, autoimmune or allergic disorders, autoimmune disease and delayed allergy caused by cellular immunity; arthropathia (for example, but not limited to, rheumatoid arthritis (RA) and osteoarthritis (OA)), inflammation (e.g., hepatitis), graft versus host reaction (GVH reaction), graft versus host disease (GVHD), immune rejection accompanying transplantation of a tissue (e.g., skin, cornea, bone) or organ (e.g., liver, heart, lung, kidney, pancreas), immune response triggered by a foreign antigen or autoantigen (for example, production of antibodies against said antigen, cell proliferation, production of cytokines), and disorders caused by the abnormal intestinal immunity (e.g., inflammatory intestinal disorders, Crohn's disease, ulcerative colitis, alimentary allergy).

Furthermore, compositions and methods described herein may be utilized for the suppression/treatment of transplant rejection or GVHD in combination with known immunosuppressive agents such as inhibitors of cytokine transcription (e.g., cyclosporin A, tacrolimus), nucleotide synthesis (e.g., azathiopurine, mycophenolate mofetil), growth factor signal transduction (e.g., sirolimus, rapamycin), and the T cell interleukin 2 receptor (e.g., daclizumab, basiliximab). In a particular embodiment, an immunosuppressant agent used in combination with compositions and methods of the invention includes one or more of the following: adriamycin, azathiopurine, busulfan, cyclophosphamide, cyclosporin A ("CyA"), cytoxin, fludarabine, 5-fluorouracil, methotrexate, mycophenolate mofetil (MOFETIL), nonsteroidal anti-inflammatories (NSAIDs), rapamycin, and tacrolimus (FK506).

The compositions and methods of the present invention can be applied to inflammatory disease for example, inflammation accompanying various arthritis (for example, rheumatoid arthritis, osteoarthritis), pneumonia, hepatitis (including viral hepatitis), inflammation accompanying infectious diseases, inflammatory bowel diseases, intestinal enteritis, nephritis (e.g., glomerular nephritis, nephrofibrosis), gastritis, angiitis, pancreatitis, peritonitis, bronchitis, myocarditis, cerebritis, inflammation in postischemic reperfusion injury (myocardial ischemic reperfusion injury), inflammation attributed to immune rejection after transplantation of tissue and organ, burn, various skin inflammation (psoriasis, allergic contact-type dermatitis, lichen planus), inflammation in multiple organ failure, inflammation after operation of PTCA or PTCR, and inflammation accompanying arteriosclerosis, and autoimmune thyroiditis.

Compositions of the invention comprising an anti-ICOS antibody with enhanced effector function as an active ingredient may be used to inhibit, treat and/or prevent a variety of diseases, for example, but not limited to rheumatoid arthritis, multiple sclerosis, autoimmune thyroiditis, allergic contact dermatitis, lichen planus, systemic lupus erythematosus, insulin dependent diabetes mellitus, psoriasis, autoimmune diseases or allergic diseases, delayed allergies mediated by cellular immunity; arthropathies (e.g., rheumatoid arthritis (RA), osteoarthritis (OA)), inflammation (e.g., hepatitis), graft versus host reaction (GVH reaction), graft versus host disease (GVHD), immunorejection associated with transplantation of tissues (e.g., skin, cornea and bone) or organs (e.g., liver, heart, lung, kidney, pancreas), inflammatory bowel disease, Crohn's disease, ulcerative colitis, and alimentary allergy.

The compositions in accordance with the present invention make it possible to treat or prevent some inflammations for which various steroidal drugs are used as anti-inflammatory drugs, for example, inflammation associated with various arthritides (e.g., rheumatoid arthritis, osteoarthritis), pneumonia, hepatitis (including viral hepatitis), inflammation associated with infectious diseases, inflammatory bowel disease, enteritis, nephritis, glomerular nephritis, inflammation associated with kidney fibrosis, gastritis, vasculitis, pancreatitis, peritonitis, bronchitis, myocarditis, encephalitis, inflammation associated with ischemia-reperfusion injury, myocaridial ischemia-reperfusion injury, inflammation associated with immunorejection after transplantation of tissues or organs, psoriasis, allergic contact dermatitis, lichen planus, inflammation associated with multiple organ failure, inflammation after operation of PTCA or PTCR, inflammation associated with atherosclerosis, and autoimmune thyroiditis.

5.21. Transplantation

According to certain aspects of the invention, the treatment regimen and dose used with compositions and methods of the invention is chosen based on a number of factors including, for example, clinical manifestation that place a patient at risk for developing transplant rejection, or clinical evidence that such a rejection is developing.

The present invention provides compositions, therapeutic formulations, methods and regimens effective to reduce the incidence, severity, or duration of GVHD, a rejection episode, or post-transplant lymphoproliferative disorder. In certain embodiments, compositions and methods of the invention are effective to attenuate the host response to ischemic reperfusion injury of a solid tissue or organ graft. In one embodiment, compositions and methods of the invention are effective to prolong survival of a graft in a transplant recipient.

The present invention encompasses grafts that are autologous, allogeneic, or xenogeneic to the recipient. The types of grafts encompassed by the invention include tissue and organ grafts, including but not limited to, bone marrow grafts, peripheral stem cell grafts, skin grafts, arterial and venous grafts, pancreatic islet cell grafts, and transplants of the kidney, liver, pancreas, thyroid, and heart. The terms "graft" and "transplant" are used interchangeably herein. In one embodiment, the autologous graft is a bone marrow graft, an arterial graft, a venous graft or a skin graft. In one embodiment, the allograft is a bone marrow graft, a corneal graft, a kidney transplant, a pancreatic islet cell transplant, or a combined transplant of a kidney and pancreas. In one embodiment, the graft is a xenograft, wherein the possible animal donors include, but are not limited to pigs. The compositions and methods of the present invention may also be used to suppress a deleterious immune response to a non-biological graft or implant, including but not limited to an artificial joint, a stent, or a pacemaker device.

Anti-ICOS antibodies, compositions, and methods of the invention may be used to treat or prevent GVHD, rejection, or post-transplant lymphoproliferative disorder without regard to the particular indications initially giving rise to the need for the transplant or the particular type of tissue transplanted.

Therapeutic formulations and regimens of the present invention are described for treating human subjects diagnosed with autoimmune diseases or disorders, including but not limited to, rheumatoid arthritis, SLE, ITP, pemphigus-related disorders, diabetes, and scleroderma.

Appropriate treatment regimens can be determined by one of skill in the art for the particular patient or patient population. In particular embodiments, the treatment regimen is a pre-transplant conditioning regimen, a post-transplant maintenance regimen, or post-transplant treatment regimen for an acute or a chronic rejection. In certain embodiments, the particular regimen is varied for a patient who is assessed as being at a high or intermediate risk of developing a rejection response, compared with the regimen for a patient who is assessed as being at a low risk of rejection.

In certain embodiments, the particular regimen is varied according to the stage of rejection, with more aggressive therapy being indicated for patients at later stages of rejection. The stages of humoral rejection may be classified according to the knowledge and skill in the art. For example, the stages of humoral rejection may be classified as one of stages I to IV according to the following criteria: Stage I Latent Response, characterized by circulating anti-donor alloantibodies, especially anti-HLA antibodies; Stage II Silent Reaction, characterized by circulating anti-donor alloantibodies, especially anti-HLA antibodies, and C4d deposition, but without histologic changes or graft dysfunction; Stage III Subclinical Rejection: characterized by circulating anti-donor alloantibodies, especially anti-HLA antibodies, C4d deposition, and tissue pathology, but without graft dysfunction; Stage IV Humoral Rejection: characterized by circulating anti-donor alloantibodies, especially anti-HLA antibodies, C4d deposition, tissue pathology, and graft dysfunction.

Anti-ICOS antibodies, compositions and methods of the invention may be practiced to treat or prevent GVHD, rejection, or post-transplantation lymphoproliferative disorders, either alone or in combination with other therapeutic agents or treatment regimens. Other therapeutic regimens for the treatment or prevention of GVHD, rejection, or post-transplantation lymphoproliferative disorders may comprise, for example, one or more of anti-lymphocyte therapy, steroid therapy, antibody depletion therapy, immunosuppression therapy, and plasmapheresis.

Anti-lymphocyte therapy may comprise the administration to the transplant recipient of anti-thymocyte globulins, also referred to as thymoglobulin. Anti-lymphocyte therapy may also comprise the administration of one or more monoclonal antibodies directed against T cell surface antigens. Examples of such antibodies include, without limitation, OKT3™ (muromonab-CD3), CAMPATH™-1H (alemtuzumab), CAMPATH™-1G, CAMPATH™-1M, SIMULECT™ (basiliximab), and ZENAPAX™ (daclizumab). In a specific embodiment, the anti-lymphocyte therapy comprises one or more antibodies directed against B cells, including, without limitation, RITUXAN™ (rituximab).

Steroid therapy may comprise administration to the transplant recipient of one or more steroids selected from the group consisting of cortisol, prednisone, methyl prednisolone, dexamethazone, and indomethacin. One or more of the steroids may be corticosteroids, including without limitation, cortisol, prednisone, and methylprednisolone.

Antibody depletion therapy may include, for example, administration to the transplant recipient of intravenous immunoglobulin. Antibody depletion therapy may also comprise immunoadsorption therapy applied to the graft ex vivo, prior to transplantation. Immunoadsorption may be accomplished using any suitable technique, for example, protein A affinity, or antibody based affinity techniques using antibodies directed against T cell or B cell surface markers such as anti-CD3 antibodies, anti-CD19 antibodies, anti-CD20 antibodies, and anti-CD22 antibodies.

Immunosuppression therapy may comprise the administration of one or more immunosuppressive agents such as inhibitors of cytokine transcription (e.g., cyclosporin A, tacrolimus), nucleotide synthesis (e.g., azathiopurine, mycophenolate mofetil), growth factor signal transduction (e.g., sirolimus, rapamycin), and the T cell interleukin 2 receptor (e.g., daclizumab, basiliximab). In a particular embodiment, an immunosuppressant agent used in combination with compositions and methods of the invention includes one or more of the following: adriamycin, azathiopurine, busulfan, cyclophosphamide, cyclosporin A ("CyA"), cytoxin, fludarabine, 5-fluorouracil, methotrexate, mycophenolate mofetil (MOFETIL), nonsteroidal anti-inflammatories (NSAIDs), rapamycin, and tacrolimus (FK506). Immunosuppressive agents may also comprise inhibitors of complement, for example, soluble complement receptor-1, anti-C5 antibody, or a small molecule inhibitor of C1s, for example as described in Buerke et al. (*J. Immunol.*, 167:5375-80 (2001).

In one embodiment, compositions and methods of the invention are used in combination with one or more therapeutic regimens for suppressing rejection, including, without limitation, tacrolimus and mycophenolate mofetil therapy, immunoadsorption, intravenous immunoglobulin therapy, and plasmapheresis.

5.22. Inflammatory Disorder

Anti-ICOS antibodies of the invention may be administered to a subject in need thereof to prevent, manage, treat or ameliorate an inflammatory disorder (e.g., asthma) or one or more symptoms thereof. Compositions of the invention may also be administered in combination with one or more other therapies, preferably therapies useful for the prevention, management, treatment or amelioration of an inflammatory disorder (including, but not limited to the prophylactic or therapeutic agents listed herein) to a subject in need thereof to prevent, manage, treat or ameliorate an inflammatory disorder or one or more symptoms thereof. In a specific embodiment, the invention provides a method of preventing, managing, treating or ameliorating an inflammatory disorder or one or more symptoms thereof, said method comprising administering to a subject in need thereof a dose of a prophylactically or therapeutically effective amount of an anti-ICOS antibody of the invention. In another embodiment, the invention provides a method of preventing, managing, treating or ameliorating an inflammatory disorder or one or more symptoms thereof, said method comprising administering to a subject in need thereof a dose of a prophylactically or therapeutically effective amount of an effector function enhanced anti-ICOS antibody of the invention and a dose of a prophylactically or therapeutically effective amount of one or more therapies (e.g., prophylactic or therapeutic agents) other than antibodies (including antibody fragments thereof) that immunospecifically bind to an ICOS polypeptide.

The invention provides methods for managing, treating or ameliorating one or more symptoms of an inflammatory disorder in a subject refractory to conventional therapies (e.g., methotrexate and a TNF-alpha antagonist (e.g., REMICADE™ or ENBREL™)) for such an inflammatory disorder, said methods comprising administering to said subject a dose of a prophylactically or therapeutically effective amount of an effector function enhanced anti-ICOS antibody of the invention. The invention also provides methods for managing, treating or ameliorating one or more symptoms of an inflammatory disorder in a subject refractory to existing single agent therapies for such an inflammatory disorder, said methods comprising administering to said subject a dose of a prophylactically or therapeutically effective amount of an effector function enhanced anti-ICOS antibody of the invention and a dose of a prophylactically or therapeutically effective amount of one or more therapies (e.g., prophylactic or therapeutic agents) other than antibodies (including antibody fragments thereof) that immunospecifically bind to an ICOS polypeptide. The invention also provides methods for managing or treating an inflammatory disorder by administering an effector function enhanced anti-ICOS antibody of the invention in combination with any other treatment to patients who have proven refractory to other treatments but are no longer on these treatments. The invention also provides alternative methods for the treatment of an inflammatory disorder where another therapy has proven or may prove too toxic, i.e., results in unacceptable or unbearable side effects, for the subject being treated. For example, a composition of the invention may be administered to a subject, wherein the subject is refractory to a TNF antagonist or methotrexate. Further, the invention provides methods for preventing the recurrence of an inflammatory disorder in patients that have been treated and have no disease activity by administering an effector function enhanced anti-ICOS antibody of the invention.

Inflammatory disorders that can be treated by the methods encompassed by the invention include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, osteoarthritis, spondyloarthropathies (e.g., psoriatic arthritis, ankylosing spondylitis, Reiter's Syndrome (reactive arthritis), inflammatory osteolysis, Wilson's disease and chronic inflammation resulting from chronic viral or bacteria infections. As described herein, some autoimmune disorders are associated with an inflammatory condition.

Anti-inflammatory therapies and their dosages, routes of administration and recommended usage are known in the art and have been described in such literature as the Physician's Desk Reference (61th ed., 2007).

5.22.1. Anti-Inflammatory Therapies

The present invention provides methods of preventing, managing, treating or ameliorating an inflammatory disorder or one or more symptoms thereof, said methods comprising administering to a subject in need thereof an effector function enhanced anti-ICOS antibody of the invention and one or more therapies (e.g., prophylactic or therapeutic agents other than antibodies (including antibody fragments thereof) that immunospecifically bind to an ICOS polypeptide. Any agent or therapy which is known to be useful, or which has been used or is currently being used for the prevention, management, treatment or amelioration of an inflammatory disorder or one or more symptoms thereof can be used in combination with an effector function enhanced anti-ICOS antibody of the invention in accordance with the invention described herein.

Any anti-inflammatory agent, including agents useful in therapies for inflammatory disorders, well-known to one of skill in the art can be used in the compositions and methods of the invention. Non-limiting examples of anti-inflammatory agents include non-steroidal anti-inflammatory drugs (NSAIDs), steroidal anti-inflammatory drugs, anticholinergics (e.g., atropine sulfate, atropine methylnitrate, and ipratropium bromide (ATROVENT™)), beta2-agonists (e.g., abuterol (VENTOLIN™ and PROVENTIL™), bitolterol (TORNALATE™), levalbuterol (XOPONEX™), metaproterenol (ALUPENT™), pirbuterol (MAXAIR™), terbutlaine (BRETHAIRE™ and BRETHINE™), albuterol (PROVENTIL™, REPETABS™, and VOLMAX™), formoterol (FORADIL AEROLIZER™), and salmeterol (SEREVEN™ and SEREVENT DISKUS™)), and methylxanthines (e.g., theophylline (UNIPHYL™, THEO-DUR™, SLO-BID™, AND TEHO-42™)). Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRON™) corticosteroids (e.g., methylprednisolone (MEDROL™)), cortisone, hydrocortisone, prednisone (PREDNISONE™ and DELTASONE™), prednisolone (PRELONE™ and PEDIAPRED™), triamcinolone, azulfidine, and inhibitors of eicosanoids (e.g., prostaglandins, thromboxanes, and leukotrienes).

In one embodiment, an effective amount of one or more compositions of the invention is administered in combination with a mast cell protease inhibitor to a subject at risk of or with an inflammatory disorder. In another embodiment, the mast cell protease inhibitor is a tryptase kinase inhibitor, such as, but not limited to GW-45, GW-58, and genisteine. In a specific embodiment, the mast cell protease inhibitor is phosphatidylinositide-3' (PI3)-kinase inhibitors, such as, but not limited to calphostin C. In another embodiment, the mast cell protease inhibitor is a protein kinase inhibitor such as, but not limited to staurosporine. In one embodiment, the mast cell protease inhibitor is administered locally to the affected area.

Specific examples of immunomodulatory agents which can be administered in combination with an effector function enhanced anti-ICOS antibody of the invention to a subject with an inflammatory disorder include, but are not limited to, methothrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies (e.g., MEDI-507 (Medlmmune, Inc., International Publication Nos. WO 02/098370 and WO 02/069904), anti-CD11a antibodies (e.g., Xanelim (Genentech)), and anti-B7 antibodies (e.g., IDEC-114) (IDEC)); anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-alpha antibodies, anti-IL-1beta antibodies, anti-IL-6 antibodies, anti-IL-8 antibodies (e.g., ABX-IL-8 (Abgenix)), and anti-IL-12 antibodies)); CTLA4-immunoglobulin; LFA-3TIP (Biogen, International Publication No. WO 93/08656 and U.S. Pat. No. 6,162,432); soluble cytokine receptors (e.g., the extracellular domain of a TNF-alpha receptor or a fragment thereof, the extracellular domain of an IL-1beta receptor or a fragment thereof, and the extracellular domain of an IL-6 receptor or a fragment thereof); cytokines or fragments thereof (e.g., interleukin (IL)-2, IL-3, IL-4, IL-5, IL-6, IL-7, IL-8, IL-9, IL-10, IL-11, IL-112, IL-15, TNF-alpha, TNF-beta, interferon (IFN)-alpha, IFN-beta, IFN-gamma, and GM-CSF); and anti-cytokine antibodies (e.g., anti-IL-2 antibodies, anti-IL-4 antibodies, anti-IL-6 antibodies, anti-IL-9 antibodies, anti-IL-10 antibodies, anti-IL-12 antibodies, anti-IL-15 antibodies, anti-IL17 antibodies, anti-TNF-alpha antibodies, and anti-IFN-gamma antibodies).

Any TNF-alpha antagonist well-known to one of skill in the art can be used in the compositions and methods of the invention. Non-limiting examples of TNF-alpha antagonists which can be administered in combination with an effector function enhanced anti-ICOS antibody of the invention to a subject with an inflammatory disorder include proteins, polypeptides, peptides, fusion proteins, antibodies (e.g., human, humanized, chimeric, monoclonal, polyclonal, Fvs, ScFvs, Fab fragments, F(ab)$_2$ fragments, and antigen-binding fragments thereof) such as antibodies that immunospecifically bind to TNF-alpha, nucleic acid molecules (e.g., antisense molecules or triple helices), organic molecules, inorganic molecules, and small molecules that blocks, reduces, inhibits or neutralizes the function, activity and/or expression of TNF-alpha. In various embodiments, a TNF-alpha antagonist reduces the function, activity and/or expression of TNF-alpha by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as phosphate buffered saline (PBS). Examples of antibodies that immunospecifically bind to TNF-alpha include, but are not limited to, infliximab (REMICADE™; Centacor), D2E7 (Abbott Laboratories/Knoll Pharmaceuticals Co., Mt. Olive, N.J.), CDP571 which is also known as HUMICADE™ and CDP-870 (both of Celltech/Pharmacia, Slough, U.K.), and TN3-19.12 (Williams et al., 1994, Proc. Natl. Acad. Sci. USA 91: 2762-2766; Thorbecke et al., 1992, Proc. Natl. Acad. Sci. USA 89:7375-7379). The present invention also encompasses the use of antibodies that immunospecifically bind to TNF-alpha disclosed in the following U.S. Patents in the compositions and methods of the invention: U.S. Pat. Nos. 5,136,021; 5,147,638; 5,223,395; 5,231,024; 5,334,380; 5,360,716; 5,426,181; 5,436,154; 5,610,279; 5,644,034; 5,656,272; 5,658,746; 5,698,195; 5,736,138; 5,741,488; 5,808,029; 5,919,452; 5,958,412; 5,959,087; 5,968,741; 5,994,510; 6,036,978; 6,114,517; and 6,171,787; each of which are herein incorporated by reference in their entirety. Examples of soluble TNF-alpha receptors include, but are not limited to, sTNF-R1 (Amgen), etanercept (ENBREL™; Immunex) and its rat homolog RENBREL™, soluble inhibitors of TNF-alpha derived from TNFrI, TNFrII (Kohno et al., 1990, Proc. Natl. Acad. Sci. USA 87:8331-8335), and TNF-alpha Inh (Seckinger et al, 1990, Proc. Natl. Acad. Sci. USA 87:5188-5192).

Other TNF-alpha antagonists encompassed by the invention include, but are not limited to, IL-10, which is known to block TNF-alpha production via interferon gamma-activated macrophages (Oswald et al. 1992, Proc. Natl. Acad. Sci. USA 89:8676-8680), TNFR-IgG (Ashkenazi et al., 1991, Proc. Natl. Acad. Sci. USA 88:10535-10539), the murine product TBP-1 (Serono/Yeda), the vaccine CytoTAb (Protherics), antisense molecule 104838 (ISIS), the peptide RDP-58 (SangStat), thalidomide (Celgene), CDC-801 (Celgene), DPC-333 (Dupont), VX-745 (Vertex), AGIX-4207 (Athero-Genics), ITF-2357 (Italfarmaco), NPI-13021-31 (Nereus), SCIO-469 (Scios), TACE targeter (Immunix/AHP), CLX- 120500 (Calyx), Thiazolopyrim (Dynavax), auranofin (Ridaura) (SmithKline Beecham Pharmaceuticals), quinacrine (mepacrine dichlorohydrate), tenidap (Enablex), Melanin (Large Scale Biological), and anti-p38 MAPK agents by Uriach.

Non-limiting examples of anti-inflammatory agents which can be administered in combination with an effector function enhanced anti-ICOS antibody of the invention to a subject with an inflammatory disorder include non-steroidal anti-inflammatory drugs (NSAIDs), steroidal anti-inflammatory drugs, beta-agonists, anticholingeric agents, and methyl xanthines. Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRON™) cortisone, hydrocortisone, prednisone (DELTASONE™), prednisolone, triamcinolone, azulfidine, and eicosanoids such as prostaglandins, thromboxanes, and leukotrienes.

In specific embodiments, patients with osteoarthritis are administered a prophylactically or therapeutically effective amount of an effector function enhanced anti-ICOS antibody of the invention in combination with other agents or therapies useful for osteoarthritis prevention, treatment, management or amelioration including but not limited to: analgesics (non-limiting examples are acetaminophen, in a dose up to 4000 mg/d; phenacetin; and tramadol, in a daily dose in the range of 200 to 300 mg); NSAIDs (non-limiting examples include but not limited to, aspirin, diflunisal, diclofenac, etodolac, fenamates, fenoprofen, flurbiprofen, ibuprofen, indomethacin, ketoprofen, methylsalicylate, nebumetone, naproxin, oxaprazin, phenylbutazone, piroxicam, sulindac, and tolmetin. Low dose NSAIDs are preferred, e.g., ibuprofen at 1200 mg/d, naproxen at 500 mg/d. A gastroprotective agent, e.g., misoprostol, famotidine or omeprazole, is preferred to use concurrently with a NSAID); nonacetylated salicylates including but not limited to salsalate; cyclooxygenase (Cox)-2-specific inhibitors (CSIs), including but not limited to, celecoxib and rofecoxib; intra- or periarticular injection of a depot glucocorticoid preparation; intra-articular injection of hyaluronic acid; capsaicin cream; copious irrigation of the osteoarthritis knee to flush out fibrin, cartilage shards and other debris; and joint replacement surgery. Compositions and methods of the invention can also be used in combination with other nonpharmacologic measures in prevention, treatment, management and amelioration of osteoarthritis including but not limited to: reduction of joint loading (non-limiting examples are correction of poor posture, support for excessive lumbar lordosis, avoid excessive loading of the involved joint, avoid prolonged standing, kneeling and squatting); application of heat to the affected joint; aerobic exercise and other physical therapies.

In specific embodiments, patients with rheumatoid arthritis are administered a prophylactically or therapeutically effective amount of an effector function enhanced anti-ICOS antibody of the invention in combination with other agents or therapies useful in prevention, treatment, management and amelioration of rheumatoid arthritis including but not limited to: NSAIDs (non-limiting examples include but not limited to, aspirin, diflunisal, diclofenac, etodolac, fenamates, fenoprofen, flurbiprofen, ibuprofen, indomethacin, ketoprofen, methylsalicylate, nebumetone, naproxin, oxaprazin, phenylbutazone, piroxicam, sulindac, and tolmetin); analgesics (non-limiting examples are acetaminophen, phenacetin and tramadol); CSIs including but not limited to, celecoxib and rofecoxib; glucocorticoids (preferably low-dose oral glucocorticoids, e.g., <7.5 mg/d prednisone, or monthly pulses with high-dose glucocorticoids, or intraarticular glucocorticoids); disease-modifying antirheumatic drugs (DMARDs) including but not limited to, methotrexate (preferably given intermittent low dose, e.g., 7.5-30 mg once weekly), gold compounds (e.g., gold salts), D-penicillamine, the antimalarials (e.g., chloroquine), and sulfasalazine; TNF-alpha neutralizing agents including but not limited to, etanercept and infliximab; immunosuppressive and cytotoxic agents (examples include but not limited to, azathioprine, leflunomide, cyclosporine, and cyclophosphamide), and surgery (examples include but not limited to, arthroplasties, total joint replacement, reconstructive hand surgery, open or arthroscopic synovectomy, and early tenosynovectomy of the wrist). The compositions and methods of the invention may also be used in combination with other measures in prevention, treatment, management and amelioration of the rheumatoid arthritis including but not limited to: rest, splinting to reduce unwanted motion of inflamed joint, exercise, used of a variety of orthotic and assistive devices, and other physical therapies. The compositions and methods of the invention may also be used in combination with some nontraditional approaches in prevention, treatment, management and amelioration of rheumatoid arthritis including but not limited to, diets (e.g., substituting omega-3 fatty acids such as eicosapentaenoic acid found in certain fish oils for dietary omega-6 essential fatty acids found in meat), vaccines, hormones and topical preparations.

In specific embodiments, patients with chronic obstructive pulmonary disease (COPD) are administered a prophylactically or therapeutically effective amount of an effector function enhanced anti-ICOS antibody of the invention in combination with other agents or therapies useful in prevention, treatment, management and amelioration of COPD including but not limited to: bronchodilators including but not limited to, short- and long-acting beta2-adrenergic agonists (examples of short-acting beta2 agonist include but not limited to, albuterol, pirbuterol, terbutaline, and metaproterenol; examples of long-acting beta2 agonist include but not limited to, oral sustained-release albuterol and inhaled salmeterol), anticholinergics (examples include but not limited to ipratropium bromide), and theophylline and its derivatives (therapeutic range for theophylline is preferably 10-20 .mu.g/mL); glucocorticoids; exogenous alpha1AT (e.g., alpha1AT derived from pooled human plasma administered intravenously in a weekly dose of 60 mg/kg); oxygen; lung transplantation; lung volume reduction surgery; endotracheal intubation, ventilation support; yearly influenza vaccine and pneumococcal vaccination with 23-valent polysaccharide; exercise; and smoking cessation.

In specific embodiments, patients with asthma are administered a prophylactically or therapeutically effective amount of an effector function enhanced anti-ICOS antibody of the invention in combination with an effective amount of one or more other agents useful for asthma therapy. Non-limiting examples of such agents include adrenergic stimulants (e.g., catecholamines (e.g., epinephrine, isoproterenol, and isoetharine), resorcinols (e.g., metaproterenol, terbutaline, and fenoterol), and saligenins (e.g., salbutamol)), adrenocorticoids, blucocorticoids, corticosteroids (e.g., beclomethadonse, budesonide, flunisolide, fluticasone, triamcinolone, methylprednisolone, prednisolone, and prednisone), other steroids, beta2-agonists (e.g., albtuerol, bitolterol, fenoterol, isoetharine, metaproterenol, pirbuterol, salbutamol, terbutaline, formoterol, salmeterol, and albutamol terbutaline), anticholinergics (e.g., ipratropium bromide and oxitropium bromide), IL-4 antagonists (including antibodies), IL-5 antagonists (including antibodies), IL-9 antagonists (including antibodies), IL-13 antagonists (including antibodies), IL__17 antagonists (including antibodies), PDE4-inhibitor, NF-Kappa-beta inhibitor, VLA-4 inhibitor, CpG, anti-CD23, selectin antagonists (TBC 1269), mast cell protease inhibitors (e.g., tryptase kinase inhibitors (e.g., GW-45, GW-58, and genisteine), phosphatidylinositide-3' (PI3)-kinase inhibitors (e.g., calphostin C), and other kinase inhibitors (e.g., staurosporine) (see Temkin et al., 2002 J Immunol 169(5):2662-2669; Vosseller et al., 1997 Mol. Biol. Cell 8(5):909-922; and Nagai et al., 1995 Biochem Biophys Res Commun 208(2): 576-581)), a C3 receptor antagonists (including antibodies), immunosuppressant agents (e.g., methotrexate and gold salts), mast cell modulators (e.g., cromolyn sodium (INTAL™) and nedocromil sodium (TILADE™)), and mucolytic agents (e.g., acetylcysteine)). In a specific embodiment, the anti-inflammatory agent is a leukotriene inhibitor (e.g., montelukast (SINGULAIR™), zafirlukast (ACCOLATE™), pranlukast (ONON™), or zileuton (ZYFLO™)).

In specific embodiments, patients with allergy are administered a prophylactically or therapeutically effective amount of an effector function enhanced anti-ICOS antibody of the invention in combination with an effective amount of one or more other agents useful for allergy therapy. Non-limiting examples of such agents include antimmediator drugs (e.g., antihistamine), corticosteroids, decongestants, sympathomimetic drugs (e.g., alpha-adrenergic and .beta-adrenergic drugs), TNX901 (Leung et al., N Engl J Med 348(11):986-993 (2003)), IgE antagonists (e.g., antibodies rhuMAb-E25 omalizumab (see Finn et al., 2003 J Allergy Clin Immuno 111(2):278-284; Corren et al., 2003 J Allergy Clin Immuno 111(1):87-90; Busse and Neaville, 2001 Curr Opin Allergy Clin Immuno 1(1):105-108; and Tang and Powell, 2001, Eur J Pediatr 160(12): 696-704), HMK-12 and 6HD5 (see Miyajima et al., 2202 Int Arch Allergy Immuno 128(1):24-32), and mAB Hu-901 (see van Neerven et al., 2001 Int Arch Allergy Immuno 124(1-3):400), theophylline and its derivatives, glucocorticoids, and immunotherapies (e.g., repeated long-term injection of allergen, short course desensitization, and venom immunotherapy).

5.23. Autoimmune Disease

According to certain aspects of the invention, the treatment regimen and dose used with compositions and methods of the invention is chosen based on a number of factors including, but not limited to, the stage of the autoimmune disease or disorder being treated. Appropriate treatment regimens can be determined by one of skill in the art for particular stages of an autoimmune disease or disorder in a patient or patient population. Dose response curves can be generated using standard protocols in the art in order to determine the effective amount of compositions of the invention for treating patients having different stages of a autoimmune disease or disorder. In general, patients having more activity of a autoimmune disease or disorder will require higher doses and/or more frequent doses which may be administered over longer periods of time in comparison to patients having less activity of an autoimmune disease or disorder.

Anti-ICOS antibodies, compositions and methods may be practiced to treat an autoimmune disease or disorder. The term "autoimmune disease or disorder" refers to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, including, but not limited to chronic inflammation. Autoimmune disorders may or may not be associated with inflammation. Moreover, inflammation may or may not be caused by an autoimmune disorder. Thus, certain disorders may be characterized as both autoimmune and inflammatory disorders. Exemplary autoimmune diseases or disorders include, but are not limited to: alopecia greata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, diabetes, eosinophilic fascites, fibromyalgia-fibromyositis, glomerulonephritis, Graves' disease, Guillain-Barre, Hashimoto's thyroiditis, Henoch-Schönlein purpura, idiopathic pulmonary fibrosis, idiopathic/autoimmune thrombocytopenia purpura (ITP), IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus-related disorders (e.g., pemphigus vulgaris), pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiffman syndrome, systemic lupus erythematosis (SLE), Sweet's syndrome, Still's disease, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, graft versus host disease, urticaria, Vogt-Koyanagi-Hareda syndrome and chronic inflammation resulting from chronic viral or bacteria infections.

5.23.1. Autoimmune Disorder Treatment

An effector function enhanced anti-ICOS antibody of the invention may be administered to a subject in need thereof to prevent, manage, treat or ameliorate an autoimmune disorder or one or more symptoms thereof. Compositions of the invention may also be administered in combination with one or more other therapies, preferably therapies useful for the prevention, management or treatment of an autoimmune disorder (including, but not limited to the prophylactic or therapeutic agents) to a subject in need thereof to prevent, manage, treat or ameliorate an autoimmune disorder or one or more symptoms thereof. In a specific embodiment, the invention provides a method of preventing, managing, treating or ameliorating an autoimmune disorder or one or more symptoms thereof, said method comprising administering to a subject in need thereof a dose of a prophylactically or therapeutically effective amount of an effector function enhanced anti-ICOS antibody of the invention. In another embodiment, the invention provides a method of preventing, managing, treating or ameliorating an autoimmune disorder or one or more symptoms thereof, said method comprising administering to a subject in need thereof a dose of a prophylactically or therapeutically effective amount of an effector function enhanced anti-ICOS antibody of the invention and a dose of a prophylactically or therapeutically effective amount of one or more therapies (e.g., prophylactic or therapeutic agents) other than antibodies (including antibody fragments thereof) that immunospecifically bind to an ICOS polypeptide.

The invention provides methods for managing, treating or ameliorating an autoimmune disorder or one or more symptoms thereof in a subject refractory to conventional therapies for such an autoimmune disorder, said methods comprising administering to said subject a dose of a prophylactically or therapeutically effective amount of an effector function enhanced anti-ICOS antibody of the invention. The invention also provides methods for managing, treating or ameliorating an autoimmune disorder or one or more symptoms thereof in a subject refractory to existing single agent therapies for such an autoimmune disorder, said methods comprising administering to said subject a dose of a prophylactically or therapeutically effective amount of an effector function enhanced anti-ICOS antibody of the invention and a dose of a prophylactically or therapeutically effective amount of one or more therapies (e.g., prophylactic or therapeutic agents) other than antibodies (including antibody fragments thereof) that immunospecifically bind to an ICOS polypeptide. The invention also provides methods for managing, treating or ameliorating an autoimmune disorder or one or more symptoms thereof by administering an effector function enhanced anti-ICOS antibody of the invention in combination with any other treatment to patients who have proven refractory to other treatments but are no longer on these treatments. The invention also provides alternative methods for the management or treatment of an autoimmune disorder where another therapy has proven or may prove too toxic, i.e., results in unacceptable or unbearable side effects, for the subject being treated. Particularly, the invention provides alternative methods for the management or treatment of an autoimmune disorder where the patient is refractory to other therapies. Further, the invention provides methods for preventing the recurrence of an autoimmune disorder in patients that have been treated and have no disease activity by administering an effector function enhanced anti-ICOS antibody of the invention.

Examples of autoimmune disorders that can be treated by the methods of the invention include, but are not limited to, alopecia greata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Mnire's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymy-algia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis.

Autoimmune therapies and their dosages, routes of administration and recommended usage are known in the art and have been described in such literature as the Physician's Desk Reference (61th ed., 2007).

5.23.2. Autoimmune Disorder Therapies

The present invention provides methods of preventing, managing, treating or ameliorating an autoimmune disorder or one or more symptoms thereof, said methods comprising administering to a subject in need thereof an effector function enhanced anti-ICOS antibody of the invention and one or more therapies (e.g., prophylactic or therapeutic agents) other than antibodies (including antibody fragments thereof) that immunospecifically bind to an ICOS polypeptide. Any agent or therapy which is known to be useful, or which has been used or is currently being used for the prevention, management, treatment or amelioration of an autoimmune disorder or one or more symptoms thereof can be used in combination with an effector function enhanced anti-ICOS antibody of the invention in accordance with the invention described herein. Examples of such agents include, but are not limited to, immunomodulatory agents, anti-inflammatory agents and TNF-alpha antagonists. Specific examples of immunomodulatory agents, anti-inflammatory agents and TNF-alpha antagonists which can be used in combination with an effector function enhanced anti-ICOS antibody of the invention for the prevention, management, treatment or amelioration of an autoimmune disorder are disclosed herein.

In specific embodiments, patients with multiple sclerosis (MS) are administered a prophylactically or therapeutically effective amount of an effector function enhanced anti-ICOS antibody of the invention in combination with other agents or therapies useful in prevention, treatment, management and amelioration of MS including but not limited to: IFN-beta1b (Betaseron) (e.g., 8.0 million international unites (MIU) is administered by subcutaneous injection every other day); IFN-beta1a (Avonex) (e.g., 6.0 MIU is administered by intramuscular injection once every week); glatiramer acetate (Copaxone) (e.g., 20 mg is administered by subcutaneous injection every day); mitoxantrone (e.g., 12 mg/m$^2$ is administered by intravenous infusion every third month); azathioprine (e.g., 2-3 mg/kg body weight is administered orally each day); methotrexate (e.g., 7.5 mg is administered orally once each week); cyclophosphamide; intravenous immunoglobulin (e.g., 0.15-0.2 g/kg body weight administered monthly for up to 2 years); glucocorticoids; methylprednisolone (e.g., administered in bimonthly cycles at high doses); 2-chlorodeoxyadenosine (cladribine); baclofen (e.g., 15 to 80 mg/d in divided doses, or orally in higher doses up to 240 mg/d, or intrathecally via an indwelling catheter); cycloenzaprine hydrochloride (e.g., 5-10 mg bid or tid); clonazepam (e.g., 0.5 to 1.0 mg tid, including bedtime dose); clonidine hydrochloride (e.g., 0.1 to 0.2 mg tid, including a bedtime dose); carbamazepine (e.g., 100-1200 mg/d in divided, escalating doses); gabapentin (e.g., 300-3600 mg/d); dilantin (e.g., 300-400 mg/d); amitriptyline (e.g., 25-150 mg/d); baclofen (e.g., 10-80 mg/d); primidone (e.g., 125-250 mg bid or tid); ondansetron (e.g., 4 to 8 mg bid or tid); isoniazid (e.g., up to 1200 mg in divided doses); oxybutynin (e.g., 5 mg bid or tid);

tolterodine (e.g., 1-2 mg bid); propantheline (e.g., 7.5 to 15 mg qid); bethanecol (e.g., 10-50 mg tid or qid); terazosin hydrochloride (e.g., 1-5 mg at bedtime); sildenafil citrate (e.g., 50-100 mg po prn); amantading (e.g., 100 mg bid); pemoline (e.g., 37.5 mg bid); high dose vitamins; calcium orotate; gancyclovir; antibiotic; and plasma exchange.

In specific embodiments, patients with psoriasis are administered a prophylactically or therapeutically effective amount of an effector function enhanced anti-ICOS antibody of the invention in combination with other agents or therapies useful in prevention, treatment, management and amelioration of psoriasis including but not limited to: topical steroid cream or ointment; tar (examples including but not limited to, Estar, Psorigel, Fototar cream, and LCD 10% in Nutraderm lotion or mixed directly with triamcinolone 0.1% cream); occlusion; topical vitamin D analogue (a non-limiting example is calcipotriene ointment); ultraviolet light; PUVA (psoralen plus ultraviolet A); methotrexate (e.g., up to 25 mg once weekly or in divided doses every 12 hours for three doses once a week); synthetic retinoid (a non-limiting examples is etretinate, e.g., in dosage of 0.5-1 mg/kg/d); immunomodulatory therapy (a non-limiting example is cyclosporine); sulfasalazine (e.g., in dosages of 1 g three times daily).

In specific embodiments, patients with Crohn's disease are administered a prophylactically or therapeutically effective amount of an effector function enhanced anti-ICOS antibody of the invention in combination with other agents or therapies useful in prevention, treatment, management and amelioration of Crohn's disease including but not limited to: antidiarrheals (e.g., loperamide 2-4 mg up to 4 times a day, diphenoxylate with atropine 1 tablet up to 4 times a day, tincture of opium 8-15 drops up to 4 times a day, cholestyramine 2-4 g or colestipol 5 g once or twice daily), antispasmodics (e.g., propantheline 15 mg, dicyclomine 10-20 mg, or hyoscyamine 0.125 mg given before meals), 5-aminosalicylic acid agents (e.g., sulfasalazine 1.5-2 g twice daily, mesalamine (ASACOL™) and its slow release form (PENTASA™), especially at high dosages, e.g., PENTASA™ 1 g four times daily and ASACOL™ 0.8-1.2 g four times daily), corticosteroids, immunomodulatory drugs (e.g., azathioprine (1-2 mg/kg), mercaptopurine (50-100 mg), cyclosporine, and methotrexate), antibiotics, TNF inhibitors (e.g., infliximab (REMICADE™)), immunosuppressive agents (e.g., tacrolimus, mycophenolate mofetil, and thalidomide), anti-inflammatory cytokines (e.g., IL-10 and IL-11), nutritional therapies, enteral therapy with elemental diets (e.g., Vivonex for 4 weeks), and total parenteral nutrition.

In specific embodiments, patients with lupus erythematosus are administered a prophylactically or therapeutically effective amount of an effector function enhanced anti-ICOS antibody of the invention in combination with other agents or therapies useful in prevention, treatment, management and amelioration of lupus erythematosus including but not limited to: antimalarials (including but not limited to, hydroxychloroquine); glucocorticoids (e.g., low dose, high dose, or high-dose intravenous pulse therapy can be used); immunosuppressive agents (including but not limited to, cyclophosphamide, chlorambucil, and azanthioprine); cytotoxic agents (including but not limited to methotrexate and mycophenolate mofetil); androgenic steroids (including but not limited to danazol); and anticoagulants (including but not limited to warfarin).

The antibody formulations of the invention or combination therapies of the invention may be used as the first, second, third, fourth, or fifth therapy to prevent, manage, treat, and/or ameliorate an autoimmune disorder or one or more symptom thereof. The invention also includes methods of preventing, treating, managing, and/or ameliorating an autoimmune disorder or one or more symptoms thereof in a patient undergoing therapies for other disease or disorders. The invention encompasses methods of preventing, managing, treating, and/or ameliorating an autoimmune disorder or one or more symptoms thereof in a patient before any adverse effects or intolerance to therapies other than antibodies of the invention develops. The invention also encompasses methods of preventing, treating, managing, and/or ameliorating an autoimmune disorder or a symptom thereof in refractory patients. The invention encompasses methods for preventing, treating, managing, and/or ameliorating a proliferative disorder or a symptom thereof in a patient who has proven refractory to therapies other than antibodies, compositions, or combination therapies of the invention. The determination of whether a patient is refractory can be made either in vivo or in vitro by any method known in the art for assaying the effectiveness of a treatment of autoimmune disorders, using art-accepted meanings of "refractory" such a context. In certain embodiments, a patent with an autoimmune disorder is refractory to a therapy when one or more symptoms of an autoimmune disorder is not prevented, managed, and/or alleviated. The invention also encompasses methods of preventing, managing, treating, and/or ameliorating an autoimmune disorder or a symptom thereof in patients who are susceptible to adverse reactions to conventional therapies.

The present invention encompasses methods for preventing, treating, managing, and/or ameliorating an autoimmune disorder or one or more symptoms thereof as an alternative to other conventional therapies. In specific embodiments, the patient being managed or treated in accordance with the methods of the invention is refractory to other therapies or is susceptible to adverse reactions from such therapies. The patient may be a person with a suppressed immune system (e.g., post-operative patients, chemotherapy patients, and patients with immunodeficiency disease, patients with broncho-pulmonary dysplasia, patients with congenital heart disease, patients with cystic fibrosis, patients with acquired or congenital heart disease, and patients suffering from an infection), a person with impaired renal or liver function, the elderly, children, infants, infants born prematurely, persons with neuropsychiatric disorders or those who take psychotropic drugs, persons with histories of seizures, or persons on medication that would negatively interact with conventional agents used to prevent, manage, treat, or ameliorate an autoimmune disease or disorder.

Autoimmune therapies and their dosages, routes of administration and recommended usage are known in the art and have been described in such literature as the Physician's Desk Reference (61th ed., 2007).

5.23.3. Diagnosis of Autoimmune Diseases or Disorders

The diagnosis of an autoimmune disease or disorder is complicated in that each type of autoimmune disease or disorder manifests differently among patients. This heterogeneity of symptoms means that multiple factors are typically used to arrive at a clinical diagnosis. Generally, clinicians use factors, such as, but not limited to, the presence of autoantibodies, elevated cytokine levels, specific organ dysfunction, skin rashes, joint swelling, pain, bone remodeling, and/or loss of movement as primarily indicators of an autoimmune disease or disorder. For certain autoimmune diseases or disorders, such as RA and SLE, standards for diagnosis are known in the art. For certain autoimmune diseases or disorders, stages of disease have been characterized and are well known in the art. These art recognized methods for diagnosing autoimmune diseases and disorders as well as stages of disease and scales of activity and/or severity of disease that are well known in the art can be used to identify patients and patient populations in need of treatment for an autoimmune disease or disorder using compositions and methods of the invention.

5.23.4. Clinical Criteria for Diagnosing Autoimmune Diseases or Disorders

Diagnostic criteria for different autoimmune diseases or disorders are known in the art. Historically, diagnosis is typically based on a combination of physical symptoms. More recently, molecular techniques such as gene-expression profiling have been applied to develop molecular definitions of autoimmune diseases or disorders. Exemplary methods for clinical diagnosis of particular autoimmune diseases or disorders are provided below. Other suitable methods will be apparent to those skilled in the art.

In certain embodiments, patients with low levels of autoimmune disease activity or patients with an early stage of an autoimmune disease (for diseases where stages are recognized) can be identified for treatment using anti-ICOS antibody compositions and methods. The early diagnosis of autoimmune disease is difficult due to the general symptoms and overlap of symptoms among diseases. In such embodiments, a patient treated at an early stage or with low levels of an autoimmune disease activity has symptoms comprising at least one symptom of an autoimmune disease or disorder. In related embodiments, a patient treated at an early stage or with low levels of an autoimmune disease has symptoms comprising at least 1, 2, 3, 4, 5, 6, 7, 8, 9, 10, 11, 12, 13, 14, or 15 symptoms of an autoimmune disease or disorder. The symptoms may be of any autoimmune diseases and disorders or a combination thereof. Examples of autoimmune disease and disorder symptoms are described below.

5.24. Immunotherapeutic Protocols

Anti-ICOS antibody compositions used in the therapeutic regimen/protocols, referred to herein as "anti-ICOS immunotherapy" can be naked antibodies, immunoconjugates and/or fusion proteins. Compositions of the invention can be used as a single agent therapy or in combination with other therapeutic agents or regimens. Anti-ICOS antibodies or immunoconjugates can be administered prior to, concurrently with, or following the administration of one or more therapeutic agents. Therapeutic agents that can be used in combination therapeutic regimens with compositions of the invention include any substance that inhibits or prevents the function of cells and/or causes destruction of cells. Examples include, but are not limited to, radioactive isotopes, chemotherapeutic agents, and toxins such as enzymatically active toxins of bacterial, fungal, plant or animal origin, or fragments thereof.

The therapeutic regimens described herein, or any desired treatment regimen can be tested for efficacy using a transgenic animal model which expresses human ICOS antigen in place of native ICOS antigen. Thus, an anti-ICOS antibody treatment regimen can be tested in an animal model to determine efficacy before administration to a human.

5.25. Anti-ICOS Immunotherapy

In accordance with the present invention "anti-ICOS immunotherapy" encompasses the administration of any of the anti-ICOS antibodies of the invention in accordance with any therapeutic regimen described herein. Anti-ICOS antibodies can be administered as naked antibodies, or immunoconjugates or fusion proteins. In one embodiment, a human subject having a T cell-mediated disease or disorder can be treated by administering an anti-ICOS antibody capable to mediate human ADCC.

Antibodies of IgG1 or IgG3 human isotypes are in some cases preferred for therapy. However, the IgG2 or IgG4 human isotypes can be used as well, provided they have the relevant effector function, for example human ADCC. Such effector function can be assessed by measuring the ability of the antibody in question to mediate target cell lysis by effector cells in vitro or in vivo.

In one embodiment, the dose of antibody used should be sufficient to deplete circulating ICOS expressing T cells. Progress of the therapy can be monitored in the patient by analyzing blood samples. Other signs of clinical improvement can be used to monitor therapy.

Methods for measuring depletion of ICOS expressing T cells that can be used in connection with compositions and methods of the invention are well known in the art and include, but are not limited to the following embodiments. In one embodiment, circulating ICOS expressing T cells depletion can be measured with flow cytometry using a reagent other than an anti-ICOS antibody that binds to ICOS expressing T cells to define the amount of ICOS expressing T cells. In another embodiment, ICOS expressing T cell depletion can be measured by immunochemical staining to identify ICOS expressing T cells. In such embodiments, ICOS expressing T cells or tissues or serum comprising ICOS expressing T cells extracted from a patient can be placed on microscope slides, labeled and examined for presence or absence. In related embodiments, a comparison is made between ICOS expressing T cells extracted prior to therapy and after therapy to determine differences in the presence of ICOS expressing T cells.

In embodiments of the invention where an anti-ICOS antibody is administered as a single agent therapy, the invention contemplates use of different treatment regimens.

According to certain aspects of the invention, an anti-ICOS antibody used in compositions and methods of the invention, is a naked antibody. In related embodiments, the dose of naked anti-ICOS antibody used is at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5 mg/kg of body weight of a patient. In certain embodiments, the dose of naked anti-ICOS antibody used is at least about 1 to 10, 5 to 15, 10 to 20, or 15 to 25 mg/kg of body weight of a patient. In certain embodiments, the dose of naked anti-ICOS antibody used is at least about 1 to 20, 3 to 15, or 5 to 10 mg/kg of body weight of a patient. In other embodiments, the dose of naked anti-ICOS antibody used is at least about 5, 6, 7, 8, 9, or 10 mg/kg of body weight of a patient.

In certain embodiments, the dose comprises about 375 mg/m$^2$ of anti-ICOS antibody administered weekly for about 1, 2, 3, 4, 5, 6, 7 or 8 consecutive weeks. In certain embodiments, the dose is at least about 1, 2, 3, 4, 5, 6, 7, 8, 9, 10, 11, 12, 13, 14, or 15 mg/kg of body weight of the patient administered weekly for about 1, 2, 3, 4, 5, 6, 7 or 8 consecutive weeks.

The exemplary doses of anti-ICOS antibody described above can be administered as described herein. In one embodiment, the above doses are single dose injections. In other embodiments, the doses are administered over a period of time. In other embodiments, the doses are administered multiple times over a period of time. The period of time may be measured in days, weeks, or months. Multiple doses of an anti-ICOS antibody can be administered at intervals suitable to achieve a therapeutic benefit while balancing toxic side effects. For example, where multiple doses are used, it may be preferred to time the intervals to allow for recovery of the patient's monocyte count prior to the repeat treatment with antibody. This dosing regimen will optimize the efficiency of treatment, since the monocyte population reflects ADCC function in the patient.

In certain embodiments, compositions of the invention are administered to a human patient as long as the patient is responsive to therapy. In other embodiments, compositions of the invention are administered to a human patient as long as the patient's disease does not progress. In related embodiments, compositions of the invention are administered to a human patient until a patient's disease does not progress or has not progressed for a period of time, then the patient is not administered compositions of the invention unless the disease reoccurs or begins to progress again. If disease progression stops or reverses, then the patient will not be administered compositions of the invention until that patient relapses, i.e., the disease being treated reoccurs or progresses. Upon this reoccurrence or progression, the patient can be treated again with the same dosing regimen initially used or using other doses described above.

In certain embodiments, compositions of the invention can be administered as a loading dose followed by multiple lower doses (maintenance doses) over a period of time. In such embodiments, the doses may be timed and the amount adjusted to maintain effective ICOS expressing T cell depletion. In certain embodiments, the loading dose is about 10, 11, 12, 13, 14, 15, 16, 17, or 18 mg/kg of patient body weight and the maintenance dose is at least about 5 to 10 mg/kg of patient body weight. In other embodiments, the maintenance dose is administered at intervals of every 7, 10, 14 or 21 days.

5.26. Combination with Chemotherapeutic Agents

Anti-ICOS immunotherapy (using naked antibody, immunoconjugates, or fusion proteins) can be used in conjunction with other therapies including but not limited to, chemotherapy, radioimmunotherapy (RIT), chemotherapy and external beam radiation (combined modality therapy, CMT), or combined modality radioimmunotherapy (CMRIT) alone or in combination, etc. In certain embodiments, an anti-ICOS antibody therapy of the present invention can be administered in conjunction with CHOP (Cyclophosphamide-Hydroxy-doxorubicin-Oncovin (vincristine)-Prednisolone) As used herein, the term "administered in conjunction with" means that an anti-ICOS immunotherapy can be administered before, during, or subsequent to the other therapy employed.

In certain embodiments, an anti-ICOS immunotherapy is in conjunction with a cytotoxic radionuclide or radiotherapeutic isotope. For example, an alpha-emitting isotope such as $^{225}$Ac, $^{224}$Ac, $^{211}$At, $^{212}$Bi, $^{213}$Bi, $^{212}$Pb, $^{224}$Ra, or $^{223}$Ra. The cytotoxic radionuclide may also be a beta-emitting isotope such as $^{186}$Re, $^{188}$Re, $^{90}$Y, $^{131}$I, $^{177}$Lu, $^{153}$Sm, $^{166}$Ho, or $^{64}$Cu. Further, the cytotoxic radionuclide may emit Auger and low energy electrons and include the isotopes $^{125}$I, $^{123}$I or $^{77}$Br. In other embodiments the isotope may be $^{198}$Au, $^{32}$P, and the like. In certain embodiments, the amount of the radionuclide administered to the subject is between about 0.001 mCi/kg and about 10 mCi/kg.

In some embodiments, the amount of the radionuclide administered to the subject is between about 0.1 mCi/kg and about 1.0 mCi/kg. In other embodiments, the amount of the radionuclide administered to the subject is between about 0.005 mCi/kg and 0.1 mCi/kg.

In certain embodiments, an anti-ICOS immunotherapy is in conjunction with a chemical toxin or chemotherapeutic agent. The chemical toxin or chemotherapeutic agent may be selected from the group consisting of an enediyne such as calicheamicin and esperamicin; duocarmycin, methotrexate, doxorubicin, melphalan, chlorambucil, ARA-C, vindesine, mitomycin C, cis-platinum, etoposide, bleomycin and 5-fluorouracil.

Suitable chemical toxins or chemotherapeutic agents that can be used in combination therapies with an anti-ICOS immunotherapy include members of the enediyne family of molecules, such as calicheamicin and esperamicin. Chemical toxins can also be taken from the group consisting of duocarmycin (see, e.g., U.S. Pat. No. 5,703,080 and U.S. Pat. No. 4,923,990), methotrexate, doxorubicin, melphalan, chlorambucil, ARA-C, vindesine, mitomycin C, cis-platinum, etoposide, bleomycin and 5-fluorouracil. Examples of chemotherapeutic agents also include Adriamycin, Doxorubicin, 5-Fluorouracil, Cytosine arabinoside ("Ara-C"), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Caminomycin, Aminopterin, Dactinomycin, Mitomycins, Esperamicins (see, U.S. Pat. No. 4,675,187), Melphalan and other related nitrogen mustards.

In other embodiments, for example, "CVB" (1.5 g/m$^2$ cyclophosphamide, 200-400 mg/m$^2$ etoposide, and 150-200 mg/m$^2$ carmustine) can be used in combination therapies of the invention. CVB is a regimen used to treat non-Hodgkin's lymphoma. Patti et al., *Eur. J. Haematol.* 51:18 (1993). Other suitable combination chemotherapeutic regimens are well-known to those of skill in the art. See, for example, Freedman et al., "*Non-Hodgkin's Lymphomas*," in CANCER MEDICINE, VOLUME 2, 3rd Edition, Holland et al. (eds.), pp. 2028-2068 (Lea & Febiger 1993). As an illustration, first generation chemotherapeutic regimens for treatment of intermediate-grade non-Hodgkin's lymphoma include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate and brostatin-1. In a multimodal therapy, both chemotherapeutic drugs and cytokines are co-administered with an antibody, immunoconjugate or fusion protein according to the present invention. The cytokines, chemotherapeutic drugs and antibody, immunoconjugate or fusion protein can be administered in any order, or together.

Other toxins that may be used in compositions and methods of the invention include poisonous lectins, plant toxins such as ricin, abrin, modeccin, botulina and diphtheria toxins. Of course, combinations of the various toxins could also be coupled to one antibody molecule thereby accommodating variable cytotoxicity. Illustrative of toxins which are suitably employed in combination therapies of the invention are ricin, abrin, ribonuclease, DNase I, Staphylococcal enterotoxin-A, pokeweed antiviral protein, gelonin, diphtherin toxin, *Pseudomonas* exotoxin, and *Pseudomonas* endotoxin. See, for example, Pastan et al., *Cell* 47:641 (1986), and Goldenberg et al., *Cancer Journal for Clinicians* 44:43 (1994). Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria*

*officinalis* inhibitor, gelonin, mitogellin, restrictocin, phenomycin, enomycin and the tricothecenes. See, for example, WO 93/21232 published Oct. 28, 1993.

Suitable toxins and chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985). Other suitable toxins and/or chemotherapeutic agents are known to those of skill in the art.

An anti-ICOS immunotherapy of the present invention may also be in conjunction with a prodrug-activating enzyme which converts a prodrug (e.g., a peptidyl chemotherapeutic agent, see, WO81/01145) to an active anti-cancer drug. See, for example, WO 88/07378 and U.S. Pat. No. 4,975,278. The enzyme component of such combinations includes any enzyme capable of acting on a prodrug in such a way so as to covert it into its more active, cytotoxic form. The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, *"Prodrugs in Cancer Chemotherapy" Biochemical Society Transactions,* 14, pp. 375-382, 615th Meeting Belfast (1986) and Stella et al., *"Prodrugs: A Chemical Approach to Targeted Drug Delivery," Directed Drug Delivery,* Borchardt et al. (ed.), pp. 247-267, Humana Press (1985). Prodrugs that can be used in combination with anti-ICOS antibodies include, but are not limited to, phosphate-containing prodrugs, thiophosphate-containing prodrugs, sulfate-containing prodrugs, peptide-containing prodrugs, D-amino acid-modified prodrugs, glycosylated prodrugs, α-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

In certain embodiments, administration of compositions and methods of the invention may enable the postponement of toxic therapy and may help avoid unnecessary side effects and the risks of complications associated with chemotherapy and delay development of resistance to chemotherapy. In certain embodiments, toxic therapies and/or resistance to toxic therapies is delayed in patients administered compositions and methods of the invention delay for up to about 6 months, 1, 2, 3, 4, 5, 6, 7, 8, 9, or 10 years.

5.27. Combination with Therapeutic Antibodies

An anti-ICOS immunotherapy described herein may be administered in combination with other antibodies, including, but not limited to, anti-CD19 mAb, anti-CD52 mAb, anti-CD22 antibody, and anti-CD20 antibodies, such as RITUXAN™ (C2B8; RITUXIMAB™; IDEC Pharmaceuticals). Other examples of therapeutic antibodies that can be used in combination with antibodies of the invention or used in compositions of the invention include, but are not limited to, HERCEPTIN™ (Trastuzumab; Genentech), MYLOTARG™ (Gemtuzumab ozogamicin; Wyeth Pharmaceuticals), CAMPATH™ (Alemtuzumab; Berlex), ZEVALIN™ (Ipritumomab tiuxetan; Biogen Idec), BEXXAR™ (Tositumomab; GlaxoSmithKline Corixa), ERBITUX™ (Cetuximab; Imclone), and AVASTIN™ (Bevacizumab; Genentech).

5.28. Combination Compounds that Enhance Monocyte or Macrophage Function

In certain embodiments of methods of the invention, a compound that enhances monocyte or macrophage function (e.g., at least about 25%, 50%, 75%, 85%, 90%, 95% or more) can be used in conjunction with an anti-ICOS immunotherapy. Such compounds are known in the art and include, without limitation, cytokines such as interleukins (e.g., IL-12), and interferons (e.g., alpha or gamma interferon).

The compound that enhances monocyte or macrophage function or enhancement can be formulated in the same pharmaceutical composition as the antibody, immunoconjugate or antigen-binding fragment. When administered separately, the antibody/fragment and the compound can be administered concurrently (within a period of hours of each other), can be administered during the same course of therapy, or can be administered sequentially (i.e., the patient first receives a course of the antibody/fragment treatment and then a course of the compound that enhances macrophage/monocyte function or vice versa). In such embodiments, the compound that enhances monocyte or macrophage function is administered to the human subject prior to, concurrently with, or following treatment with other therapeutic regimens and/or compositions of the invention. In one embodiment, the human subject has a blood leukocyte, monocyte, neutrophil, lymphocyte, and/or basophil count that is within the normal range for humans. Normal ranges for human blood leukocytes (total) is about 3.5-about 10.5 ($10^9$/L). Normal ranges for human blood neutrophils is about 1.7-about 7.0 ($10^9$/L), monocytes is about 0.3-about 0.9 ($10^9$/L), lymphocytes is about 0.9-about 2.9 ($10^9$/L), basophils is about 0-about 0.3 ($10^9$/L), and eosinophils is about 0.05-about 0.5 ($10^9$/L). In other embodiments, the human subject has a blood leukocyte count that is less than the normal range for humans, for example at least about 0.01, 0.05, 0.1, 0.2, 0.3, 0.4, 0.5, 0.6, 0.7, or 0.8 ($10^9$/L) leukocytes.

5.29. Combination with Immunoregulatory Agents

The anti-ICOS immunotherapy of the present invention may also be in conjunction with an immunoregulatory agent. The term "immunoregulatory agent" as used herein for combination therapy refers to substances that act to suppress, mask, or enhance the immune system of the host.

Examples of immunomodulatory agents include, but are not limited to, proteinaceous agents such as cytokines, peptide mimetics, and antibodies (e.g., human, humanized, chimeric, monoclonal, polyclonal, Fvs, ScFvs, Fab or F(ab)$_2$ fragments or epitope binding fragments), nucleic acid molecules (e.g., antisense nucleic acid molecules, RNAi and triple helices), small molecules, organic compounds, and inorganic compounds. In particular, immunomodulatory agents include, but are not limited to, methothrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steriods, mycophenolate mofetil, rapamycin (sirolimus), mizoribine, deoxyspergualin, brequinar, malononitriloamindes (e.g., leflunamide), T cell receptor modulators, and cytokine receptor modulators. Examples of immunosupressant, include, but are not limited to, mycophenolate mofetil (CELLCEPT™), D-penicillamine (CUPRIMINE™, DEPEN™), methotrexate (RHEUMATREX™, TREXALL™), and hydroxychloroquine sulfate (PLAQUENIL™).

Immunomodulatory agents would also include substances that suppress cytokine production, downregulate or suppress self-antigen expression, or mask the MHC antigens. Examples of such agents include 2-amino-6-aryl-5-substituted pyrimidines (see, U.S. Pat. No. 4,665,077), azathioprine (or cyclophosphamide, if there is an adverse reaction to azathioprine); bromocryptine; glutaraldehyde (which masks the MHC antigens, as described in U.S. Pat. No. 4,120,649); anti-idiotypic antibodies for MHC antigens and MHC fragments; cyclosporin A; steroids such as glucocorticosteroids, e.g., prednisone, methylprednisolone, and dexamethasone; cytokine or cytokine receptor antagonists including anti-interferon-gamma, -beta, or -alpha antibodies; anti-tumor necrosis factor-alpha antibodies; anti-tumor necrosis factor-beta antibodies; anti-interleukin-2 antibodies and anti-IL-2 receptor antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990); streptokinase; TGF-.beta.; streptodomase; RNA or DNA from the host; FK506; RS-61443; deoxyspergualin; rapamycin; T-cell receptor (U.S. Pat. No. 5,114,721); T-cell receptor fragments (Offner et al., *Science* 251:430-432 (1991); WO 90/11294; and WO 91/01133); and T-Cell receptor antibodies (EP 340,109) such as T10B9.

Examples of cytokines include, but are not limited to lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha; mullerian-inhibiting substance; mouse gonadotropin-associated peptide; inhibin; activin; vascular endothelial growth factor; integrin; thrombopoiotin (TPO); nerve growth factors such as NGF-alpha; platelet-growth factor; transforming growth factors (TGFs) such as TGF-alpha and TGF-alpha; insulin-like growth factor-I and -II; erythropoietin (EPO); osteoinductive factors; interferons; colony stimulating factors (CSFs) such as macrophage-CSF (M-CSF); granulocyte-macrophage-CgP (GM-CSP); and granulocyte-CSF (G-CSF); interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines. In certain embodiments, the methods further include administering to the subject one or more immunomodulatory agents, preferably a cytokine. Preferred cytokines are selected from the group consisting of interleukin-1 (IL-1), IL-2, IL-3, IL-12, IL-15, IL-18, G-CSF, GM-CSF, thrombopoietin, and gamma interferon.

In certain embodiments, the immunomodulatory agent is a cytokine receptor modulator. Examples of cytokine receptor modulators include, but are not limited to, soluble cytokine receptors (e.g., the extracellular domain of a TNF-alpha receptor or a fragment thereof, the extracellular domain of an IL-1beta receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-alpha, TNF-beta, interferon (IFN)-alpha, IFN-beta, IFN-gamma, and GM-CSF), anti-cytokine receptor antibodies (e.g., anti-IL-2 receptor antibodies, anti-IL-4 receptor antibodies, anti-IL-6 receptor antibodies, anti-IL-10 receptor antibodies, and anti-IL-12 receptor antibodies), anti-cytokine antibodies (e.g., anti-IFN receptor antibodies, anti-TNF-alpha antibodies, anti-IL-1beta antibodies, anti-IL-6 antibodies, anti-IL-9, anti-IL-17 antibodies, antibodies, and anti-IL-12 antibodies). In a specific embodiment, a cytokine receptor modulator is IL-4, IL-10, or a fragment thereof. In another embodiment, a cytokine receptor modulator is an anti-IL-1beta antibody, anti-IL-6 antibody, anti-IL-12 receptor antibody, anti-TNF-alpha antibody. In another embodiment, a cytokine receptor modulator is the extracellular domain of a TNF-alpha receptor or a fragment thereof. In certain embodiments, a cytokine receptor modulator is not a TNF-alpha antagonist.

In certain embodiments, the immunomodulatory agent is a T cell receptor modulator. Examples of T cell receptor modulators include, but are not limited to, anti-T cell receptor antibodies (e.g., anti-CD4 antibodies (e.g., cM-T412 (Boeringer), IDEC-CE9.1 (IDEC and SKB), mAB 4162W94, Orthoclone and OKTcdr4a (Janssen-Cilag)), anti-CD3 antibodies, anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies, anti-CD52 antibodies (e.g., CAM-PATH 1H (Ilex)), anti-CD2 monoclonal antibodies) and CTLA4-immunoglobulin.

In certain embodiments, the immunomodulatory agent is a TNF-alpha antagonist. Examples of TNF-alpha antagonists include, but are not limited to, antibodies (e.g., infliximab (REMICADE™; Centocor), D2E7 (Abbott Laboratories/Knoll Pharmaceuticals Co., Mt. Olive, N.J.), CDP571 which is also known as HUMIRA™ and CDP-870 (both of Celltech/Pharmacia, Slough, U.K.), and TN3-19.12 (Williams et al., 1994, Proc. Natl. Acad. Sci. USA 91: 2762-2766; Thorbecke et al., 1992, Proc. Natl. Acad. Sci. USA 89:7375-7379)) soluble TNF-alpha receptors (e.g., sTNF-R1 (Amgen), etanercept (ENBREL™; Immunex) and its rat homolog RENBREL™, soluble inhibitors of TNF-alpha derived from TNFrI, TNFrII (Kohno et al., 1990, Proc. Natl. Acad. Sci. USA, 87:8331-8335), and TNF-alpha Inh (Seckinger et al, 1990, Proc. Natl. Acad. Sci. USA, 87:5188-5192)), IL-10, TNFR-IgG (Ashkenazi et al., 1991, Proc. Natl. Acad. Sci. USA, 88:10535-10539), the murine product TBP-1 (Serono/Yeda), the vaccine CytoTAb (Protherics), antisense molecule 104838 (ISIS), the peptide RDP-58 (SangStat), thalidomide (Celgene), CDC-801 (Celgene), DPC-333 (Dupont), VX-745 (Vertex), AGIX-4207 (AtheroGenics), ITF-2357 (Italfarmaco), NPI-13021-31 (Nereus), SCIO-469 (Scios), TACE targeter (Immunix/AHP), CLX-120500 (Calyx), Thiazolopyrim (Dynavax), auranofin (Ridaura) (SmithKline Beecham Pharmaceuticals), quinacrine (mepacrine dichlorohydrate), tenidap (Enablex), Melanin (Large Scale Biological), and anti-p38 MAPK agents by Uriach.

An anti-ICOS immunotherapy may also be in conjunction with an immunoregulatory agent. In this approach, a chimeric, human or humanized anti-ICOS antibody can be used. The term "immunoregulatory agent" as used herein for combination therapy refers to substances that act to suppress, mask, or enhance the immune system of the host. This would include substances that suppress cytokine production, down-regulate or suppress self-antigen expression, or mask the MHC antigens. Examples of such agents include 2-amino-6-aryl-5-substituted pyrimidines (see, U.S. Pat. No. 4,665,077), azathioprine (or cyclophosphamide, if there is an adverse reaction to azathioprine); bromocryptine; glutaraldehyde (which masks the MHC antigens, as described in U.S. Pat. No. 4,120,649); anti-idiotypic antibodies for MHC antigens and MHC fragments; cyclosporin A; steroids such as glucocorticosteroids, e.g., prednisone, methylprednisolone, and dexamethasone; cytokine or cytokine receptor antagonists including anti-interferon-γ, -β, or -α antibodies; anti-tumor necrosis factor-α antibodies; anti-tumor necrosis factor-β antibodies; anti-interleukin-2 antibodies and anti-IL-2 receptor antibodies; anti-L3T4 antibodies; heterologous anti-lymphocyte globulin; pan-T antibodies, for example anti-CD3 or anti-CD4/CD4a antibodies; soluble peptide containing a LFA-3 binding domain (WO 90/08187 published Jul. 26, 1990); streptokinase; TGF-β; streptodornase; RNA or DNA from the host; FK506; RS-61443; deoxyspergualin; rapamycin; T-cell receptor (U.S. Pat. No. 5,114,721); T-cell receptor fragments (Offner et al., *Science* 251:430-432 (1991); WO 90/11294; and WO 91/01133); and T-cell receptor antibodies (EP 340,109) such as T10B9. Examples of cytokines include, but are not limited to lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α; mullerian-inhibiting substance; mouse gonadotropin-associated peptide; inhibin; activin; vascular endothelial growth factor; integrin; thrombopoietin (TPO); nerve growth factors such as NGF-α; platelet-growth factor; transforming growth factors (TGFs) such as TGF-α and TGF-α; insulin-like growth factor-I and -II; erythropoietin (EPO); osteoinductive factors; interferons; colony stimulating factors (CSFs) such as macrophage-CSF (M-CSF); granulocyte-macrophage-CgP (GM-CSP); and granulocyte-CSF (G-CSF); interleukins (ILs) such as IL-1, IL-1a, IL-2, IL-3, IL-4, IL-5, IL-6, IL-7, IL-8, IL-9, IL-1 I, IL-12, IL-15; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines. In certain embodiments, the methods further include administering to the subject one or more immunomodulatory agents, for example a cytokine. Suitable cytokines may be selected from the group consisting of interleukin-1 (IL-1), IL-2, IL-3, IL-12, IL-15, IL-18, G-CSF, GM-CSF, thrombopoietin, and γ interferon.

These immunoregulatory agents are administered at the same time or at separate times from anti-ICOS antibodies. The preferred immunoregulatory agent will depend on many factors, including the type of disorder being treated, as well as the patient's history, but the agent frequently may be selected from cyclosporin A, a glucocorticosteroid (for example prednisone or methylprednisolone), azathioprine, bromocriptine, heterologous anti-lymphocyte globulin, or a mixture thereof.

5.30. Combination with Other Therapeutic Agents

Agents that act on the tumor neovasculature can also be used in conjunction with anti-ICOS immunotherapy and include tubulin-binding agents such as combrestatin A4 (Griggs et al., *Lancet Oncol.* 2:82, (2001)) and angiostatin and endostatin (reviewed in Rosen, *Oncologist* 5:20 (2000), incorporated by reference herein) Immunomodulators suitable for use in combination with anti-ICOS antibodies include, but are not limited to, of α-interferon, γ-interferon, and tumor necrosis factor alpha (TNFα). In certain embodiments, the therapeutic agents used in combination therapies using compositions and methods of the invention are peptides.

In certain embodiments, an anti-ICOS immunotherapy is in conjunction with one or more calicheamicin molecules. The calicheamicin family of antibiotics are capable of producing double-stranded DNA breaks at sub-picomolar concentrations. Structural analogues of calicheamicin which may be used include, but are not limited to, $\gamma 1^I$, $\gamma 2^I$, $\gamma 3^I$, N-acetyl-$\gamma 1^I$, PSAG and 011 Hinman et al., *Cancer Research* 53:3336-3342 (1993) and Lode et al., *Cancer Research* 58: 2925-2928 (1998)).

In certain embodiments, a treatment regimen includes compounds that mitigate the cytotoxic effects of an anti-ICOS antibody composition. Such compounds include analgesics (e.g., acetaminophen), bisphosphonates, antihistamines (e.g., chlorpheniramine maleate), and steroids (e.g., dexamethasone, retinoids, deltoids, betamethasone, cortisol, cortisone, prednisone, dehydrotestosterone, glucocorticoids, mineralocorticoids, estrogen, testosterone, progestins).

In certain embodiments, the therapeutic agent used in combination with an anti-ICOS immunotherapy is a small molecule (i.e., inorganic or organic compounds having a molecular weight of less than about 2500 daltons). For example, libraries of small molecules may be commercially obtained from Specs and BioSpecs B.V. (Rijswijk, The Netherlands), Chembridge Corporation (San Diego, Calif.), Comgenex USA Inc. (Princeton, N.J.), and Maybridge Chemicals Ltd. (Cornwall PL34 OHW, United Kingdom).

In certain embodiments an anti-ICOS immunotherapy can be administered in combination with an anti-bacterial agent. Non-limiting examples of anti-bacterial agents include proteins, polypeptides, peptides, fusion proteins, antibodies, nucleic acid molecules, organic molecules, inorganic molecules, and small molecules that inhibit and/or reduce a bacterial infection, inhibit and/or reduce the replication of bacteria, or inhibit and/or reduce the spread of bacteria to other cells or subjects. Specific examples of anti-bacterial agents include, but are not limited to, antibiotics such as penicillin, cephalosporin, imipenem, axtreonam, vancomycin, cycloserine, bacitracin, chloramphenicol, erythromycin, clindamycin, tetracycline, streptomycin, tobramycin, gentamicin, amikacin, kanamycin, neomycin, spectinomycin, trimethoprim, norfloxacin, rifampin, polymyxin, amphotericin B, nystatin, ketocanazole, isoniazid, metronidazole, and pentamidine.

In certain embodiments an anti-ICOS immunotherapy can be administered in combination with an anti-fungal agent. Specific examples of anti-fungal agents include, but are not limited to, azole drugs (e.g., miconazole, ketoconazole (NIZORAL®), caspofungin acetate (CANCIDAS®), imidazole, triazoles (e.g., fluconazole (DIFLUCAN®)), and itraconazole))(SPORANOX®, polyene (e.g., nystatin, amphotericin B) (FUNGIZONE®, amphotericin B lipid complex ("ABLC") (ABELCET®), amphotericin B colloidal dispersion ("ABCD") (AMPHOTEC®), liposomal amphotericin B (AMBISONE®)), potassium iodide (KI), pyrimidine (e.g., flucytosine (ANCOBON®) and voriconazole (VFEND®). Administration of anti bacterial and anti-fungal agents can mitigate the effects or escalation of infectious disease that may occur in methods of the invention where a patient's ICOS expressing T cells are significantly depleted.

In certain embodiments of the invention, an anti-ICOS immunotherapy can be administered in combination with one or more of the agents described above to mitigate the toxic side effects that may accompany administration of compositions of the invention. In other embodiments, an anti-ICOS immunotherapy can be administered in combination with one or more agents that are well known in the art for use in mitigating the side effects of antibody administration, chemotherapy, toxins, or drugs.

In embodiments of the invention where an anti-ICOS immunotherapy is administered in combination with another antibody or antibodies and/or agent, the additional antibody or antibodies and/or agents can be administered in any sequence relative to the administration of the antibody of this invention. For example, the additional antibody or antibodies can be administered before, concurrently with, and/or subsequent to administration of an anti-ICOS antibody or immunoconjugate to the human subject. The additional antibody or antibodies can be present in the same pharmaceutical composition as an antibody of the invention, and/or present in a different pharmaceutical composition. The dose and mode of administration of an antibody of this invention and the dose of the additional antibody or antibodies can be the same or different, in accordance with any of the teachings of dosage amounts and modes of administration as provided in this application and as are well known in the art.

5.31. Use of Anti-ICOS Antibodies in Diagnosing T Cell Malignancies

The present invention also encompasses anti-ICOS antibodies, and compositions thereof, that immunospecifically bind to the human ICOS antigen, which anti-ICOS antibodies are conjugated to a diagnostic or detectable agent. In certain embodiments, the antibodies are anti-ICOS antibodies with enhanced effector function. Such anti-ICOS antibodies can be useful for monitoring or prognosing the development or progression of a T cell malignancy as part of a clinical testing procedure, such as determining the efficacy of a particular therapy. Such diagnosis and detection can be accomplished by coupling an anti-ICOS antibody that immunospecifically binds to the human ICOS antigen to a detectable substance including, but not limited to, various enzymes, such as but not limited to, horseradish peroxidase, alkaline phosphatase, beta-galactosidase, or acetylcholinesterase; prosthetic groups, such as but not limited to, streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd) molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, noradioactive paramagnetic metal ions, and molecules that are radiolabelled or conjugated to specific radioisotopes. Any detectable label that can be readily measured can be conjugated to an anti-ICOS antibody and used in diagnosing T cell malignancies. The detectable substance may be coupled or conjugated either directly to an antibody or indirectly, through an intermediate (such as, for example, a linker known in the art) using techniques known in the art. See, e.g., U.S. Pat. No. 4,741,900 for metal ions which can be conjugated to antibodies for use as a diagnostics according to the present invention. In certain embodiments, the invention provides for diagnostic kits comprising an anti-ICOS antibody conjugated to a diagnostic or detectable agent.

5.32. Use of Anti-ICOS Antibodies in Monitoring Immune Reconstitution

The present invention also encompasses anti-ICOS antibodies, and compositions thereof, that immunospecifically bind to the human ICOS antigen, which anti-ICOS antibodies are conjugated to a diagnostic or detectable agent. Such anti-ICOS antibodies can be useful for monitoring immune system reconstitution following immunosuppressive therapy or bone marrow transplantation. Such monitoring can be accomplished by coupling an anti-ICOS antibody that immunospecifically binds to the human ICOS antigen to a detectable substance including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as, but not limited to, luciferase, luciferin, and aequorin; radioactive materials, such as, but not limited to, iodine ($^{131}$I, $^{125}$I, $^{123}$I, $^{121}$I) carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{163}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron-emitting metals using various positron-emission tomographies, noradioactive paramagnetic metal ions, and molecules that are radiolabelled or conjugated to specific radioisotopes. Any detectable label that can be readily measured can be conjugated to an anti-ICOS antibody and used in diagnosing an autoimmune disease or disorder. The detectable substance may be coupled or conjugated either directly to an antibody or indirectly, through an intermediate (such as, for example, a linker known in the art) using techniques known in the art. See, e.g., U.S. Pat. No. 4,741,900 for metal ions which can be conjugated to antibodies for use as a diagnostics according to the present invention. In certain embodiments, the invention provides for diagnostic kits comprising an anti-ICOS antibody conjugated to a diagnostic or detectable agent.

5.33. Use of Anti-ICOS Antibodies in Diagnosing Autoimmune Diseases or Disorders The present invention also encompasses anti-ICOS antibodies, and compositions thereof, that immunospecifically bind to the human ICOS antigen, which anti-ICOS antibodies are conjugated to a diagnostic or detectable agent. In certain embodiments, the antibodies are anti-ICOS antibodies with enhanced effector function. Such anti-ICOS antibodies can be useful for monitoring or prognosing the development or progression of an autoimmune disease or disorder as part of a clinical testing procedure, such as determining the efficacy of a particular therapy. Such diagnosis and detection can be accomplished by coupling an anti-ICOS antibody that immunospecifically binds to the human ICOS antigen to a detectable substance including, but not limited to, various enzymes, such as but not limited to, horseradish peroxidase, alkaline phosphatase, beta-galactosidase, or acetylcholinesterase; prosthetic groups, such as but not limited to, streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, noradioactive paramagnetic metal ions, and molecules that are radiolabelled or conjugated to specific radioisotopes. Any detectable label that can be readily measured can be conjugated to an anti-ICOS antibody and used in diagnosing an autoimmune disease or disorder. The detectable substance may be coupled or conjugated either directly to an antibody or indirectly, through an intermediate (such as, for example, a linker known in the art) using techniques known in the art. See, e.g., U.S. Pat. No. 4,741,900 for metal ions which can be conjugated to antibodies for use as a diagnostics according to the present invention. In certain embodiments, the invention provides for diagnostic kits comprising an anti-ICOS antibody conjugated to a diagnostic or detectable agent.

5.34. Kits

The invention provides a pharmaceutical pack or kit comprising one or more containers filled with a composition of the invention for the prevention, treatment, management or amelioration of a T cell-mediated disease and disorder, such as, but not limited to, chronic infection, autoimmune disease or disorder, inflammatory disease or disorder, graft-versus-host disease (GVHD), transplant rejection, and T cell proliferative disorder, or one or more symptoms thereof, potentiated by or potentiating a T cell-mediated disease and disorder.

The present invention provides kits that can be used in the above-described methods. In one embodiment, a kit comprises a composition of the invention, in one or more containers. In another embodiment, a kit comprises a composition of the invention, in one or more containers, and one or more other prophylactic or therapeutic agents useful for the prevention, management or treatment of a T cell-mediated disease and disorder, or one or more symptoms thereof, potentiated by or potentiating a T cell-mediated disease and disorder in one or more other containers. The kit may further comprise instructions for preventing, treating, managing or ameliorating a T cell-mediated disease and disorder, as well as side effects and dosage information for method of administration. Optionally associated with such container(s) can be a notice in the form prescribed by a governmental agency regulating the manufacture, use or sale of pharmaceuticals or biological products, which notice reflects approval by the agency of manufacture, use or sale for human administration.

6. SPECIFIC EMBODIMENTS

1. An isolated anti-ICOS antibody comprising a VH domain, a VK domain and a variant Fc region, wherein the antibody mediates enhanced ADCC activity as compared to the level of ADCC activity mediated by a parent antibody comprising the VH and VK domains and a wild type Fc region.

2. The antibody of embodiment 1, wherein the EC50 of the antibody as measured in an in vitro ADCC assay is at least about 7× lower than the EC50 value of the parent antibody.

3. The antibody of embodiments 1 or 2, wherein the variant Fc region has a higher affinity for an Fc receptor than the wild type Fc region.

4. The antibody of embodiment 3, wherein the Fc receptor is human FcgammaRIIIA

5. The antibody of embodiment 1, wherein the variant Fc region comprises at least one substitution of an amino acid residue selected from the group consisting of: residue 239, 330, and 332, wherein the amino acid residue positions are determined according to the EU convention.

6. The antibody of embodiment 1, wherein the variant Fc region comprises at least on amino acid substitution selected from the group consisting of: S239D, A330L, and I332E; wherein the amino acid residue positions are determined according to the EU convention.

7. An isolated anti-ICOS antibody comprising a VH domain, a VK domain and an engineered Fc region, wherein the antibody has complex N-glycoside-linked sugar chains bound to the engineered Fc region in which fucose is not bound to N-acetylglucosamine in the reducing end in the sugar chain.

8. The antibody of embodiment 7, wherein the antibody mediates enhanced ADCC activity as compared to the level of ADCC activity mediated by a parent antibody comprising the VH and VK domains and a non-engineered Fc region.

9. The antibody of embodiment 8, wherein the EC50 of the antibody as measured in an in vitro ADCC assay is at least about 7× lower than the EC50 value of the parent antibody.

10. The antibody of any one of the embodiments 1-7, wherein the VH domain comprises the amino acid sequence of SEQ ID NO:7 and the VK domain comprises the amino acid sequence of SEQ ID NO:2.

11. A nucleic acid encoding the amino acid sequence of the antibody as in any one of the embodiments 1-10.

12. The nucleic acid of embodiment 11, wherein the nucleic acid comprises a nucleotide sequence selected from the group consisting of SEQ ID NO:28-31.

13. A vector comprising the nucleic acid of embodiment 11.

14. The vector of embodiment 13, wherein the vector comprises a nucleotide sequence selected from the group consisting of SEQ ID NO:28-31.

15. An isolated cell comprising the vector of embodiment 13.

16. The isolated cell of embodiment 15, wherein said cell lacks the activity of a glycosylation enzyme.

17. The glycosylation enzyme of embodiment 16, wherein said enzyme is selected from the group consisting of FUT8 or GnTIII.

18. The isolated cell of embodiment 16, wherein the enzyme is selected from the group consisting of FUT8 or GnTIII, and wherein the cell comprises a vector comprising the nucleotide sequence selected from the group consisting of SEQ ID NO:28-31.

19. An isolated cell expressing the antibody as in any one of the embodiments 1-10.

20. A method of producing an antibody comprising culturing the isolated cell of embodiment 19 under conditions sufficient for the production of the antibody and recovering the antibody from the culture.

21. A pharmaceutical composition comprising the antibody as in any one of the embodiments 1-10 in a pharmaceutically-acceptable carrier.

22. The pharmaceutical composition of embodiment 21, wherein the antibody is of the IgG1, IgG2, IgG3, or IgG4 human isotype.

23. A method of treating an autoimmune disease or disorder in a human, comprising administering to a human in need thereof a therapeutically-effective amount of the antibody as in any one of the embodiments 1-10.

24. The method of embodiment 23, wherein the autoimmune disease or disorder is SLE or scleroderma.

25. A method of treating or preventing rejection in a human transplant patient, comprising administering to a human in need thereof a therapeutically-effective amount of the antibody as in any one of the embodiments 1-10.

26. A method of treating a T cell malignancy in a human comprising administering to a human in need thereof a therapeutically-effective amount of the antibody as in any one of the embodiments 1-10.

27. A method of treating an inflammatory disease or disorder in a human, comprising administering to a human in need thereof a therapeutically-effective amount of the antibody as in any one of the embodiments 1-10.

28. The method of embodiment 27, wherein the inflammatory disease or disorder is myositis.

29. The method of embodiment 28, wherein the myositis is inclusion-body myositis (IBM), polymyositis (PM) or dermatomyositis (DM).

30. A method of depleting ICOS expressing T cells in a human patient comprising administering to a human in need thereof a therapeutically-effective amount of the antibody as in any one of the embodiments 1-10.

31. The method of embodiment 30, wherein the depletion substantially persists for at least about 1, at least about 2, at least about 3 or at least about 4 weeks following the administration of the antibody.

32. The method of embodiment 30, wherein at least about 95% of the T cells are depleted.

33. The method of embodiment 30, wherein the ICOS expressing T cell is a memory T cell.

34. The method of embodiment 30, wherein the ICOS expressing T cell is a circulating T cell.

35. A method of disrupting germinal center architecture in a secondary lymphoid organ of a primate, comprising administering an effective amount of the antibody as in any one of the embodiments 1-10.

36. The method of embodiment 35, wherein the primate is a non-human primate.

37. A method of depleting germinal center B cells from a secondary lymphoid organ of a primate comprising administering an effective amount of the antibody as in any one of the embodiments 1-10.

38. The method of embodiment 37, wherein the primate is a non-human primate.

39. The method of embodiment 37, wherein the primate is a human.

40. The method of embodiment 37, wherein the depletion substantially persists for at least about 1, at least about 2, at least about 3 or at least about 4 weeks following the administration of the antibody.

41. A method of depleting circulating class switched B cells in a primate comprising administering an effective amount of the antibody as in any one of the embodiments 1-10.

42. The method of embodiment 41, wherein the primate is a non-human primate.

43. The method of embodiment 41, wherein the primate is a human.

44. The method of embodiment 41, wherein the depletion substantially persists for at least about 1, at least about 2, at least about 3 or at least about 4 weeks following the administration of the antibody.

45. The method of embodiment 41, wherein at least about 95% of the circulating class switched B cells are depleted.

46. An isolated anti-ICOS antibody comprising a VH domain, a VK domain and a variant Fc region, wherein the antibody mediates enhanced ADCC activity as compared to the level of ADCC activity mediated by a parent antibody comprising the VH and VK domains and a wild type Fc region, and wherein said antibody is capable of depleting germinal center B cells from a secondary lymphoid organ of a primate.

47. The antibody of embodiment 46, wherein the primate is a non-human primate.

48. The antibody of embodiment 46, wherein the primate is a human.

49. The antibody of embodiment 46, wherein the depletion substantially persists for at least about 1, at least about 2, at least about 3 or at least about 4 weeks following the administration of the antibody.

50. An isolated anti-ICOS antibody comprising a VH domain, a VK domain and a variant Fc region, wherein the antibody mediates enhanced ADCC activity as compared to the level of ADCC activity mediated by a parent antibody comprising the VH and VK domains and a wild type Fc region, and wherein said antibody is capable of depleting circulating class switched B cells in a primate.

51. The antibody of embodiment 50, wherein the primate is a non-human primate.

52. The antibody of embodiment 50, wherein the primate is a human.

53. The antibody of embodiment 50, wherein the depletion substantially persists for at least about 1, at least about 2, at least about 3 or at least about 4 weeks following the administration of the antibody.

54. The antibody of embodiment 50, wherein at least about 95% of the circulating class switched B cells are depleted.

55. An isolated anti-ICOS antibody comprising a VH domain, a VK domain and an engineered Fc region, wherein the antibody has complex N-glycoside-linked sugar chains bound to the engineered Fc region in which fucose is not bound to N-acetylglucosamine in the reducing end in the sugar chain, wherein the antibody mediates enhanced ADCC activity as compared to the level of ADCC activity mediated by a parent antibody comprising the VH and VK domains and a non-engineered Fc region, and wherein said antibody is capable of depleting germinal center B cells from a secondary lymphoid organ of a primate.

56. The antibody of embodiment 55, wherein the primate is a non-human primate.

57. The antibody of embodiment 55, wherein the primate is a human.

58. The antibody of embodiment 55, wherein the depletion substantially persists for at least about 1, at least about 2, at least about 3 or at least about 4 weeks following the administration of the antibody.

59. An isolated anti-ICOS antibody comprising a VH domain, a VK domain and an engineered Fc region, wherein the antibody has complex N-glycoside-linked sugar chains bound to the engineered Fc region in which fucose is not bound to N-acetylglucosamine in the reducing end in the sugar chain, wherein the antibody mediates enhanced ADCC activity as compared to the level of ADCC activity mediated by a parent antibody comprising the VH and VK domains and a non-engineered Fc region, and wherein said antibody is capable of depleting class switched B cells in a primate.

60. The antibody of embodiment 59, wherein the primate is a non-human primate.

61. The antibody of embodiment 59, wherein the primate is a human.

62. The antibody of embodiment 59, wherein the depletion substantially persists for at least about 1, at least about 2, at least about 3 or at least about 4 weeks following the administration of the antibody.

63. The antibody of embodiment 59, wherein at least about 95% of the circulating class switched B cells are depleted.

7. EXAMPLES

7.1. Construction of ADCC Enhanced Anti-ICOS Antibodies

The following sections describe the design of an ADCC enhanced anti-ICOS antibody comprising a human IgHγ1 constant region. An ADCC enhanced anti-ICOS antibody may comprise variant Fc regions with increased effector function (see, US Patent Publication No's: US 2007-0003546 A1, US20060160996A9, US 2005-0054832 A1, US 2004-0132101 A1, and US 2004-0110226 A1). An ADCC enhanced anti-ICOS antibody may comprise complex N-glycoside-linked sugar chains linked to Asn297 of the Fc region in which fucose is not bound to N-acetylglucosamine in the reducing end (see, U.S. Pat. No. 6,946,292, US Patent Publication No's: US 2006-0223147 A1, US 2006-0021071 A1, US 2005-0272916 A1, US 2004-0259150 A1, US 2004-0132140 A1, US 2004-0110704 A1, and US 2004-0110282 A1). The ADCC enhanced anti-ICOS antibodies described in the Examples comprise the heavy and light chain variable domains of the JMab-136 anti-ICOS antibody described in U.S. Pat. No. 6,803,039. The amino acid sequence of the JMab anti-ICOS antibody VH and VK domains are disclosed herein as SEQ ID NO: 7 and 2, respectively. The anti ICOS antibody comprising JMab-136 VH and VL domains and further comprising the IgHγ2 constant region is hereinafter referred to as IC009. The anti ICOS antibody comprising JMab-136 VH and VL domains and further comprising the IgHγ1 constant region is hereinafter referred to as as IC9G1. Those skilled in the art recognize that the experimental methods described herein may also be applied to any other anti-ICOS antibody, for example, but not limited to, those described in U.S. Pat. No. 6,803,039.

7.1.1. Sequence Optimization

Amino acid sequence: The amino acid sequence of the VK domain (SEQ ID NO:1) comprises the following motifs: a potential o-glycosylation site at amino acid position 5, and a potential deamidation motif at amino acid position 92 in the VK CDR3. The amino acid sequence of the VH domain (SEQ ID NO: 6) comprises the following motifs: a potential o-glycosylation site at amino acid position 17, and a potential isoaspartate formation motif at amino acid position 99 in the VH CDR3. Amino acid positions are determined according to the Kabat consensus. The amino acid sequence of the VH or VK domain may be changed to eliminate any one of these sequence motifs and thus eliminate the potential for post-translational modification at the altered sequence motifs. For example, an NG potential deamidation motif may be eliminated by substituting the N residue with a Y, D or G residue. Methods for introducing a substitution into the amino acid sequence of the anti-ICOS antibody are described below. The antigen binding properties of an amino acid substitution comprising anti-ICOS antibody may be ascertained using the methods described herein.

Nucleic acid sequence: The polynucleotides encoding the heavy and light chains of the anti-ICOS antibody may be subjected to nucleic acid sequence optimization. The final goal of the sequence optimization process is to create a coding region that is transcribed and translated at the highest possible efficiency. Sequence optimization is achieved by a combination of: (i) codon usage optimization, (ii) G/C content adaptation, (iii) elimination of internal splicing sites and premature polyadenylation sites, (iv) disruption of stable RNA secondary structures, (v) elimination of direct repeat sequences, (vi) elimination of sequences that may form stable dsRNA with host cell transcripts, (vii) eliminate sequences targeted by host cell micro RNAs, and (viii) introduction of RNA stabilizing and RNA translocation signals. Detailed sequence optimization methods are described in WO2004059556A2, WO2006015789A2, Bradel-Tretheway et al., *J. Virol. Methods* 111:145-56 (2003), Valencik & McDonald, *Transgenic Res.* 3:269-75 (2001). Alternatively, a sequence may be optimized by a commercial provider (e.g., GENEART Inc.).

Nucleotide sequences encoding the VH, VK, heavy chain and light chain of the IC9G1 were optimized following the methods described herein. The optimized nucleotide sequences encoding the VH, VK, heavy chain and light chain of IC9G1 is disoclosed as SEQ ID NO:28-31, respectively.

7.1.2. Gene Assembly and Expression Cloning

Constructs may be generated by a PCR-based gene assembly method first described by Stemmer (Stemmer, W. P. et al. 1995 *Gene*, 164:49-53). This method consists of four steps: oligonucleotide synthesis; gene assembly; gene amplification and cloning. Eight VH gene specific primers and six VK gene specific primers that may be used for PCR mediated gene assembly are listed in Table 2. Primer sets for variant VH and VK regions comprising specific amino acid substitutions may be generated by modifying the nucleic acid sequence of the primer encoding the given amino acid residue. Primers are designed to overlap by 15-20 nucleotides and are ligated into a complete variable region during thermal cycling. In case of VH, an additional vector specific primer (Universal VH FW in Table 2) is included in the PCR mediated gene assembly process. The external 5' and 3' primers for VH region incorporate a unique recognition site for the XbaI and ApaI restriction endonuclease, respectively, to help with the subsequent cloning steps. The external 5' and 3' primers for VK incorporate a unique recognition site for the XmaI and BsiWI restriction endonuclease, respectively, to help with the subsequent cloning steps. PCR products of the correct size are restriction digested and ligated in frame into an expression vector wherein VH regions are digested with XbaI and ApaI, and VK regions are digested with XmaI and BsiWI according to the manufacturer's instructions. The heavy chain assembly vector comprises eukaryotic transcription control elements operably linked to a polynucleotide encoding the MGDNDIHFAFLSTGVHS VH leader (SEQ ID NO: 26) and a human IgHγ1 constant region wherein said transcription control elements comprise a CMV immediate early promoter and a SV40 poly A addition signal. The use of appropriately designed primers for VH assembly ensures that the polynucleotide sequences encoding the VH leader, VH region and IgHγ1 constant region are joined in frame within the final heavy chain expression vector. The light chain assembly vector comprises eukaryotic transcription control elements operably linked to a polynucleotide encoding the human VK1-L12 leader (amino acid sequence MDMRVPAQLLGLLLLWLPGAKC (SEQ ID NO:27); Bentley, D. L. & Rabbitts, T. H., *Nature* 288, 730-733 (1980)) and a human IgLκ constant region wherein said transcription control elements comprise a CMV immediate early promoter and a SV40 poly A addition signal. The use of appropriately designed primers for VK assembly ensures that the polynucleotide sequences encoding the VK1-L12 leader, VK region and IgLκ constant region are joined in frame within the final light chain expression vector. The ligation product is used to transform DH10B competent *E. coli* cells according to the manufacturer's protocols. Colonies containing the plasmid and a correct sized insert can be identified using various methods known in the art (e.g. restriction digest of vector DNA preparation, PCR amplification of vector sequences). Plasmid clones with correct sized insert may be sequenced using dideoxy sequencing reaction (e.g., Big-Dye® Terminator v3.0 Cycle Sequencing Ready Reaction Kit, ABI). Plasmid DNA is prepared from selected clones using the QIAGEN Mini and Maxi Plasmid Kit according to the manufacturer's protocols.

DNA plasmid expression vector preparations encoding the anti-ICOS heavy chain and light chain polypeptides are used to co-transfect HEK293 cells. The co-transfected HEK293 cells are cultured under standard conditions. Antibody-containing conditioned medium is harvested 72 and 144 hours post-transfection. The secreted, soluble human IgG is purified from the conditioned media directly using 1 ml HiTrap protein A columns according to the manufacturer's instructions (APBiotech, Inc., Piscataway, N.J.). Purified human IgG (typically >95% pure, as judged by SDS-PAGE) is dialyzed against phosphate buffered saline (PBS), flash frozen and stored at −70° C.

IgG concentration of the purified preparation is quantified using a capture ELISA assay. Briefly, IgG molecules are captured on a 96-well plate via an immobilized goat anti-human IgG H+L specific antibody, and detected with an HRP conjugated anti-human kappa light chain antibody. The assay is calibrated using a reference IgG1 mAb of irrelevant specificity.

7.1.3. ADCC Enhanced Anti-ICOS Antibody Comprising a Variant Fc Domain

An antibody expression vector encoding an ADCC enhanced anti-ICOS antibody having a variant Fc domain comprising the S239D, A330L, and I332E amino acid substitutions (hereinafter referred to as "IC9G1-3M") may be generated using the methods described in US Patent Publications 2004/0132101 and 2005/0054832, both to Lazar et al. Briefly, the above described antibody expression vector encoding the JMab136 VH and VL domains is modified using a site directed mutagenesis kit (e.g., QuickChange (Promega)) to introduce the necessary nucleotide residue substitutions into the polynucleotide sequence encoding the heavy chain constant region to generate the IC9G1-3M antibody expression vector. Purified IC9G1-3M antibody is generated by transfecting HEK239F cells with the IC9G1-3M antibody expression vector. Transfected cells are fed at day 3 and 6 and the antibody-containing conditioned medium is harvested at day 9. Antibody is purified from the conditioned medium using a pre-cast protein A column (GE Healthcare). Antibody is eluted from the column with low pH buffer, neutralized, and dialyzed against PBS. The concentration of the purified antibody is calculated from the solution's optical density at 280 nm.

TABLE 2

Representative primer sets for VH and VK region assembly. Gene specific nucleotides are printed in upper case, vector specific nucleotides are printed in lower case. Recognition sites for restriction endonucleases used for VH and VK fragment cloning are underlined.

| | |
|---|---|
| Univ VH FW | tatatatatctagacatatatatgggtgacaatgacatccactttgcctttctctcc (SEQ ID NO: 11) |
| VH FW1 | tccactttgcctttctctccacaggtgtccactccCAGGTGCAGCTGGTGCAGTCTGGGG CTGAGGTGAAGAAGCCTGGGGCCTCAGTG (SEQ ID NO: 12) |
| VH RE2 | CATATAGTAGCCGGTGAAGGTGTATCCAGAAGCCTTGCAGGAGAC CTTCACTGAGGCCCCAGGCTTC (SEQ ID NO: 13) |
| VH FW3 | CACCGGCTACTATATGCACTGGGTGCGACAGGCCCCTGGACAAGG GCTTGAGTGGATGGGATGGATC (SEQ ID NO: 14) |
| VH RE4 | CTGCCCTGAAACTTCTGTGCATAGTTTGTGCCACCACTGTGAGGGT TGATCCATCCCATCCAC (SEQ ID NO: 15) |
| VH FW5 | CAGAAGTTTCAGGGCAGGGTCACCATGACCAGGGACACGTCCATC AGCACAGCCTACATGGAGCTGAG (SEQ ID NO: 16) |
| VH RE6 | GTCCTCGCACAGTAATACACGGCCGTGTCGTCGGATCTCAGCCTG CTCAGCTCCATGTAGGCTG (SEQ ID NO: 17) |
| VH FW7 | GTATTACTGTGCGAGGACGTATTACTATGATAGTAGTGGTTATTAC CATGATGCTTTTGATATCTG (SEQ ID NO: 18) |
| VH RE8 | tatatatagggcccttggtggaggcCTGAAGAGACGGTGACCATTGTCCCTTGGC CCCAGATATCAAAAGCATC (SEQ ID NO: 19) |
| VK FW1 | tatatataccccgggccaaatgtGACATCCAGATGACCCAGTCTCCATCTTCCG TGTCTGCATCTGTAGGAGACAGAG (SEQ ID NO: 20) |
| VK RE2 | GATACCAGGCTAACAACCTGCTAATACCCTGACTCGCCCGACAAG TGATGGTGACTCTGTCTCCTACAGA (SEQ ID NO: 21) |
| VK FW3 | GTTAGCCTGGTATCAGCAGAAACCAGGGAAAGCCCCTAAACTCCT GATCTATGTTGCATCCAGTTTGCAAAGTG (SEQ ID NO: 22) |
| VK RE4 | GTGAAATCTGTCCCAGATCCACTGCCGCTGAACCTTGATGGGACC CCACTTTGCAAACTGGATG (SEQ ID NO: 23) |
| VK FW5 | CTGGGACAGATTTCACTCTCACCATCAGCAGCCTGCAGCCTGAAG ATTTTGCAACTTACTATTGTCAACAG (SEQ ID NO: 24) |
| VK RE6 | tatatatacgtacgTTTGATTTCCACCTTGGTCCCTTGGCCGAACGTCCACG GGAAACTGTTAGCCTGTTGACAATAGTAAG (SEQ ID NO: 25) |

7.1.4. ADCC Null Anti-ICOS Fc Variant Antibody

An antibody expression vector encoding an anti-ICOS antibody with reduced ADCC activity having an Fc region comprising the L234F, L235E, and P331S amino acid substitutions (hereinafter referred to as "IC9G1-TM") is generated using methods described in US 2004/0132101 and US 2005/0054832, both to Lazar et al. Briefly, the above described antibody expression vector encoding the JMab136 VH and VL domains is modified using a site directed mutagenesis kit (e.g., QuickChange (Promega)) to introduce the necessary nucleotide residue substitutions into the polynucleotide sequence encoding the heavy chain constant region to generate the IC9G1-TM antibody expression vector. Purified IC9G1-TM antibody is generated by transfecting HEK239F cells with the IC9G1-TM antibody expression vector. Transfected cells are fed at day 3 and 6 and the antibody-containing conditioned medium is harvested at day 9. Antibody is purified from the conditioned medium using a pre-cast protein A column (GE Healthcare). Antibody is eluted from the column with low pH buffer, neutralized, and dialyzed against PBS. The concentration of the purified antibody is calculated from the solution's optical density at 280 nm.

7.1.5. Afucosylated Anti-ICOS Antibody with Increased ADCC

An IC9G1 antibody composition (hereinafter referred to as IC9G1-aFuc) comprising a plurality of antibodies having complex N-glycoside-linked sugar chains linked to Asn297 of the Fc region in which fucose is not bound to N-acetylglucosamine in the reducing end was prepared according to the methods set forth in U.S. Pat. No. 6,946,292 to Kanda et al. Briefly, fucosyltransferase knock-out CHO cells are transfected with a DNA plasmid expression vector preparation encoding the heavy and light chains of JMab136. Transfected cells are fed at day 3 and 6 and the antibody-containing conditioned medium is harvested at day 9. Antibody is purified from the conditioned medium using a pre-cast protein A column (GE Healthcare). Antibody is eluted from the column with low pH buffer, neutralized, and dialyzed against PBS. The concentration of the purified antibody is calculated from the solution's optical density at 280 nm.

7.2. Binding Profile Characterization of ADCC Enhanced Anti-ICOS Antibodies

The binding profile of ADCC enhanced anti-ICOS antibodies may be characterized by a number of methods known to one of skill in the arts. The antibodies may be characterized by using, for example, but not limited to, cell based ELISA assays, ELISA assays using a recombinant ICOS molecule as capture reagent, flow cytometry, Biacore analysis.

The ability of an ADCC enhanced anti-ICOS antibody to bind ICOS may be assessed by a cell based ICOS binding assay utilizing stable transfectants cells expressing recombinant ICOS protein on their cell surface as a capture agent. U.S. Pat. No. 6,803,039 describes an ICOS transgenic CHO cell line and an ICOS transgenic HPB-ALL cell line, each of which may be used in a cell based ELISA assay. A cell based ELISA may be performed by using any one of the methods known to one skilled in the arts. For example, HPB-ALL h-ICOS+ cells are cultured according to standard protocols in RPMI 1640 medium containing L-glutamine and supplemented with 10% Fetal Calf Serum. Individual wells of a 96 well U bottom plate are seeded with 1×10e5 stable transfectants HPB-ALL hICOS cells and incubated overnight. Cells are washed once with ELISA buffer prior to incubation on ice with various amounts of anti-ICOS antibodies. Binding reactions are performed in triplicates for each antibody concentration tested. Negative control wells using an isotype matched antibody of irrelevant specificity should be included in the assay. Additional negative control wells seeded with non-transfected HPB-ALL cells may also be used to further demonstrate the binding specificity the anti-ICOS antibody. Following incubation with the antibody, HPB-ALL hICOS-cells are washed three times with 200 micro liter of ELISA buffer. The amount of anti-ICOS antibodies bound to HPB-ALL hICOS cells may be detected using a goat anti-human kappa antibody conjugated with horseradish peroxidase following standard protocols. An ICOS specific antibody should give a dose dependent ELISA signal with the HPB-ALL hICOS cells but not with the parental HPB-ALL cells. The ELISA signal is expected to reach a maximum at an antibody concentration where all available epitopes on the cell surface are bound.

Anti-ICOS antibodies may also be characterized by an ELISA assay that uses a recombinant ICOS-Fc fusion protein (R&D Systems) as a capture reagent. ELISA assays may be performed according to any one of the established protocols known to one of skill in the art. For example, microtiter plates are coated with ICOS-Fc fusion protein (e.g., 100 µl of 0.25 pg/ml ICOS-Fc protein) and incubated at 4° C. overnight. Any remaining binding sites are blocked with 4% skimmed milk in PBS buffer (blocking buffer) for 1 h at 37° C. Approximately 25-50 µl of anti-ICOS antibody solution of various concentrations is added to each well and incubated for 1 h at 37° C. After washing the wells, a goat anti-human kappa antibody conjugated with horseradish peroxidase is used for the detection of ICOS-Fc fusion protein bound anti-ICOS antibody following the manufacturer's directions. Detection is carried out by adding 30 µl of tetramethylbenzidine (TMB) substrate (Pierce) followed by neutralization with 30 µl of 0.2 M $H_2SO_4$. The absorbance is read at 450 nm. Negative control wells using an isotype matched antibody of irrelevant specificity should be included in the assay. In addition, negative control wells without ICOS-Fc protein may also be included in the assay. An ICOS specific antibody should give a dose dependent ELISA signal with the ICOS-Fc coated wells but not with the uncoated negative control wells. The ELISA signal is expected to reach a maximum at an antibody concentration where all available epitopes are occupied.

The antigen specificity of ADCC enhanced anti-ICOS antibodies may also be characterized by flow cytometry assays. Isolated cells expressing human ICOS on their cell surface (e.g., stable transfectant CHO hICOS cells, activated T lymphocytes) are incubated with a fluorescently conjugated anti-ICOS antibody following a standard protocols. Negative control cell that do not display ICOS on the cell surface are stained as well using the same protocol. Immuno stained cells are analyzed on a flow cytometer. Cells incubated with a negative control antibody of unrelated specificity may also be included in the assay. An ICOS expressing cell stained with a fluorescently conjugated anti-ICOS antibody should have a mean fluorescence intensity that is higher than that of either a non-ICOS expressing cell stained with the same antibody or an ICOS expressing cell stained with a negative control antibody of irrelevant specificity.

The binding affinity of ADCC enhanced anti-ICOS antibodies may also be determined using the Biacore System (see, U.S. Pat. No. 6,803,039).

7.3. Antigen Binding Affinity of Deamidated Anti-ICOS Antibodies

Deamidation of asparagines residue may significantly contribute to the chemical degradation of antibody pharmaceuticals (see, Chelius et al., *Anal. Chem.* 77:6004-11 (2005)). Deamidation may be especially important when the potential deamidation site is located within the CDR regions of an antibody. CDR3 of the JMAb136 light chain variable domain comprises a NS potential deamidation site at Kabat position 92. The effect of deamidation on the antigen binding affinity of an anti-ICOS antibody may be assessed using methods known to one of skills in the art. Briefly, an anti-ICOS antibody is stored under conditions known to enhance the chemical deamidation process. For example, an anti-ICOS antibody may be stored for two weeks at 40° C. in a buffer with a pH of 8.5 or 9.5 to accelerate the deamidation process. As deamidation of an asparagine residue changes the overall charge of the protein, the extent of deamidation in a given purified antibody sample may be assessed by a number of analytical methods, for example, but not limited to, ion exchange chromatography (IEC), isoelectro focusing (IEF), Liquid Chromatography/Mass Sprectometry (LC-MS). The effect of deamidation on ICOS binding affinity may be ascertained by comparing the binding properties of IC9G1 antibody preparations with high and low levels of deamidation. Binding affinity of the various antibody preparations may be analaysed by for example, but not limited to, cell based ELISA assays, ELISA assays using a recombinant ICOS molecule as capture reagent, flow cytometry, Biacore analysis. A significant decrease in the ICOS binding activity of a IC9G1 anti-ICOS antibody preparations upon deamidation would suggest that deamidation plays a major role in the chemical degradation of the antibody. Alternatively, the ICOS binding activity of non-deamidated and deamidated IC9G1 antibody preparations may be very similar suggesting that deamidation is not a major concern when considering the degradation pathways of the antibody. If deamidation poses a problem for the long term stability of the IC9G1 anti-ICOS antibody, then the deamidation site may be eliminated from the amino acid sequence by generating single amino acid substitution variants using the methods described above. The ICOS binding affinity of any deamidation null anti-ICOS antibody variant may be characterized by using the methods described herein.

7.4. In Vitro ADCC Activity of ADCC Enhanced Anti-ICOS Antibodies

The ADCC activity of various anti-ICOS antibodies may be determined by an in vitro ADCC assay, such as that described in U.S. Pat. No. 5,500,362 or 5,821,337. The ADCC assay may be performed using a commercially available assay kit, for example, but not limited to CytoTox 96® Non-Radioactive Cytotoxicity Assay (Promega). The CytoTox 96® Non-Radioactive Cytotoxicity Assay (Promega) is a colorimetric alternative to $^{51}$Cr release cytotoxicity assays. The CytoTox 96® Assay quantitatively measures lactate dehydrogenase (LDH), a stable cytosolic enzyme that is released upon cell lysis. Released LDH in culture supernatants is measured with a 30-minute coupled enzymatic assay, which results in the conversion of a tetrazolium salt (INT) into a red formazan product. The amount of color formed is proportional to the number of lysed cells.

The assays are performed according to the manufacturer's directions. Briefly, target cells are washed with PBS, resuspended in RPMI-5 Phenol Free media at a cell density of $0.4 \times 10^6$/ml. NK effector cells are washed once in PBS and resuspended in RPMI-5 Phenol Free media at a cell density $1 \times 10^6$/ml. Assays are performed in U bottom 96 well plates. Each assay plate includes a combination of experimental and control wells. Experimental wells are set up by combining 50 μl of the appropriate antibody dilution, 50 ul of target cell suspension and 50 ul of effector cell suspension. The cell densities described above result in a 1:2.5 target to effector cell ratio; effector cell stock may be further diluted or concentrated if a different target to effector ratio is desired. Several different types of control wells are used to account for (i) the spontaneous LDH release form target cells (Target Spontaneous), (ii) the spontaneous LDH release from effector cells (Effector Spontaneous), (iii) the maximum LDH release from the target cells (Target Maximum), and (iv) the presence of contaminants in the culture medium (Background). All wells in use on a 96 well plate contain the same final volume. Reactions are set up in triplicates. Following set up, plates are spun at 120×g for 3 minutes to pellet the cells. Incubate plate at 37° C./5% $CO_2$ for 4 hours. Forty five minutes prior to the end of incubation 15 μl of manufacturer provided Lysis Buffer is added to the Target Cell Maximum Release Control well. After incubation the plate is centrifuged at 120×g for 4 minutes. 50 μl of the supernatant from each well is transferred to a new flat bottom 96 well plate. 50 μl of reconstituted substrate mix (assembled from manufacturer provided components) is added and the plate is incubated at room temperature 10-20 minutes protected from light. 50 μl of manufacturer provided stop buffer is added and absorbance at 490 or 492 nm is measured in a plate reader. % cytotoxicity equals (Experimental-Effector spontaneous−Target Spontaneous)/ (Target Maximum−Target Spontaneous). Prior to calculating the % cytotoxicity all other values are reduced by the Background.

Potential target cells for an anti-ICOS antibody dependent cytotoxicity assay include, but are not limited to, stable transfectant hICOS expressing cell lines (e.g., human ICOS expressing CHO cell line and human ICOS expressing HPB-ALL cell line described in U.S. Pat. No. 6,803,039). Alternatively, freshly isolated cells displaying human ICOS on their cell surface (e.g., activated T cells) may also be used as target cells. Suitable effector cells include, but are not limited to, freshly isolated natural killer cells (NK cells), and peripheral blood mononuclear cells (PMBC). NK cell lines expressing a transgenic Fc receptor (e.g. CD16) and associated signaling polypeptide (e.g. FCεRI-γ) may also serve as effector cells (see, e.g. WO 2006/023148 A2 to Campbell).

ADCC assays are performed in parallel using unmodified anti-ICOS antibody (e.g., IC9G1), ADCC enhanced anti-ICOS antibody (e.g., IC9G1-aFuc, IC9G1-3M). ADCC enhanced antibodies are expected to mediate the lysis of a higher percentage of target cells than that of mediated by the unmodified antibody. An anti-ICOS antibody with reduced ADCC activity (e.g., IC9G1-TM) may also be include in the assay as a negative control. Target specificity of the anti-ICOS mediated ADCC assay may be demonstrated by using target cells not expressing hICOS. The background cytotxicity in ADCC assays performed using target cells not expressing hICOS is expected to be similar between reactions using ADCC enhanced and unmodified anti-ICOS antibodies.

7.5. Human ICOS Expression in Transgenic Mice

Human ICOS transgenic mice, which can be developed using methods well known to persons trained in the art, or other transgenic animals expressing human ICOS can be used to assess different therapeutic regimens comprising anti-ICOS antibodies, such as variations in dosing concentration, amount, and timing. The efficacy in human patients of different therapeutic regimens can be predicted using, e.g., the two indicators described below, i.e., T cell depletion in certain bodily fluids and/or tissues and the ability of an anti-ICOS antibody to bind T cells. In particular embodiments, treatment regimens that are effective in human ICOS transgenic mice could be used with compositions and methods of the invention to treat human T cell disorders and disease including, but not limited to, autoimmune diseases or disorders, inflammatory diseases or disorders, and T cell malignancies.

In order to determine whether human ICOS is expressed on T cell subpopulations from transgenic mice (hICOStg) comprising the human ICOS transgene, T cells could be extracted from the thymus, peripheral blood, spleen, lymph node and peritoneal lavage of these mice. Human ICOS and mouse ICOS expression could be assessed in these cells by contacting the cells with anti-ICOS antibodies that specifically bind human ICOS (e.g., IC9G1) or mouse ICOS (mICOS) (e.g., clone 15F9, BioLegend, CA). Binding of the antibody to T lineage cell subpopulations could be detected using four-color immunofluorescence staining with flow cytometry analysis. The relative expression levels of mICOS and hICOS, could then be assessed by measuring mean fluorescence intensity (anti-hICOS for hICOS and anti-mICOS for mICOS) respectively.

7.6. Anti-ICOS Antibody Mediated Depletion of T Cells in Vivo

Anti-ICOS antibodies of the invention, which bind to human ICOS, can be assessed for their ability to deplete hICOStg thymic, peripheral blood, splenic, and lymph node T cell subpopulations in vivo. For example, each antibody would be given to mice at either 250 or 50 µg/mouse, a single dose about 10 to 50-fold lower than a 375 mg/m$^2$ dose given to a human subject. T cell depletion from thymus, blood, spleen and lymph nodes of hICOStg mice would be determined by immunofluorescence staining with flow cytometry analysis. The results using anti-ICOS antibodies identified as capable of depleting T cells can be correlated to use in humans and antibodies with properties of the identified antibodies can be used in the compositions and methods of the invention for the treatment of human T cell disorders and disease including, but not limited to, autoimmune diseases or disorders, inflammatory diseases or disorders, and T cell malignancies.

7.6.1. Determination Whether Tissue T Cell Depletion is FCγR-Dependent

Should administration of an anti-ICOS mAb of the invention result in tissue T cell depletion, the following assays can be used to demonstrate dependence upon FcγR expression. Through a process of interbreeding hICOStg mice with mice lacking expression of certain FcγR, mice can be generated that express hICOS and lack expression of certain FcγR. Such mice can be used in assays to assess the ability of anti-ICOS antibodies to deplete T cells through pathways that involve FcγR expression, e.g., ADCC. Thus, anti-ICOS antibodies identified in these assays can be used to engineer anti-ICOS antibodies with enhanced effector function using the techniques described above. Such antibodies can in turn be used in the compositions and methods of the invention for the treatment of human T cell disorders and disease including, but not limited to, autoimmune diseases or disorders, inflammatory diseases or disorders, and T cell malignancies.

Mouse effector cells express four different FcγR classes for IgG, the high-affinity FcγRI (CD64), and the low-affinity FcγRII (CD32), FcγRIII (CD16), and FcγRIV molecules. FcγRI, FcγRIII and FcγRIV are hetero-oligomeric complexes in which the respective ligand-binding α chains associate with a common γ chain (FcRγ). FcRγ chain expression is required for FcγR assembly and for FcγR triggering of effector functions, including phagocytosis by macrophages. Since FcRγ$^{-/-}$ mice lack high-affinity FcγRI (CD64) and low-affinity FcγRIII (CD16) and FcγRIV molecules, FcRγ$^{-/-}$ mice expressing hICOS can be used to assess the role of FcγR in tissue T cell depletion following anti-ICOS antibody treatment.

7.6.2. Durability of Anti-ICOS Antibody-Induced T Cell Depletion

To assess the efficacy and duration of T cell depletion, hICOStg mice can be administered a single low dose (e.g. 250 µg) injection of anti-ICOS antibody and the duration and dose response of T cell depletion followed as a function of time. The results are expected to demonstrate that circulating T cells are depleted for a substantial amount of time (e.g. one week to six months), followed by a gradual recovery of ICOS expressing T cells.

7.7. Therapeutic Efficacy of Subcutaneous (S.C.) Administration of an Anti-ICOS Antibody of the Invention The assay described herein can be used to determine whether a subcutaneous route of administration of an anti-ICOS antibody of the invention can effectively deplete T cell subpopulations. The results of the efficacy of different delivery routes tested in animal models can be correlated to humans by means well-known in the art.

For example, hICOStg mice can be treated with an anti-ICOS antibody of the invention at 250 µg either by subcutaneous (s.c.), intraperitoneal (i.p.) or intravenous (i.v.) administration. Values are determined for the mean (±SEM) blood (per mL), thymus, spleen, lymph node, and peritoneal cavity ICOS positive T cell numbers on day seven as assessed using flow cytometry. Results are expected to demonstrate that subcutaneous (s.c.), intraperitoneal (i.p.) and intravenous (i.v.) administration of an anti-ICOS antibody of the invention will effectively deplete ICOS expressing circulating and tissue T cells in vivo.

7.8. Use of Anti-ICOS Antibodies in Reducing Tumor Growth in an In Vivo Lymphoma Model Anti-ICOS antibodies of the invention, which bind to human ICOS, may be assessed for their ability to reduce tumor growth in in vivo animal models. For example, SCID mice would be injected with human ICOS expressing cell lines to establish a tumor xenograft (e.g., stable transfectant HBP-ALL hICOS cells). Subsequently, the mice would be given several doses of an anti-ICOS antibody of the invention (e.g., 100 µg antibody/mouse 5 times). Tumor growth would be followed using standard methods (e.g., tumor volume, animal weight, paralysis) The effect of anti-ICOS treatment on tumor growth may be determined by comparing animals receiving anti-ICOS or control antibody treatment. The results obtained using anti-ICOS antibodies identified as capable of reducing tumor growth can be correlated to use in humans, and antibodies capable of reducing tumor growth can be used in the compositions and methods of the invention for the treatment of human T cell disorders and diseases including, but not limited to, autoimmune diseases or disorders, inflammatory diseases or disorders, and T cell malignancies.

To determine whether an anti-ICOS antibody's ability to reduce tumor growth is dependent on ICOS density, tumor cell lines with different ICOS expression profiles may be tested in the above described in vivo tumor growth assay. The results obtained may demonstrate whether human ICOS density on the tumor cell surface can influence the tumor growth reducing activity of an anti-ICOS antibody. The results can be correlated to treatment of human patients with varying levels of ICOS expression. Thus, the methods for examining ICOS presence and density, described herein, can be used in human subjects to identify patients or patient populations for which certain anti-ICOS antibodies can reduce the growth of malignant T cells and/or to determine suitable dosages.

To determine whether an anti-ICOS antibody's ability to reduce tumor growth is dependent FcγR, the above described in vivo tumor growth assay would be performed using SCID mice with compromised Fcγ receptor activity (e.g., FcRγ$^{-/-}$). Through a process of interbreeding SCID mice with mice lacking expression of certain FcRγ$^{-/-}$, SCID mice can be generated that also lack expression of certain FcγR (e.g., SCID, FcRγ$^{-/-}$ mice). Such mice can be used in assays to assess the ability of anti-ICOS antibodies to reduce tumor growth through pathways that involve FcγR expression, e.g., ADCC. Based on the results, anti-ICOS antibodies with increased ADCC can be engineered using the techniques described above. Such antibodies can in turn be used in the compositions and methods of the invention for the treatment of human T cell disorders and diseases including, but not limited to, autoimmune diseases or disorders, inflammatory diseases or disorders, and T cell malignancies.

7.8.1. IC9G1-aFuc Binding to Fcgamma Receptors.

The equilibrium binding constants of IC009, IC9G1 and IC9G1-aFuc to human and cynomolgus FcγRIIIA-V158, FcγRIIIA-F158, FcγRIIA and FcγRIIB are measured on a BIAcore 3000 instrument (Uppsala, Sweden). The measurements are performed according to standard protocols. Briefly, all IgGs are immobilized onto separate flow cells of two CM5 sensor chips using standard amino coupling chemistry as recommended by the manufacturer. Immobilized IgG levels range from 8194 to 8725 RUs. Stock solutions of the recombinantly expressed extracellular domains of all FcγRs at either 4000 or 16000 nM are prepared and then serially diluted down to the desired concentrations using the instrument buffer (50 mM HBS buffer containing 0.01 M HEPES, pH 7.4, 0.15 M NaCl, 3 mM EDTA and 0.005% P-20). Duplicate injections of each concentration of FcγR ared then injected over all of the IgG surfaces at a flow rate of 5 μL/min. Binding data are collected for approximately 50 min, followed by a 30 sec. pulse of 5 mM HCl between injections to regenerate the IgG surfaces. Several buffer injections are also interspersed throughout the injection series. One of these buffer injections is used along with the reference cell data to correct the raw data sets. After all binding data is collected, individual data sets are averaged for each γ concentration, then fit to a 1:1 binding isotherm from which the equilibrium binding constants, $K_D$, are derived. Analysis is carried out using the BIAevaluation software. The $K_D$ values (nM) are presented in FIG. 2.

7.9. IC9G1-aFuc Inhibits Anti-CD3/ICOSL Induced Human T Cell Proliferation 96-well tissue culture plates are coated with 25 microL 2 μg/ml B7h-Fc protein and 25 microL of 0.2 μg/ml anti-CD3 antibody (OKT3). Isolated T cells are plated on the pre-coated plates in the presence of various concentration (0.1-20 μg/ml) of IC009, IC9G1 and IC9G1-aFuc antibody. T cell proliferation is ascertained by measuring after 72 hours of incubation the number of viable cells in each well using a luminescence assay. The proliferation of T cells in uncoated wells, and wells coated with either anti-CD3 antibody or B7h-Fc protein alone is determined as a control.

An example of the results obtained is shown in FIG. 3. Unstimulated T cells or T cells stimulated by anti-CD3 or B7h-Fc alone displayed a very limited baseline proliferation. T cell induction by surface bound anti-CD3 and B7h-Fc in the presence of 0.01 mg/ml antibody resulted in cell proliferation significantly above the baseline. Anti-CD3/B7h-Fc induced T cell proliferation is inhibited by all three anti-ICOS antibody tested (IC009, IC9G1 and IC9G1-aFuc) in a dose dependent manner. The inhibitory activity of IC009, IC9G1 and IC9G1-aFuc antibodies was substantially identical in the assay.

7.10. IC9G1-aFuc does not Inhibit Anti-CD3/Anti-CD28 Induced Human T Cell Proliferation 96-well tissue culture plates are coated with anti-CD3 (OKT3) and anti-CD28 antibodies. Isolated tonsillar T cells are plated on the pre-coated plates in the presence of 10 μg/ml of IC9G1-aFuc antibody. T cell proliferation is ascertained by measuring after 72 hours of incubation the number of viable cells in each well using a luminescence assay. The proliferation of T cells in uncoated wells, and wells coated with either anti-CD3 or anti-CD28 antibody only is determined as a control.

An example of the results obtained is shown in FIG. 4. Unstimulated T cells or T cells stimulated by anti-CD3 or anti-CD28 antibody alone displayed a very limited baseline proliferation. T cell induction by surface bound anti-CD3 and anti-CD28 antibodies resulted in cell proliferation significantly above the baseline (αCd3+αCD28). The IC9G1-aFuc antibody (10 μg/ml) did not inhibit the anti-CD3/anti-CD28 induced T cell proliferation (αCd3+αCD28+IC9G1-aFuc).

7.11. IC9G1-aFuc has Enhanced ADCC Activity

The ADCC activity of IC9G1-aFuc is ascertained by an in vitro ADCC assay using various ICOS expressing primary cells and cell lines. The ADCC assays are performed following a standard protocol. Briefly, target cells and effector cells (e.g., transgenic NK cells expressing CD16 and associated signaling polypeptide FCεRI-ε) are plated at a predetermioned ratio (e.g., 2.5:1 effector to target ratio) in the presence of the IC9G1-aFuc antibody. The plates are incubated for a pre-determined length of time (e.g. 4 hrs). Cell death is ascertained by measuring LDH release into the supernatant using a commercially available LDH detetction kit. Antibody mediated cytotoxicity is calculated by subtracting from the LDH levels detected in the antibody containing wells the background LDH levels detected in antibody-free control wells. Antibody mediated cytotoxicity is expressed as a % of maximum cytotoxicity achievable. The maximum cytotoxicity value is derived from the LDH levels measured in wells containing chemically lysed cells (e.g. Triton-X 100 treated well). ADCC activity is presented by plotting antibody mediated cytotoxicity as a function of the antibody concentration. EC50 values correspond to the antibody concentration resulting in a 50% maximum antibody mediated cytotoxicity in the particular assay.

Figure 5A:
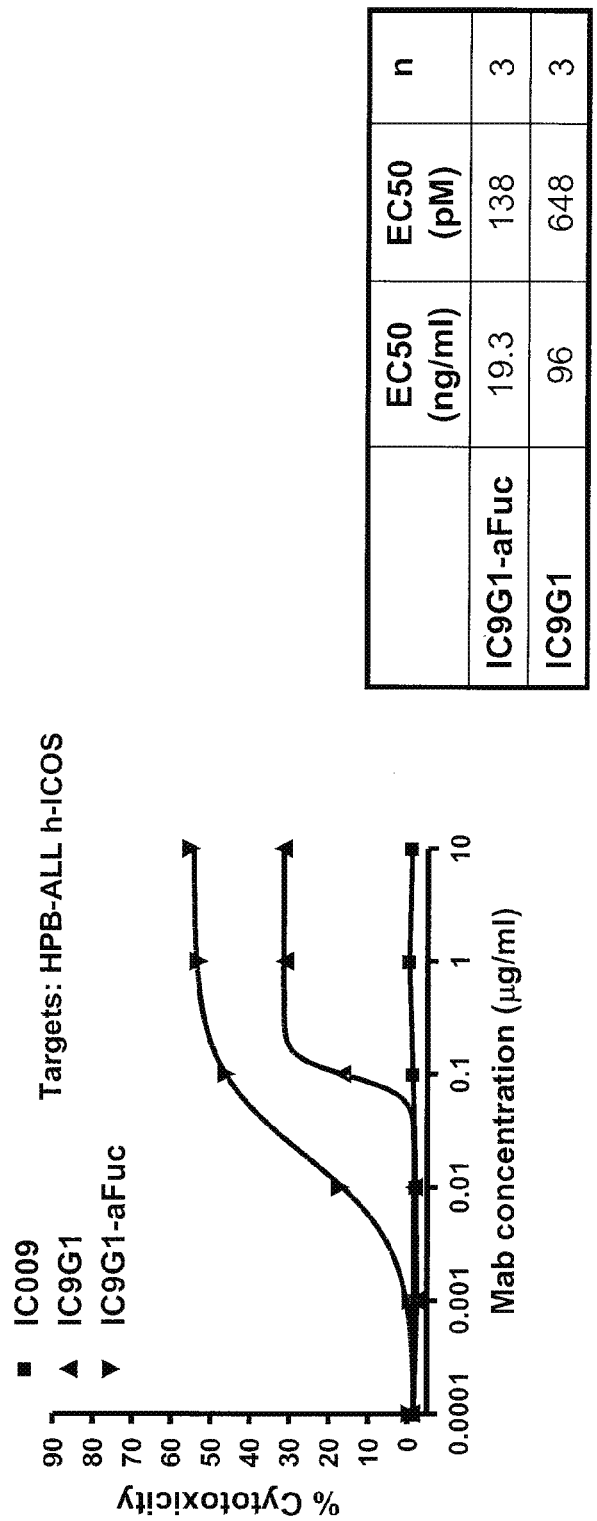

FIG. 5A shows an example of ADCC activity measurements performed using stable transfectant HPB-ALL hICOS cells as target cells. The generation of human ICOS transgenic HPB-ALL cell line is described in U.S. Pat. No. 6,803,039. The ADCC assay was performed using CD16/FCεRI-γ transgenic NK cells as effector cells at a 2.5:1 effector to target ratio. The ADCC reaction was allowed to proceed for 4 hrs. The ADCC activity of IC009, IC9G1 and IC9G1-aFuc antibodies was ascertained. IC009 mediated ADCC activity was below the detection level. The ADCC activity of IC9G1-aFuc was significantly higher than that of the IC9G1 antibody. The EC50 values of IC9G1-aFuc and IC9G1 antibodies were 138 pM and 648 pM, respectively, in this assay.

Figure 5B:
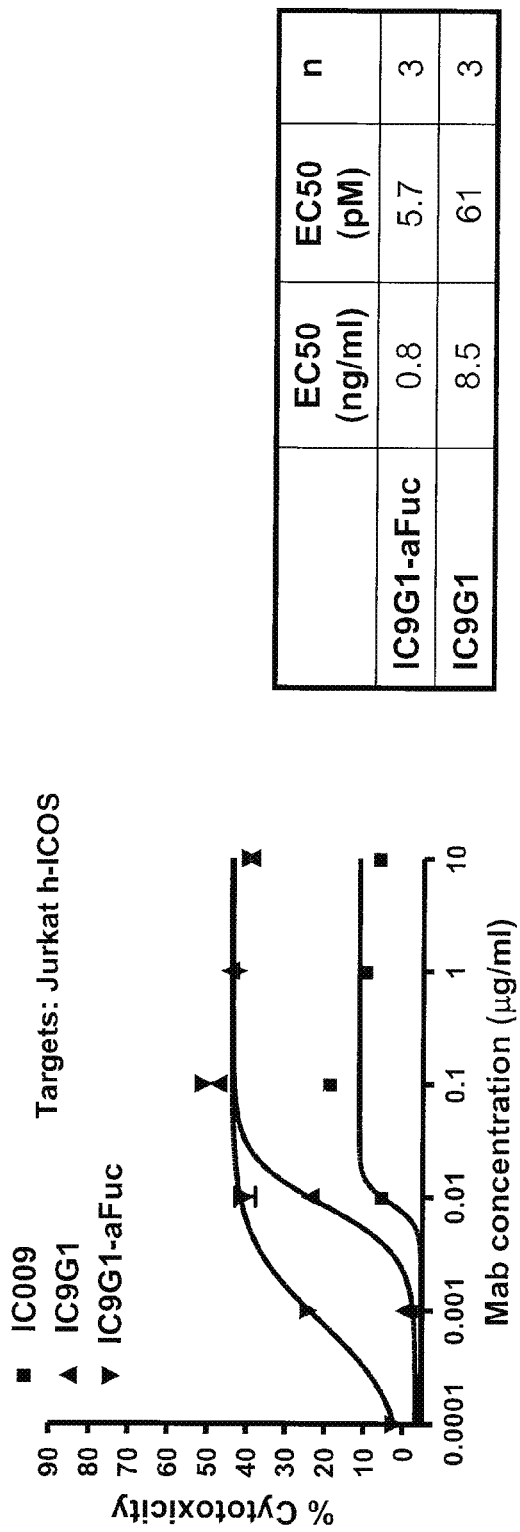

FIG. 5B shows an example of ADCC activity measurements performed using human ICOS transgenic Jurkat cells as target cells. The ADCC assay was performed using CD16/FCϵRI-γ transgenic NK cells as effector cells at a 2.5:1 effector to target ratio. The ADCC reaction was allowed to proceed for 4 hrs. The ADCC activity of IC009, IC9G1 and IC9G1-aFuc antibodies was ascertained. All three antibodies displayed measurable ADCC activity. Maximum % ADCC activity of IC9G1-aFuc and IC9G1 was higher then that of IC009. Maximum % ADCC activity of IC9G1-aFuc and IC9G1 were substantially identical. The EC50 values of IC9G1-aFuc and IC9G1 antibodies were 5.7 pM and 61 pM, respectively, in this assay.

FIG. 7 shows an example of ADCC activity measurements performed using isolated human tonsillar T cells as target cells. ICOS expression of human tonsillar T cells was restricted to the CD4+CD45RO+CD45RA−CXCR5+ memory $T_{FH}$ cell population (FIG. 6). Human tonsillar T cells were isolated with the help of a commercially available kit (Miltenyi MACS human PanT cell isolation kit). The ADCC assay was performed using isolated human NK cells as effector cells ar a 2:1 effector to target ratio; the reaction was incubated overnight. The ADCC activity of IC009, IC9G1 and IC9G1-aFuc antibodies was ascertained. IC009 mediated ADCC activity was slightly above detection level. The IC9G1-aFuc and IC9G1 antibodies displayed a dose dependent ADCC activity in this assay. The ADCC activity of IC9G1-aFuc was significantly higher than that of the IC9G1 antibody. The EC50 values of IC9G1-aFuc and IC9G1 antibodies were 8.2 pM and 60.4 pM, respectively, in this assay.

FIG. 8 shows an example of ADCC activity measurements performed using isolated cynomolgus splenic T cells as target cells. ICOS expression was substantially restricted to the CD4+CD45RA− memory T cell population in the spleen (FIG. 8A). Cynomolgus splenic T target cells were isolated using a non-human primate T cell isolation kit (Miltenyi). The ADCC assay was performed using isolated human NK cells as effector cells ar a 2:1 effector to target ratio; the reaction was incubated overnight. The ADCC activity of IC009, IC9G1 and IC9G1-aFuc antibodies was ascertained. IC009 mediated ADCC activity was below detection level. The IC9G1-aFuc and IC9G1 antibodies displayed a dose dependent ADCC activity in this assay. The ADCC activity of IC9G1-aFuc was significantly higher than that of the IC9G1 antibody. The EC50 values of IC9G1-aFuc and IC9G1 antibodies were 14.6 pM and 236 pM, respectively, in this assay.

FIG. 8 shows an example of ADCC activity measurements performed using isolated cynomolgus mesenteric lymph node (MLN) T cells as target cells. ICOS expression was substantially restricted to the CD4+CD45RA− activated T cell population in the MLN (FIG. 9A). Cynomolgus splenic T target cells were isolated using a non-human primate T cell isolation kit (Miltenyi). The ADCC assay was performed using isolated human NK cells as effector cells ar a 2:1 effector to target ratio; the reaction was incubated overnight. The ADCC activity of IC009, IC9G1 and IC9G1-aFuc antibodies was ascertained. IC009 mediated ADCC activity was at detection level. The IC9G1-aFuc and IC9G1 antibodies displayed a dose dependent ADCC activity in this assay. The ADCC activity of IC9G1-aFuc was significantly higher than that of the IC9G1 antibody. The EC50 values of IC9G1-aFuc and IC9G1 antibodies were 17.1 pM and 198 pM, respectively, in this assay.

7.12. Pharmacokinetic Profile of IC9G1-aFuc in Cynomolgus Monkeys

Cynomolgus monkeys were administered a single IV dose of IC9G1-aFuc antibody on day 0 of the experiment. Experimental design is outlined in Table 3.

TABLE 3

Experimental design of in vivo studies of IG9G1-aFuc in cynomolgus monkeys.

| Group | Agent | Dose (mg/kg) | Number |
|---|---|---|---|
| 1 | Carrier only | 0 | 5 males |
| 2 | IC9G1-aFuc | 0.01 | 5 males |
| 3 | IC9G1-aFuc | 0.1 | 5 males |
| 4 | IC9G1-aFuc | 1 | 5 males |
| 5 | IC9G1-aFuc | 10 | 5 males |
| 6 | IC009 | 10 | 5 males |

The pharmacokinetic profile of IC9G1-aFuc was analyzed by delivering a single dose of the antibody and monitoring its serum concentration over time. Serum concentration of IC9G1-aFuc was measured by ELISA according to standard protocols. ICG91-aFuc serum concentration as a function of time is presented in FIG. 10. Systemic exposure based on estimates of $AUC_{LAST}$ for IC9G1-aFuc and $C_{max}$ increased in a dose proportional manner with increasing the dose, reflecting the linearity in the antibody pharmacokinetic properties. Mean terminal half-life (t½ lz) values of 4.36±1.52 days, 6.34±1.44 days and 7.87±1.09 days were observed following bolus infusions of 0.1 mg/kg, 1 mg/kg and 10 mg/kg, respectively.

7.13. In Vivo T Cell Depletion Following the Administration of a Single Dose of IC9G1-aFuc Cynomolgus monkeys were administered a single IV dose of IC9G1-aFuc antibody. Antibody dose administered to the various animals is described in Table 3. Two animals from each group were sacrificed on day 8 post-dosing. Three animals from each group were sacrificed on day 29 post-dosing. The level of circulating, splenic and mesnteric lymph node (MLN) ICOS+ T cells were monitored for four weeks following the delivery of the single antibody dose. ICOS+ T cells were monitored by flow cytometry.

FIG. 11 shows the changes in circulating ICOS+ memory T cell level following the administration of a single dose of IC9G1-aFuc antibody. Circulating memory T cells were defined as CD3+CD4+CD45RA−ICOS+ cells for the purposes of this study. Absolute numbers of circulating memory T cells detected were normalized to the circulating memory T cell numbers detected on day 0 prior to antibody administration. Administration of a single dose of 0.01 mg/kg of IC9G1-aFuc antibody resulted in a significant reduction in circulating memory T cell count by day 4. Administration of a single dose of 0.1 mg/kg, 1 mg/kg or 10 mg/kg of IC9G1-aFuc antibody resulted in the complete elimination of circulating memory T cells by day 4 of the experiment. Recovery of the circulating memory T cell compartment over time was dose dependent.

Figure 13A:
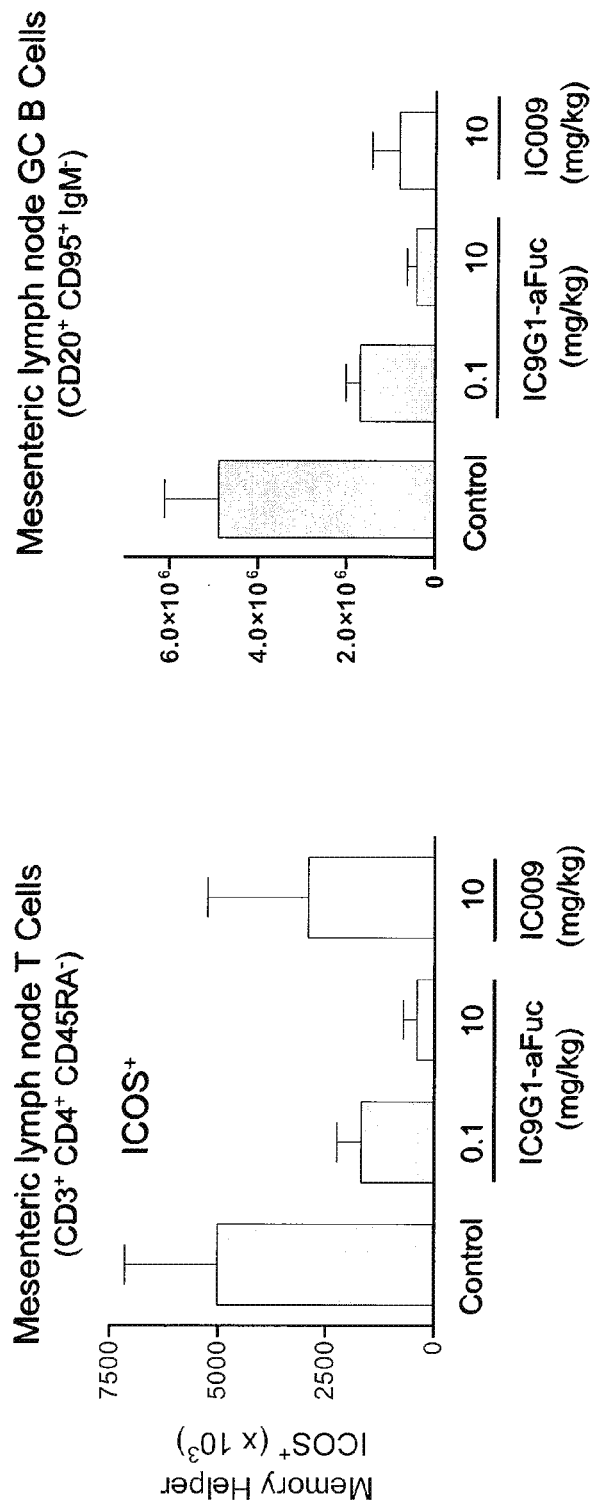
Figure 13B:
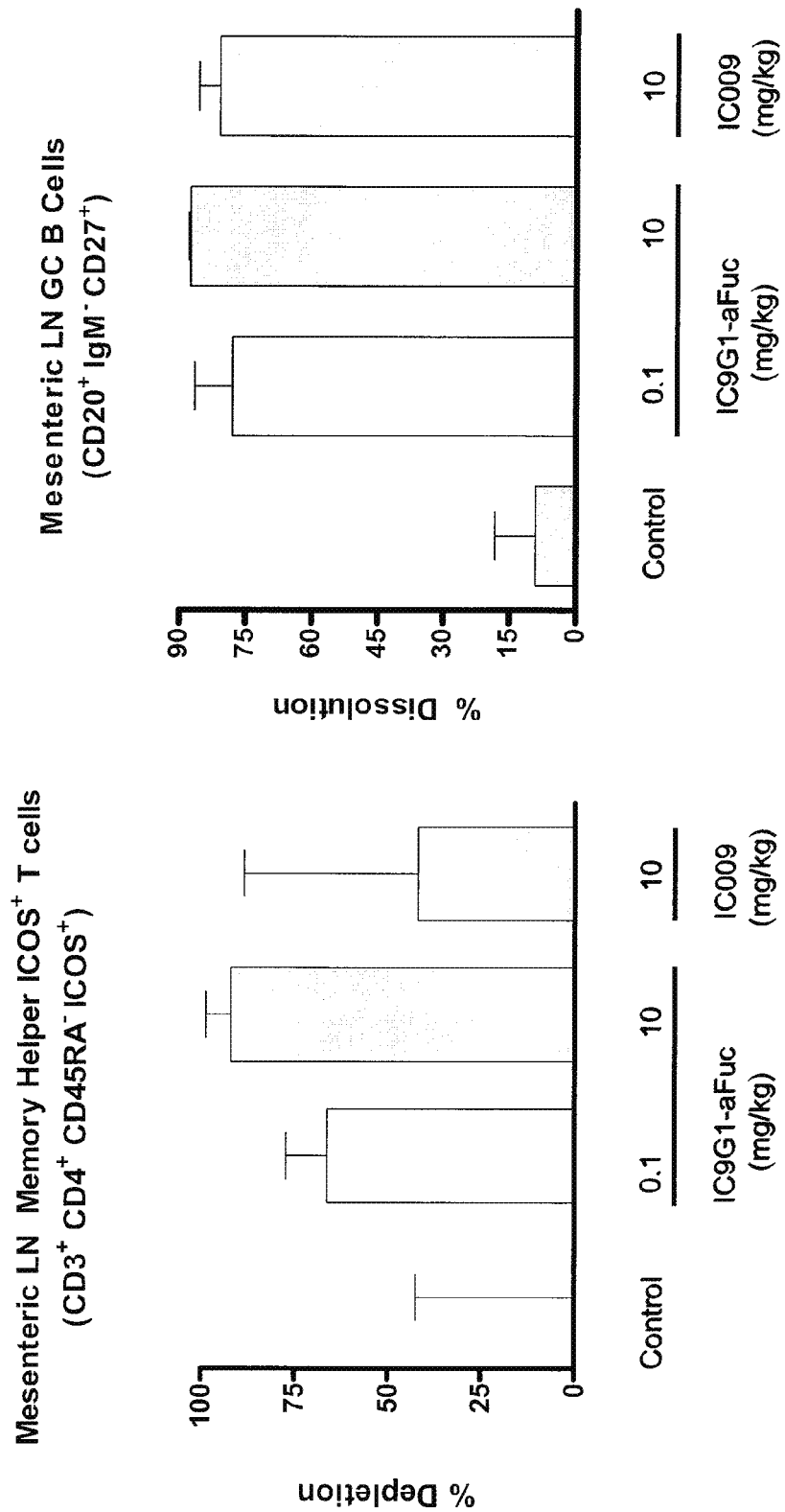

FIG. 13 provides an example of the depletion results seen in the mesenteric lymph node (MLN) T cell compartment. MLN T cells were isolated from animals sacrificed on day 8 and day 29 of the experiment. Absolute numbers of ICOS+ memory helper T cells isolated from the MLN were determined by flow cytometry. Memory helper T cells were defined as CD3+CD4+CD45RA− for the purposes of the experiment. Absolute numbers of ICOS+ memory T cells isolated from the MLN on day 8 are displayed in FIG. 13A. Administration of a single dose of 0.1 mg/kg and 10 mg/kg of IC9G1-aFuc antibody resulted in a significant dose dependent depletion of ICOS+ memory helper T cells from the mesenteric lymph node. Similar depletion of ICOS+ memory helper T cells was detected in the tonsil and mandibular lymph node. FIG. 13B presents the % depletion of ICOS+ memory helper T cells in the mesenteric lymph node on day 8. % depletion was calculated by normalizing the absolute ICOS+ memory helper T cell numbers detected in IC9G1-aFuc treated animals to the cell numbers detected in the carrier only treated control animals. Administration of a single dose of 0.1 mg/kg and 10 mg/kg of IC9G1-aFuc antibody resulted in the depletion of greater than 60% and 90%, respectively, of ICOS+ memory helper T cells from the mesenteric lymph node by day 8.

Figure 14A:
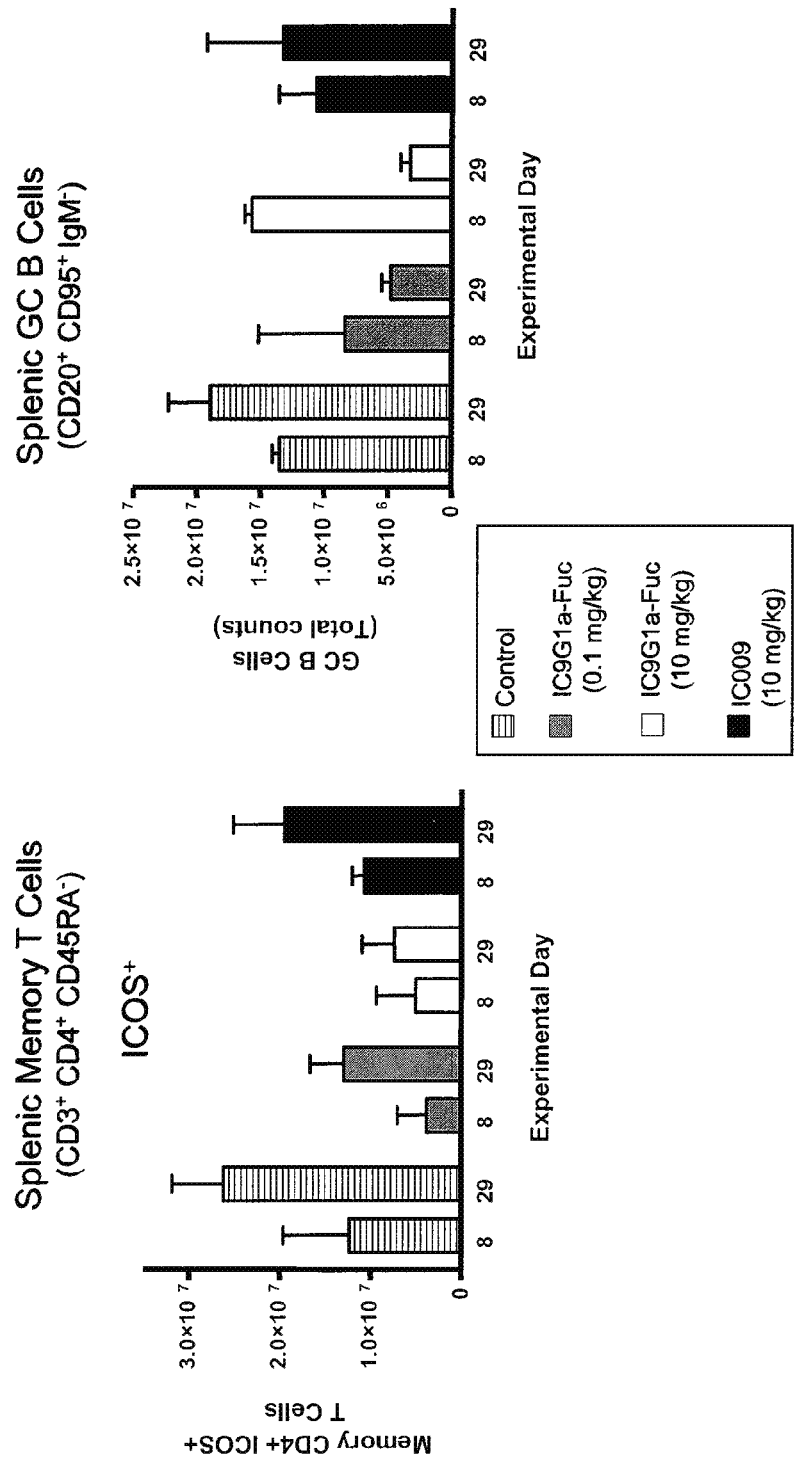
Figure 14B:
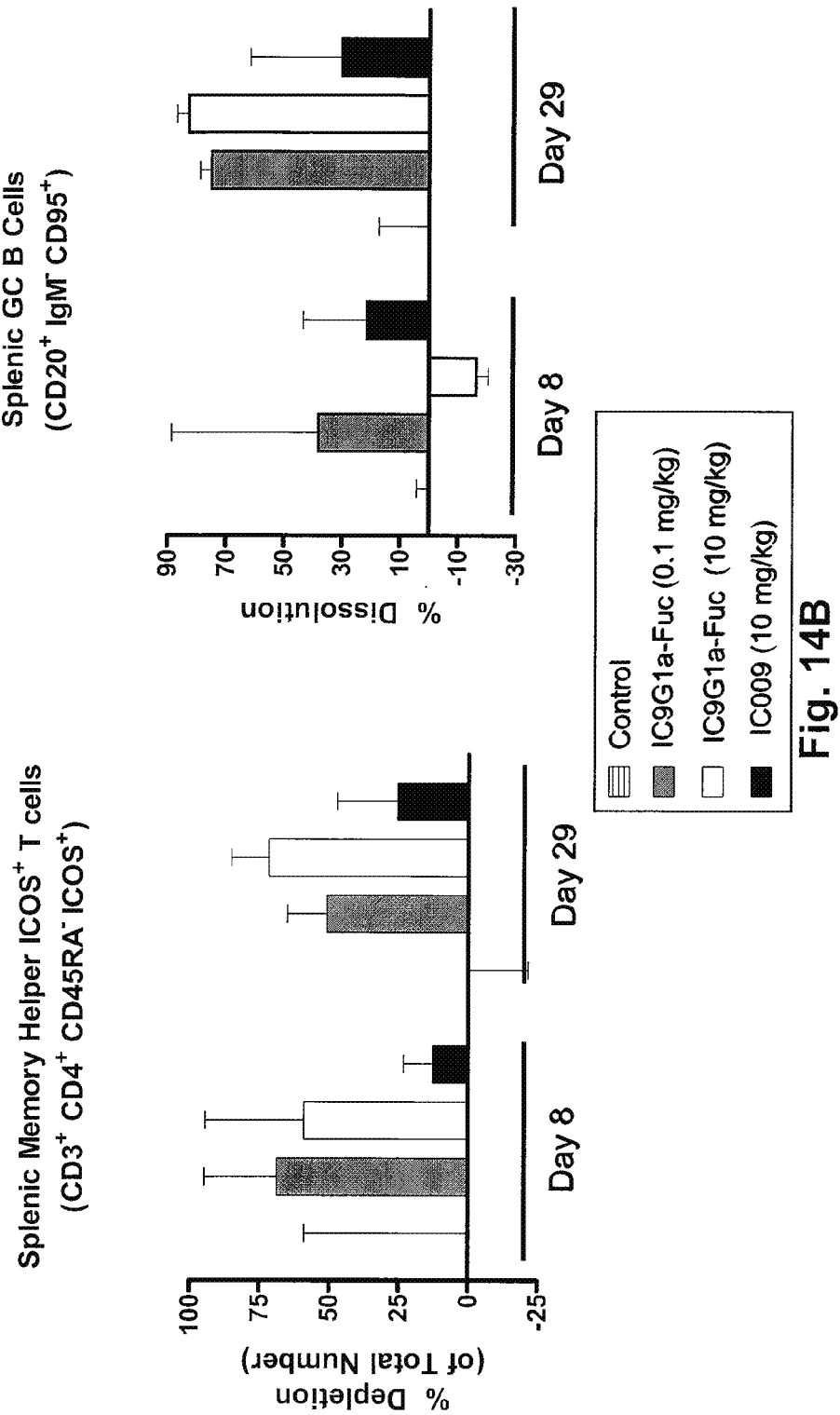

FIG. 14 provides an example of the depletion results seen in the splenic T cell compartment. Splenic T cells were isolated from animals sacrificed on day 8 and day 29 of the experiment. Absolute numbers of splenic ICOS+ memory helper T cells were determined by flow cytometry. Memory helper T cells were defined as CD3+CD4+CD45RA− for the purposes of the experiment. Absolute numbers of ICOS+ memory T cells isolated from the MLN on day 8 and 29 are displayed in FIG. 14A. Administration of a single dose of 0.1 mg/kg and 10 mg/kg of IC9G1-aFuc antibody resulted in a significant depletion of splenic ICOS+ memory helper T cells by day 8. The recovery of splenic ICOS+ memory helper T cells were dose dependent; splenic ICOS+ T cell recovery on day 28 was more pronounced in animals dosed with 0.1 mg/kg IC9G1-aFuc than in animals dosed with 10 mg/kg IC9G1-aFuc. FIG. 14B presents the % depletion of splenic ICOS+ memory helper T cells in the mesenteric lymph node on day 8 and 29. % depletion was calculated by normalizing the absolute ICOS+ memory helper T cell numbers detected in IC9G1-aFuc treated animals to the cell numbers detected in the carrier only treated control animals. Administration of a single dose of 0.1 mg/kg and 10 mg/kg of IC9G1-aFuc antibody resulted in the depletion of greater than 60% of splenic ICOS+ memory helper T cells by day 8. By day 29, the splenic ICOS+ memory helper T cell compartment of animals dosed with 0.1 mg/kg of IC9G1-aFuc started to recover. The splenic ICOS+ memory helper T cell compartment of animals dosed with 10 mg/kg of IC9G1-aFuc was more depleted on day 29 than on day 8.

7.14. In Vivo Administration of a Single Dose of IC9G1-aFuc Results in the Dissolution of Already Formed Germinal Centers Cynomolgus monkeys were administered a single IV dose of IC9G1-aFuc antibody. Antibody dose administered to the various animals is described in Table 3. Two animals from each group were sacrificed on day 8 post-dosing. Three animals from each group were sacrificed on day 29 post-dosing. The architecture of splenic white pulp was examined on day 8 and 29 using standard histology protocols. The number of mesenteric lymp node and splenic germinal center B cells were measured on day 8 and 29 by flow cytometry.

Figure 15A:
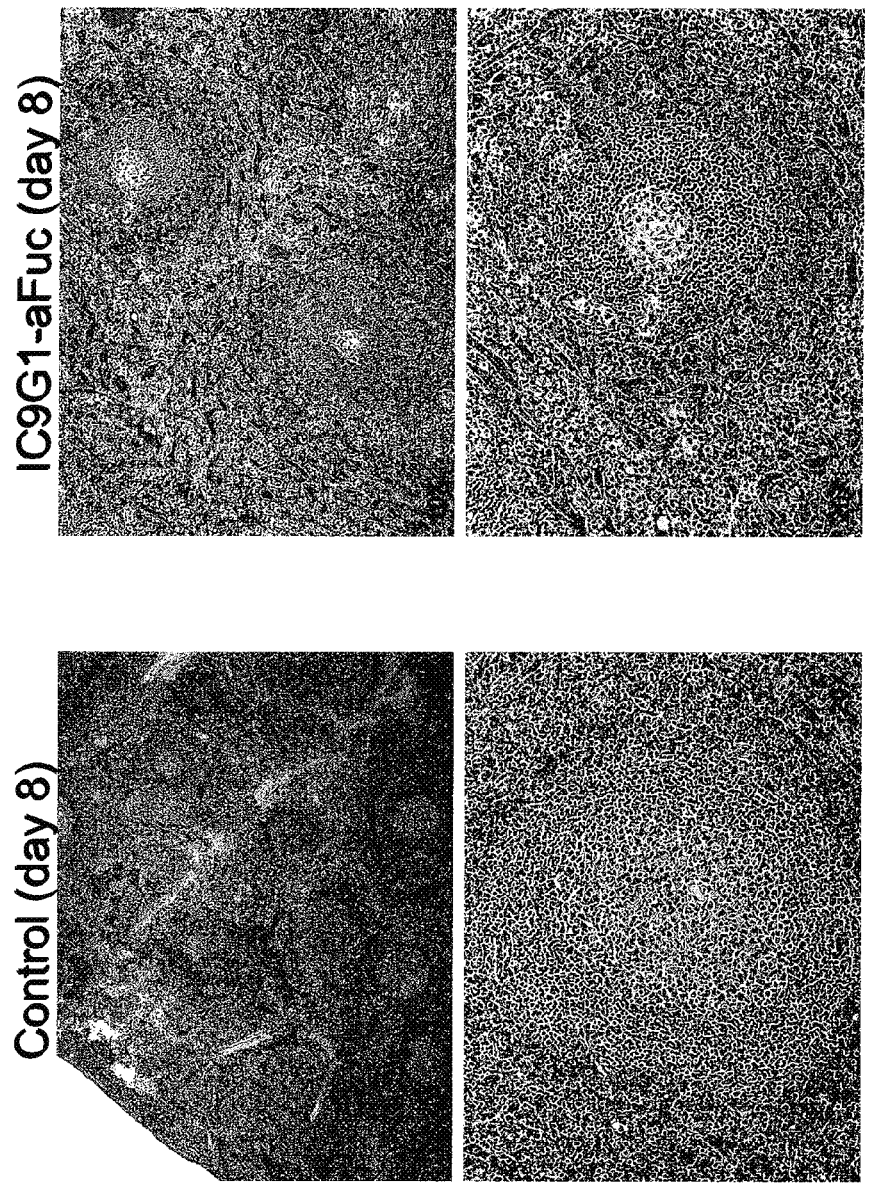
Figure 15B:
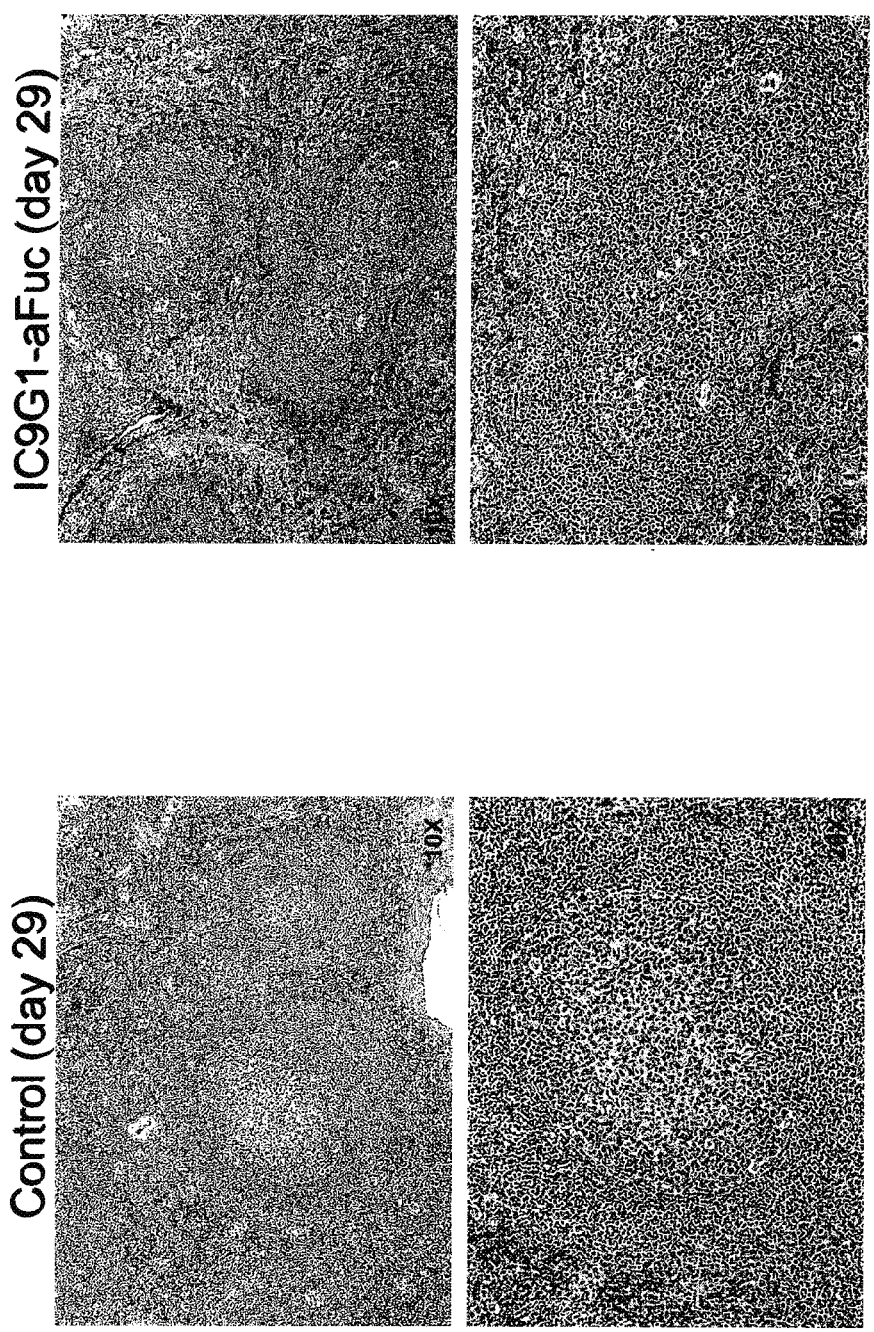

FIG. 15 presents an example of the architectural changes to the splenic white pulp caused by the administration of a single IV dose of IC9G1-aFuc. Low (10×) and high (20×) magnification of histological sections of white pulp isolated from control and IC9G1-aFuc dosed animals on day 8 (FIG. 15A) and day 29 (FIG. 15B) of the experiment is shown. Splenic follicles were atrophied on day 29 after administration of a single dose of IC9G1-aFuc antibody to cynomolgus monkeys. The morphology of splenic white pulp was examined following the administration of a single dose f IC9G1-aFuc antibody. Histological sections of the spleen isolated on day 8 (A) and day 29 (B) after IC9G1-aFuc antibody administration are shown. IC9G1-aFuc administration results in severe atrophy of splenic follicles by day 29.

FIG. 12 shows the flow cytometry protocol that was used to identify germinal center B cells. Lymphocytes were isolated from lymphatic organs of sacrificed animals following standard protocols. Isolated lymphocytes were immunostained with anti-CD3, anti-CD20, anti-IgM and anti CD95 or anti-CD27 antibodies. Dead cells were excluded from the analysis with the aid of 7AAD staining. Germinal center N cells were defined as either CD3-CD20+IgM−CD95+ or CD3-CD20+ IgM− CD27+ cells.

FIG. 13 provides an example of the effects on the mesenteric lymph node (MLN) germinal center B cell compartment caused by the administration of a single dose of IC9G1-aFuc. MLN lymphocytes were isolated from animals sacrificed on day 8 and day 29 of the experiment. Absolute numbers of germinal center B cells were determined by flow cytometry. Germinal center B cells were defined as CD20+IgM− CD95+ cells for the purposes of the experiment. Absolute numbers of germinal center B cells isolated from the MLN on day 8 are displayed in FIG. 13A. Administration of a single dose of 0.1 mg/kg and 10 mg/kg of IC9G1-aFuc antibody resulted in a significant dose dependent loss of germinal center B cells from the mesenteric lymph node. The administration of a single dose of the IC009 antibody resulted in a comparable loss of germinal center B cells from the MLN on day 8. FIG. 13B presents the % dissolution of germinal centers in the mesenteric lymph node on day 8. % dissolution was calculated by normalizing the absolute germinal center B cell numbers detected in IC9G1-aFuc treated animals to the cell numbers detected in the carrier only treated control animals. Administration of a single dose of 0.1 mg/kg and 10 mg/kg of IC9G1-aFuc antibody resulted in the dissolution of greater than 75% and 90%, respectively, of germinal centers from the mesenteric lymph node by day 8. Administration of a single dose of 10 mg/kg of IC009 antibody resulted in the dissolution of greater than 80% of germinal centers from the mesenteric lymph node by day 8. The germinal center B cells in this model system were present in the MLN prior to administration of the IC9G1-aFuc antibody. The loss of germinal center B cells from the MLN therefore indicates that the depletion of ICOS+ memory helper T cells leads to the dissolution of previously formed germinal centers.

FIG. 14 provides an example of the effects on the splenic germinal center B cell compartment caused by the administration of a single dose of IC9G1-aFuc. Splenic lymphocytes were isolated from animals sacrificed on day 8 and day 29 of the experiment. Absolute numbers of germinal center B cells were determined by flow cytometry. Germinal center B cells were defined as CD20+IgM− CD95+ cells for the purposes of this experiment. Absolute numbers of germinal center B cells isolated from the spleen on day 8 and 29 are displayed in FIG. 14A. Administration of a single dose of 0.1 mg/kg and 10 mg/kg of IC9G1-aFuc antibody did not significantly affect splenic germinal center B cells numbers on day 8. By day 29, however, the splenic germinal center B cell numbers were significantly reduced in IC9G1-aFuc treated animals, In contrast, no significant change in splenic germinal center B cell numbers were detected in IC009 treated animals. FIG. 14B presents the % dissolution of splenic germinal centers on day 8 and 29. % dissolution was calculated by normalizing the absolute germinal center B cell numbers detected in IC9G1- aFuc treated animals to the cell numbers detected in the carrier only treated control animals. Administration of a single dose of IC9G1-aFuc antibody did not result in significant dissolution of splenic germinal centers by day 8. By day 29, however, approximately 80% of splenic germinal centers were dissolved in the IC9G1-aFuc treated animals. No significant dissolution of splenic germinal centers were detected on either day 8 or 29 following the administration of 10 mg/kg of IC009. The germinal center B cells in this model system were present in the spleen prior to administration of the IC9G1-aFuc antibody. The loss of germinal center B cells from the spleen therefore indicates that the depletion of ICOS+ memory helper T cells leads to the dissolution of previously formed germinal centers.

7.15. ICOS and ICOSL mRNA Expression is Elevated in Patients Affected by Inflammatory or Autoimmune Diseases

7.16. ICOS is a Therapeutic Target in Systemic Lupus Erythematosus

Inducible costimulator (ICOS) is involved in the regulation of autoimmune and proinflammatory responses and may play important roles in the pathogenesis of SLE. We used a genomics approach to evaluate the mRNA expression levels of a panel of cytokines and immune regulators in lesional skin of active SLE patients with cutaneous involvement.

We profiled lesional skin and whole blood (WB) from a large panel of SLE patients with cutaneous involvement using the Affymetrix® human whole genome array (WGA) platform. TaqMan® QRT-PCR using a BioMark™ 48.48 dynamic array from Fluidigm was used to measure the mRNA levels of both long and short alternative splicing forms of ICOS, along with a large panel of cytokines.

ICOS mRNA was overexpressed in lesional skin for approximately 50-60% of the SLE patients evaluated in the study (FIG. 20). Positive correlations between ICOS and the ICOS ligand mRNA overexpression, and between ICOS and IL-10 mRNA overexpression were observed. Robust overexpression of these mRNAs was not observed in peripheral uninvolved tissues of SLE patients. Additionally, we used TaqMan QRT-PCR to determine whether the short or long alternative splicing form of ICOS is overexpressed in SLE, and also evaluated miR-101 expression in ICOS+ memory T cells purified from WB of SLE patients.

Two protein isoforms of ICOS were identified from the cDNA database (see FIG. 16). Full length of ICOS (SEQ ID NO:32) has 199 amino acids. It contains a signal peptide, an extracellular domain, a transmembrane domain and a cytoplasmic domain. In the cytoplasmic domain, it contains YMFM (residues 180-183 of SEQ ID NO:32) conserved motif for PI3K binding. The short form of ICOS (SEQ ID NO:33) has 168 amino acids. The short form has a in frame truncation in cytoplasmic domain caused by exon 4 skipping. The truncation generated a much shorter cytoplasmic domain and lost PI3K binding site that may have functional impacts on ICOS function.

In silico analysis of ICOS 3' UTR (residues 238-2284 of SEQ ID NO:34) using a MiRanda revealed several putative miRNA target sites (FIG. 17). MicroRNA target region one (MTR1), a 47 bp region containing target sequences for miR-101, 103/107 and 338, and miRNA target region two (MTR2), a 47 bp region containing the target sequence for miR-149. Complementarity of ICOS cDNA and the identified miRNA molecules is shown in FIG. 17. (Di Yu, & Carola G. Vinuesa et al. Nature (2007) 450, 299-303).

Affymetrix GeneChip and qRT-PCR Profiling—SLE: We profiled lesional skin and whole blood (WB) from a panel of SLE patients with cutaneous involvement using the Affymetrix® human whole genome array (WGA) platform. TaqMan@ qRT-PCR using a BioMark™ 48.48 dynamic array from Fluidigm was used to measure the mRNA levels of ICOS, along with a large panel of cytokines.

Figure 20A:
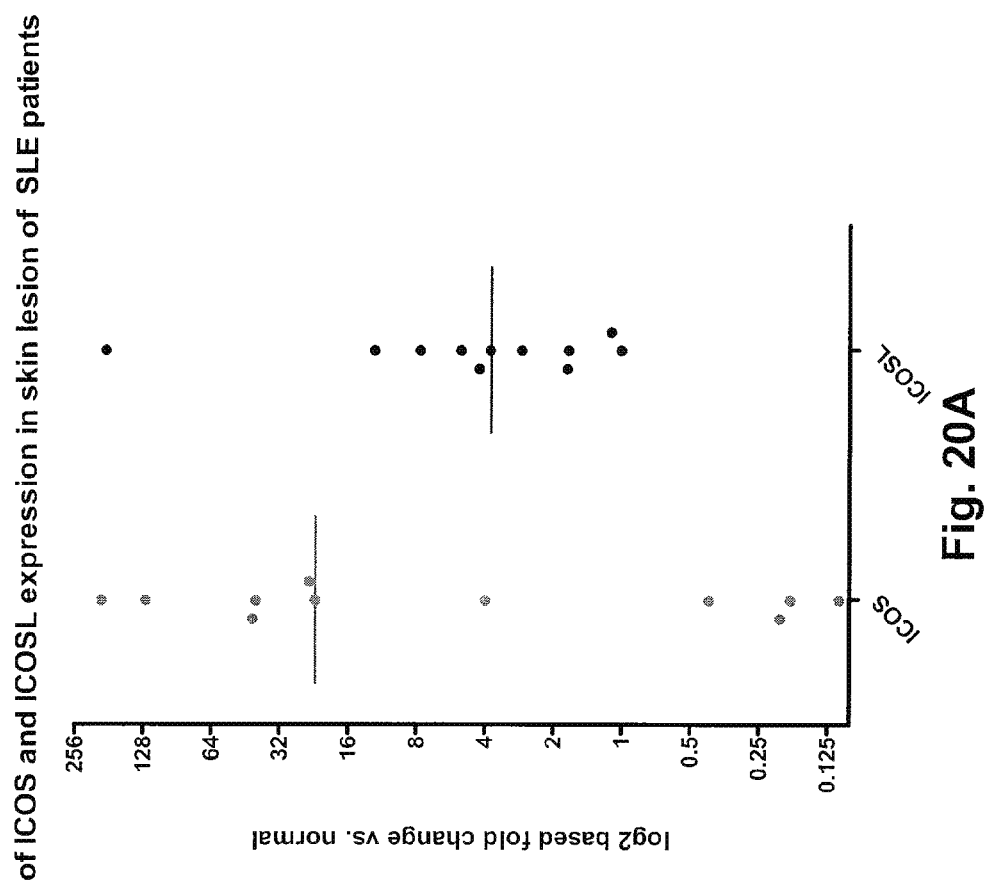
Figure 20B:
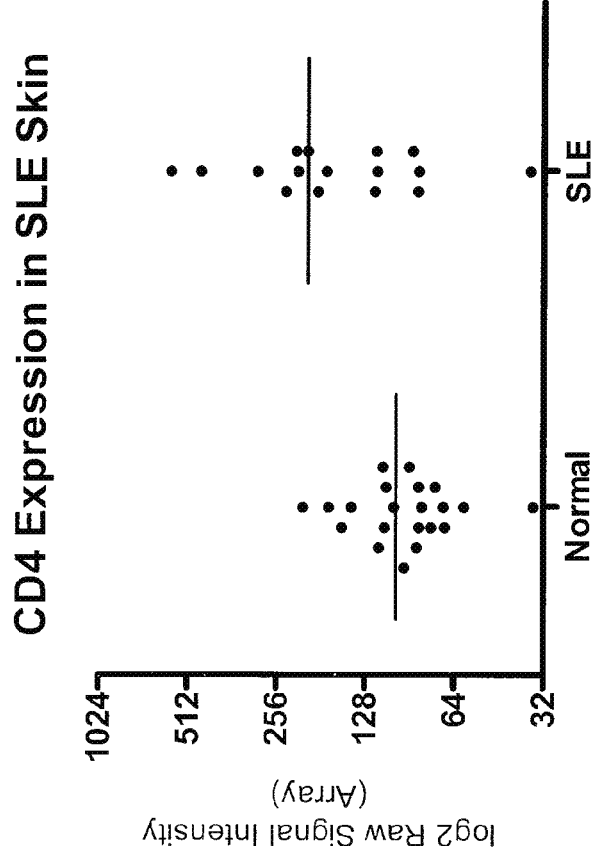
Figure 20C:
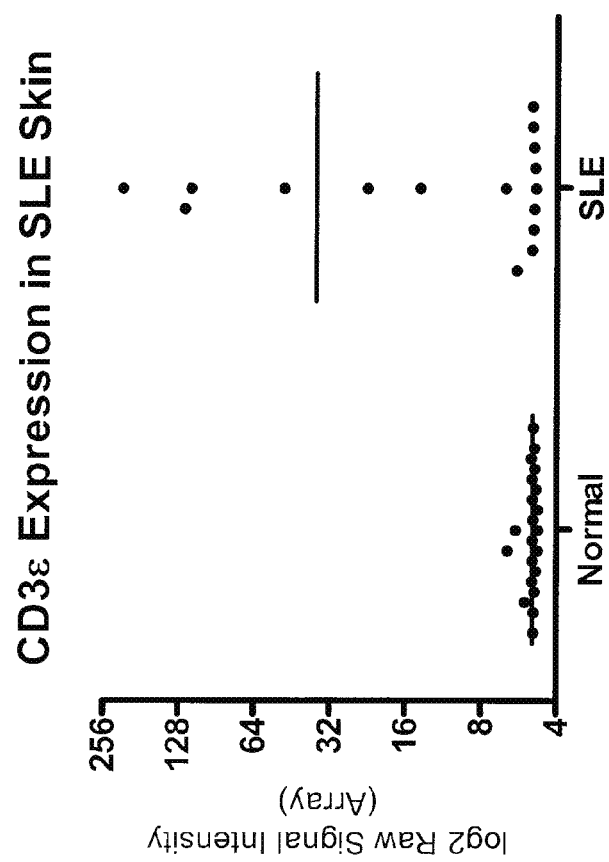

FIG. 20A shows ICOS and ICOSL mRNA relative expression (log 2 scale) in SLE (Systemic Lupus Erythematosus) skin lesion specimens. Individual fold-change values were determined relative to a normal skin sample control. Data was generated on Fluidigm's BioMark™ 48.48 dynamic array. Bars represent mean of relative expression (fold-change) for each transcript (ICOS or ICOSL) examined.

Raw signal intensity values (log 2 scale) for CD4 (FIG. 20B) and CDR3ε mRNA (FIG. 20C) in normal and SLE (Systemic Lupus Erythematosus) skin specimens. Data (GC-RMA normalized) was generated on the Affymetrix Human Genome U133 Plus 2.0 Array. Bars represent mean of raw signal intensity for normal and SLE samples.

Figure 21A:
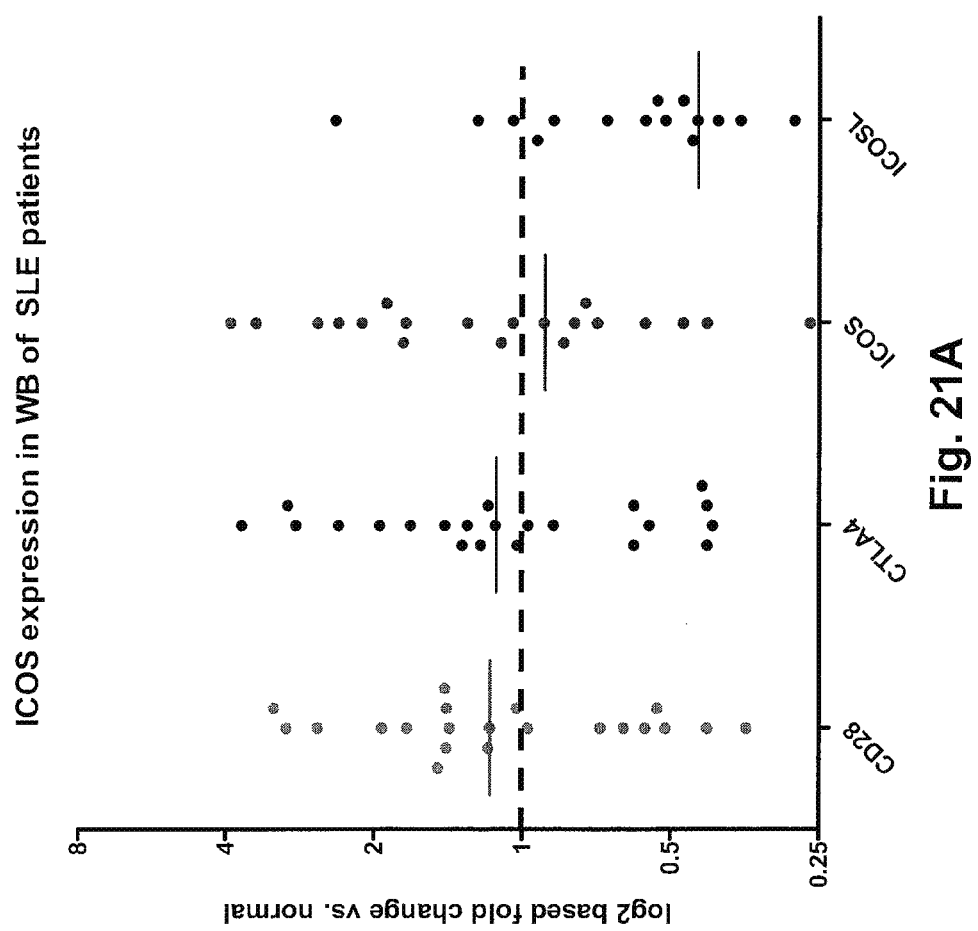
Figure 21B:
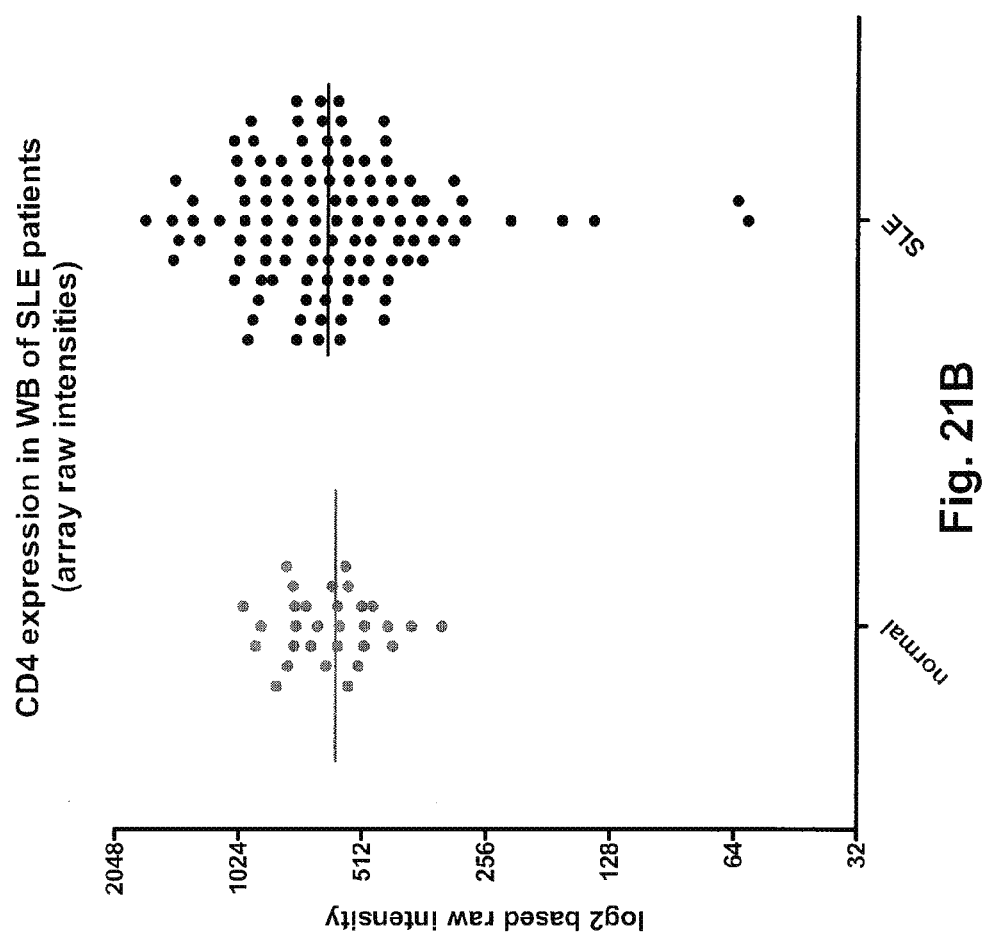

FIG. 21A: CD28, CTLA4, ICOS and ICOSL mRNA relative expression (log 2 scale) in SLE (Systemic Lupus Erythematosus) whole blood specimens. Individual fold-change values were determined relative to a pooled normal whole blood sample control. Data was generated on Fluidigm's BioMark™ 48.48 dynamic array. Bars represent mean of relative expression (fold-change) for each transcript (CD28, CTLA4, ICOS or ICOSL) analyzed.

Raw signal intensity values (log 2 scale) for CD4 (FIG. 21B) and CDR3ε mRNA (FIG. 21C) in normal and SLE (Systemic Lupus Erythematosus) whole blood specimens. Data (GC-RMA normalized) was generated on the Affymetrix Human Genome U133 Plus 2.0 Array. Bars represent mean of raw signal intensity for normal and SLE samples.

7.17. ICOS Expression in Inclusion Body Myositis (IBM) and Dermatomyositis (DM).

Inducible costimulator (ICOS), a receptor on activated T-cells, plays a central role in humoral immunity. Elevated levels of ICOS are present in patients with autoimmune diseases (e.g., rheumatoid arthritis and systemic lupus) and effector cytokines have been shown to correlate with increased levels of this protein. We used genomics technologies to investigate the over-expression of ICOS and the ICOS ligand (ICOSL) in muscle tissue taken from patients with inclusion body myositis (IBM), dermatomyositis (DM) and polymyositis (PM) and present results consistent with a regulatory mechanism of ICOS by the T-cell expressed miRNA, miR-101.

We profiled muscle specimens from myositis patients using TaqMan® QRT-PCR (Fluidigm's BioMark™ 48.48 dynamic array). MiRNAs (noncoding RNAs expressed by T lymphocytes and known to regulate gene expression) that potentially regulate ICOS were identified by 2 criteria: (1) their sequences were complementary to the 3' UTR region of ICOS, and (2) they were significantly differentially expressed in the opposite direction of ICOS mRNA in IBM, PM and DM muscle, compared with normal control muscle.

ICOS mRNA in IBM muscle specimens were highly up-regulated by an average of 40-fold, with mRNAs of ICOSL up-regulated by an average of 3.5-fold, compared to normal controls. In DM muscle specimens, ICOS mRNAs were up-regulated by an average of 5-fold; ICOSL mRNA showed no significant upregulation compared with normal controls. ICOS mRNA in IBM muscle specimens were highly up-regulated (over 70 fold upregulation), with ICOSL mRNAs up-regulated by ~2-fold, compared to normal controls. Overexpression of ICOS and ICOSL mRNA was not observed in whole blood from IBM or DM muscle. CD4 and CD3ε mRNAs were strongly over-expressed in IBM muscle specimens, whereas only CD4 mRNA was over-expressed in muscle specimens of DM patients. The presence of ARE sites (AU rich region for protein binding) and sequence complementarity between the 3' UTR domain in ICOS and miR-101 suggest that miR-101 is a potential regulator of ICOS. We subsequently evaluated the expression level of miR-101, as well as the feasibility of this miRNA to regulate this transcript. The expression of miR-101 was significantly down-regulated by an average of 4-fold and 2.5-fold, respectively, in IBM and DM muscle compared with normal control muscle.

ICOS mRNA is overexpressed in muscle tissue from IBM, DM and PM patients. Strong over-expression of mRNAs of CD4 and CD3ε suggest an increase in CD4+ T cell infiltration at the disease site of IBM patients as has been previously noted. The significant under-expression of miR-101 in muscle tissue from IBM and DM patients confirmed the observation from sanroque mice previously reported.

Affymetrix GeneChip, qRT-PCR and microRNA Profiling—Myositis: We profiled muscle biopsy and whole blood (WB) from a panel of myositis patients using the Affymetrix® human whole genome array (WGA) platform. Additionally, we profiled muscle specimens from myositis patients using both TaqMan® qRT-PCR (Fluidigm's BioMark™ 48.48 dynamic array) and the Applied Biosystem MicroRNA TaqMan Human MicroRNA Array v1.0 platforms. MiRNAs (noncoding RNAs expressed by T lymphocytes and known to regulate gene expression) that potentially regulate ICOS were identified by 2 criteria: (1) their sequences were complementary to the 3' UTR region of ICOS, and (2) they were significantly differentially expressed in the opposite direction of ICOS mRNA in IBM, PM and DM muscle, compared with normal control muscle.

FIG. 18 shows miR-101 relative expression in muscle specimens from myositis patients (IBM=Inclusion-body myositis, PM=polymyositis, DM=Dermatomyositis). Individual expression values were determined relative to a normal muscle sample control. Data was generated on ABI's Human MicroRNA Array v1.0 platform. Bars represent mean of relative expression for each disease sub-type.

Figure 19A:
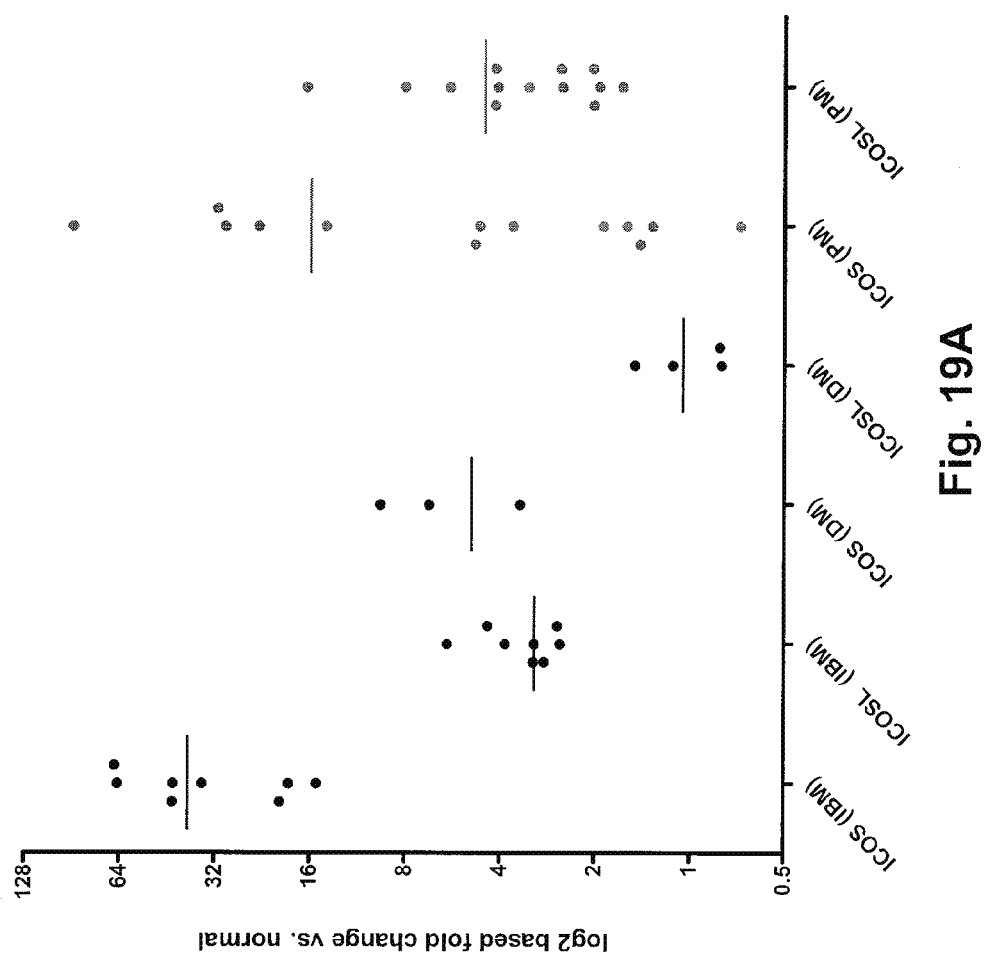
Figure 19B:
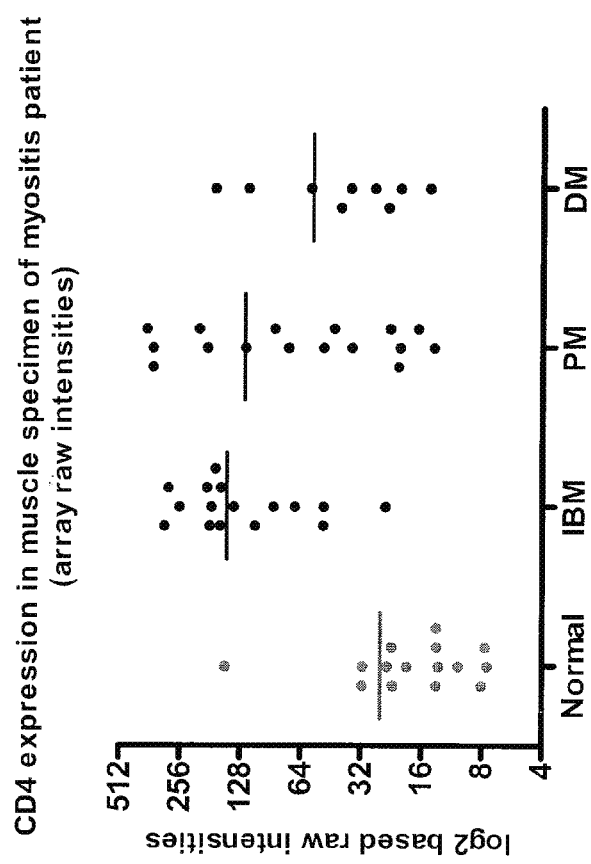
Figure 19C:
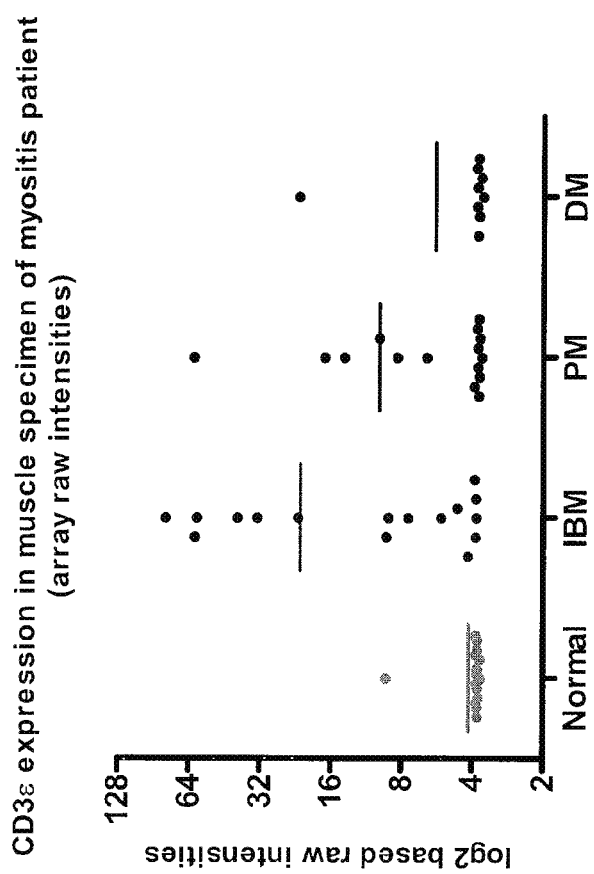

FIG. 19A shows ICOS and ICOSL mRNA relative expression (log 2 scale) in myositis muscle specimens (IBM=Inclusion-body myositis, PM=polymyositis, DM=Dermatomyositis). Individual fold-change values were determined relative to a normal muscle sample control. Data was generated on Fluidigm's BioMark™ 48.48 dynamic array. Bars represent mean of relative expression (fold-change) for each disease sub-type and transcript (ICOS or ICOSL) combination.

Raw signal intensity values (log 2 scale) for CD4 (FIG. 19B) and CD3ζ (FIG. 19C). mRNA in normal and myositis muscle specimens (IBM=Inclusion-body myositis, PM=polymyositis, DM=Dermatomyositis). Data (GC-RMA normalized) was generated on the Affymetrix Human Genome U133 Plus 2.0 Array. Bars represent mean of raw signal intensity for normals and each disease sub-type.

Figure 19D:
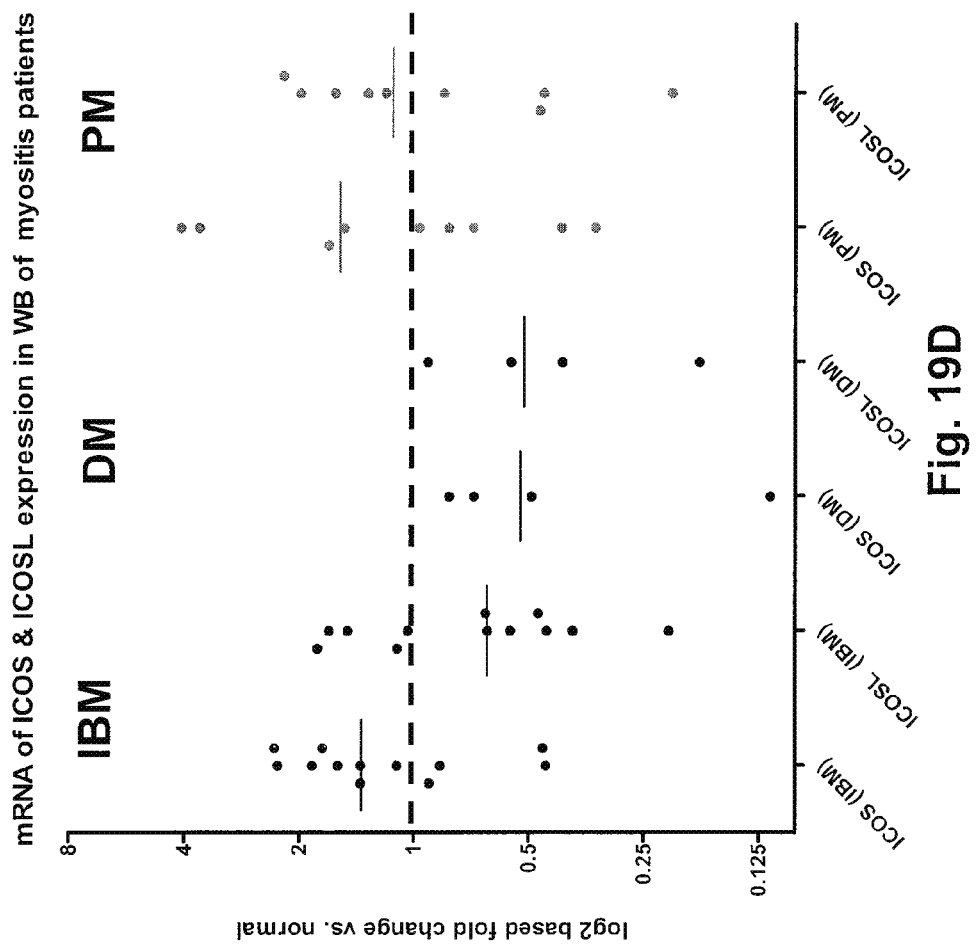

FIG. 19D shows ICOS and ICOSL mRNA relative expression (log 2 scale) in myositis whole blood samples (IBM=Inclusion-body myositis, PM=polymyositis, DM=Dermatomyositis). Individual fold-change values were determined relative to a normal muscle sample control. Data was generated on Fluidigm's BioMark™ 48.48 dynamic array. Bars represent mean of relative expression (fold-change) for each disease sub-type and transcript (ICOS or ICOSL) combination.

Those skilled in the art will recognize, or be able to ascertain using no more than routine experimentation, many equivalents to the specific embodiments of the invention described herein. Such equivalents are intended to be encompassed by the following claims.

Various publications are cited herein, the disclosures of which are incorporated by reference in their entireties.

Although the foregoing invention has been described in some detail by way of illustration and example for purposes of clarity of understanding, it will be obvious that certain changes and modifications may be practiced within the scope of the appended claims.

What is claimed is:

1. An isolated human anti-ICOS antibody comprising a VH domain of an amino acid sequence of SEQ ID NO: 7, a VK domain of an amino acid sequence of SEQ ID NO: 2, and an engineered IgG1 Fc region, wherein the engineered IgG1 Fc region comprises complex N-glycoside-linked sugar chains in which fucose is not bound to N-acetylglucosamine in the reducing end of the sugar chain, wherein the antibody mediates enhanced ADCC activity as compared to the level of ADCC activity mediated by a parent antibody comprising the same VH and VK domains and a wild type Fc region, wherein said antibody depletes circulating ICOS-expressing T cells in vivo in a mammal for at least 14 days when administered as a single dose of 125 mg/m².

2. A pharmaceutical composition comprising the antibody of claim 1 in a pharmaceutically acceptable carrier.

3. A method of treating an autoimmune disease or disorder in a human, comprising administering to a human in need thereof a therapeutically-effective amount of the antibody of claim 1.

4. The method of claim 3, wherein the autoimmune disease or disorder is SLE or scleroderma.

5. A method of treating or preventing rejection in a human transplant patient, comprising administering to a human in need thereof a therapeutically-effective amount of the antibody of claim 1.

6. A method of depleting ICOS expressing T cells in a human patient comprising administering to a human in need thereof a therapeutically-effective amount of the antibody of claim 1.

7. The method of claim 6, wherein the depletion substantially persists for at least about 1, at least about 2, at least about 3 or at least about 4 weeks following the administration of the antibody.

8. The method of claim 6, wherein at least about 95% of the T cells are depleted.

9. The method of claim 6, wherein the ICOS expressing T cell is a memory T cell.

10. The method of claim 6, wherein the ICOS expressing T cell is a circulating T cell.

11. A method of depleting circulating class switched B cells in a primate comprising administering an effective amount of the antibody of claim 1.

12. The method of claim 11, wherein the depletion substantially persists for at least about 1, at least about 2, at least about 3 or at least about 4 weeks following the administration of the antibody.

13. The method of claim 11, wherein at least about 95% of the circulating class switched B cells are depleted.

14. An isolated anti-ICOS antibody comprising a VH domain of an amino acid sequence of SEQ ID NO: 7, a VK domain of an amino acid sequence of SEQ ID NO:2, and a modified IgG1 Fc region, wherein the antibody has complex N-glycoside-linked sugar chains bound to the modified IgG1 Fc region in which fucose is not bound to N-acetylglucosamine in the reducing end in the sugar chain, wherein the antibody mediates enhanced ADCC activity as compared to the level of ADCC activity mediated by a parent antibody comprising the same VH and VK domains and a non-modified Fc region, and wherein said antibody depletes circulating ICOS-expressing T cells in vivo and depletes class switched B cells in a primate.

15. The antibody of claim 14, wherein the primate is a non-human primate.

16. The antibody of claim 14, wherein the primate is a human.

17. The antibody of claim 14, wherein the depletion substantially persists for at least about 1, at least about 2, at least about 3 or at least about 4 weeks following the administration of the antibody.

18. The antibody of claim 14, wherein at least about 95% of the circulating class switched B cells are depleted.

19. A method of treating a T cell malignancy in a human, comprising administering to a human in need thereof a therapeutically effective amount of the antibody of claim 1.

20. An isolated anti-ICOS antibody comprising a VH domain of an amino acid sequence of SEQ ID NO: 7, a VK domain of an amino acid sequence of SEQ ID NO:2, and a variant IgG1 Fc region comprising complex N-glycoside-linked sugar chains in which fucose is not bound to N-acetylglucosamine in the reducing end of the sugar chain, wherein the antibody depletes circulating ICOS-expressing T cells in vivo.

\* \* \* \* \*

SEQUENCE LISTING

```
<160> NUMBER OF SEQ ID NOS: 39

<210> SEQ ID NO 1
<211> LENGTH: 321
<212> TYPE: DNA
<213> ORGANISM: Homo sapiens

<400> SEQUENCE: 1
gacatccaga tgacccagtc tccatcttcc gtgtctgcat ctgtaggaga cagagtcacc      60
atcacttgtc gggcgagtca gggtattagc aggttgttag cctggtatca gcagaaacca     120
gggaaagccc ctaaactcct gatctatgtt gcatccagtt tgcaaagtgg ggtcccatca     180
aggttcagcg gcagtggatc tgggacagat ttcactctca ccatcagcag cctgcagcct     240
gaagattttg caacttacta ttgtcaacag gctaacagtt tcccgtggac gttcggccaa     300
gggaccaagg tggaaatcaa a                                               321

<210> SEQ ID NO 2
<211> LENGTH: 107
<212> TYPE: PRT
<213> ORGANISM: Homo sapiens

<400> SEQUENCE: 2
```

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Leu
            20                  25                  30

Leu Ala Trp Tyr Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Ala Asn Ser Phe Pro Trp
                85                  90                  95

Thr Phe Gly Gln Gly Thr Lys Val Glu Ile Lys
            100                 105
```

```
<210> SEQ ID NO 3
<211> LENGTH: 11
<212> TYPE: PRT
<213> ORGANISM: Homo sapiens

<400> SEQUENCE: 3

Arg Ala Ser Gln Gly Ile Ser Arg Leu Leu Ala
1               5                   10

<210> SEQ ID NO 4
<211> LENGTH: 7
<212> TYPE: PRT
<213> ORGANISM: Homo sapiens

<400> SEQUENCE: 4

Val Ala Ser Ser Leu Gln Ser
1               5

<210> SEQ ID NO 5
<211> LENGTH: 9
<212> TYPE: PRT
<213> ORGANISM: Homo sapiens

<400> SEQUENCE: 5

Gln Gln Ala Asn Ser Phe Pro Trp Thr
1               5

<210> SEQ ID NO 6
<211> LENGTH: 376
<212> TYPE: DNA
<213> ORGANISM: Homo sapiens

<400> SEQUENCE: 6
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccctc acagtggtgg cacaaactat     180
gcacagaagt ttcagggcag ggtcaccatg accagggaca cgtccatcag cacagcctac     240
atggagctga gcaggctgag atccgacgac acggccgtgt attactgtgc gaggacgtat     300
tactatgata gtagtggtta ttaccatgat gcttttgata tctggggcca agggacaatg     360
gtcaccgtct cttcag                                                     376

<210> SEQ ID NO 7
```

```
<211> LENGTH: 125
<212> TYPE: PRT
<213> ORGANISM: Homo sapiens

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro His Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Thr Tyr Tyr Tyr Asp Ser Ser Gly Tyr Tyr His Asp Ala Phe
            100                 105                 110

Asp Ile Trp Gly Gln Gly Thr Met Val Thr Val Ser Ser
        115                 120                 125

<210> SEQ ID NO 8
<211> LENGTH: 5
<212> TYPE: PRT
<213> ORGANISM: Homo sapiens

<400> SEQUENCE: 8

Gly Tyr Tyr Met His
1               5

<210> SEQ ID NO 9
<211> LENGTH: 17
<212> TYPE: PRT
<213> ORGANISM: Homo sapiens

<400> SEQUENCE: 9

Trp Ile Asn Pro His Ser Gly Gly Thr Asn Tyr Ala Gln Lys Phe Gln
1               5                   10                  15

Gly

<210> SEQ ID NO 10
<211> LENGTH: 16
<212> TYPE: PRT
<213> ORGANISM: Homo sapiens

<400> SEQUENCE: 10

Thr Tyr Tyr Tyr Asp Ser Ser Gly Tyr Tyr His Asp Ala Phe Asp Ile
1               5                   10                  15

<210> SEQ ID NO 11
<211> LENGTH: 57
<212> TYPE: DNA
<213> ORGANISM: Artificial
<220> FEATURE:
<223> OTHER INFORMATION: nucleotide primer

<400> SEQUENCE: 11
tatatatatc tagacatata tatgggtgac aatgacatcc actttgcctt tctctcc      57

<210> SEQ ID NO 12
```

```
<211> LENGTH: 89
<212> TYPE: DNA
<213> ORGANISM: Artificial
<220> FEATURE:
<223> OTHER INFORMATION: nucleotide primer

<400> SEQUENCE: 12
tccactttgc ctttctctcc acaggtgtcc actcccaggt gcagctggtg cagtctgggg    60
ctgaggtgaa gaagcctggg gcctcagtg                                       89

<210> SEQ ID NO 13
<211> LENGTH: 67
<212> TYPE: DNA
<213> ORGANISM: Artificial
<220> FEATURE:
<223> OTHER INFORMATION: nucleotide primer

<400> SEQUENCE: 13
catatagtag ccggtgaagg tgtatccaga agccttgcag agaccttca ctgaggcccc      60 aggcttc                                                               67

<210> SEQ ID NO 14
<211> LENGTH: 67
<212> TYPE: DNA
<213> ORGANISM: Artificial
<220> FEATURE:
<223> OTHER INFORMATION: nucleotide primer

<400> SEQUENCE: 14
caccggctac tatatgcact gggtgcgaca ggcccctgga caagggcttg agtggatggg    60
atggatc                                                               67

<210> SEQ ID NO 15
<211> LENGTH: 63
<212> TYPE: DNA
<213> ORGANISM: Artificial
<220> FEATURE:
<223> OTHER INFORMATION: nucleotide primer

<400> SEQUENCE: 15
ctgccctgaa acttctgtgc atagtttgtg ccaccactgt gagggttgat ccatcccatc    60
cac                                                                   63

<210> SEQ ID NO 16
<211> LENGTH: 68
<212> TYPE: DNA
<213> ORGANISM: Artificial
<220> FEATURE:
<223> OTHER INFORMATION: nucleotide primer

<400> SEQUENCE: 16
cagaagtttc agggcagggt caccatgacc agggacacgt ccatcagcac agcctacatg    60
gagctgag                                                              68

<210> SEQ ID NO 17
<211> LENGTH: 64
<212> TYPE: DNA
<213> ORGANISM: Artificial
<220> FEATURE:
<223> OTHER INFORMATION: nucleotide primer

<400> SEQUENCE: 17
gtcctcgcac agtaatacac ggccgtgtcg tcggatctca gcctgctcag ctccatgtag    60
``` gctg                                                                    64

<210> SEQ ID NO 18
<211> LENGTH: 66
<212> TYPE: DNA
<213> ORGANISM: Artificial
<220> FEATURE:
<223> OTHER INFORMATION: nucleotide primer

<400> SEQUENCE: 18
gtattactgt gcgaggacgt attactatga tagtagtggt tattaccatg atgcttttga     60
tatctg                                                                  66

<210> SEQ ID NO 19
<211> LENGTH: 74
<212> TYPE: DNA
<213> ORGANISM: Artificial
<220> FEATURE:
<223> OTHER INFORMATION: nucleotide primer

<400> SEQUENCE: 19
tatatatagg gcccttggtg gaggcctgaa gagacggtga ccattgtccc ttggccccag     60
atatcaaaag catc                                                         74

<210> SEQ ID NO 20
<211> LENGTH: 79
<212> TYPE: DNA
<213> ORGANISM: Artificial
<220> FEATURE:
<223> OTHER INFORMATION: nucleotide primer

<400> SEQUENCE: 20
tatatatacc ccggggccaa atgtgacatc cagatgaccc agtctccatc ttccgtgtct     60
gcatctgtag gagacagag                                                    79

<210> SEQ ID NO 21
<211> LENGTH: 70
<212> TYPE: DNA
<213> ORGANISM: Artificial
<220> FEATURE:
<223> OTHER INFORMATION: nucleotide primer

<400> SEQUENCE: 21
gataccaggc taacaacctg ctaataccct gactcgcccg acaagtgatg gtgactctgt     60
ctcctacaga                                                              70

<210> SEQ ID NO 22
<211> LENGTH: 74
<212> TYPE: DNA
<213> ORGANISM: Artificial
<220> FEATURE:
<223> OTHER INFORMATION: nucleotide primer

<400> SEQUENCE: 22
gttagcctgg tatcagcaga aaccagggaa agcccctaaa ctcctgatct atgttgcatc     60
cagtttgcaa agtg                                                         74

<210> SEQ ID NO 23
<211> LENGTH: 64
<212> TYPE: DNA
<213> ORGANISM: Artificial
<220> FEATURE:

<223> OTHER INFORMATION: nucleotide primer

<400> SEQUENCE: 23
gtgaaatctg tcccagatcc actgccgctg aaccttgatg gaccccact ttgcaaactg    60 gatg    64

<210> SEQ ID NO 24
<211> LENGTH: 71
<212> TYPE: DNA
<213> ORGANISM: Artificial
<220> FEATURE:
<223> OTHER INFORMATION: nucleotide primer

<400> SEQUENCE: 24
ctgggacaga tttcactctc accatcagca gcctgcagcc tgaagatttt gcaacttact    60
attgtcaaca g    71

<210> SEQ ID NO 25
<211> LENGTH: 82
<212> TYPE: DNA
<213> ORGANISM: Artificial
<220> FEATURE:
<223> OTHER INFORMATION: nucleotide primer

<400> SEQUENCE: 25
tatatatacg tacgtttgat ttccaccttg gtcccttggc cgaacgtcca cgggaaactg    60
ttagcctgtt gacaatagta ag    82

<210> SEQ ID NO 26
<211> LENGTH: 17
<212> TYPE: PRT
<213> ORGANISM: Homo sapiens

<400> SEQUENCE: 26

Met Gly Asp Asn Asp Ile His Phe Ala Phe Leu Ser Thr Gly Val His
1               5                   10                  15

Ser

<210> SEQ ID NO 27
<211> LENGTH: 22
<212> TYPE: PRT
<213> ORGANISM: Homo sapiens

<400> SEQUENCE: 27

Met Asp Met Arg Val Pro Ala Gln Leu Leu Gly Leu Leu Leu Leu Trp
1               5                   10                  15

Leu Pro Gly Ala Lys Cys
            20

<210> SEQ ID NO 28
<211> LENGTH: 375
<212> TYPE: DNA
<213> ORGANISM: Artificial
<220> FEATURE:
<223> OTHER INFORMATION: optimized coding sequence

<400> SEQUENCE: 28
caggtgcagc tggtgcagag cggcgctgag gtgaagaagc ctggcgccag cgtcaaggtg    60
tcctgcaagg ccagcggcta caccttcacc ggctactaca tgcactgggt gcggcaggct    120
ccaggacagg gcctggaatg gatgggctgg atcaaccccc acagcggcgg caccaactac    180

```
gcccagaagt tccagggcag ggtcaccatg accagggaca ccagcatcag caccgcctac      240
atggaactgt ccaggctgag aagcgacgac accgccgtgt actactgcgc caggacctac      300
tactacgaca gcagcggcta ctaccacgac gccttcgaca tctggggcca gggcaccatg      360
gtgaccgtga gcagc                                                       375

<210> SEQ ID NO 29
<211> LENGTH: 321
<212> TYPE: DNA
<213> ORGANISM: Artificial
<220> FEATURE:
<223> OTHER INFORMATION: optimized coding sequence

<400> SEQUENCE: 29
gacatccaga tgacccagag ccccagcagc gtgagcgcca gcgtgggcga cagggtgacc       60
atcacctgca gggccagcca gggcatcagc aggctgctgg cctggtatca gcagaagccc      120
ggcaaggccc ccaagctgct gatctacgtg gcctccagcc tccagagcgg cgtgcccagc      180
aggttcagcg gcagcggctc cggcaccgac ttcaccctga ccatcagctc cctgcagccc      240
gaggacttcg ccacctacta ctgccagcag gccaacagct cccctggac cttcggccag       300 ggcaccaagg tggagatcaa g                                                321

<210> SEQ ID NO 30
<211> LENGTH: 1368
<212> TYPE: DNA
<213> ORGANISM: Artificial
<220> FEATURE:
<223> OTHER INFORMATION: optimized coding sequence

<400> SEQUENCE: 30
caggtgcagc tggtgcagag cggcgctgag gtgaagaagc ctggcgccag cgtcaaggtg       60
tcctgcaagg ccagcggcta caccttcacc ggctactaca tgcactgggt gcggcaggct      120
ccaggacagg gcctggaatg gatgggctgg atcaaccccc acagcggcgg caccaactac      180
gcccagaagt tccagggcag ggtcaccatg accagggaca ccagcatcag caccgcctac      240
atggaactgt ccaggctgag aagcgacgac accgccgtgt actactgcgc caggacctac      300
tactacgaca gcagcggcta ctaccacgac gccttcgaca tctggggcca gggcaccatg      360
gtgaccgtga gcgccag caccaagggg cccagcgtgt tccccctggc ccccagcagc         420
aagagcacct ccggcggcac agccgccctg ggctgcctgg tgaaggacta cttccccgaa      480
ccggtgaccg tgtcctggaa cagcggcgct ctgaccagcg gcgtgcacac cttccccgcc      540
gtgctgcaga gcagcggcct gtacagcctg agcagcgtgg tgacagtgcc cagcagcagc      600
ctgggcaccc agacctacat ctgcaacgtg aaccacaagc ccagcaacac caaggtggac      660
aagagagtgg agcccaagag ctgcgacaag acccacacct gcccccctg ccctgcccct       720 gagctgctgg gcgacctag cgtgttcctg ttcccccca gcccaagga caccctgatg         780 atcagcagga cccccgaggt gacctgcgtg gtggtggacg tgagccacga ggaccctgag      840
gtgaagttca attggtacgt ggacggcgtg gaggtgcaca acgccaagac caagcccaga      900
gaggagcagt acaacagcac ctacagggtg gtgtccgtgc tgaccgtgct gcaccaggac      960
tggctgaacg gcaaggaata caagtgcaag gtctccaaca aggccctgcc tgccccatc     1020 gaaaagacca tcagcaaggc caagggccag cctcgggagc ccaggtgta caccctgccc     1080 cctagccggg aggagatgac caagaaccag gtgtccctga cctgtctggt gaagggcttc     1140 tacccccagcg acatcgccgt ggagtgggag agcaacggcc agcccgagaa caactacaag     1200
```

```
accacccccc ctgtgctgga cagcgacggc agcttcttcc tgtacagcaa gctgaccgtg    1260
gacaagtcca ggtggcagca gggcaacgtg ttcagctgca gcgtgatgca cgaggccctg    1320
cacaaccact acacccagaa gagcctgagc ctgtcccccg gcaagtaa                 1368
```

<210> SEQ ID NO 31
<211> LENGTH: 645
<212> TYPE: DNA
<213> ORGANISM: Artificial
<220> FEATURE:
<223> OTHER INFORMATION: optimized coding sequence

<400> SEQUENCE: 31

```
gacatccaga tgacccagag ccccagcagc gtgagcgcca gcgtgggcga cagggtgacc     60
atcacctgca gggccagcca gggcatcagc aggctgctgg cctggtatca gcagaagccc    120
ggcaaggccc ccaagctgct gatctacgtg gcctccagcc tccagagcgg cgtgcccagc    180
aggttcagcg gcagcggctc cggcaccgac ttcaccctga ccatcagctc cctgcagccc    240
gaggacttcg ccacctacta ctgccagcag gccaacagct cccctggac cttcggccag    300 ggcaccaagg tggagatcaa cgtacggtg gccgctccca gcgtgttcat cttcccccc    360 agcgacgagc agctgaagag cggcaccgcc tccgtggtgt gcctgctgaa caacttctac    420
ccccgcgagg ccaaggtgca gtggaaggtg gacaacgccc tgcagtccgg caacagccag    480
gagagcgtca ccgagcagga cagcaaggac tccacctaca gcctgagcag caccctgacc    540
ctgagcaagg ccgactacga gaagcacaag gtgtacgcct gcgaggtgac ccaccagggc    600
ctgtccagcc ccgtgaccaa gagcttcaac aggggcgagt gctga                    645
```

<210> SEQ ID NO 32
<211> LENGTH: 199
<212> TYPE: PRT
<213> ORGANISM: Homo saoiens

<400> SEQUENCE: 32

```
Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175
```

```
Asn Gly Glu Tyr Met Phe Met Arg Ala Val Asn Thr Ala Lys Lys Ser
            180                 185                 190

Arg Leu Thr Asp Val Thr Leu
        195

<210> SEQ ID NO 33
<211> LENGTH: 168
<212> TYPE: PRT
<213> ORGANISM: Homo saoiens

<400> SEQUENCE: 33

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Val Cys Ile Leu Gly Cys Ile Leu
145                 150                 155                 160

Ile Cys Trp Leu Thr Lys Lys Met
                165

<210> SEQ ID NO 34
<211> LENGTH: 2609
<212> TYPE: DNA
<213> ORGANISM: Homo saoiens

<400> SEQUENCE: 34
ctgaacgcga ggactgttaa ctgtttctgg caaacatgaa gtcaggcctc tggtatttct     60
ttctcttctg cttgcgcatt aaagttttaa caggagaaat caatggttct gccaattatg    120
agatgtttat atttcacaac ggaggtgtac aaattttatg caaatatcct gacattgtcc    180
agcaatttaa aatgcagttg ctgaaagggg gcaaatact ctgcgatctc actaagacaa    240
aaggaagtgg aaacacagtg tccattaaga gtctgaaatt ctgccattct cagtyatcca    300
acaacagtgt ctctttttttt ctatacaact tggaccattc tcatgccaac tattacttct    360
gcaacctatc aatttttgat cctcctcctt ttaaagtaac tcttacagga ggatatttgc    420
atatttatga atcacaactt tgttgccagc tgaagttctg gttacccata ggatgtgcag    480
cctttgttgt agtctgcatt ttgggatgca tacttatttg ttggcttaca aaaagaagt    540 attcatccag tgtgcacgac cctaacggtg aatacatgtt catgagagca gtgaacacag    600
ccaaaaaatc tagactcaca gatgtgaccc tataatatgg aactctggca cccaggcatg    660
aagcacgttg gccagttttc ctcaacttga agtgcaagat tctcttattt ccgggaccac    720
```

```
ggagagtctg acttaactac atacatcttc tgctggtgtt ttgttcaatc tggaagaatg    780
actgtatcag tcaatgggga ttttaacaga ctgccttggt actgccgagt cctctcaaaa    840
caaacaccct cttgcaacca gctttggaga agcccagct cctgtgtgct cactgggagt     900
ggaatccctg tctccacatc tgctcctagc agtgcatcag ccagtaaaac aaacacattt    960
acaagaaaaa tgttttaaag atgccagggg tactgaatct gcaaagcaaa tgagcagcca   1020
aggaccagca tctgtccgca tttcactatc atactacctc ttctttctgt agggatgaga   1080
attcctcttt taatcagtca agggagatgc ttcaaagctg gagctatttt atttctgaga   1140
tgttgatgtg aactgtacat tagtacatac tcagtactct ccttcaattg ctgaacccca   1200
gttgaccatt ttaccaagac tttagatgct ttcttgtgcc ctcaattttc ttttaaaaa    1260
tacttctaca tgactgcttg acagcccaac agccactctc aatagagagc tatgtcttac   1320
attctttcct ctgctgctca atagttttat atatctatgc atacatatat acacacatat   1380
gtatataaaa ttcataatga atatatttgc ctatattctc cctacaagaa tattttttgct  1440
ccagaaagac atgttctttt ctcaaattca gttaaaatgg tttactttgt tcaagttagt   1500
ggtaggaaac attgcccgga attgaaagca aatttatttt attatcctat tttctaccat   1560
tatctatgtt ttcatggtgc tattaattac aagtttagtt cttttttgtag atcatattaa   1620
aattgcaaac aaaatcatct ttaatgggcc agcattctca tggggtagag cagaatattc   1680
atttagcctg aaagctgcag ttactatagg ttgctgtcag actataccca tggtgcctct   1740
gggcttgaca ggtcaaaatg gtccccatca gcctggagca gccctccaga cctgggtgga   1800
attccagggt tgagagactc ccctgagcca gaggccacta ggtattcttg ctcccagagg   1860
ctgaagtcac cctgggaatc acagtggtct acctgcattc ataattccag gatctgtgaa   1920
gagcacatat gtgtcagggc acaattccct ctcataaaaa ccacacagcc tggaaattgg   1980
ccctggccct tcaagatagc cttctttaga atatgatttg gctagaaaga ttcttaaata   2040
tgtggaatat gattattctt agctggaata ttttctctac ttcctgtctg catgcccaag   2100
gcttctgaag cagccaatgt cgatgcaaca acatttgtaa ctttaggtaa actgggatta   2160
tgttgtagtt taacattttg taactgtgtg cttatagttt acaagtgaga cccgatatgt   2220
cattatgcat acttatatta tcttaagcat gtgtaatgct ggatgtgtac agtacagtac   2280
tgaacttgta atttgaatct agtatggtgt tctgttttca gctgacttgg acaacctgac   2340
tggctttgca caggtgttcc ctgagttgtt tgcaggtttc tgtgtgtggg gtggggtatg   2400
gggaggagaa ccttcatggt ggcccacctg gcctggttgt ccaagctgtg cctcgacaca   2460
tcctcatccc cagcatggga cacctcaaga tgaataataa ttcacaaaat ttctgtgaaa   2520
tcaaatccag ttttaagagg agccacttat caaagagatt ttaacagtag taagaaggca   2580
aagaataaac atttgatatt cagcaactg                                     2609
```

<210> SEQ ID NO 35
<211> LENGTH: 23
<212> TYPE: RNA
<213> ORGANISM: Homo sapiens

<400> SEQUENCE: 35
aguuguuuua gugacuacga ccu                                             23

<210> SEQ ID NO 36
<211> LENGTH: 23
<212> TYPE: RNA

```
<213> ORGANISM: Homo sapiens

<400> SEQUENCE: 36
aguaucggga cauguuacga cga                                               23

<210> SEQ ID NO 37
<211> LENGTH: 23
<212> TYPE: RNA
<213> ORGANISM: Homo sapiens

<400> SEQUENCE: 37
acuaucggga cauguuacga cga                                               23

<210> SEQ ID NO 38
<211> LENGTH: 22
<212> TYPE: RNA
<213> ORGANISM: Homo sapiens

<400> SEQUENCE: 38
gaagucaaua gugucaugac au                                                22

<210> SEQ ID NO 39
<211> LENGTH: 22
<212> TYPE: RNA
<213> ORGANISM: Homo sapiens

<400> SEQUENCE: 39
ccucacuucu gugccucggu cu                                                22
```